(12) United States Patent
Anversa et al.

(10) Patent No.: US 7,547,674 B2
(45) Date of Patent: Jun. 16, 2009

(54) METHODS AND COMPOSITIONS FOR THE REPAIR AND/OR REGENERATION OF DAMAGED MYOCARDIUM

(75) Inventors: Piero Anversa, New York, NY (US); Donald Orlic, Bethesda, MD (US)

(73) Assignee: New York Medical College, Valhalla, NY (US)

(*) Notice: Subject to any disclaimer, the term of this patent is extended or adjusted under 35 U.S.C. 154(b) by 0 days.

(21) Appl. No.: 10/162,796

(22) Filed: Jun. 5, 2002

(65) Prior Publication Data
US 2003/0054973 A1 Mar. 20, 2003

Related U.S. Application Data

(63) Continuation-in-part of application No. 09/919,732, filed on Jul. 31, 2001, now abandoned.

(60) Provisional application No. 60/295,807, filed on Jun. 6, 2001, provisional application No. 60/295,806, filed on Jun. 6, 2001, provisional application No. 60/295,805, filed on Jun. 6, 2001, provisional application No. 60/295,804, filed on Jun. 6, 2001, provisional application No. 60/295,803, filed on Jun. 6, 2001.

(51) Int. Cl.
| A61K 38/00 | (2006.01) |
| A61K 38/19 | (2006.01) |
| C12N 5/00 | (2006.01) |
| A61K 38/20 | (2006.01) |

(52) U.S. Cl. .......................... 514/2; 424/85.1; 435/375
(58) Field of Classification Search ................ 424/85.1; 514/2; 435/375, 377
See application file for complete search history.

(56) References Cited

U.S. PATENT DOCUMENTS

| 5,197,985 | A | | 3/1993 | Caplan et al. |
| 5,199,942 | A | | 4/1993 | Gillis |
| 5,202,120 | A | | 4/1993 | Silver et al. |
| 5,543,318 | A | | 8/1996 | Smith et al. |
| 5,580,779 | A | | 12/1996 | Smith et al. |
| 5,602,301 | A | * | 2/1997 | Field ............................. 800/8 |
| 5,833,975 | A | | 11/1998 | Paoletti et al. |
| 5,906,934 | A | | 5/1999 | Grande et al. |
| 5,942,235 | A | | 8/1999 | Paoletti |
| 5,990,091 | A | | 11/1999 | Tartaglia et al. |
| 6,001,934 | A | | 12/1999 | Yamanaka et al. |
| 6,004,777 | A | | 12/1999 | Tartaglia et al. |
| 6,099,832 | A | | 8/2000 | Mickle et al. |
| 6,110,459 | A | | 8/2000 | Mickle et al. |
| 6,117,675 | A | | 9/2000 | van der Kooy et al. |
| 6,130,066 | A | | 10/2000 | Tartaglia et al. |
| 6,174,333 | B1 | | 1/2001 | Kadiyala et al. |
| 6,255,292 | B1 | | 7/2001 | Liang |
| 6,265,189 | B1 | | 7/2001 | Paoletti et al. |
| 6,329,348 | B1 | | 12/2001 | Crystal et al. |
| 6,547,787 | B1 | * | 4/2003 | Altman et al. ................. 606/41 |
| 2002/0122792 | A1 | * | 9/2002 | Stegmann ................... 424/94.1 |

FOREIGN PATENT DOCUMENTS

| WO | WO 95/14079 | | 5/1995 |
| WO | 96/04314 | | 2/1996 |
| WO | WO 9945775 A1 | * | 9/1999 |
| WO | 00/06701 | | 2/2000 |
| WO | 00/57922 | | 10/2000 |

OTHER PUBLICATIONS

Taylor et al. Cardiac chimerism as a mechanism for self-repair: does it happen and if so to what degree? Circulation. 106(1):2-4, Jul. 2002.*
Foley et al. Heart induction: embryology to cardiomyocyte regeneration. Trends Cardiovasc Med. 14(3):121-5, Apr. 2004.*
Burkitt et al. Wheater's Functional Histology: A Text and Colour Atlas. Third Ed. New York: Churchill Livingstone, 1996, pp. 107-111.*
Nagai et al. Promotion of cardiac regeneration by cardiac stem cells. Circulation Research, vol. 97, pp. 615-617, 2005.*
Kanellakis et al. Granulocyte colony-stimulating factor and stem cell factor improve endogenous repair after myocardial infarction. Cardiovascular Research, vol. 70, pp. 117-125, 2006.*
Denten et al. Hematopoietic stem cells do not repair the infarcted mouse heart. Cardiovascular Research, vol. 65, pp. 52-63, 2005.*
Mohri et al. Leukemia inhibitory factor induces endothelial differentiation in cardiac stem cells. The Journal of Biological Chemistry, vol. 281, No. 10, pp. 6442-6447, Mar. 2006.*
Stedman's Online Medical Dictionary, 27th Edition, entry for "biotechnology", http://www.stedmans.com/, printed on Oct. 24, 2007.*
Merriam-Webster Online Dictionary, entry for "biotechnology", http://www.m-w.com/, printed on Oct. 24, 2007.*
On-line Medical Dictionary, entry for "cardiology", http://cancerweb.ncl.ac.uk/omd/index.html, printed on Oct. 24, 2007.*
Encarta World English Dictionary [North American Edition], entry for "cardiology", http://encarta.msn.com, Microsoft Corporation, 2007.*
Yasuda et al. Single low-dose administration of human recombinant heptocyte growth factor attenuates intimal hyperplasia in a balloon-injured rabbit iliac artery model. Circulation, vol. 101, pp. 2546-2549, May 2000.*
Huang, Jul-Han, et al., "Protein Transfer of Preformed MHC-Peptide Complexes Sensitizes Tartet Cells to T Cell Cytolysis," Immunity, vol. 1, No. 7, 607-613, Oct. 1994.
Ross, Russell, "The pathogenesis of atherosclerosis: a perspective for the 1990s," Nature, vol. 362, 801-809, Apr. 1993.

(Continued)

*Primary Examiner*—Celine X Qian
*Assistant Examiner*—Jennifer Dunston
(74) *Attorney, Agent, or Firm*—Cooley Godward Kronish LLP

(57) ABSTRACT

Methods, compositions, and kits for repairing damaged myocardium and/or myocardial cells including the administration cytokines are disclosed and claimed.

22 Claims, 87 Drawing Sheets
(56 of 87 Drawing Sheet(s) Filed in Color)

OTHER PUBLICATIONS

Sensebe, Luc, et al., The Broad Spectrum of Cytokine Gene Expression by Myoid Cells from the Human Marrow Microenvironment, Stem Cells, vol. 15, 133-143, Nov. 2, 1997.

Wartiovaara, Ulla, et al., "Peripheral Blood Platelets Express VEGF-C and VEGF which are Released during Platelet Activation," Thromb Haemost, vol. 80, 171-175, 1998.

Mohle, Robert, et al., "Constitutive production and thrombin-induced release of vascular endothelial growth factor by human megakaryocytes and platelets," Proc. Natl. Acad. Sci. USA, vol. 94, No. 2, 663-8, Jan. 21, 1997.

Boyden, Stephen, "The Chemotactic Effect of Mixtures of Antibody and Antigen on Polymorphonuclear Leucocytes," J. Exptl. Med. vol. 115, 453-456, 1962.

American Heart Association. *2001 Heart and Stroke Statistical Update*. Dallas, Texas: American Heart Association, 2000.

Bautz, F. et al., "Expression and secretion of vascular endothelial growth factor-A by cytokine stimulated hematopoietic progenitor cells. Possible role in the hematopoietic microenvironment." *Exp Hematol* Jun. 2000; 28(6):700-6, abstract only.

Beardsle, M. A. et al., "Rapid turnover of connexin43 in the adult rat heart." *Circ. Res.* (1998) 83, 629-635.

Beltrami, C.A. et al., "Structural basis of end-stage failure in ischemic cardiomyopathy in humans." *Circulation* (1994) 89, 151-163.

Bianco, P. et al. "Bone marrow stromal stem cells: nature, biology, and potential applications." *Stem Cells* (2001) 19:180-192.

Blume et al., "A review of autologous hematopoetic cell transplantation." Biology of Blood & Marrow Transplantation, (2000) 6: 1-12.

Bodine, D.M. et al., "Efficient retrovirus transduction of mouse pluripotent hematopoietic stem cells mobilized into the peripheral blood by treatment with branulocyte colony-stimulating factor and stem cell factor." *Blood* (1994) 84, 1482-1491.

Brier, G. et al., "Molecular cloning and expression of murine vascular endothelial-cadherin in early stage development of cardiovascular system." *Blood* (1996) 87, 630-641.

Brugger et al., "Ex vivo manipulation of hematopoetic stem and progenitor cells. Seminars in Hematology." (2000), 37 (1): 42-49.

Caceres-Cortes, J.R. et al., "Steel factor sustains SCL expression and the survival of purified CD34+ bone marrow cells in the absence of detectable cell differentiation." *Stem Cells* (Jan. 2001);19(1):59-70, abstract only.

Chiu et al., "Cellular Cardiomyoplasty: Mycardial Regeneration With Satellite Cell Implantation." *Ann. Thorac. Surg.*(1995) 60: 12-18.

Clutterbuck, R.D. et al., "G-CSF mobilization of haemopoietic cell populations in SCID mice engrafted with human leukaemia." *Bone Marrow Transplant* (Aug. 1997); 20(4);325-32, abstract only.

Coles, J.G. et al., "Inhibition of Human Xenogenic or Allogenic Antibodies to Reduce Xenograft or Allograft Rejection in Human Recipients". Patent No. WO 95/34581A1, published Dec. 21, 1995, abstract only.

Couper, L.L. et al., "Vascular endothelial growth factor increases the mitogenic response to fibroblast growth factor-2 in vascular smooth muscle cells in vivo via expression of fms-like tyrosine kinase-1." (1997) *Circ. Res.* 81, 932-939.

Dinsmore, J. "Procine Cardiomyocytes and Their Use in Treatment of Insufficient Cardiac Function". Patent No. WO 96/38544, published Dec. 5, 1996, abstract only.

Durocher, D. et al., "The cardiac transciption factors Nkx2-5 and GATA-4 are mutual cofactors." *EMBO J.* 16, 5687-5696 (1997).

Fielding et al., "Autologous bone marrow transplantation." Curr. Opin. Hematology, 1994, 1: 412-417.

Gussoni et al., "Normal dystrophin transcripts detected in Duchenne muscular dystrophy patients after myoblast transplantation." Nature 356:435-438 (1992).

Hermann, H. and Aebi, U. "In Subcellular Biochemistry: Intermediate Filaments." vol. 31 (ed. Herrmann, H. & Harris, E.) 319-362 (Plenum Press, New York, 1998).

Huang H.M. et al., "Optimal proliferation of a hematopoietic progenitor cell line requires either costimulation with stem cell factor or increase of receptor expression that can be replaced by over expression of Bcl-2. Blood." Apr. 15, 1999;93(8):2569-77.

Ikuta, K. et al., "Mouse hematopoietic stem cells and the interaction of c-kit receptor and steel factor." *International Journal of Cell Cloning* 1991; 9:451-460, abstract only.

Janowska-Wieczorek, A. et al., "Autocrine/paracrine mechanisms in human hematopoiesis." *Stem Cells* 2001; 19:99-107.

Jo, D.Y. et al., "Chemotaxis of primitive hematopoietic cells in response to stromal cell-derived factor-1." *The Journal of Clinical Investigation* Jan. 2000; 105(1):101-111.

Kachinsky, A.M. et al., "Intermediate filaments in cardiac myogenesis: nestin in the developing mouse heart." (1995) *J. Histochem. Cytochem.* 43, 843-847.

Kanj et al., "Myocardial ischemia associated with high-dose carmustine infusion." Cancer, 1991, 68 (9): 1910-1912.

Kajstura, J. et al., "The cellular basis of pacing-induced dilated cardiomyopathy. Myocyte cell loss and myocyte cellular reactive hypertrophy." (1995) *Circulation* 92, 2306-2317.

Kasahara, H. et al., "Cardiac and extracardiac expression of Csx/Nkx2.5 homeodomain protein." (1998) *Circ. Res.* 82, 936-946.

Kedes, L.H. et al., "Compositions and Methods for Transduction of Cells." Patent No. WO 95/12979A1, published May 18, 1995, abstract only.

Keil F. et al., "Effect of interleukin-3, stem cell factor and granulocyte-macrophage colony-stimulating factor on committed stem cells, long-term culture initiating cells and bone marrow stroma in a one-step long-term bone marrow culture." Ann Hematol. May 2000;79(5):243-8.

Kempermann, G. et al., "Activity-dependent regulation of neuronal plasticity and self repair." *Prog Brain Res* 2000; 127:35-48, abstract only.

Kim, C.H. and Broxmeyer H.E., "In vitro behavior of hematopoietic progenitor cells under the influence of chemoattractants: stromal cell-derived factor-1, steel factor, and the bone marrow environment." *Blood* Jan. 1, 1998; 91(1):100-10.

Koh et al., "Differentiation and long-term survival of C2C12 myoblast grafts in heart." Journal of Clinical Investigation 92:1548-1554 (1993).

Krause, D.S. et al., "Multi-organ, multi-lineage engraftment by a single bone marrow-derived stem cell." *Cell* (May 2001);105(3)369-370.

Kronenwett, R. et al., "The role of cytokines and adhesion molecules for mobilization of peripheral blood stem cells." *Stem Cells* 2000; 18:320-330.

LaIuppa, J.A. et al., "Evaluation of cytokines for expansion of the megakaryocyte and ranulocyte lineages." *Stem Cells* (May 1997):15(3):198-206, abstract only.

Leor et al., "Transplantation of Fetal Myocardial Tissue Into the Infarcted Myocardium of Rat, A Potential Method for Repair of Infarcted Myocardium?" Circulation 94:(Supplement II) II-332-II-336 (1996).

Li et al., "Method of Culturing Cardiomyocytes from Human Pediatric Ventricular Myocardium." (1992) *J. Tiss. Cult. Meth.*; 93-100.

Li, Q. et al. "Overexpression of insulin-like growth factor-1 in mice protects from myocyte death after infarction, attenuating ventricular dilation, wall stress, and cardiac hypertrophy." *J Clin Invest.* 100, 1991-1999 (1997).

Li, B et al., "Insulin-like growth factor-1 attenuates the detrimental impact of nonocclusive coronary artery constriction on the heart." (1999) *Circ. Res.* 84, 1007-1019.

Li et al., "In Vivo Survival and Function of Transplanted Rat Cardiomyocytes" *Circulation Research* 78:283-288 (1996).

Li et al., "Cardiomyocyte Transplantation Improves Heart Function" (1996) *The Society of Thoracic Surgeons*; 62: 654-661.

Li et al., "Human Pediatric and Adult Ventricular Cardiomyocytes in Culture: Assessment of Phenotypic Changes with Passaging" Feb. 20, 1996 *Cardiovascular Research*; 32(2):362-373.

Lin, Q. et al., "Control of mouse cardiac morphogenesis and myogenesis by transcription factor MEF2C." (1997) *Science* 276, 1404-1407.

Malouf, N.N. et al., "Adult derived stem cells from the liver become myocytes in the heart in vivo." *Am J Pathology* Jun. 2001; 158(6)1929-35, abstract only.

Menasche, P. et al., (2000) *Lancet* 357, 279-280.

Morin, S. et al., "GATA-dependent recruitment of MEF2 proteins to target promoters." (2000) *EMBO J.* 19, 2046-2055.

Murray et al., "Skeletal Myobalst Transplantation for Repair of Myocardial Necrosis" *J. Clin. Invest.* 98:2512-2523 (1996).

Musil, L. S. et al., "Regulation of connexin degradation as a mechanism to increase gap junction assembly and function." (2000) *J. Biol. Chem.* 275, 25207-25215.

National Institutes of Health. "Stem Cells : A Primer." *National Institutes of Health*: May 2000.

Noishiki et al., "Angiogenic growth factor release system for in vivo tissue engineering: a trial of bone marrow transplantation into ischemic myocardium." (1999) *J. Artif. Organs*, 2: 85-91.

Olivetti, G. et al., "Cellular basis of chronic ventricular remodeling after myocardial infarction in rats." (1991) *Circ. Res.* 68(3), 856-869.

Orlic, D. et al., (1993) *Blood* 91, 3247-3254.

Orlic, D. et al., "Bone marrow cells regenerate infarcted myocardium." (2001) *Nature* 410, 701-705.

Patchen, ML et al. "Mobilization of peripheral blood progenitor cells by Betafectin® PGG-glucan alone and in combination with granulocyte colony-stimulating factor." *Stem Cells* (May 1998); 16(3):208-217, abstract.

Pfeffer, M. A. and Braunwald, E. "Ventricular remodeling after myocardial infarction." *Circulation* 81, 1161-1172 (1990).

Pollick, C. et al., "Echocardiographic and cardiac Doppler assessment of mice." (1995) *J. Am. Soc. Echocardiogr.* 8, 602-610 (1995).

Reiss, K. et al., "Overexpression of insulin-like growth factor-1 in the heart is coupled with myocyte proliferation in transgenic mice." (1996) *Proc. Natl. Acad. Sci. USA* 93(16), 8630-8635.

Roberts M.M., et al., "Prolonged release and c-kit expression of haemopoietic precursor cells mobilized by stem cell factor and granulocyte colony stimulating factor." Br J Haematol. Mar. 1999;104(4):778-84.

Rosenthal, N. and Tsao, L. "Helping the heart to heal with stem cells." *Nature Medicine* Apr. 2001; 7(4):412-413.

Scholzen, T., and Gerdes, J. "The ki-67 protein: from the known and the unknown." *J. Cell. Physiol.* 182, 311-322 (2000).

Shimomura T., et al., "Thrombopoietin stimulates murine lineage negative, Sca-1+, C-Kit+, CD34– cells: comparative study with stem cell factor or interleukin-3." *Int J Hematol.* (Jan. 2000);71(1):33-9.

Soonpaa et al. "Formation of nascent intercalated disks between grafted fetal cardiomyocytes and host myocardium." (1994) *Science* 264(5155):98-101.

Simnett et al. "Autologous stem cell transplantation for malignancy: a systemic review of the literature." Clin. Lab Haem. 2000, 22:61-72.

Strobel, ES et al. "Adhesion and migration are differentially regulated in hematopoietic progenitor cells by cytokines and extracellular matrix." *Blood* (Nov. 1, 1997); 90(9):3524-3532.

Taylor, D.A. et al. (1998) *Nature Med.* 4, 929-933.

Temple, S. "Opinion: Stem cell plasticity—building the brain of our dreams." *Nat Rev Neurosci* Jul. 2001;2(7):513-520, abstract only.

Thompson et al. *Science* 257:868-870 (1992).

Tomita, S et al. (1999) *Circulation* 100(suppl II), II-247-II-256.

Vaughn et al. "Incorporating bone marrow transplantation into NCCN guidelines." (1998) *Oncology*, 12 (11A): 390-392.

Yamaguchi, T.P. et al., "Flk-1, an flt-related receptor tyrosine kinase is an early marker for endothelial cell precursors. Development." (1993) *Development* 118(2), 489-498.

Quaini, F. et al. "Chimerism of the transplanted heart." (2002) *N Engl J Med.*346(1):5-15 N.

Anversa, P. and Nadal-Ginard, B., "Myocyte renewal and ventricular remodeling." *Nature.* (2002); 415(6868):240-3.

Reya, T. et al., "Stem Cells, cancer, and cancer stem cells." (2001) *Nature* 414(6859):105-11.

Jackson, K.A. et al., "Hematopoietic potential of stem cells isolated from murine skeletal muscle." *Proc Natl Acad Sci U S A.* (1999) 96(25):14482-6.

Orlic, D. et al., "Mobilized bone marrow cells repair the infarcted heart, improving function and survival." *Proc Natl Acad Sci U S A.* (2001) 98(18):10344-9v.

Blau, H.M. et al., "The evolving concept of a stem cell: entity or function?" *Cell.* (2001);105(7):829-41.

S. P. Monga, S.P. et al. "Expansion of hepatic and hematopoietic stem cells utilizing mouse embryonic liver explants." (2001) *Cell Transplant.* Jan.-Feb.;10(1), 81-89.

Weimar, I.S. et al., ",Hepatocyte growth factor/scatter factor (HGF/SF) is produced by human bone marrow stromal cells and promotes proliferation, adhesion and survival of human hematopoietic progenitor cells (CD34+)." *Exp Hematol.* (1998) 26(9):885-94.

Yu, C.Z. et al., *Stem Cells* 16, 66-77 (1998).

Birchmeier, C. and Brohmann, H., *Curr. Opin. Cell Biol.* 12, 725 (2001).

Xin, X. et al., *Am. J. Pathol.* 158, 1111 (2001).

Hamasuna, R. et al. "Regulation of matrix metalloproteinase-2 (MMP-2) by hepatocyte growth factor/scatter factor (HGF/SF) in human glioma cells: HGF/SF enhances MMP-2 expression and activation accompanying up-regulation of membrane type-1 MMP." *Int J Cancer.* (1999) 82(2):274-81.

Wang, H. and Keiser, J.A., "Hepatocyte growth factor enhances MMP activity in human endothelial cells." *Biochem Biophys Res Commun.* 2000 ;272(3):900-5.

Arsenijevic, Y. et al., "Insulin-like growth factor-I is necessary for neural stem cell proliferation and demonstrates distinct actions of epidermal growth factor and fibroblast growth factor-2." *J Neurosci.* (2001) 21(18):7194-202.

Arsenijevic, Y. and Weiss, S., J. Neurosci. "Insulin-like growth factor-I is a differentiation factor for postmitotic CNS stem cell-derived neuronal precursors: distinct actions from those of brain-derived neurotrophic factor." *J Neurosci.* (1998) 18(6):2118-28.

Brooker, G.J. et al., "Endogenous IGF-1 regulates the neuronal differentiation of adult stem cells." *J Neurosci Res.* (2000) 59(3):332-41.

Page, D.L. et al., "Myocardial changes associated with cardiogenic shock." *N Engl J Med.* (1971) 285(3):133-7.

Pasumarthi, K.B.S. et al., "Coexpression of mutant p53 and p193 renders embryonic stem cell-derived cardiomyocytes responsive to the growth-promoting activities of adenoviral E1A." *Circ Res.* (2001) 88(10):1004-11.

Condorelli, G. et al., "Cardiomyocytes induce endothelial cells to trans-differentiate into cardiac muscle: implications for mycardium regeneration." *Proc Natl Acad Sci U S A.* (2001) 98(19):10733-8.

Beltrami, A.P. et al. "Evidence that human cardiac myocytes divide after myocardial infarction." *N Engl J Med.* (2001) 344(23):1750-7.

Jackson, K.A. et al., *J. Clin. Invest.* (2001) 107, 1395.

MacLellan, W.R. and Schneider, M.D. "Genetic dissection of cardiac growth control pathways." *Annu. Rev. Physiol.* (2000) 62, 289-319.

Ol, H. et al. "Telomerase reverse transcriptase promotes cardiac muscle cell proliferation, hypertrophy, and survival." *Proc. Natl. Acad. Sci. USA* 98, 10308-10313 (2001).

Anversa, P. and Kajstura, J. "Ventricular myocytes are not terminally differentiated in the adult mammalian heart." *Circ. Res.* (1998) 83, 1-14.

Rao, M.S. and Mattson, M.P. Stem cells and aging: expanding the possibilities. *Mech. Ageing Dev.* (1998) 122, 713-734.

Zaucha, J.M. et al. "Hematopoietic responses to stress conditions in young dogs compared with elderly dogs." *Blood* (2001) 98, 322-327.

Gritti, A. et al. "Epidermal and fibroblast growth factors behave as mitogenic regulators for a single multipotent stem cell-like population from the subventricular region of the adult mouse forebrain." *J. Neurosci.* (1999) 19, 3287-3297.

Shihabuddin, L.S. et al., "Adult spinal cord stem cells generate neurons after transplantation in the adult dentate gyrus." *J. Neurosci.* (2000) 20, 8727-8735.

Cheng, W. et al. "Aging does not affect the activation of the myocyte IGF-1 autocrine system after infarction and ventricular failure in Fischer 344 rats." *Circ. Res.* (1996) 78, 536-546.

Kajstura, J. et al. "Apoptotic and necrotic myocyte cell deaths are independent contributing variables of infarct size in rats." *Lab. Invest.* (1996) 74, 86-107.

Mikawa, T. & Fishman, D.A. "The polyclonal origin of myocyte lineages." *Annu. Rev. Physiol.* (1996) 58, 509-521.

Stainer, D.Y.R. et al., "Cardiovascular development in zebrafish. I. Myocardial fate and heart tube formation." *Development* (1993) 119, 31-40.

Hillebrands, J-L. et al. "Origin of neointimal endothelium and α-actin-positive smooth muscle cells in transplant arteriosclerosis." *J. Clin. Invest.* (2001) 107, 1411-1422.

Eisenberg, C.A. & Bader, D. "QCE-6: a clonal cell line with cardiac myogenic and endothelial cell potentials." *Dev. Biol.* (1995) 167, 469-481.

Kehat, I. et al. "Human embryonic stem cells can differentiate into myocytes with structural and functional properties of myocytes." *J. Clin. Invest.* (2001) 108, 407-414.

Anderson, D.J. "Stem cells and pattern formation in the nervous system: the possible versus the actual." *Neuron* (2001) 30, 19-35.

Lee, J.Y. et al. "Clonal isolation of muscle-derived cells capable of enhancing muscle regeneration and bone healing." *J. Cell Biol.* (2000) 150, 1085-1099.

Seale, P. et al. "Pax7 is required for the specification of myogenic satellite cells." *Cell* (2000) 102, 777-786.

Broudy, V.C. "Stem cell factor and hematopoiesis." *Blood* (1997) 90, 1345-1364.

Tropepe, V. et al. "Distinct neural stem cells proliferate in response to EGF and FGF developing mouse telencephalon." *Dev. Biol.* (1999) 208, 166-188.

Li, P. et. al. "Myocyte performance during evolution of myocardial infarction in rats: effects of propionyl-L-carnitine." *Am. J. Physiol.* (1995) 208, H1702-H1713.

Bunting, K.D. et al., *Blood* 96, 902 (2000).

Block, G.D. et al., *J. Cell Biol.* 132, 1133 (1996).

Rappolee, D.A. et al., *Circ. Res.* 78, 1028 (1996).

Powell, E.M. et al., *Neuron.* 30, 79 (2001).

Leri, A. et al., *Circ. Res.* 84, 752 (1999).

Capasso, J.M. and Anversa, P., *Am. J. Physiol.* 263, H841 (1992).

\* cited by examiner

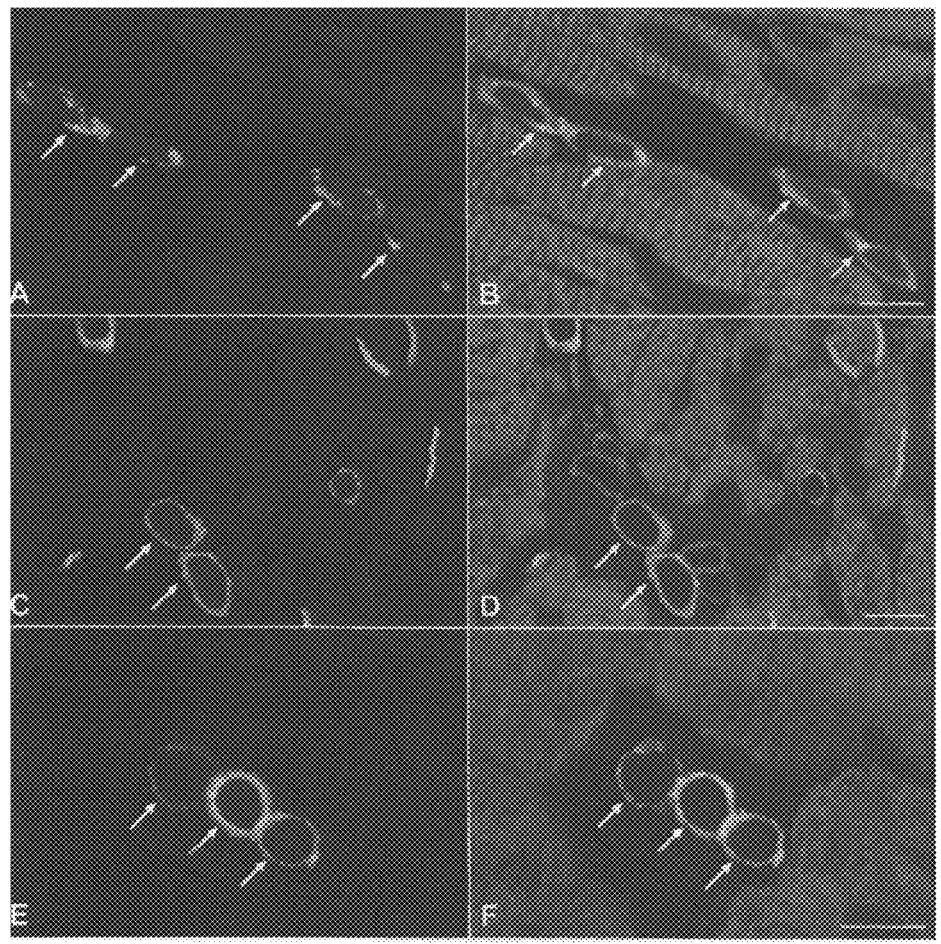
FIGURE 22A-F

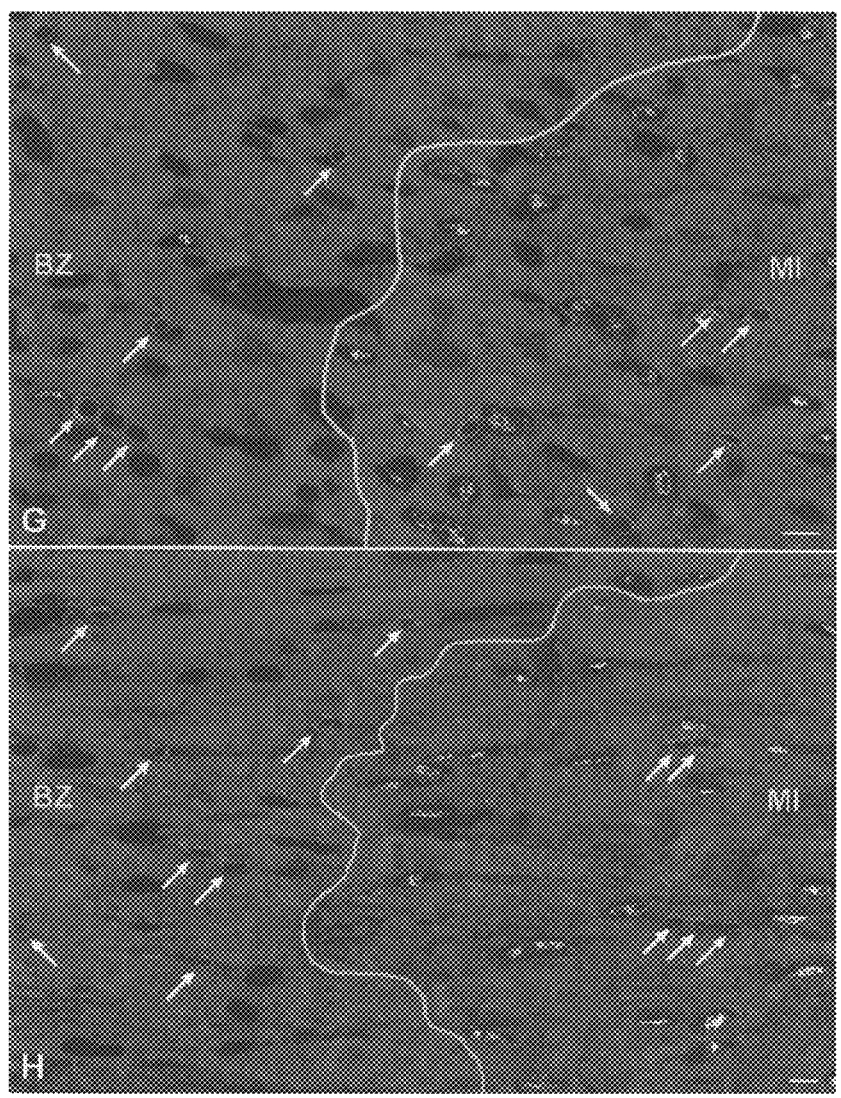
FIGURE 22G-H

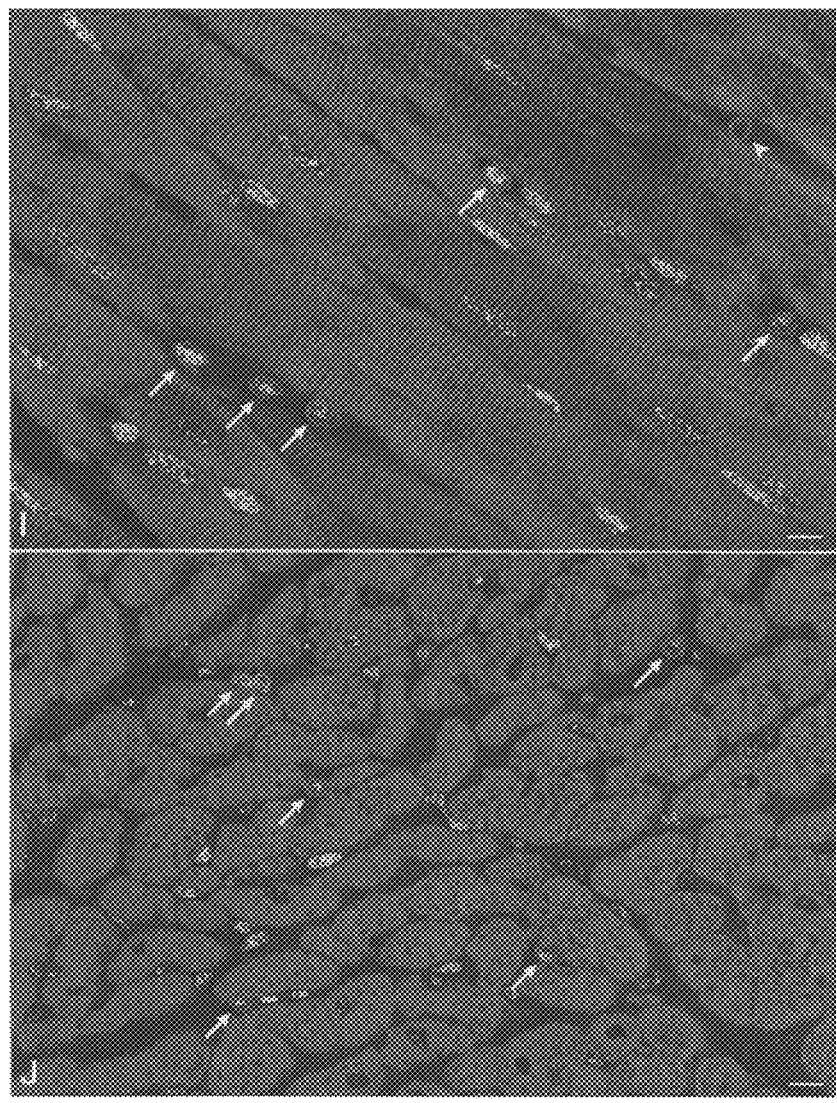
FIGURE 22I-J

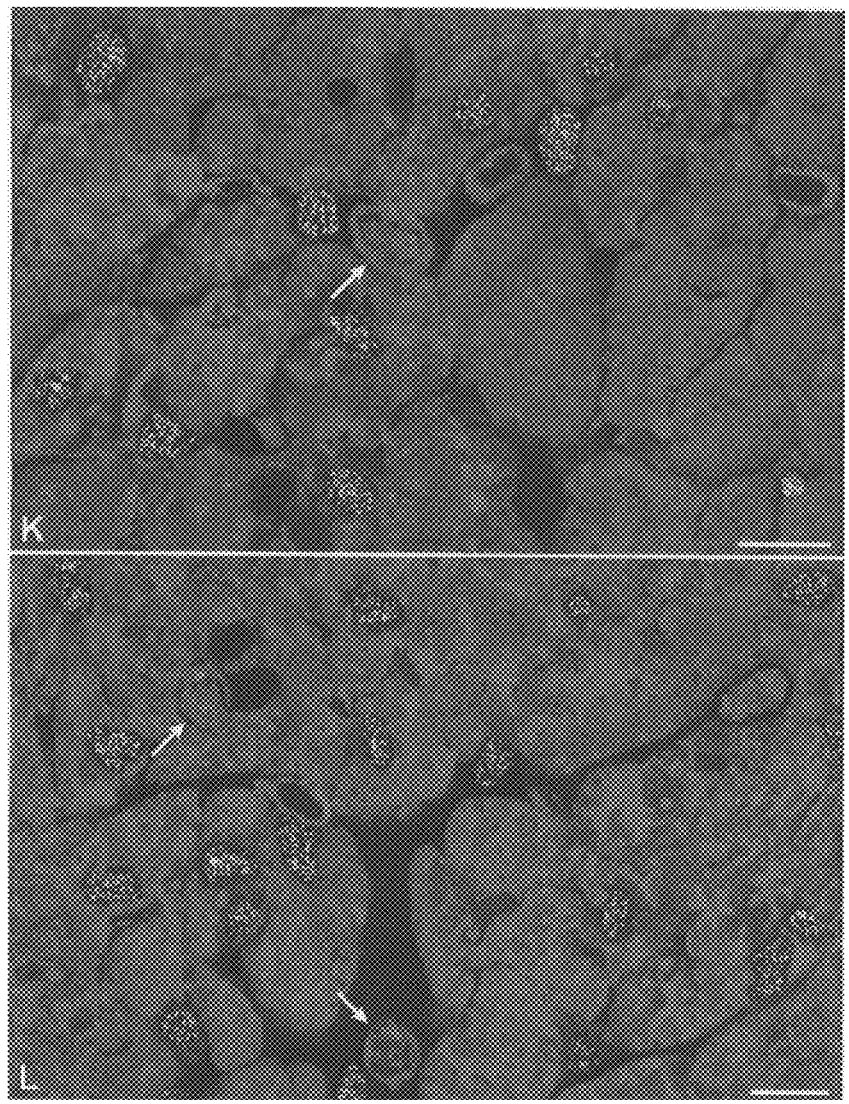
FIGURE 22K-L

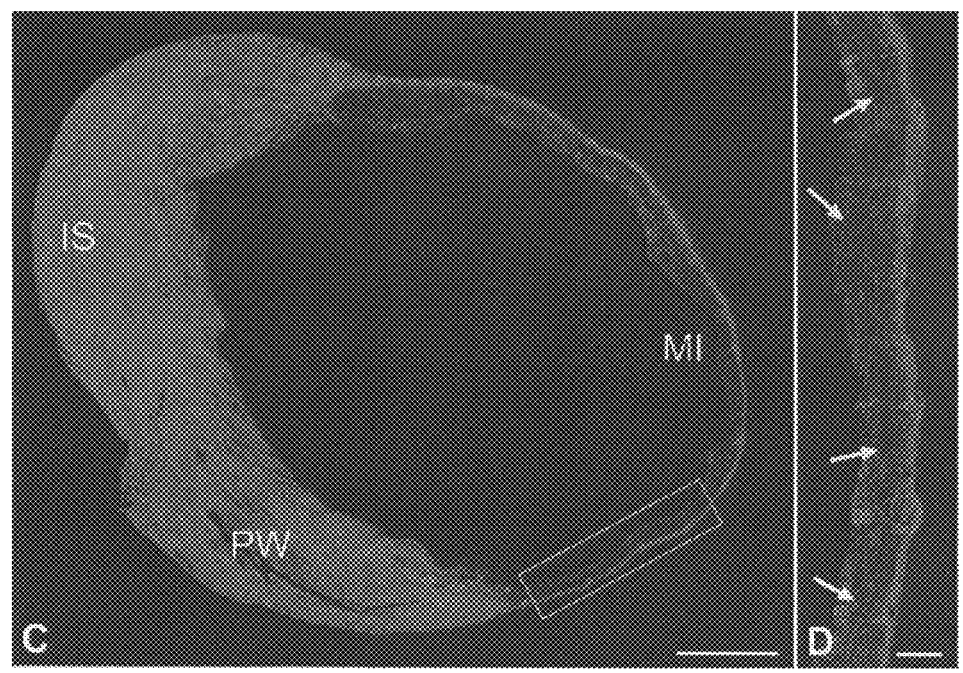
FIGURE 23C-D

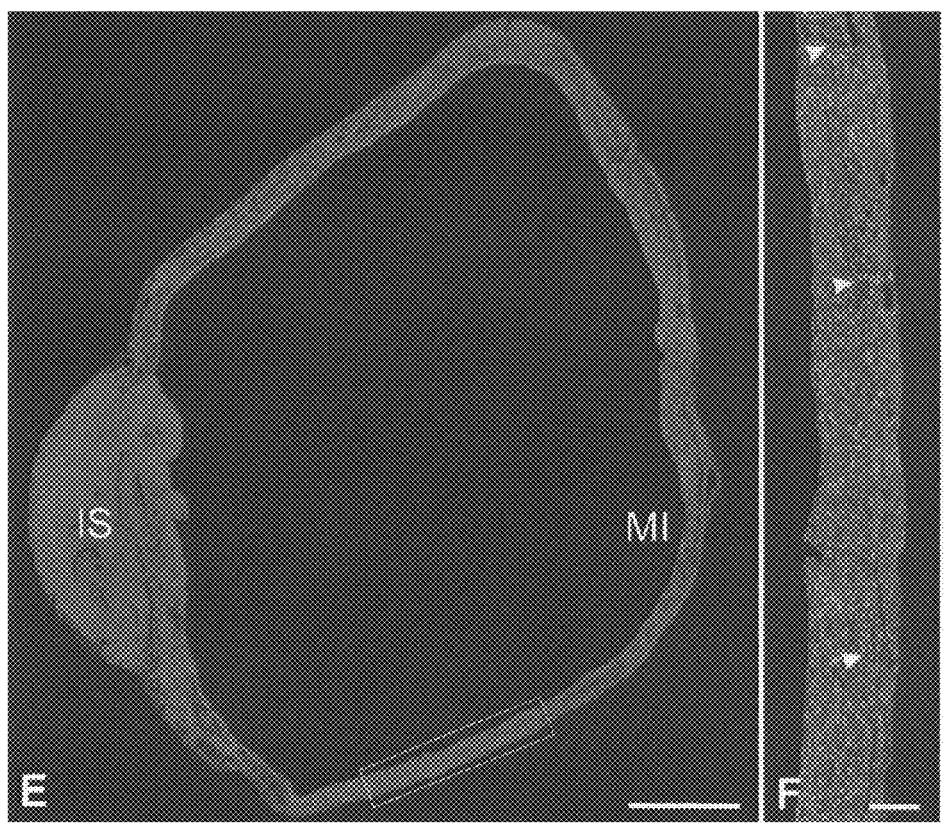
FIGURE 23E-F

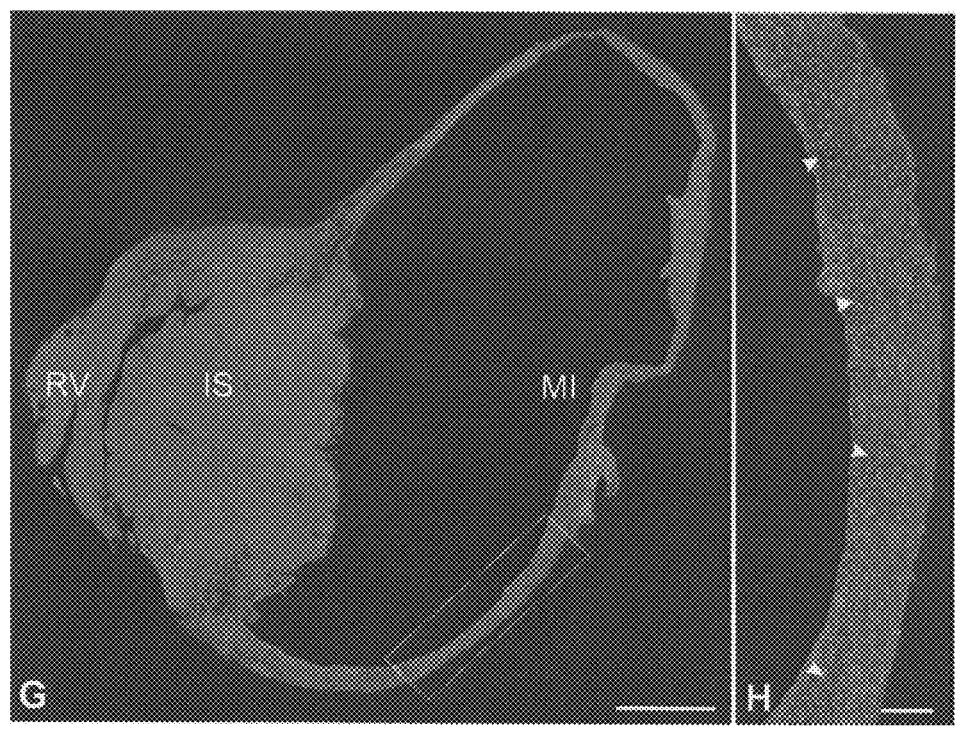
FIGURE 23G-H

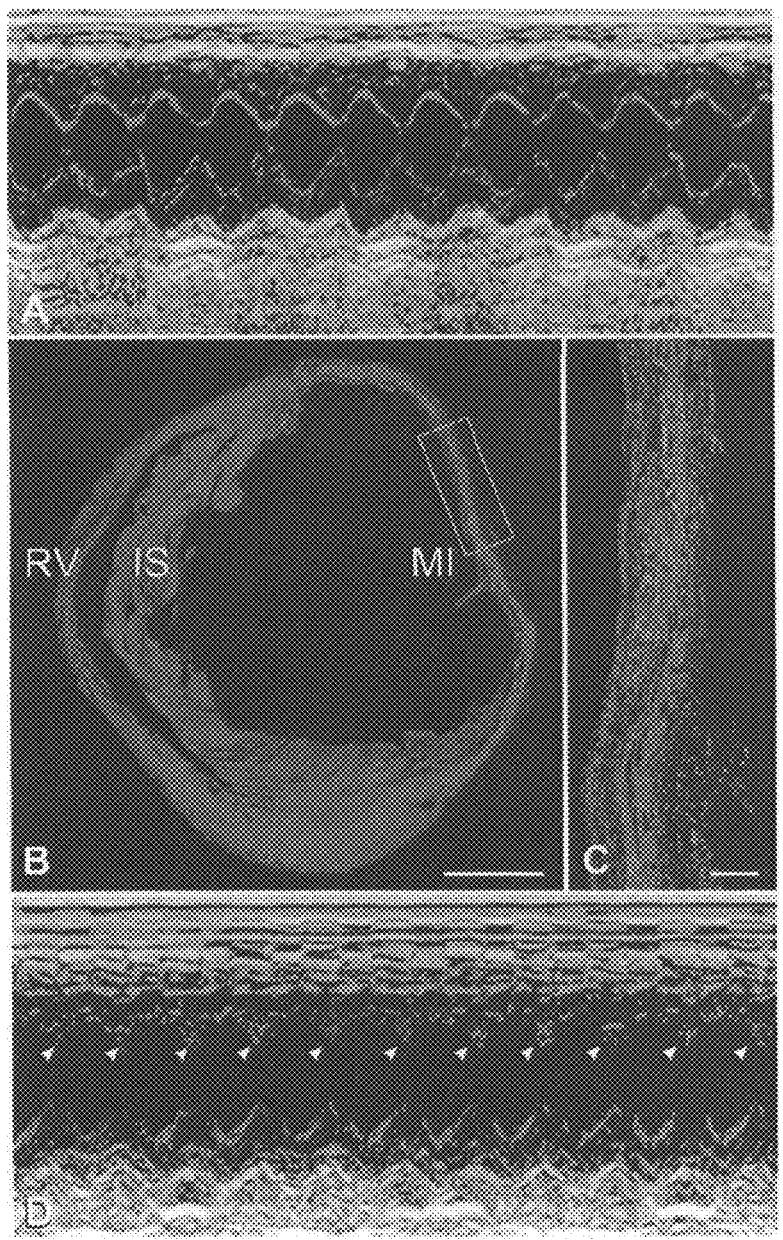
FIGURE 24A-D

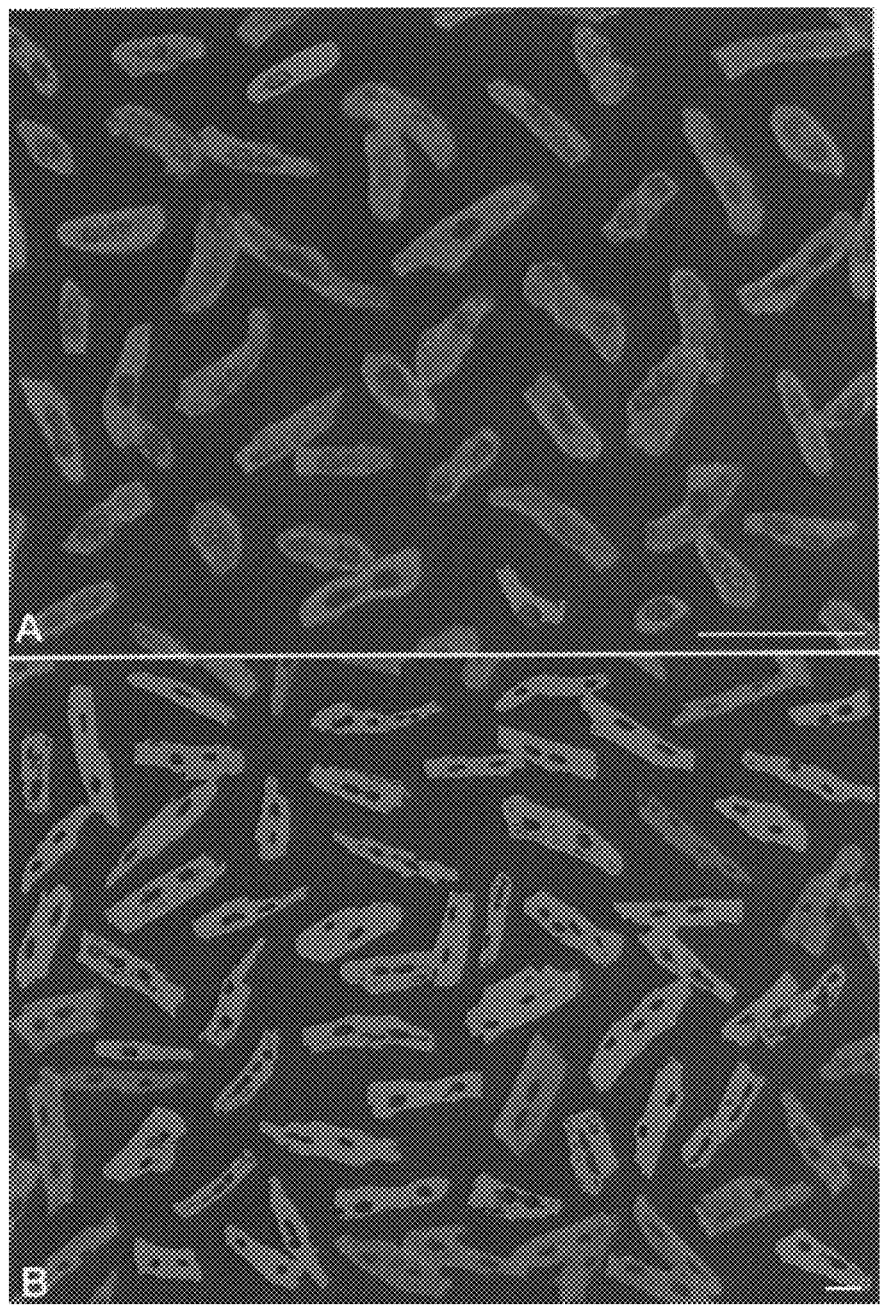
FIGURE 25A-B

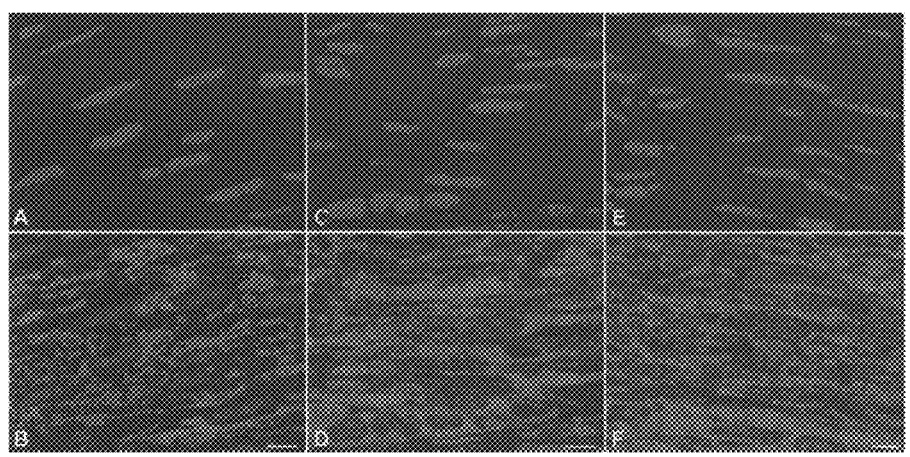
FIGURE 26A-F

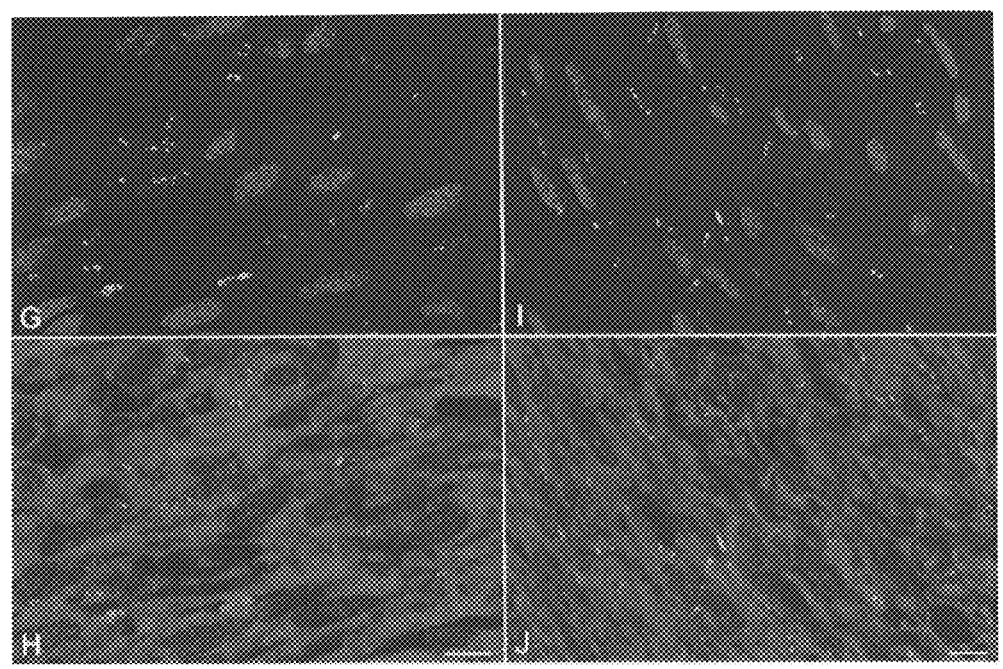
FIGURE 26G-J

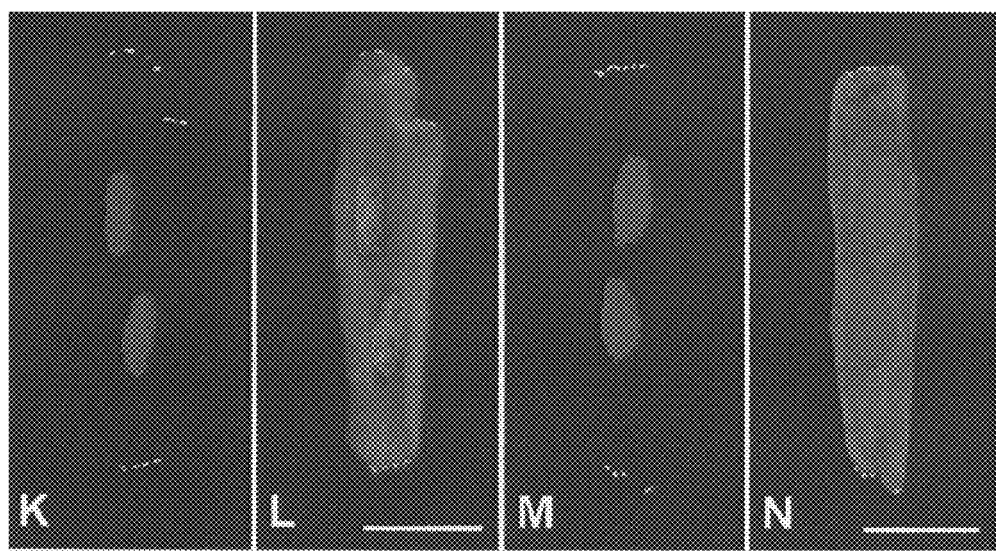
FIGURE 26K-N

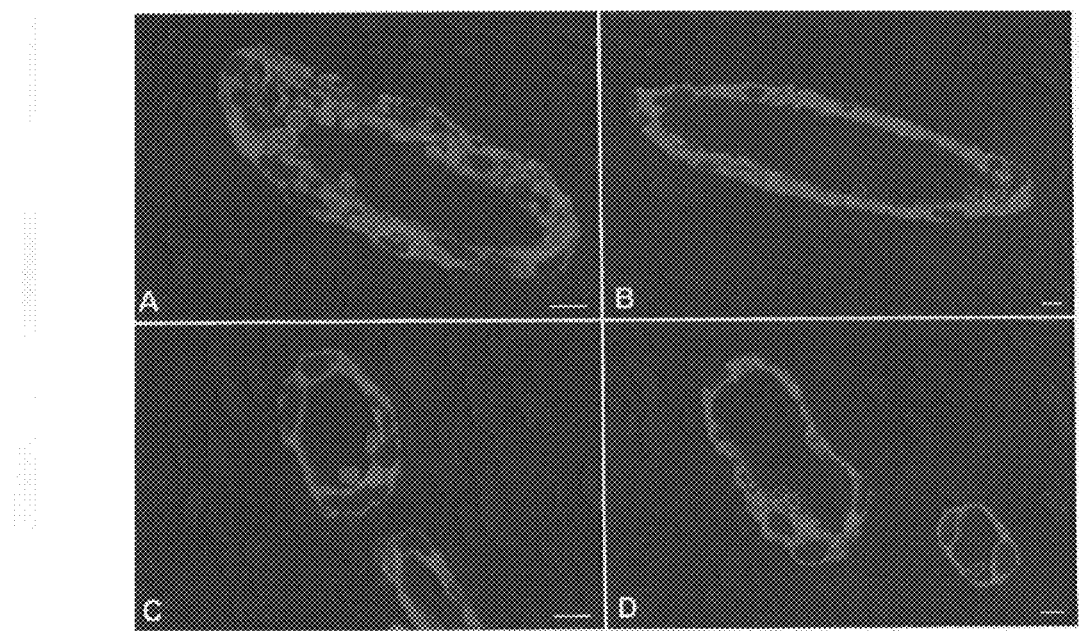
FIGURE 27A-D

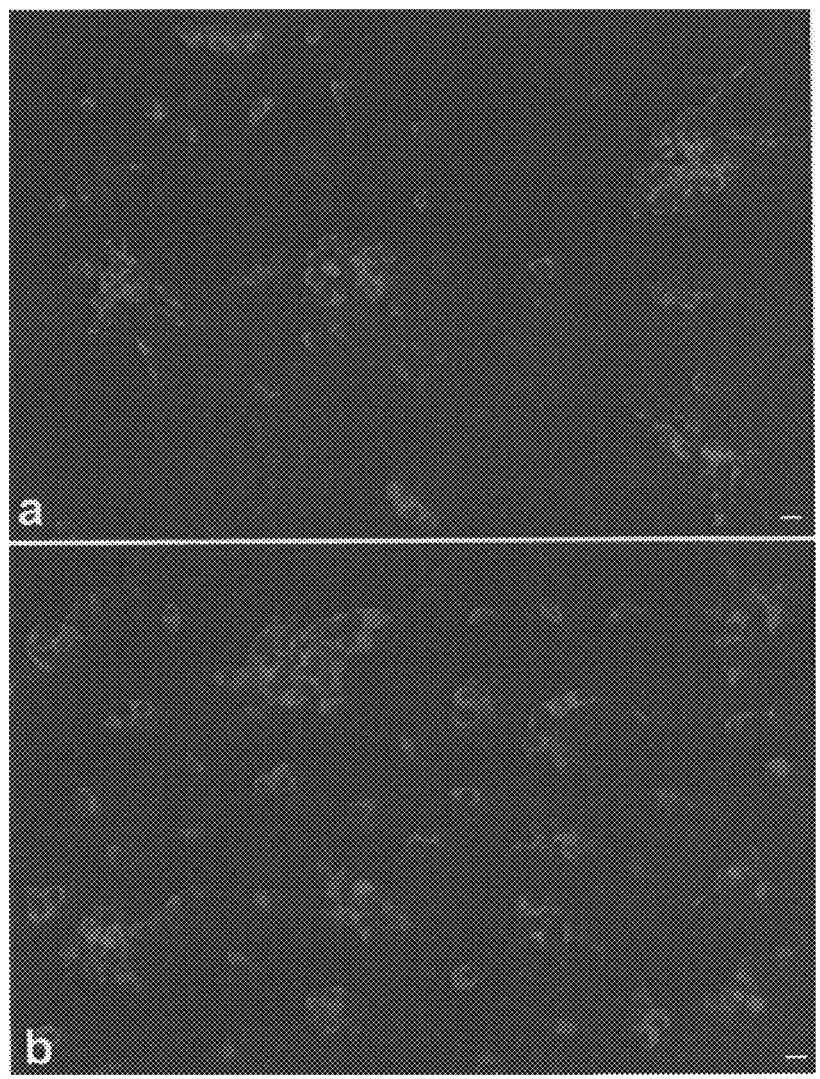
FIGURE 28A-B

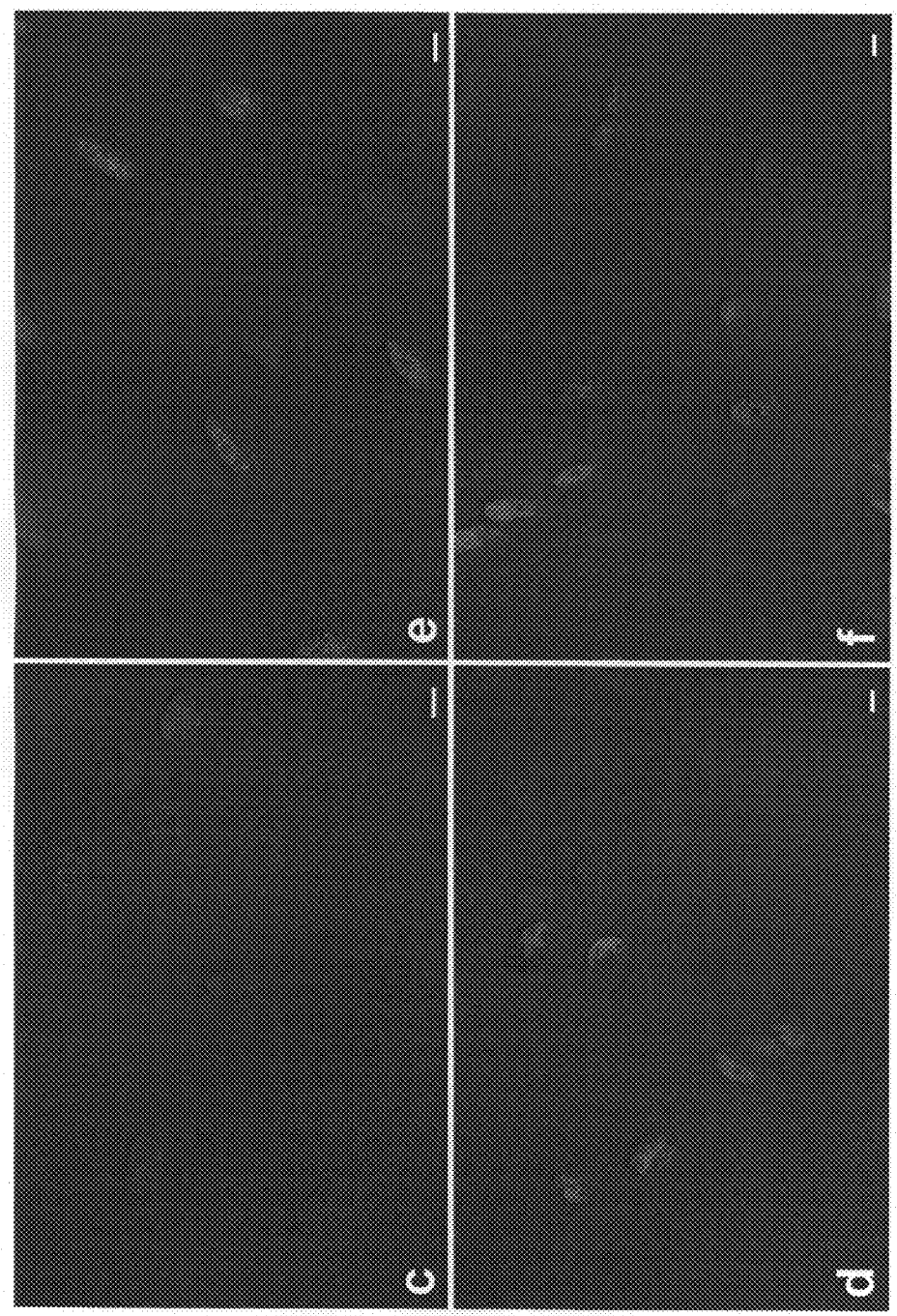
FIGURE 28C-F

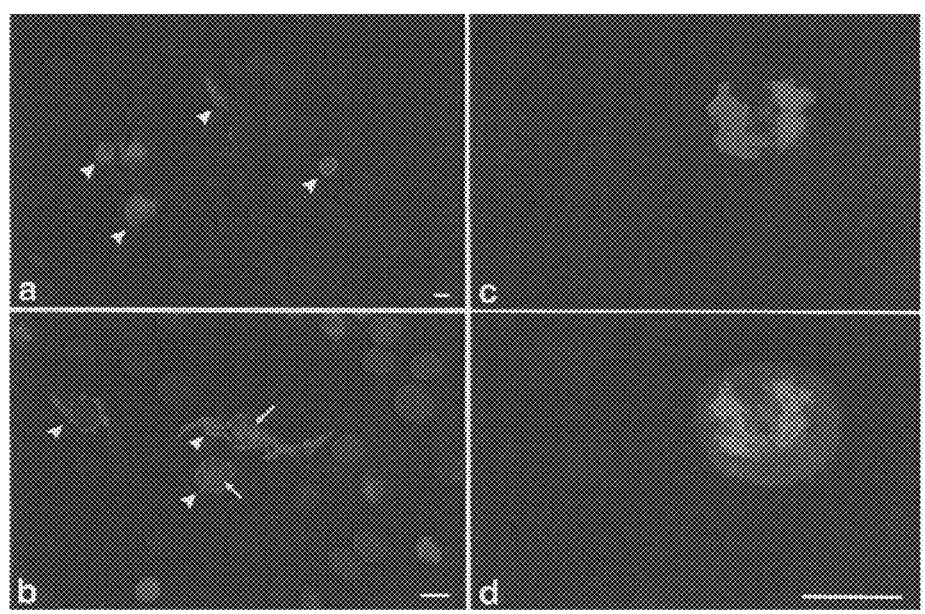
FIGURE 29A-D

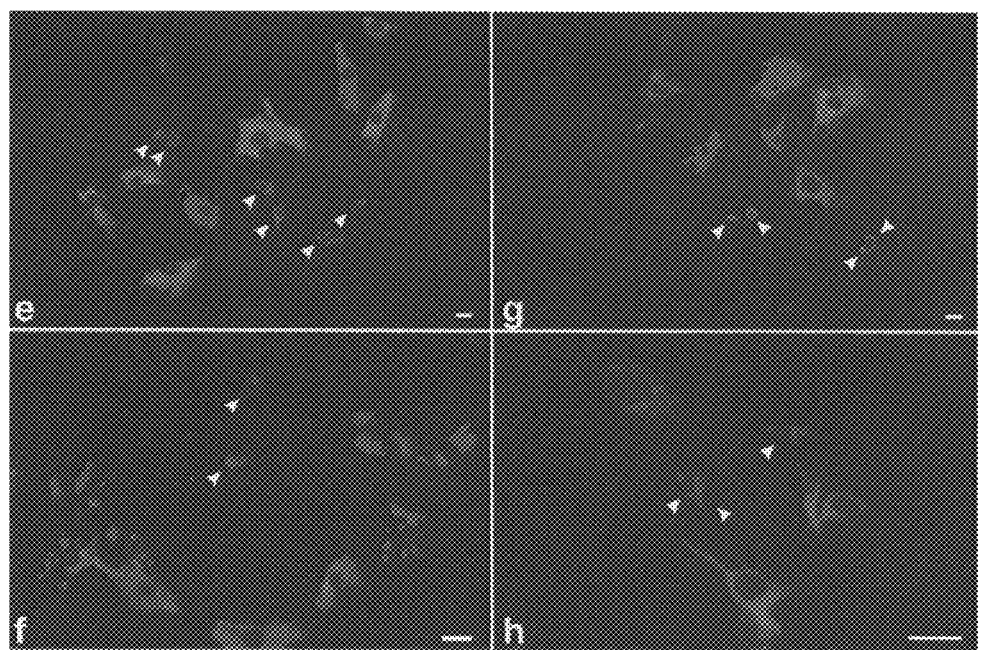
FIGURE 29E-H

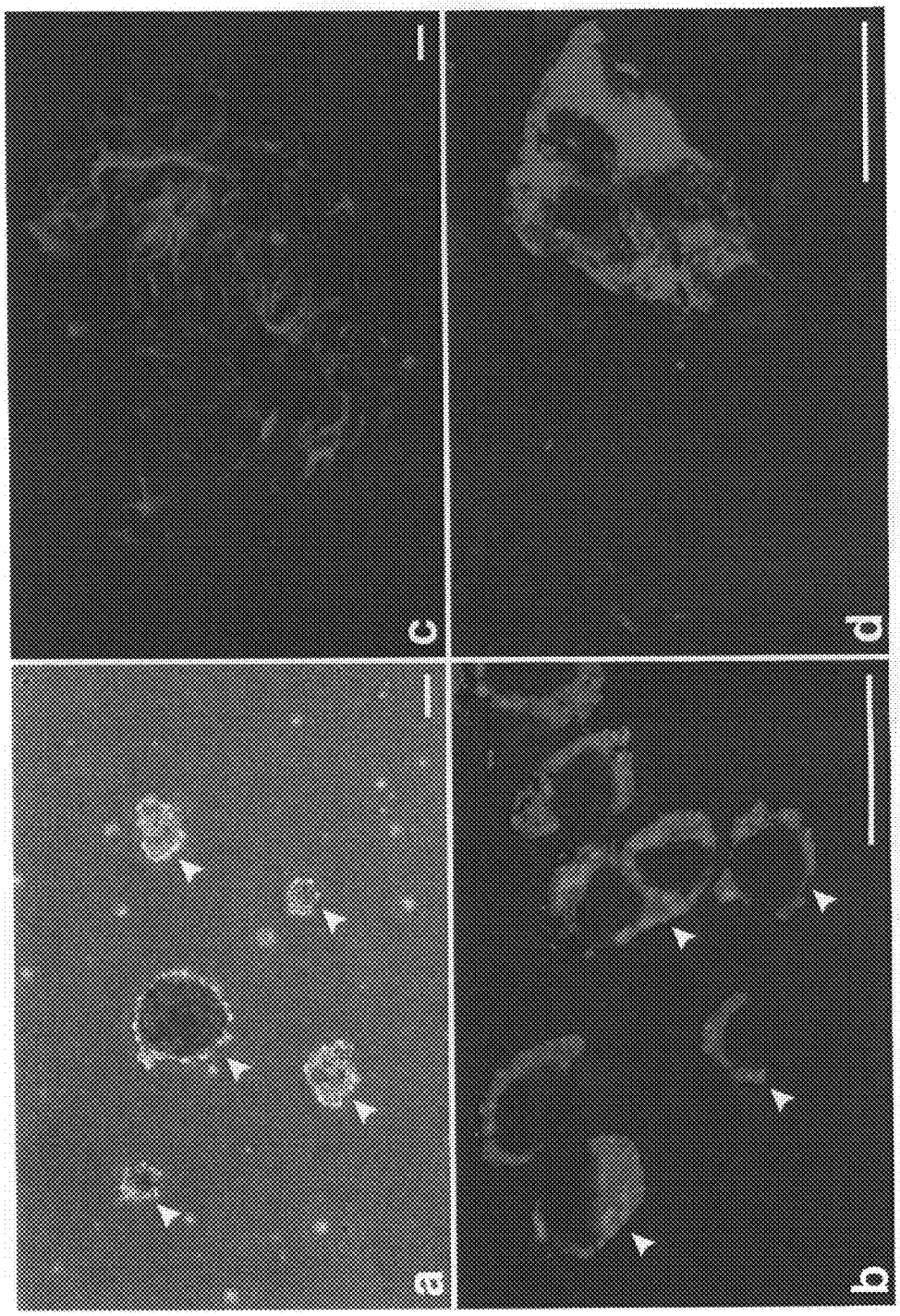
FIGURE 30A-D

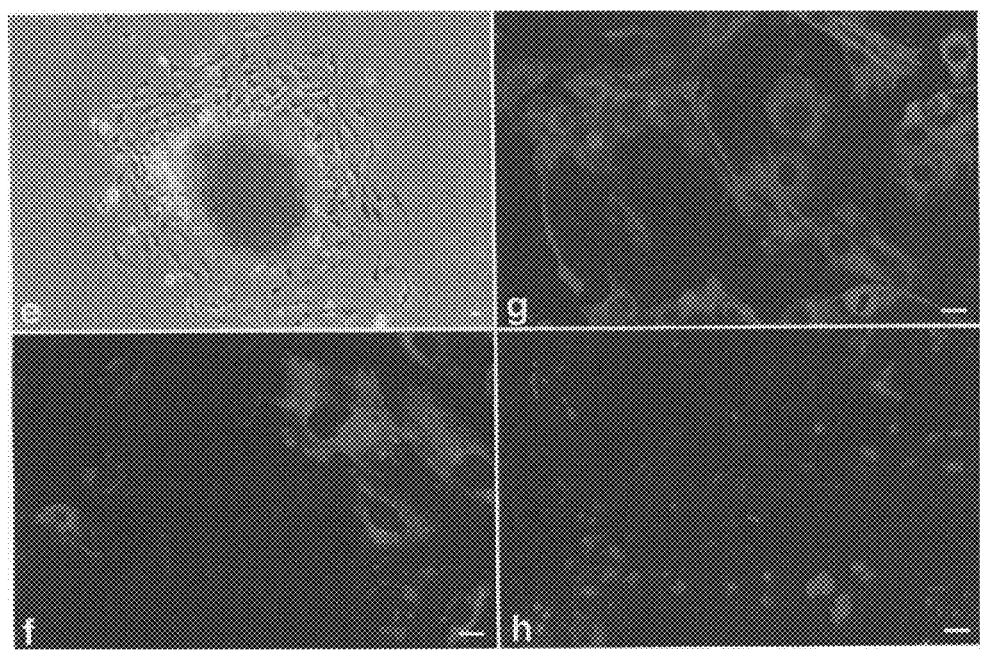
FIGURE 30E-H

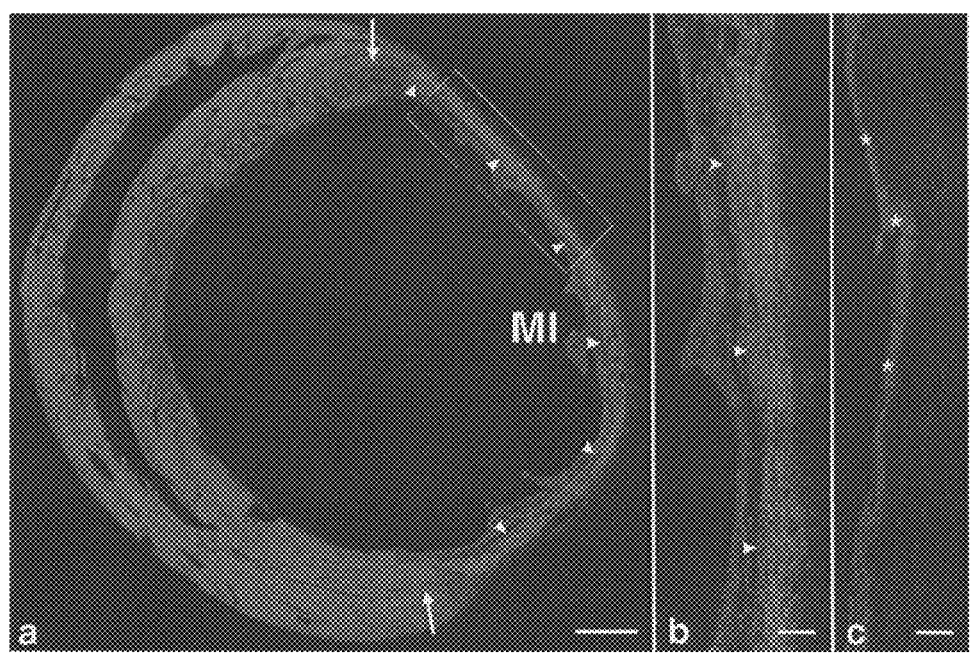
FIGURE 31A-C

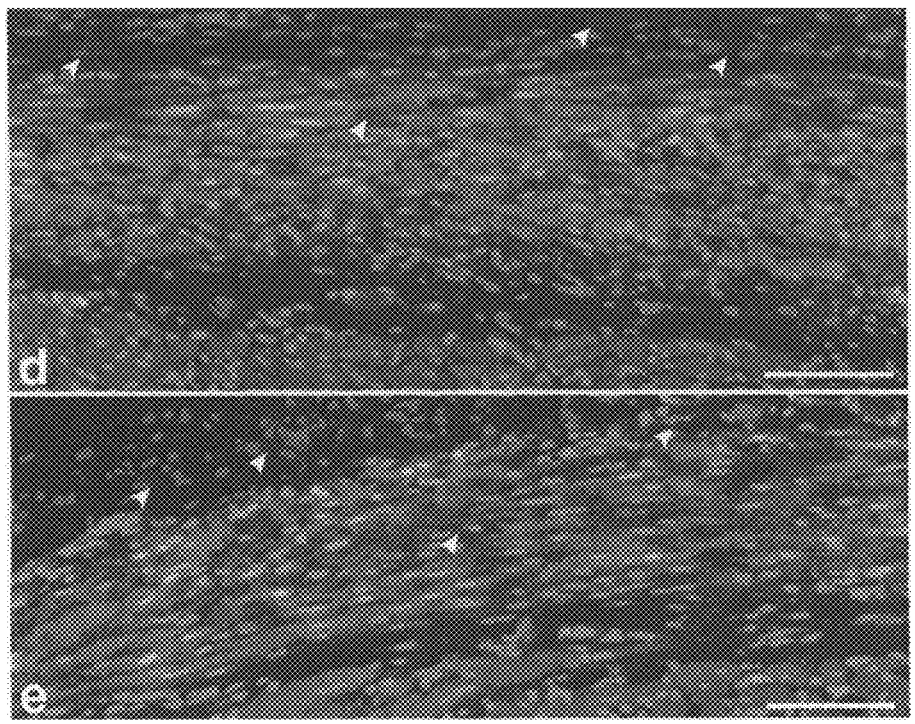
FIGURE 31D-E

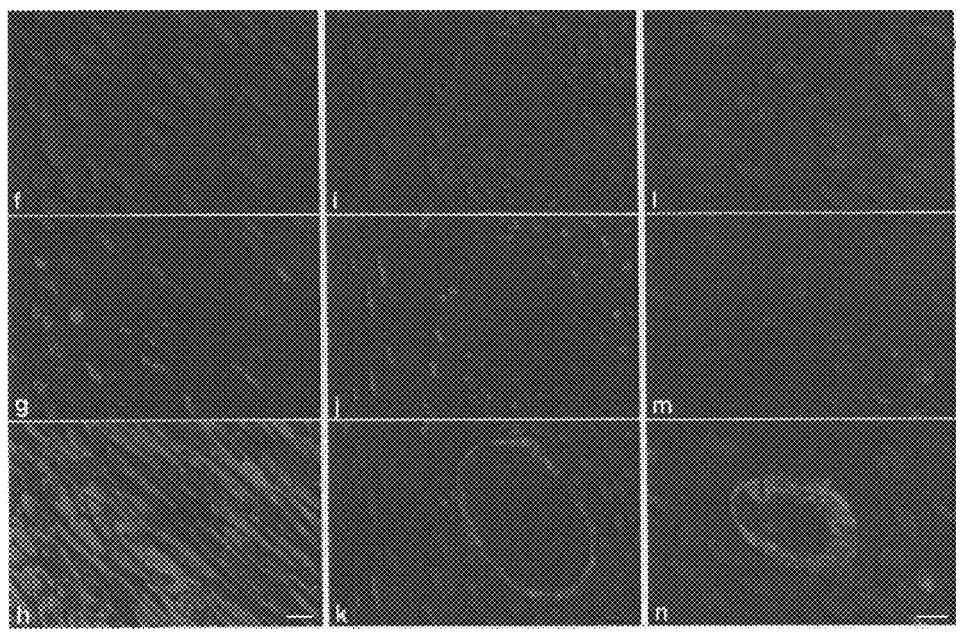
FIGURE 31F-N

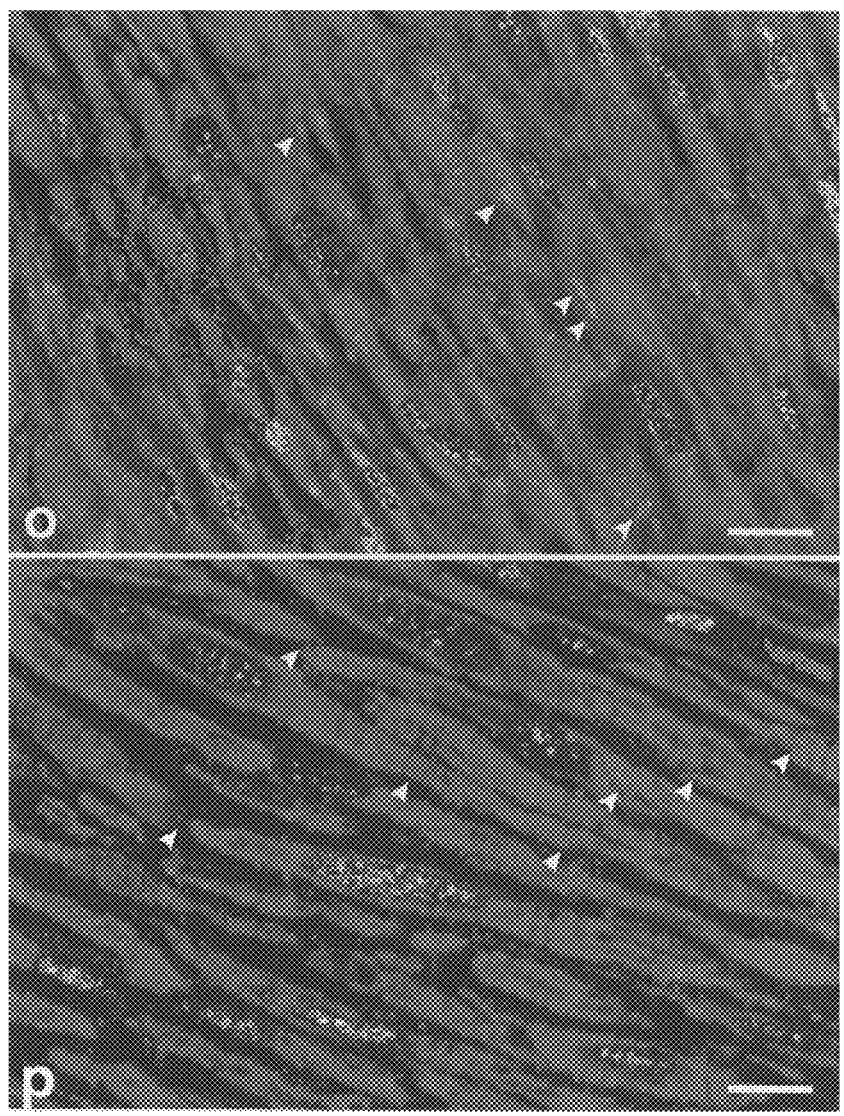
FIGURE 310-P

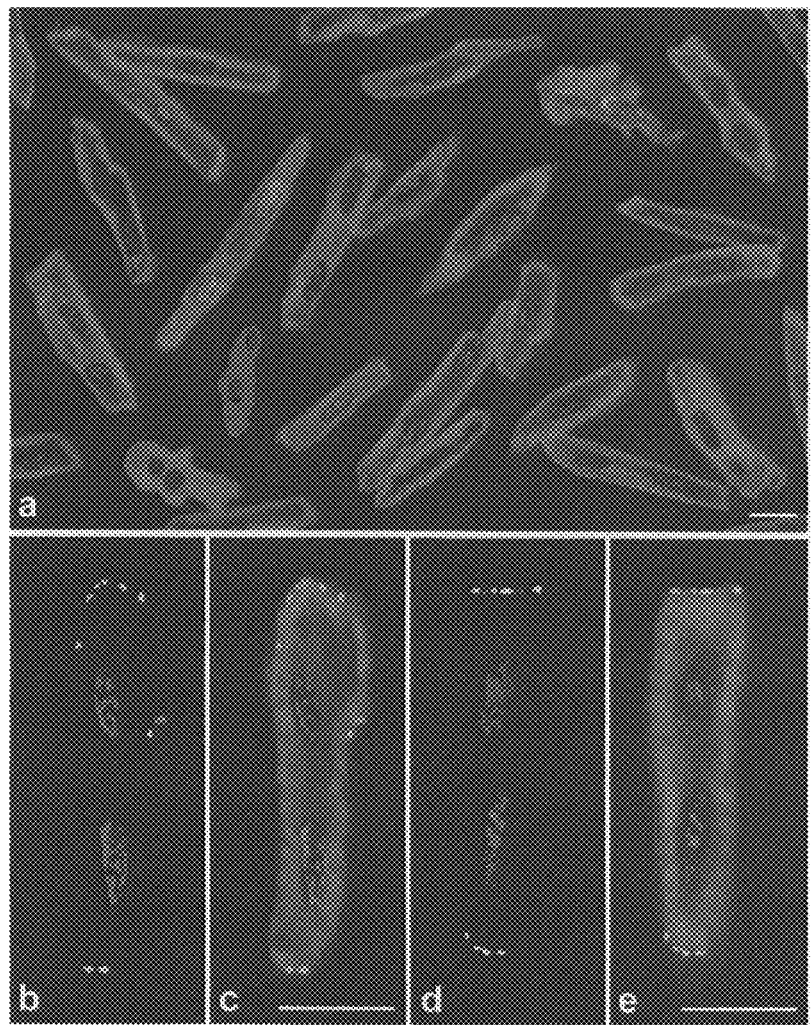
FIGURE 32A-E

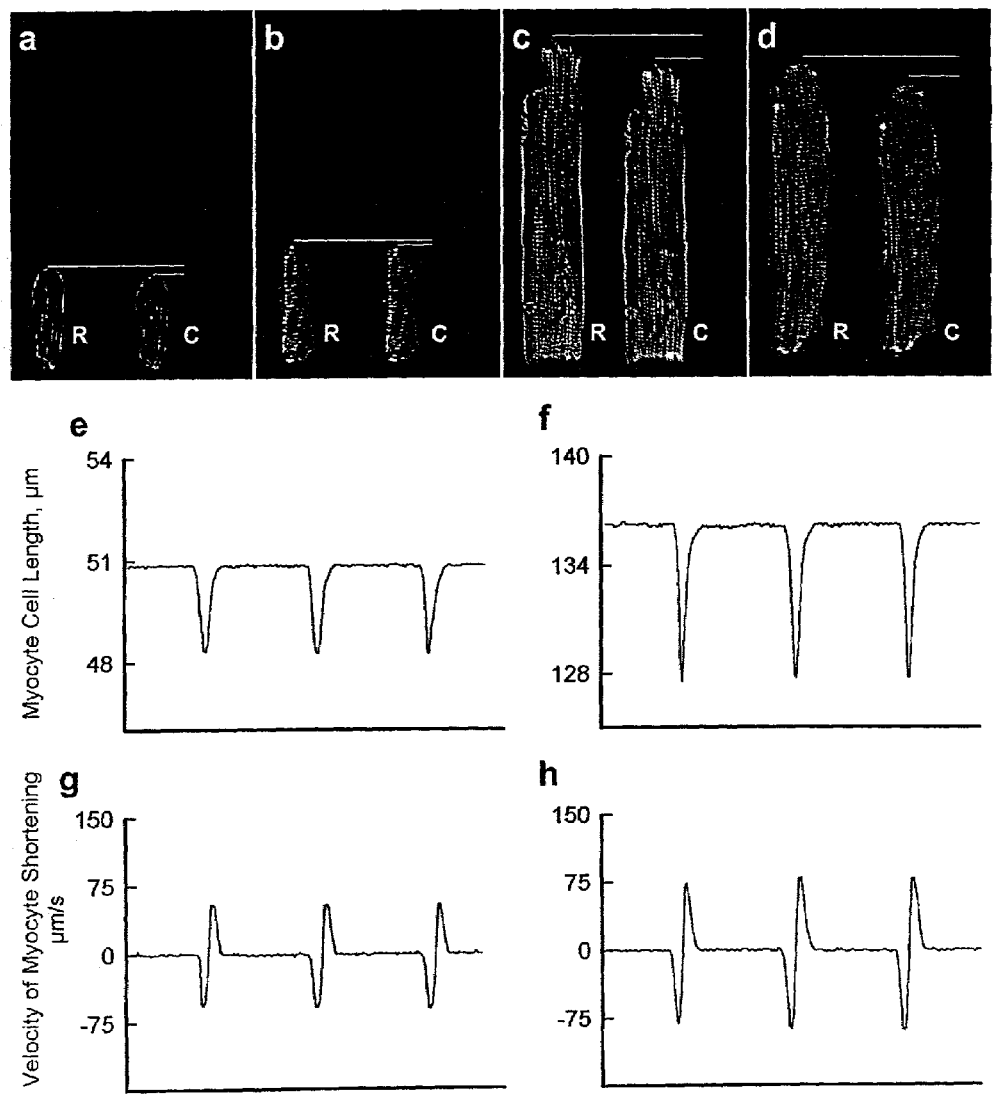
FIGURE 33A-H

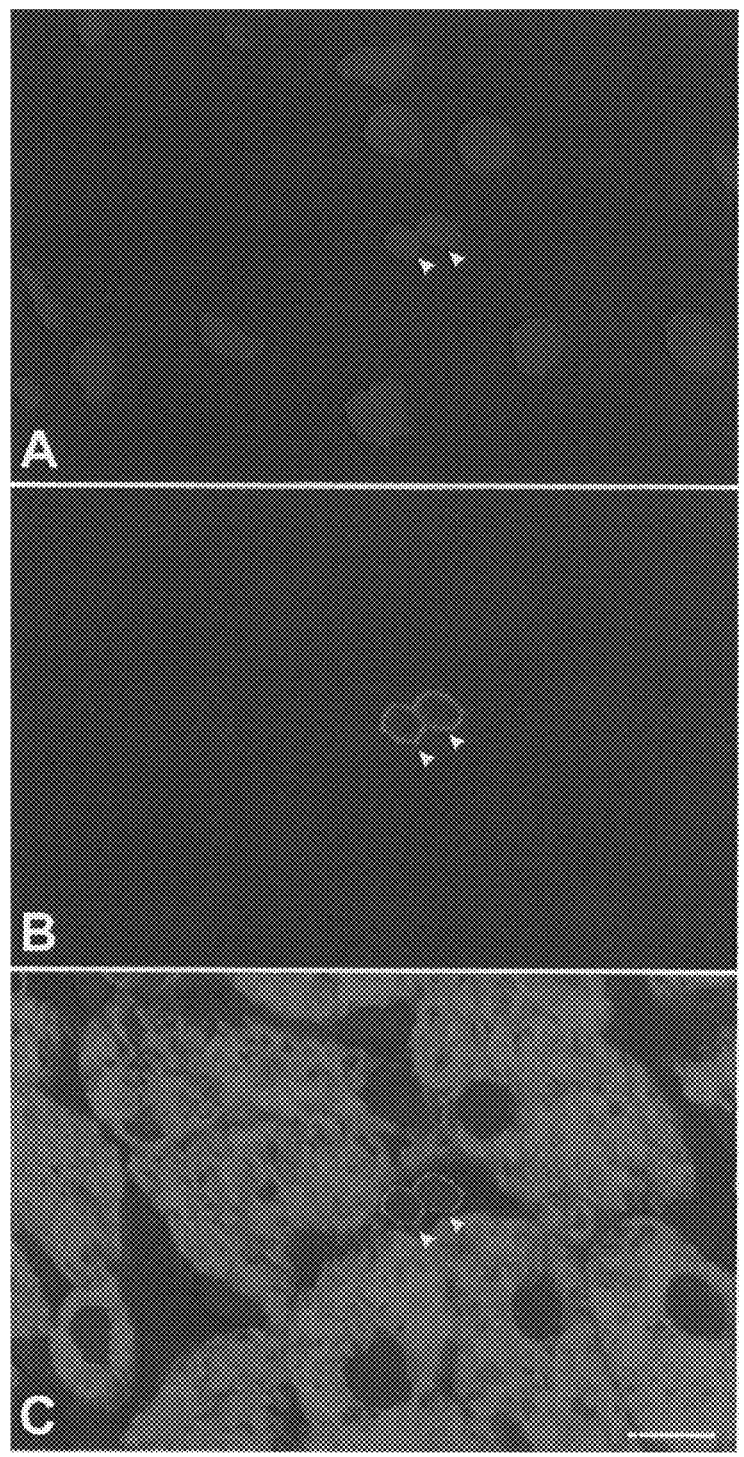
FIGURE 34A-C

FIGURE 36A-B

Transcription Factors of Cardiomyocyte Differentiation

Cytoplasmic Markers of Neural Cells

Myocardial Repair

Spared Myocytes in the Infarcted Ventricle

FIGURE 60A-D

METHODS AND COMPOSITIONS FOR THE REPAIR AND/OR REGENERATION OF DAMAGED MYOCARDIUM

RELATED APPLICATIONS/PATENT & INCORPORATION BY REFERENCE

This application is a continuation in part of U.S. patent application Ser. No. 09/919,732 filed Jul. 31, 2001 now abandoned and claims priority from Provisional U.S. Patent Application Ser. Nos. 60/295,807, 60/295,806, 60/295,805, 60/295,804, and 60/295,803 filed Jun. 6, 2001.

Each of the applications and patents cited in this text, including each of the foregoing cited applications, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, various documents or references are cited in this text, either in a Reference List before the claims or in the text itself; and, each of the documents or references ("herein cited documents") and all of the documents cited in this text (also "herein cited documents"), as well as each document or reference cited in each of the herein cited documents (including any manufacturer's specifications, instructions, etc. for products mentioned herein and in any document incorporated herein by reference), is hereby expressly incorporated herein by reference. There is no admission that any of the various documents cited in this text are prior art as to the present invention. Any document having as an author or inventor person or persons named as an inventor herein is a document that is not by another as to the inventive entity herein. Also, teachings of herein cited documents and documents cited in herein cited documents and more generally in all documents incorporated herein by reference can be employed in the practice and utilities of the present invention.

FIELD OF THE INVENTION

The present invention relates generally to the field of cardiology, and more particularly relates to methods and cellular compositions for treatment of a patient suffering from a cardiovascular disease, including, but not limited to, artherosclerosis, ischemia, hypertension, restenosis, angina pectoris, rheumatic heart disease, congenital cardiovascular defects and arterial inflammation and other disease of the arteries, arterioles and capillaries.

Moreover, the present invention relates to any one or more of:

Methods and/or pharmaceutical composition comprising a therapeutically effective amount of somatic stem cells alone or in combination with a cytokine such as a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor or Interleukin-3 or any cytokine capable of the stimulating and/or mobilizing stem cells. Cytokines may be administered alone or in combination of with any other cytokine capable of: the stimulation and/or mobilization of stem cells; the maintenance of early and late hematopoiesis (see below); the activation of monocytes (see below), macrophage/monocyte proliferation; differentiation, motility and survival (see below) and a pharmaceutically acceptable carrier, diluent or excipient (including combinations thereof). The stem cells are advantageously adult stem cells, such as hematopoietic or cardiac stem cells or a combination thereof or a combination of cardiac stem cells and any other type of stem cells.

The implanting, depositing, administering or causing of implanting or depositing or administering of stem cells, such as adult stem cells, for instance hematopoietic or cardiac stem cells or a combination thereof or any combination of cardiac stem cells (e.g., adult cardiac stem cells) and stem cells of another type of (e.g., adult stem cells of another type), alone or with a cytokine such as a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor or Interleukin-3 or any cytokine capable of the stimulating and/or mobilizing stem cells (wherein "with a cytokine . . . " can include sequential implanting, depositing administering or causing of implanting or depositing or administering of the stem cells and the cytokine or the co-implanting co-depositing or co-administering or causing of co-implanting or co-depositing or co-administering or the simultaneous implanting, depositing administering or causing of implanting or depositing or administering of the stem cells and the cytokine), in circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta. This implanting, depositing, or administering or causing of implanting, depositing or administering can be in conjunction with grafts. Such implanting, depositing or administering or causing of implanting, depositing or administering is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other e.g., genetic, conditions that impart weakness or scarring to the heart (see also cardiac conditions mentioned infra).

The use of such stem cells alone or in combination with said cytokine(s), in the formulation of medicaments for such treatment, therapy or prevention.

Medicaments for use in such treatment, therapy or prevention comprising the stem cells and optionally the cytokine(s).

Kits comprising the stem cells and optionally the cytokine(s) for formulations for use in such treatment, therapy or prevention.

Compositions comprising such stem cells and optionally at least one cytokine and kits for preparing such compositions.

Methods of making the kits and compositions described herein.

Methods of implanting or depositing stem cells or causing the implanting or depositing of stem cells.

Methods and/or pharmaceutical compositions comprising a therapeutically effective amount of one or more cytokines for causing the migration and/or proliferation of cardiac stem cells or cardiac primative cells into circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta. This migration and/or proliferation is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other e.g., genetic, conditions that impart weakness or scarring to the heart (see also cardiac conditions mentioned infra).

Medicaments for use in such treatment, therapy or prevention comprising the two or more cytokines.

Kits comprising the cytokines for formulations for use in such treatment, therapy or prevention.

Compositions comprising the cytokines and kits for preparing such compositions.

Methods of making the kits and compositions described herein.

Methods and/or pharmaceutical compositions comprising a therapeutically effective amount of one or more cytokines for causing the migration and/or proliferation of cardiac stem cells or cardiac primative cells into circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta in combination with a therapeutically effective amount of a pharmaceutical agent useful in treating hypertension, myocardial infarction, ischemia, angina, or other coronary or vascular ailments, such as $AT_1$ receptor blockers such as losartan, streptokinase, ReoPro (abciximab), enalapril maleate, Rapilysin (reteplase), Dilatrend (carvedilol), Activase (alteplase), and other drugs for similar uses which would be known by one skilled in the art.

Methods of treating a patient suffering from hypertension, myocardial infarction, ischemia, angina or other coronary or vascular ailments, utilizing the above pharmaceutical compositions.

Kits comprising one or more cytokines in combination with a pharmaceutical agent useful in treating hypertension, myocardial infarction, ischemia, angina, or other coronary or vascular ailments.

Methods of making and using the above kits and compositions.

BACKGROUND OF THE INVENTION

Cardiovascular disease is a major health risk throughout the industrialized world. Atherosclerosis, the most prevalent of cardiovascular diseases, is the principal cause of heart attack, stroke, and gangrene of the extremities, and thereby the principal cause of death in the United States. Atherosclerosis is a complex disease involving many cell types and molecular factors (for a detailed review, see Ross, 1993, Nature 362: 801-809).

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is myocardial infarction (MI), commonly known as a heart attack, is one of the most well-known types of cardiovascular disease. 1998 estimates show 7.3 million people in the United States suffer from MI, with over one million experiencing an MI in a given year (American Heart Association, 2000). Of these individuals, 25% of men, and 38% of females will die within a year of their first recognized MI (American Heart Association, 2000). MI is caused by a sudden and sustained lack of blood flow to an area of the heart, commonly caused by narrowing of a coronary artery. Without adequate blood supply, the tissue becomes ischemic, leading to the death of myocytes and vascular structures. This area of necrotic tissue is referred to as the infarct site, and will eventually become scar tissue. Survival is dependent on the size of this infarct site, with the probability of recovery decreasing with increasing infarct size. For example, in humans, an infarct of 46% or more of the left ventricle triggers irreversible cardiogenic shock and death (99).

Current treatments for MI focus on reperfusion therapy, which attempts to start the flow of blood to the affected area to prevent the further loss of tissue. The main choices for reperfusion therapy include the use of anti-thrombolytic agents, or performing balloon angioplasty, or a coronary artery bypass graft. Anti-thrombolytic agents solubilize blood clots that may be blocking the artery, while balloon angioplasty threads a catheter into the artery to the site of the occlusion, where the tip of the catheter is inflated, pushing open the artery. Still more invasive procedures include the bypass, where surgeons remove a section of a vein from the patient, and use it to create a new artery in the heart, which bypasses the blockage, and continues the supply of blood to the affected area. In 1998, there were an estimated 553,000 coronary artery bypass graft surgeries and 539,000 percutaneous transluminal coronary angioplastys. These procedures average $27,091 and $8,982 per patient, respectively (American Heart Association, 2000).

These treatments may succeed in reestablishing the blood supply, however tissue damage that occurred before the reperfusion treatment began has been thought to be irreversible. For this reason, eligible MI patients are started on reperfusion therapy as soon as possible to limit the area of the infarct.

As such, most studies on MI have also focused on reducing infarct size. There have been a few attempts to regenerate the necrotic tissue by transplanting cardiomyocytes or skeletal myoblasts (Leor et al., 1996; Murray, et al., 1996; Taylor, et al., 1998; Tomita et al., 1999; Menasche et al., 2000). While the cells may survive after transplantation, they fail to reconstitute healthy myocardium and coronary vessels that are both functionally and structurally sound.

All of the cells in the normal adult originate as precursor cells which reside in various sections of the body. These cells, in turn, derive from very immature cells, called progenitors, which are assayed by their development into contiguous colonies of cells in 1-3 week cultures in semisolid media such as methylcellulose or agar. Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the well-known role of stem cells in the development of blood cells, stem cells also give rise to cells found in other tissues, including but not limited to the liver, brain, and heart.

Stem cells have the ability to divide indefinitely, and to specialize into specific types of cells. Totipotent stem cells, which exist after an egg is fertilized and begins dividing, have total potential, and are able to become any type of cell. Once the cells have reached the blastula stage, the potential of the cells has lessened, with the cells still able to develop into any cell within the body, however they are unable to develop into the support tissues needed for development of an embryo. The cells are considered pluripotent, as they may still develop into many types of cells. During development, these cells become more specialized, committing to give rise to cells with a specific function. These cells, considered multipotent, are found in human adults and referred to as adult stem cells. It is well known that stem cells are located in the bone marrow, and that there is a small amount of peripheral blood stem cells that circulate throughout the blood stream (National Institutes of Health, 2000).

Due to the regenerative properties of stem cells, they have been considered an untapped resource for potential engineering of tissues and organs. It would be an advance to provide uses of stem cells with respect to addressing cardiac conditions.

Mention is made of:

U.S. Pat. No. 6,117,675 which relates to the differentiation of retinal stem cells into retinal cells in vivo or in vitro, which can be used as a therapy to restore vision.

U.S. Pat. No. 6,001,934 involving the development of functional islets from islets of Langerhans stem cells.

U.S. Pat Nos. 5,906,934 and 6,174,333 pertaining to the use of mesenchymal stem cells for cartilage repair, and the use of mesenchymal stem cells for regneration of ligaments; for instance, wherein the stem cells are embedded in a gel matrix, which is contracted and then implanted to replace the desired soft tissue.

U.S. Pat. Nos. 6,099,832, and 6,110,459 involving grafts with cell transplantation.

PCT Application Nos. PCT/US00/08353 (WO 00/57922) and PCT/US99/17326 WO 00/06701) involving intramyocardial injection of autologous bone marrow and mesenchymal stem cells which fails to teach or suggest administering, implanting, depositing or the use of hematopoietic stem cells as in the present invention, especially as hematopoietic stem cells as in the present invention are advantageously isolated and/or purified adult hematopoietic stem cells.

Furthermore, at least certain of these patent documents fail to teach or suggest the present invention for additional reasons. The source of the stem cells of interest is limited to the known precursors of the type of tissue for which regeneration is required. Obtaining and purifying these specific cells can be extremely difficult, as there are often very few stem cells in a given tissue. In contrast, a benefit of the present invention results from the ability of various lineages of stem cells to home to the myocardium damage and differentiate into the appropriate cell types—an approach that does not require that the stem cells are recovered directly from myocardium, and, a variety of types of stem cells may be used without compromising the functionality of the regenerated tissue. And, other of these patent documents utilize stem cells as the source of various chemical compositions, without utilizing their proliferative capabilities, and thereby fail to teach or suggest the invention.

Only recent literature has started to investigate the potentials for stem cells to aid in the repair of tissues other than that of known specialization. This plasticity of stem cells, the ability to cross the border of germ layers, is a concept only in its infancy (Kempermann et al, 2000, Temple, 2001). Kocher et al (2001) discusses the use of adult bone marrow to induce neovascularization after infarction as an alternative therapy for left ventricle remodeling (reviewed in Rosenthal and Tsao, 2001). Other studies have focused on coaxing specific types of stem cells to differentiate into myocardial cells, i.e. liver stem cells as shown in Malour et al (2001). Still other work focuses on the possibilities of bone-marrow derived stem cells (Krause, et al., 2001).

One of the oldest uses of stem cells in medicine is for the treatment of cancer. In these treatments, bone marrow is transplanted into a patient whose own marrow has been destroyed by radiation, allowing the stem cells in the transplanted bone marrow to produce new, healthy, white blood cells.

In these treatments, the stem cells are transplanted into their normal environment, where they continue to function as normal. Until recently, it was thought that any particular stem cell line was only capable of producing three or four types of cells, and as such, they were only utilized in treatments where the stem cell was required to become one of the types of cells for which their ability was already proven. Researchers are beginning to explore other options for treatments of myriad disorders, where the role of the stem cell is not well defined. Examples of such work will be presented in support of the present invention.

Organ transplantation has been widely used to replace diseased, nonfunctional tissue. More recently, cellular transplantation to augment deficiencies in host tissue function has emerged as a potential therapeutic paradigm. One example of this approach is the well publicized use of fetal tissue in individuals with Parkinsonism (reviewed in Tompson, 1992), where dopamine secretion from transplanted cells alleviates the deficiency in patients. In other studies, transplanted myoblasts from uneffected siblings fused with endogenous myotubes in Duchenne's patients; importantly the grafted myotubes expressed wild-type dystrophin (Gussoni et al., 1992).

Despite their relevance in other areas, these earlier studies do not describe any cellular transplantation technology that can be successfully applied to the heart, where the ability to replace damaged myocardium would have obvious clinical relevance. Additionally, the use of intra-cardiac grafts to target the long-term expression of angiogenic factors and ionotropic peptides would be of therapeutic value for individuals with myocardial ischemia or congestive heart failure, respectively.

In light of this background there is a need for the improvement of myocardial regeneration technology in the heart. Desirably, such technology would not only result in tissue regeneration in the heart but also enable the delivery of useful compositions directly to the heart. The present invention addresses these needs.

It is therefore believed that heretofore the administration, implanting, depositing, causing to be deposited, implanted or administered of stem cells, alone or in combination with at least one cytokine, as well as the use of such stem cells alone or in combination with said cytokine(s), in the formulation of medicaments for treatment, therapy or prevention, as in this disclosure and as in the present invention, has not been taught, or suggested in the art and that herein methods, compositions, kits and uses are novel, nonobvious and inventive, i.e., that the present invention has not been taught or suggested in the art and that the present invention is novel, nonobvious and inventive.

OBJECT AND SUMMARY OF THE INVENTION

It has surprisingly been found that the implantation of somatic stem cells into the myocardium surrounding an infarct following a myocardial infarction, migrate into the damaged area, where they differentiate into myocytes, endothelial cells and smooth muscle cells and then proliferate and form structures including myocardium, coronary arteries, arterioles, and capillaries, restoring the structural and functional integrity of the infarct.

It has also surprisingly been found that following a myocardial infarction, the administration of a cytokine to the patient, stimulates the patient's own resident and/or circulating stem cells, causing them to enter the blood stream and home to the infarcted area. It has also been found that once the cells home to the infarct, they migrate into the damaged tissue, where they differentiate into myocytes, endothelial cells and smooth muscle cells and then proliferate and form structures including myocardium, coronary arteries, arterioles and capillaries, restoring structural and functional integrity to the infracted area.

Surprisingly, resident cardiac stem cells (CSCs) have recently been identified in the human (82) and rat (83, 84) heart. These primitive cells tend to accumulate in the atria (82) although they are also present throughout the ventricular myocardium (82, 83, 84). CSCs express surface antigens commonly found in hematopoietic and skeletal muscle stem cells (85, 86). CSCs are clonogenic, self-renewing and multipotent giving rise to all cardiac lineages (84). Because of the growth properties of CSCs, the injured heart has the potential to repair itself. However, this possibility had been limited by our lack of understanding of CSC colonization, proliferation and differentiation in new organized, functioning myocardium (61, 87). Identical obstacles apply to any other source of stem cells in the organism (88).

The identification of c-Met on hematopoietic and hepatic stem cells (89, 90, 91) and, most importantly, on satellite skeletal muscle cells (92) has prompted the determining of whether its ligand, hepatocyte growth factor (HGF), has a biological effect on CSCs. Assuming that HGF mobilize and promote the translocation of CSCs from anatomical storage areas to the site of damage acutely after infarction. HGF positively influences cell migration (93) through the expression and activation of matrix metalloproteinase-2 (94, 95). This enzyme family destroys barriers in the extracellular matrix thereby facilitating CSC movement, homing and tissue restoration.

Similarly, insulin-like growth factor-1 (IGF-1) is mitogenic, antiapoptotic and is necessary for neural stem cell multiplication and differentiation (96, 97, 98). In a comparable manner, IGF-1 impacts CSCs by increasing their number and protecting their viability. IGF-1 overexpression is characterized by myocyte proliferation in the adult mouse heart (65) and this cell growth may depend on CSC activation, differentiation and survival.

Consequently, the invention provides methods and/or compositions for repairing and/or regenerating damaged myocardium and/or myocardial cells comprising the administration of an effective amount of one or more cytokines, e.g. HGF and IGF-1 for causing the migration and/or proliferation of cardiac stem cells or cardiac primative cells into circulatory tissue or muscle tissue or circulatory muscle tissue. For example, HGF may be administered at varying concentrations of between 0 and 400 ng/ml, or preferably varying concentrations less than 400 ng/ml, or most preferably varying concentrations between 50 and 200 ng/ml. IGF-1 may be administered at a concentration less than 500 ng/ml, between 150 and 250 ng/ml, or most preferably at 200 ng/ml. The This migration and/or proliferation of cardiac stem cells induced by cytokine administration is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other, e.g. genetic, conditions that impart weakness or scarring to the heart.

It is reasonable to suggest that the protocol used here is superior to the procedure employed to replace the necrotic or scarred myocardium by transplanting cardiomyocytes (42, 79), skeletal myoblasts (55, 76) or the prospective utilization of embryonic cells (100, 101). Although these attempts have been successful in the survival of many of the grafted cells, they have failed to reconstitute healthy myocardium and coronary vessels integrated structurally and functionally with the spared portion of the ventricular wall. CSCs are programmed to regulate the normal cell turnover of the heart and, under stressful conditions, participate in the recovery of the injured ventricle structurally and mechanically (82, 102).

In accordance with one aspect of the present invention, insulin-like growth factor-1 is administered at a concentration between 0 and 500 ng/ml, preferably between 150 to 250 ng/ml as at about 200 ng/ml. Hepatocyte growth factor is administered at variable concentrations between 0 and 400 ng/ml and preferably between 50 and 200 ng/ml.

The invention also provides methods and/or compositions comprising a therapeutically effective amount of one or more cytokines for causing the migration and/or proliferation of cardiac stem cells or cardiac primative cells into circulatory tissue or muscle tissue or circulatory muscle tissue. This migration and/or proliferation is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other, e.g. genetic, conditions that impart weakness or scarring to the heart.

The invention also provides medicaments for use in such treatment, therapy or prevention.

The invention further provides kits comprising one or more cytokines for formulation for use in such treatment, therapy or prevention.

The invention still further provides methods of making the kits and compositions described herein.

The invention further provides compositions and/or kits comprising one or more cytokines in combination with a therapeutic agent for treating cardiac or vascular conditions for formulation for use in such treatment, therapy or prevention.

The invention provides to methods and/or compositions for repairing and/or regenerating recently damaged myocardium and/or myocardial cells comprising the administration of somatic stem cells, e.g., adult stem cells or cardiac stem cells or hematopoietic stem cells or a combination thereof, such as adult cardiac or adult hematopoietic stem cells or a combination thereof or a combination of cardiac stem cells and a stem cell of another type, such as a combination of adult cardiac stem cells and adult stem cells of another type.

The invention further provides a method and/or compositions for repairing and/or regenerating recently damaged myocardium and/or myocardial cells comprising the administration of at least one cytokine.

The invention further provides methods and/or compositions for repairing and/or regenerating recently damaged myocardium and/or myocardial cells comprising the administration of at least one cytokine in combination with a pharmaceutical agent useful in the treatment of cardiac or vascular conditions.

The invention still further relates to a method and/or compositions for repairing and/or regenerating recently damaged myocardium comprising the administration of somatic stem cells, e.g., adult stem cells or cardiac stem cells or hematopoietic stem cells or a combination thereof, such as adult cardiac or adult hematopoietic stem cells or a combination thereof or a combination of cardiac stem cells and a stem cell of another type, such as a combination of adult cardiac stem cells and adult stem cells of another type and a cytokine.

The invention yet further provides a method for preparing any of the aforementioned or herein disclosed compositions comprising admixing the pharmaceutically acceptable carrier and the somatic stem cells and/or cytokines.

The invention also provides to a kit comprising a pharmaceutical composition for use in repairing and/or regenerating recently damaged myocardium and/or myocardial cells.

The invention provides methods involving implanting, depositing, administering or causing the implanting or depositing or administering of stem cells, such as adult stem cells, for instance hematopoietic or cardiac stem cells or a combination thereof or any combination of cardiac stem cells (e.g., adult cardiac stem cells) and stem cells of another type of (e.g., adult stem cells of another type), alone or with a cytokine such as a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor or interleukin-3 or any cytokine capable of the stimulating and/or mobilizing stem cells (wherein "with a cytokine . . . " can include sequential implanting, depositing administering or causing of implanting or depositing or administering of the stem cells and the cytokine or the co-implanting co-depositing or co-administering or causing of co-implanting or co-depositing or co-administering or the simultaneous implanting, depositing administering or causing of implanting or depositing or administering of the stem cells and the cytokine), in circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta. This implanting, depositing, or administering or causing of implanting, depositing or administering can be in conjunction with grafts.

Such implanting, depositing or administering or causing of implanting, depositing or administering is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other e.g., genetic, conditions that impart weakness or scarring to the heart (see also cardiac conditions mentioned supra).

The invention additionally provides the use of such stem cells alone or in combination with said cytokine(s), in the formulation of medicaments for such treatment, therapy or prevention.

And thus, the invention also provides medicaments for use in such treatment, therapy or prevention comprising the stem cells and optionally the cytokine(s).

Likewise the invention provides kits comprising the stem cells and optionally the cytokine(s) for formulations for use in such treatment, therapy or prevention. The stem cells and the cytokine(s) can be in separate containers in a package or in one container in a package; and, the kit can optionally include a device for administration (e.g., syringe) and/or instructions for administration and/or admixture.

The invention also provides compositions comprising such stem cells and optionally the cytokine(s) and kits for preparing such compositions (e.g., kits comprising the stem cells and optionally the cytokine(s); stem cells and the cytokine(s) can be in separate containers in a package or in one container in a package; and, the kit can optionally include a device for administration (e.g., syringe) and/or instructions for administration and/or admixture), as well as methods of making the aforementioned compositions.

The invention also provides a means of generating and/or regenerating myocardium ex vivo, wherein somatic stem cells and heart tissue are cultured in vitro, optionally in the presence of a ctyokine. The somatic stem cells differentiate into myocytes, smooth muscle cells and endothelial cells, and proliferate in vitro, forming myocardial tissue and/or cells. These tissues and cells may assemble into cardiac structures including arteries, arterioles, capillaries, and myocardium. The tissue and/or cells formed in vitro may then be implanted into a patient, e.g. via a graft, to restore structural and functional integrity.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

These and other embodiments are disclosed or are obvious from and encompassed by, the following Detailed Description.

BRIEF DESCRIPTION OF FIGURES

The patent or application file contains at least one drawing executed in color. Copies of this patent or patent application publication with color drawing(s) will be provided by the U.S. Patent and Trademark Office upon request and payment of the necessary fee.

The following Detailed Description, given to describe the invention by way of example, but not intended to limit the invention to specific embodiments described, may be understood in conjunction with the accompanying Figures, incorporated herein by reference, in which:

FIG. 3A is stained to show the presence of EGFP (green). Magnification is 250×. FIG. 3B is stained to show the presence of cardiac myosin (red). Magnification is 250×. FIG. 3C is stained to show the presence of both EGFP and myosin (red-green), as well as PI-stained nuclei (blue). Magnification is 250×);

FIG. 5B is stained to show the presence of α-smooth muscle actin in arterioles (red). Magnification is 300×. FIG. 5C is stained to show the presence of both EGFP and α-smooth muscle actin (yellow-red), as well as PI-stained nuclei (blue). Magnification is 300×. FIGS. 5D-F and G-I depict the presence of MEF2 and Csx/Nkx2.5 in cardiac myosin positive cells. FIG. 5D shows PI-stained nuclei (blue). Magnification is 300×. FIG. 5E is stained to show MEF2 and Csx/Nkx2.5 labeling (green). Magnification is 300×. FIG. 5F is stained to show cardiac myosin (red), as well as MEF2 or Csx/Nkx2.5 with PI (bright fluorescence in nuclei). Magnification is 300×. FIG. 5G shows PI-stained nuclei (blue). Magnification is 300×. FIG. 5H is stained to show MEF2 and Csx/Nkx2.5 labeling (green). Magnification is 300×. FIG. 5I is stained to show cardiac myosin (red), as well as MEF2 or Csx/Nkx2.5 with PI (bright fluorescence in nuclei). Magnification is 300×);

FIG. 6A has been stained to show PI-labeled nuclei (blue). Magnification is 900×. FIG. 6B has been stained to show BrdU- and Ki67-labeled nuclei (green). Magnification is 900×. FIG. 6C has been stained to show the presence of α-sarcomeric actin (red). Magnification is 900×. FIGS. 6D-F shows tissue that has been incubated in the presence of antibodies to Ki67. FIG. 6D has been stained to show PI-labeled nuclei (blue). Magnification is 500×. FIG. 6E has been stained to show BrdU- and Ki67-labeled nuclei (green). Magnification is 500×. FIG. 6F has been stained to show the presence of α-smooth muscle actin (red). Magnification is 500×. Bright fluorescence: combination of PI with BrdU (C) or Ki67 (F));

FIG. 7A is stained to show the presence of EGFP (green). Magnification is 280×. FIG. 7B is stained to show the presence of cardiac myosin (red). Magnification is 280×. FIG. 7C is stained to show the presence of both EGFP and myosin (red-green), as well as PI-stained nuclei (blue). Magnification is 280×);

FIG. 8B is stained to show the presence of cardiac myosin (red). Magnification is 650×. FIG. 8C is stained to show both the presence of EGFP and myosin (yellow), as well as PI-stained nuclei (blue). Magnification is 650×. FIG. 8D is stained to show the presence of EGFP (green). Magnification is 650×. FIG. 8E is stained to show the presence of α-smooth muscle actin in arterioles (red). Magnification is 650×. FIG. 8F is stained to show the presence of both EGFP and α-smooth muscle actin (yellow-red) as well as PI-stained nuclei (blue). Magnification is 650×);

(FIG. 9A is stained to show the presence of cardiac myosin (red) Magnification is 400×. FIG. 9B is stained to show the presence of the Y chromosome (green). Magnification is 400×. FIG. 9C is stained to show both the presence of the Y chromosome (light blue) and PI-labeled nuclei (dark blue). Note the lack of Y chromosome in infarcted tissue (IT) in subendocardium and spared myocytes (SM) in subepicardium. Magnification is 400×);

FIG. 10B shows the presence of GATA-4 labeling (green). Magnification is 650×. FIG. 10C is stained to show cardiac myosin (red) in combination with GATA-4 and PI (bright fluorescence in nuclei). Magnification is 650×);

FIG. 11B shows regenerating myocardium. Magnification is 800×. FIG. 11C is stained to show the presence of connexin 43 (yellow-green), and the contacts between myocytes are shown by arrows. Magnification is 800×. FIG. 11D is stained to show both α-sarcomeric actin (red) and PI-stained nuclei (blue). Magnification is 800×);

FIG. 12B is the same as FIG. 12A at a magnification of 700×);

FIG. 13B shows a MI in a non-treated mouse. Healing comprises the entire infarct (arrowheads) (Magnification is 50×). Scarring is seen at higher magnification (80×—adjacent panel). Red=cardiac myosin; yellow-green=propidium iodide (PI) labeling of nuclei; blue-magenta=collagen types I and III);

FIGS. 16E-G show mural thickness (e), chamber diameter (f) and longitudinal axis (g) measured anatomically at sacrifice in SO (n=9), MI (n=9) and MI-C (n=10). ***p<0.05 vs SO and MI, respectively;

FIG. 18B shows the amount of cellular hypertrophy in spared myocardium. FIG. 18C shows cell proliferation in the regenerating myocardium. Myocytes (M), EC and SMC labeled by BrdU and Ki67; n=11. *,**p<0.05 vs M and EC. FIGS. 18D-E depict the volume, number (n=11) and class distribution (bucket size, 100 μm³; n=4,400) of myocytes within the formed myocardium;

FIGS. 18G-H are magnified at 1,200×);

FIG. 19B shows labeling of SMC by α-smooth muscle actin. Bright fluorescence of nuclei reflects the combination of PI and Ki67. Magnification is 1,200×. FIG. 19C shows labeling of SMC by α-smooth muscle actin. Bright fluorescence of nuclei reflects the combination of PI and BrdU. Magnification is 1,200×. FIG. 19D shows labeling of EC in the forming myocardium by factor VIII. Bright fluorescence of nuclei reflects the combination of PI and BrdU. Magnification is 1,600×;

FIG. 20B is stained to show labeling of desmin (red). Magnification is 800×. FIG. 20C is stained to show labeling of connexin 43 (green). Red fluorescence indicates cardiac myosin. Magnification is 1,400×. FIG. 20D shows VE-cadherin and yellow-green fluorescence reflects labeling of EC by flk-1 (arrows). Magnification is 1,800×. FIG. 20E shows red fluorescence indicating factor VIII in EC and and yellow-green fluorescence reflects labeling of EC by flk-1 (arrows). Magnification is 1,200×. FIG. 20F shows green fluorescence labeling of SMC cytoplasms by flk-1 and endothelial lining labeled by flk-1. Red fluorescence indicates α-smooth muscle actin. Blue fluorescence indicates PI labeling of nuclei. Magnification is 800×; FIG. 21B uses bright fluorescence to depict the combination of PI labeling of nuclei with GATA-4. Magnification is 1,200×. FIG. 21C uses bright fluorescence to depict the combination of PI labeling of nuclei with MEF2. Magnification is 1,200× (Red fluorescence shows cardiac myosin antibody staining and blue fluorescence depicts PI labeling of nuclei. The fraction of myocyte nuclei labeled by Csx/Nkx2.5, GATA-4 and MEF2 was 63±5% (nuclei sampled=2,790; n=11), 94±9% (nuclei sampled=2,810; n=11) and 85±14% (nuclei sampled=3,090; n=11), respectively).

FIG. 22A-L are confocal micrographs which show cardiac primitive cells in normal and growth factor-treated and untreated infarcted hearts. FIG. 22A-F shows sections of atrial myocardium from sham-operated mice. FIGS. 22A and B, 22C and D, and 22E and F are pairs of micrographs showing the same area of atrial myocardium with different stains. c-Met (22A, yellow) is expressed in c-kit$^{POS}$ (22B, green) cells (22B, yellow-green). Similarly, IGF-1R (22C, yellow) is detected in MDR1$^{POS}$ (22D, green) cells (22D, yellow-green). Colocalization of c-Met (22E, red) and IGF-1R (22E, yellow) are found in MDR1$^{POS}$ (22F, green) cells (22F, red-yellow-green). Arrows point to c-Met and IGF-1R in c-kit$^{POS}$ and MDR1$^{POS}$ cells. Myocyte cytoplasm is stained red-purple and contains cardiac myosin. 22G: The yellow line separates the infarcted myocardium (MI) with apoptotic myocytes (bright nuclei, PI and hairpin 1) from the border zone (BZ) with viable myocytes (blue nuclei, PI only) in a mouse treated with growth factors. Viable c-kit$^{POS}$ cells (blue nuclei, PI; c-kit, green) are present in MI and BZ (arrows). Myocyte cytoplasm is stained red and contains cardiac myosin. 22H: The yellow line separates the MI with necrotic myocytes (bright nuclei, PI and hairpin 2) from the BZ with viable myocytes (blue nuclei, PI only) in a mouse treated with growth factors. Viable MDR1$^{POS}$ cells (blue nuclei, PI; MDR1, green) are present in MI and BZ (arrows). Myocyte cytoplasm is stained red and contains cardiac myosin). 22I and 22J: Apoptotic myocytes (22I and 22J, bright nuclei, PI and hairpin 1) and c-kit$^{POS}$ (22I, green ring) and MDR1$^{POS}$ (22J, green ring) cells undergo apoptosis (22I and 22J, bright nuclei, PI and hairpin 1; arrows) in the infarcted region of two untreated mice. Viable cells have blue nuclei (PI only). A viable c-kit$^{POS}$ cell is present within the infarcted myocardium (22I, green ring, blue nucleus, PI only; arrowhead).

Myocyte cytoplasm is stained red and shows cardiac myosin. 22K and 22L: Cycling c-kit$^{POS}$ (22K, green ring; arrows) and MDR1$^{POS}$ (22L, green ring; arrows) cells are present in the infarcted myocardium (yellow dots are apoptotic nuclei) of mice treated with growth factors. Bright fluorescence in c-kit$^{POS}$ (22K) and MDR1$^{POS}$ (22L) cells corresponds to Ki67 labeling of their nuclei. 22A-L, bar=10 µm. 22M and 22N are graphs depicting the distribution of viable and dead c-kit$^{POS}$ (22M) and MDR1$^{POS}$ (22N) cells in the various regions of the heart in sham-operated (SO), infarcted-treated (Treated) and infarcted-untreated (Untreated) mice sacrificed 7-8 hours after surgery and 2-3 hours after the administration of growth factors (Treated) or saline (SO; Untreated). Abbreviations are as follows: A, atria; LV, left ventricle; R, viable myocardium remote from the infarct; B, viable myocardium bordering the infarct; I, non-viable infarcted myocardium. Results in both 22M and 22N are presented as the mean ±SD. *,** Indicates P<0.05 vs. SO and vs. Treated, respectively.

Figure 23A:
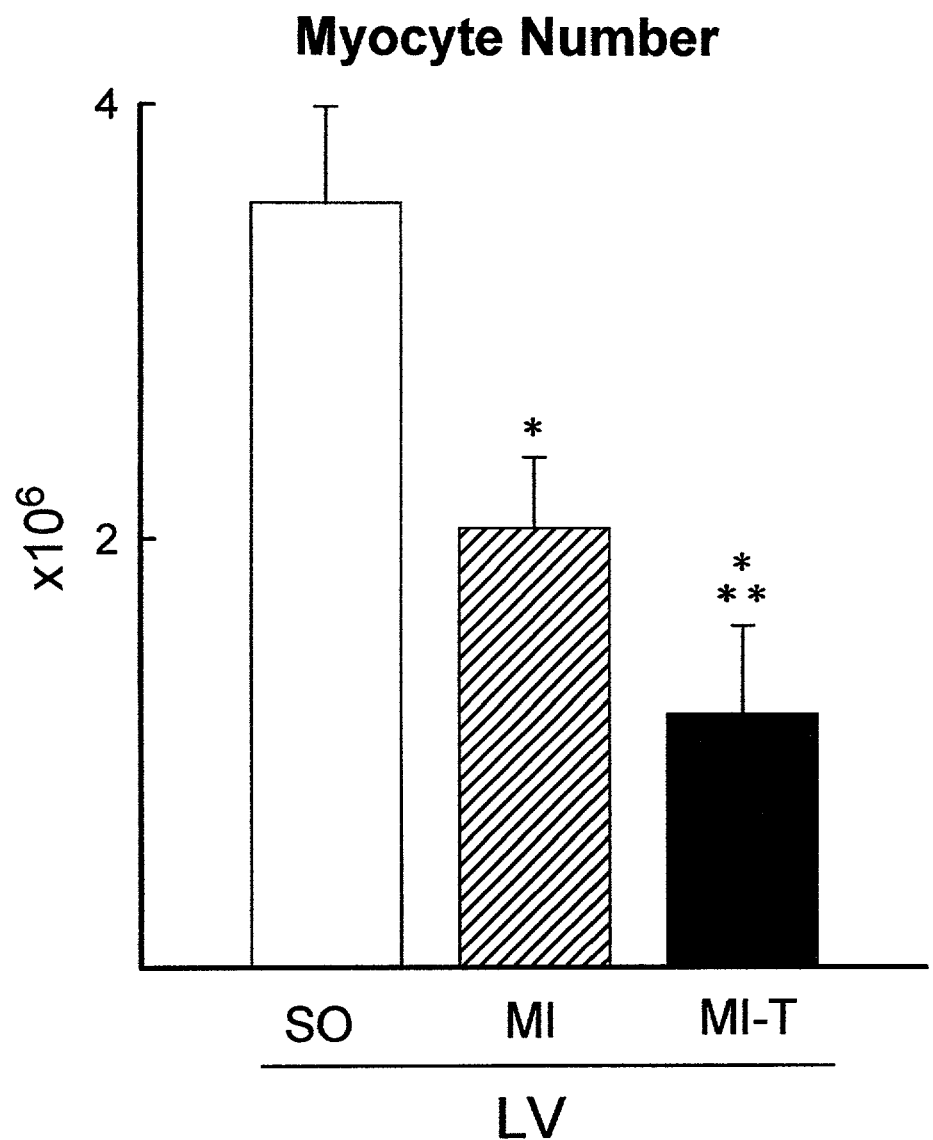
Figure 23B:
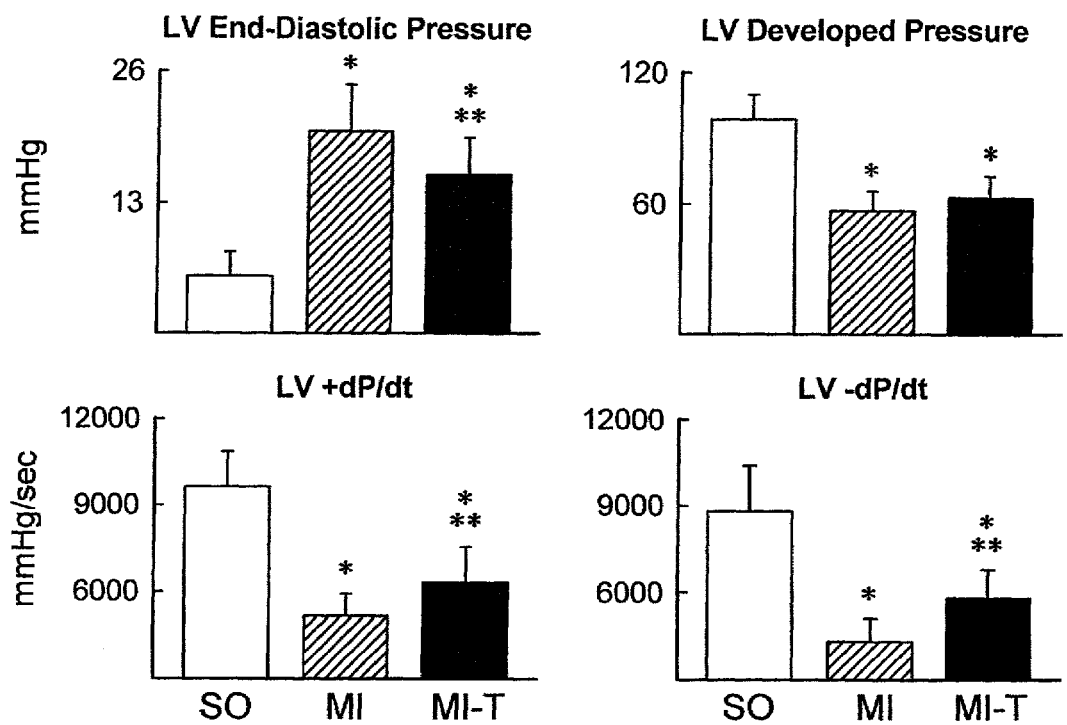

FIGS. 23A-B are graphs depicting the size of infarct and the evaluation of left ventricle hemodynamics. Results are presented as the mean±SD. *,** signifies a value of p<0.05 vs. sham-operated mice (SO) and untreated infarcted mice (MI), respectively. Abbreviations are as follows: MI-T, treated infarcted mice; LV, left ventricle and septum. 23A: To minimize the effects of cardiac hypertrophy in the surviving myocardium and healing of the necrotic region with time on infarct size, infarct dimension was measured by the loss of myocytes in the left ventricle and septum. This measurement is independent from reactive hypertrophy in the viable tissue and shrinkage of the necrotic myocardium with scar formation (87). 23B: Evaluation of LV hemodynamics is presented by data from LV end-diastolic pressure, LV developed pressure, LV +dP/dt and LV −dP/dt. 23C to 23H are confocal micrographs which depict large infarcts of the left ventricle in an untreated mouse (23C and 23D) and in two treated mice (23E to 23H). The area defined by a gate in 23C, 23E and 23G (bars=1 mm) is illustrated at higher magnification in 23D, 23F and 23H (bars=0.1 mm). In 23C and 23D the lack of myocardial regeneration is illustrated by the accumulation of collagen type I and collagen type III (blue) in the infarcted region of the wall (arrows). Nuclei of spared myocytes and inflammatory cells are apparent (green, PI). A small layer of viable myocytes is present in the subepicardium (red, cardiac myosin). In 23E to 23H, myocyte regeneration is illustrated by the red fluorescence of cardiac myosin antibody. Small foci of collagen type I and type III (blue, arrowheads) are detected in the infarcted region. Nuclei are yellow-green (PI). Abbreviations are as follows: IS, interventricular septum; MI, myocardial infarct; RV, right ventricle.

FIG. 24 shows echocardiography results from a single mouse heart before coronary artery ligation and 15 days after ligation. Confocal microscopy shows a cross section of the same heart. 24A shows the baseline echocardiography results before coronary artery ligation. 24B and 24C show confocal microscopy at low (24B, bar=1 mm) and higher (24C, bar=0.1 mm) magnification of a cross section of the heart assessed in 24A and 24D. Abbreviations used are as follows: RV, right ventricle; IS, interventricular septum; MI, myocardial infarct. 24D shows the echocardiographic documentation of contractile function in the same heart 15 days after infarction (arrowheads). 24E is a graph depicting the ejection fraction with results reported as the mean±SD. *,** p<0.05 vs. sham-operated mice (SO) and untreated infarcted mice (MI), respectively. MI-T refers to treated infarcted mice.

FIGS. 25A-F shows confocal micrographs detailing properties of regenerating myocytes. These properties are quantified in the graphs of 25G-J. 25A and 25B depict enzymatically dissociated myocytes from the regenerating portion (25A) and surviving myocardium (25B) of the infarcted ventricle of a heart treated with growth factors. 25A is stained to show small myocytes (red, cardiac myosin), bright nuclei (PI and BrdU), and blue nuclei (PI only). 25B shows large, hypertrophied myocytes (red, cardiac myosin), bright nuclei (PI and BrdU) and blue nuclei (PI only). In both 25A and 25B, the bar equals 50 µm.

Mechanical properties of new (25C and 25D) and spared (25E and 25F) myocytes are shown after infarction in mice treated with growth factors. R refers to the relaxed state of they myocytes, C is the contracted state. The effects of stimulation on cell shortening (G), velocity of shortening (H), time to peak shortening (I) and time to 50% re-lengthening (J) are depicted with results given for N (new small myocytes) and S (spared hypertrophied myocytes). Results are presented as the mean±SD. * indicates a value of P<0.05 vs S.

FIG. 26 shows pairs of confocal micrographs showing various markers of maturing myocytes (26A to 26N, bar=10 µm). In 26A to 26F, BrdU labeling of nuclei is shown in 26A, 26C and 26E as green coloration, and localization of nestin (26B, red), desmin (26D, red), cardiac myosin (26F, red) is shown in myocytes of tissue sections of regenerating myocardium. Nuclei are labeled by PI only in 26B, 26D and 26F (blue), and by BrdU and PI together in 26B, 26D and 26F (bright). 26G to 26N show the identification of connexin 43 (26G, 26H, 26K and 26L, yellow) and N-cadherin (26I, 26J, 26M and 26N, yellow) in sections of developing myocardium (26G to 26J) and in isolated myocytes (26K to 26N). Myocytes are stained by cardiac myosin (26H, 26J, 26L and 26N, red) and nuclei by BrdU only (26G, 26I, 26K and 26M, green), PI only (26H and 26J, blue) and by BrdU and PI together (26H, 26J, 26L and 26N, bright).

FIG. 27 is a series of confocal micrographs showing newly formed coronary vasculature. In 27A to 27D, arterioles are shown with TER-119-labeled erythrocyte membrane (green), PI staining of nuclei (blue), and α-smooth muscle actin staining of smooth muscle cell (red). In all micrographs, the bar equals 10 µm.

FIG. 28: Identification and growth of cardiac Lin⁻c-kit$^{POS}$ cells obtained with immunomagnetic beads (a) and FACS (b). a,b, c-kit$^{POS}$ cells in NSCM scored negative for cytoplasmic proteins of cardiac cell lineages; nuclei are stained by PI (blue) and c-kit (green) by c-kit antibody. c-f, In DM at P1, cultured cells showed by purple fluorescence in their nuclei Nkx2.5 (c), MEF2 (d), GATA-4 (e) and GATA-5 (f) labeling. g,h, Stem cells selected by NSCM and plated at low density (g) develop small individual colonies (h). Bar=10 µm.

FIG. 29: Self-renewal and multipotentiality of clonogenic cells. a, c-kit$^{POS}$ cells in a clone: nuclei=blue, c-kit=green (arrowheads). b, Two of the 3 c-kit$^{POS}$ cells (green, arrowheads) express Ki67 (purple, arrows) in nuclei (blue). c,d, Ki67 positive (c) metaphase chromosomes (red). d, metaphase chromosomes labeled by Ki67 and PI (purple) in a c-kit$^{POS}$ cell (green). e-h, In the clone, the cytoplasm (red) of M (e), EC (f), SMC (g) and F (h) is stained by cardiac myosin, factor VIII, α-smooth muscle actin and vimentin, respectively. Nuclei=blue. Lin⁻c-kit$^{POS}$ cells (green, arrowheads) are present. Bar=10 µm.

FIG. 30: Clonogenic cells and spherical clones. a, Spherical clones (arrowheads) in suspension in NSCM. b, Cluster of c-kit$^{POS}$ (green, arrowheads) and negative cells within the clone. Nuclei=blue. c, Spheroid with packed cell nuclei (blue) and large amount of nestin (red). d, Accumulation of non-degraded nestin (red) within the spheroid. Nuclei=blue. e, Spheroid plated in DM with cells migrating out of the sphere. f-h, M (f), SMC (g) and EC (h) migrating out of the spheroid and differentiating have the cytoplasm (red) stained respectively by cardiac myosin, α-smooth muscle actin and factor VIII. Nuclei=blue. Bar=10 μm.

FIG. 31: Myocardial repair. a-c, Generating myocardium (a,b, arrowheads) in an infarcted treated rat (MI). New M=myosin (red); nuclei=yellow-green. Sites of injection (arrows). c, Myocardial scarring (blue) in an infarcted untreated rat. *Spared myocytes. d-n, Myocytes h, myosin) and coronary vessels (k EC=factor VIII; n, SMC=α-smooth muscle actin) arising from the implanted cells are identified by BrdU (green) positive nuclei (g, i, m). Blue nuclei=PI (f, i, l). o-p, Myocytes at 20 days (p) are more differentiated than at 10 (o). Connexin 43=green (arrowheads); Myosin=red; Nuclei=blue; BrdU=white. Bar=1 mm (a), 100 μM (b,c), 10 μM (d-p).

FIG. 32: Newly generated myocytes. a, enzymatically dissociated cells from the repairing myocardial band. Cardiac myosin=red; Brdu=green; nuclei=blue. b-e, differentiation of new myocytes. Connexin 43=yellow (b,c); N-cadherin=yellow (d,e). Cardiac myosin=red; Brdu=green; nuclei=blue. Bar=10 μm.

FIG. 33: Mechanical properties of myocytes. a-d, new (N) and spared (S) myocytes obtained, respectively, from the regenerating and remaining myocardium after infarction in treated rats; R=relaxed, C=contracted. e-h, effects of stimulation on cell shortening and velocity of shortening of N (e,g) and S (f,h) myocytes. i-l, Results are mean±SD. *P<0.05 vs S.

FIG. 34: Primitive Cells in the Rat Heart. Section of left ventricular myocardium from a Fischer rat at 22 months of age. A, Nuclei are illustrated by the blue fluorescence of propidium iodide (PI). B, Green fluorescence documents c-kit positive cells. C, The combination of PI and c-kit is shown by green and blue fluorescence. The myocyte cytoplasm is recognized by the red fluorescence of α-sarcomeric actin antibody staining. Confocal microscopy; bar=10 μm.

Figure 35:
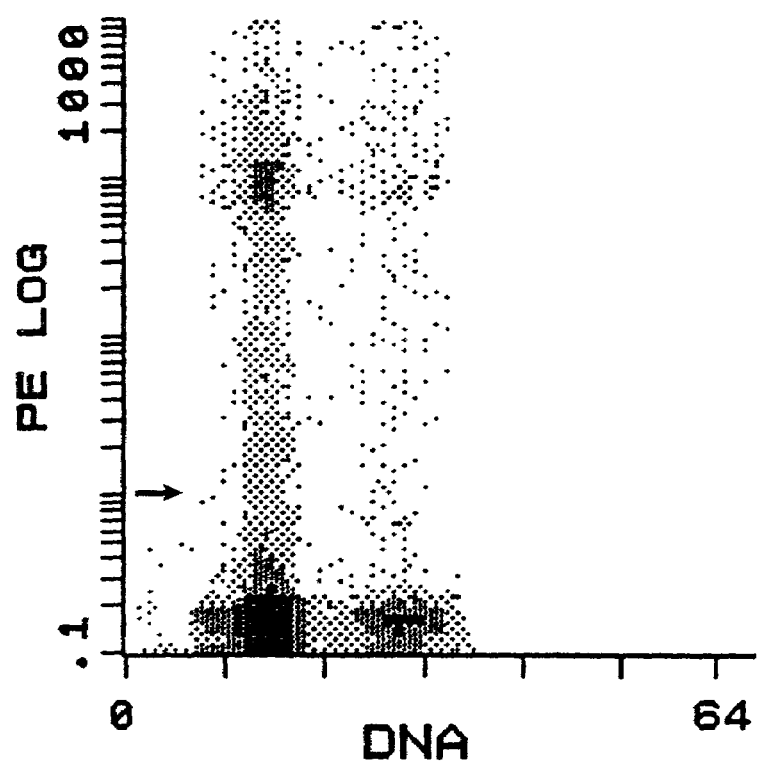

FIG. 35: FACS Analysis of c-kit$^{POS}$ Cells. Bivariate distribution of cardiac cells obtained from the left ventricle of a female Fischer 344 rat showing the level of c-kit expression versus cellular DNA. The cells were suspended at a concentration of $10^6$ cells/ml of PBS. Cellular fluorescence was measured with the ELITE ESP flow cytometer/cell sorter (Coulter Inc.) using an argon ion laser (emission at 488 nm) combined with a helium-cadmium laser, emitting UV light. Arrow indicates a threshold representing minimal c-kit level. For FACS analysis, cells were incubated with r-phycoerythrin (R-PE)-conjugated rat monoclonal c-kit antibody (Pharmingen). R-PE isotype standard was used as a negative control.

Figure 36:
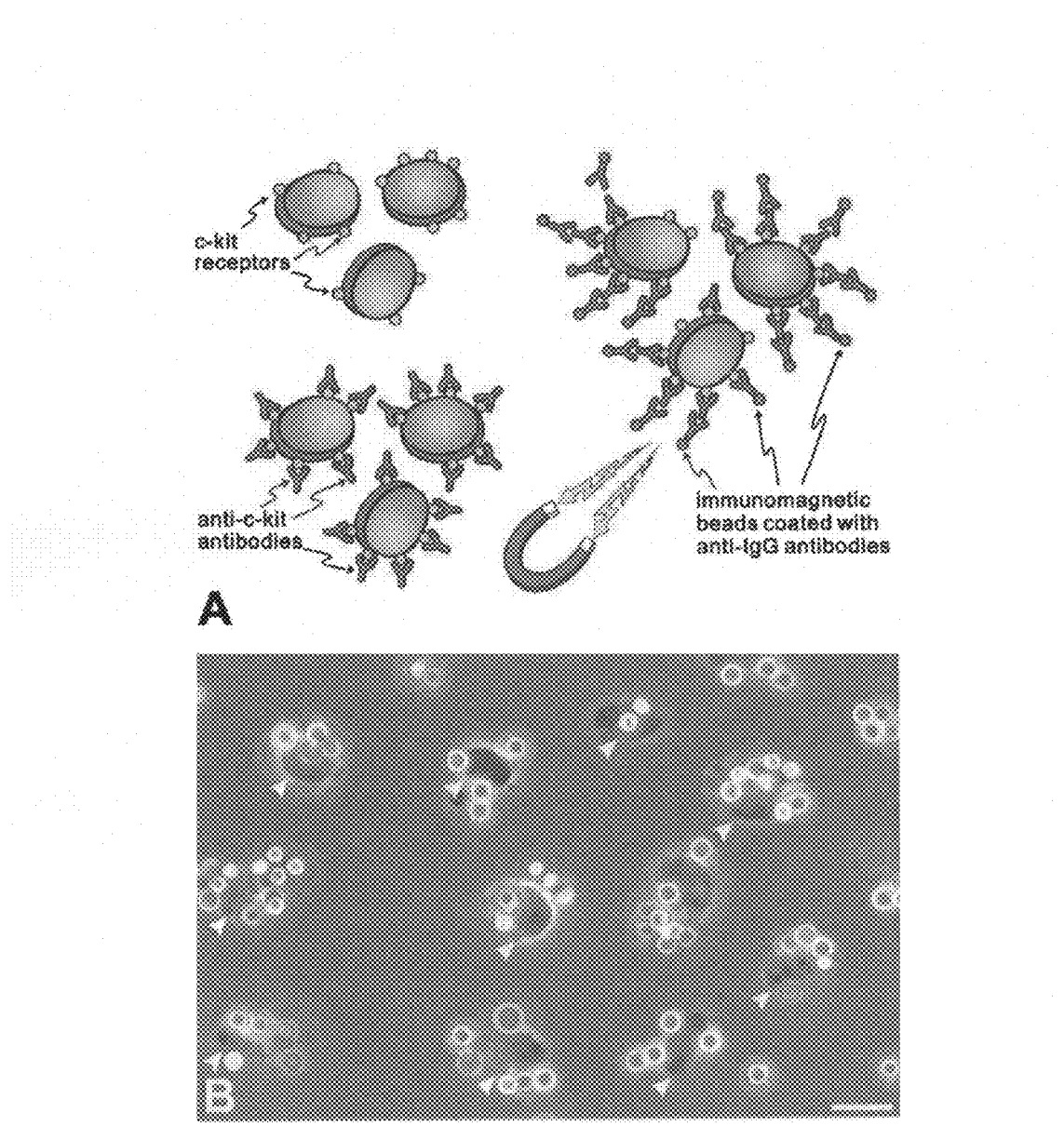

FIG. 36: Scheme for Collection of Cardiac c-kit$^{POS}$ Cells (A) and Culture of Cardiac c-kit$^{POS}$ Cells in NSCM (B). A, Undifferentiated cells expressing c-kit surface receptors are exposed to c-kit antibody and subsequently to immunomagnetic beads coated by IgG antibody. c-kit$^{POS}$ cells are collected with a magnet and cultured in NSCM. B, Immunomagnetic beads are attached on the surface of c-kit$^{POS}$ cells (arrowheads). The absence of c-kit$^{NEG}$ cells is apparent. Phase contrast microscopy; bar=10 μm.

Figure 37:
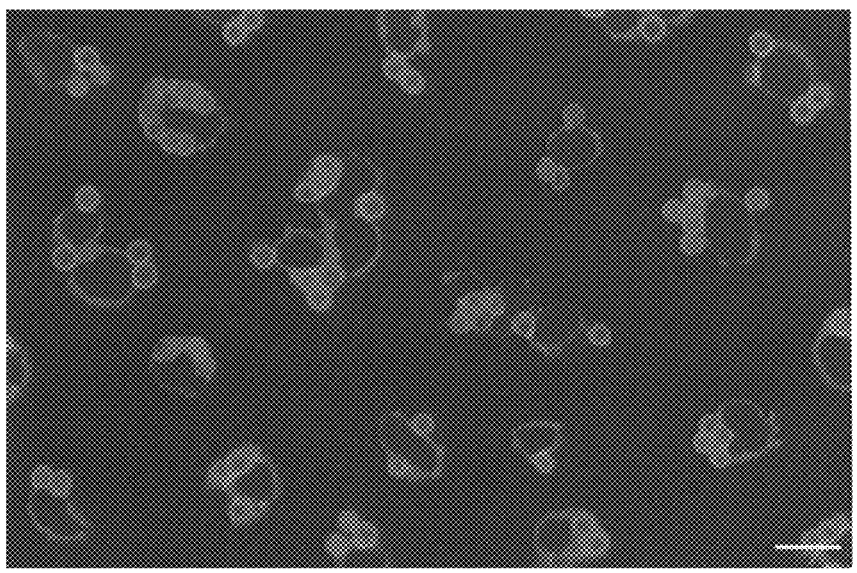

FIG. 37: c-kit Protein in Freshly Isolated Cells Collected with Immunomagnetic Beads. c-kit protein is shown by the green fluorescence of c-kit antibody. Beads adherent to the cells are illustrated by red fluorescence. Blue fluorescence reflects PI labeling of nuclei. Thus, cells selected with beads were found to be c-kit$^{POS}$. Confocal microscopy; bar=10 μm.

Figure 38:
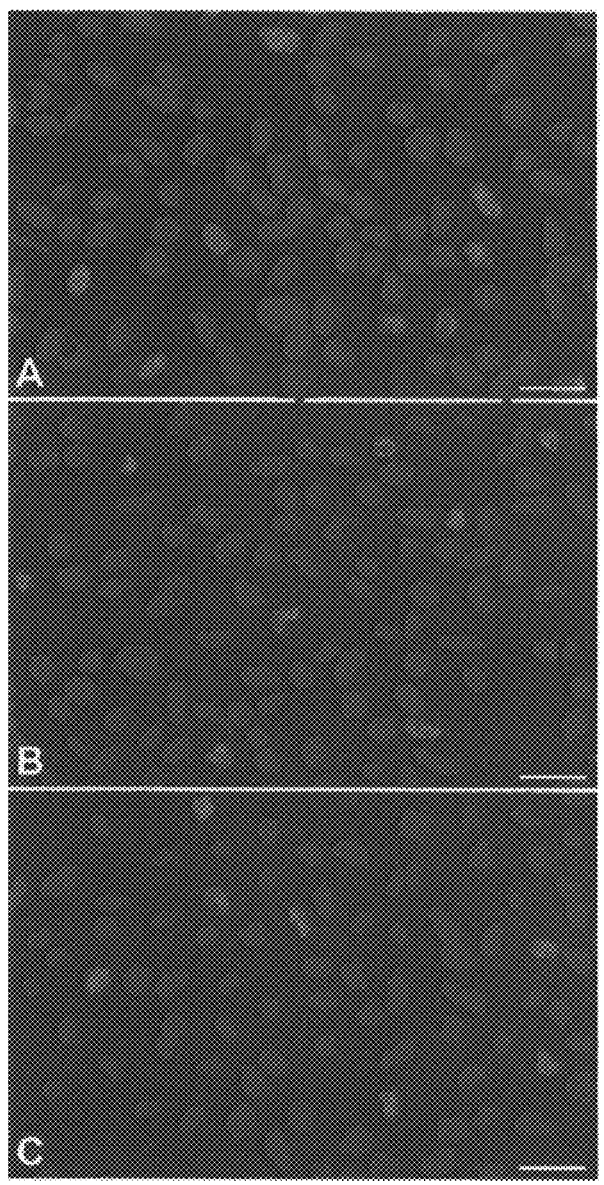

FIG. 38: Transcription Factors of Cardiomyocyte Differentiation. After removal of the beads, or immediately after FACS separation, smears were made and cells were stained for the detection of Nkx2.5, MEF2 and GATA-4. Blue fluorescence in panels A-C corresponds to PI labeling of nuclei. Purple fluorescence in nuclei reflects the expression of Nkx2.5 (A), MEF2 (B) and GATA-4 (C). Confocal microscopy; bar=10 μm.

Figure 39:
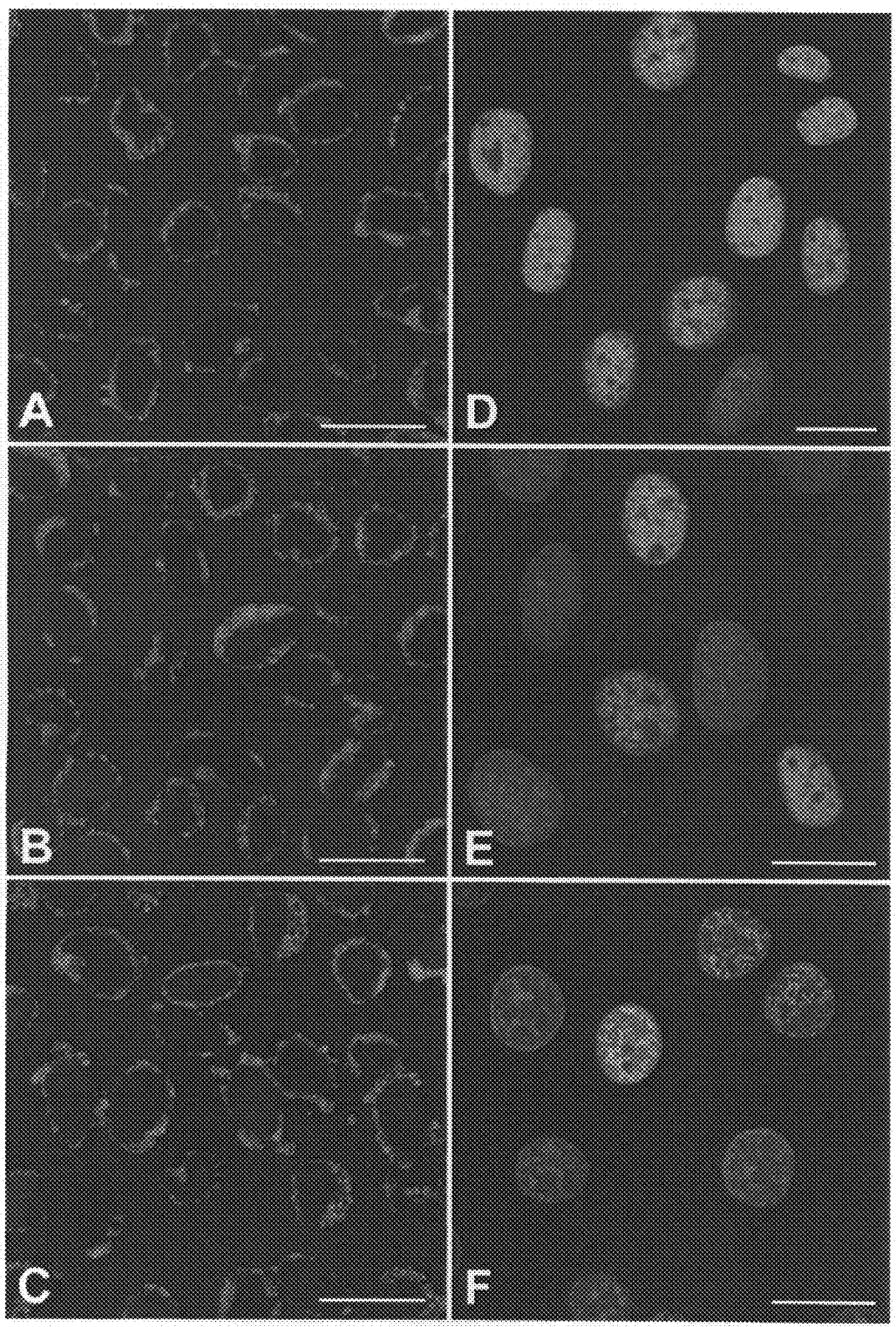

FIG. 39: c-kit$^{POS}$ Cells and Transcription Factors of Skeletal Muscle Differentiation. Panels A-C shows c-kit$^{POS}$ cells (green fluorescence, c-kit antibody; blue fluorescence, PI labeling). Panels D-F illustrate positive controls (C2C12 myoblast cell line) for MyoD (D), myogenin (E), and Myf5 (F) by green fluorescence within nuclei (red fluorescence, PI labeling). c-kit$^{POS}$ cells were negative for these skeletal muscle transcription factors. Confocal microscopy; bar=10 μm.

Figure 40:
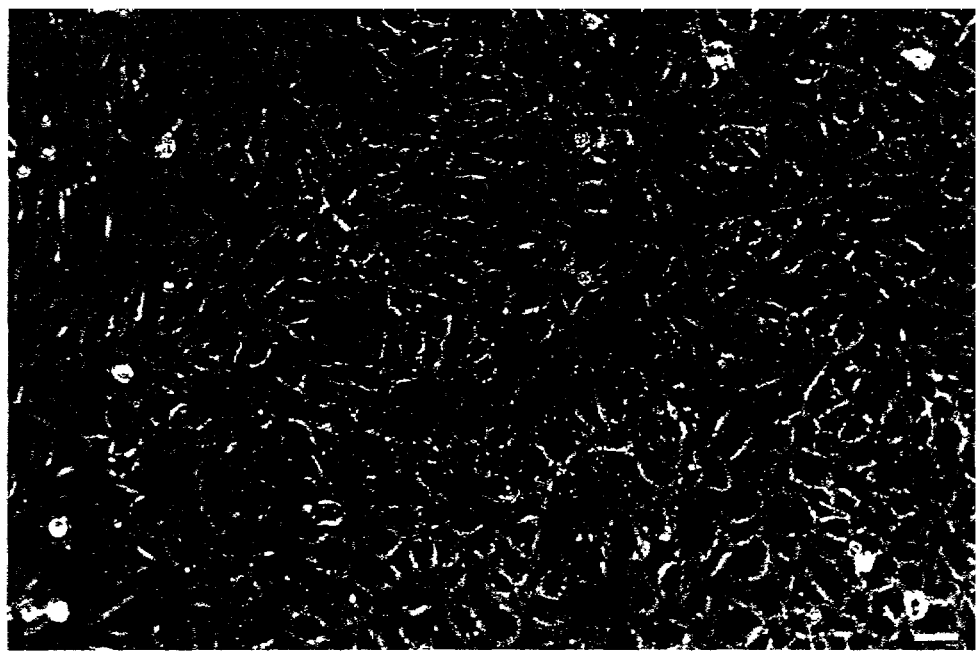

FIG. 40: Growth of c-kit$^{POS}$ Cells in Differentiating Medium (DM). Monolayer of confluent cells obtained from plating c-kit positive cells. Immunomagnetic beads were removed by gentle digestion of the cells with DNase I. This procedure degraded the short DNA linker between the bead and the anti-IgG antibody. Phase contrast microscopy; bar=20 μm.

Figure 41:
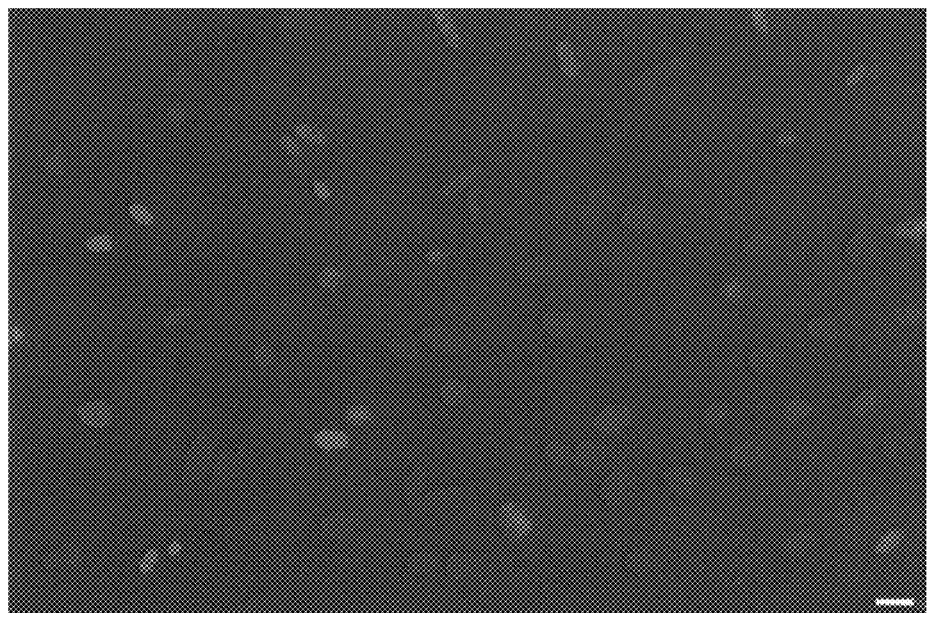

FIG. 41: Cycling Cell Nuclei in DM. Ki67 (purple fluorescence) is expressed in the majority of nuclei contained in the field. Blue fluorescence reflects PI labeling of nuclei. Confocal microscopy; bars=10 μm.

Figure 42:
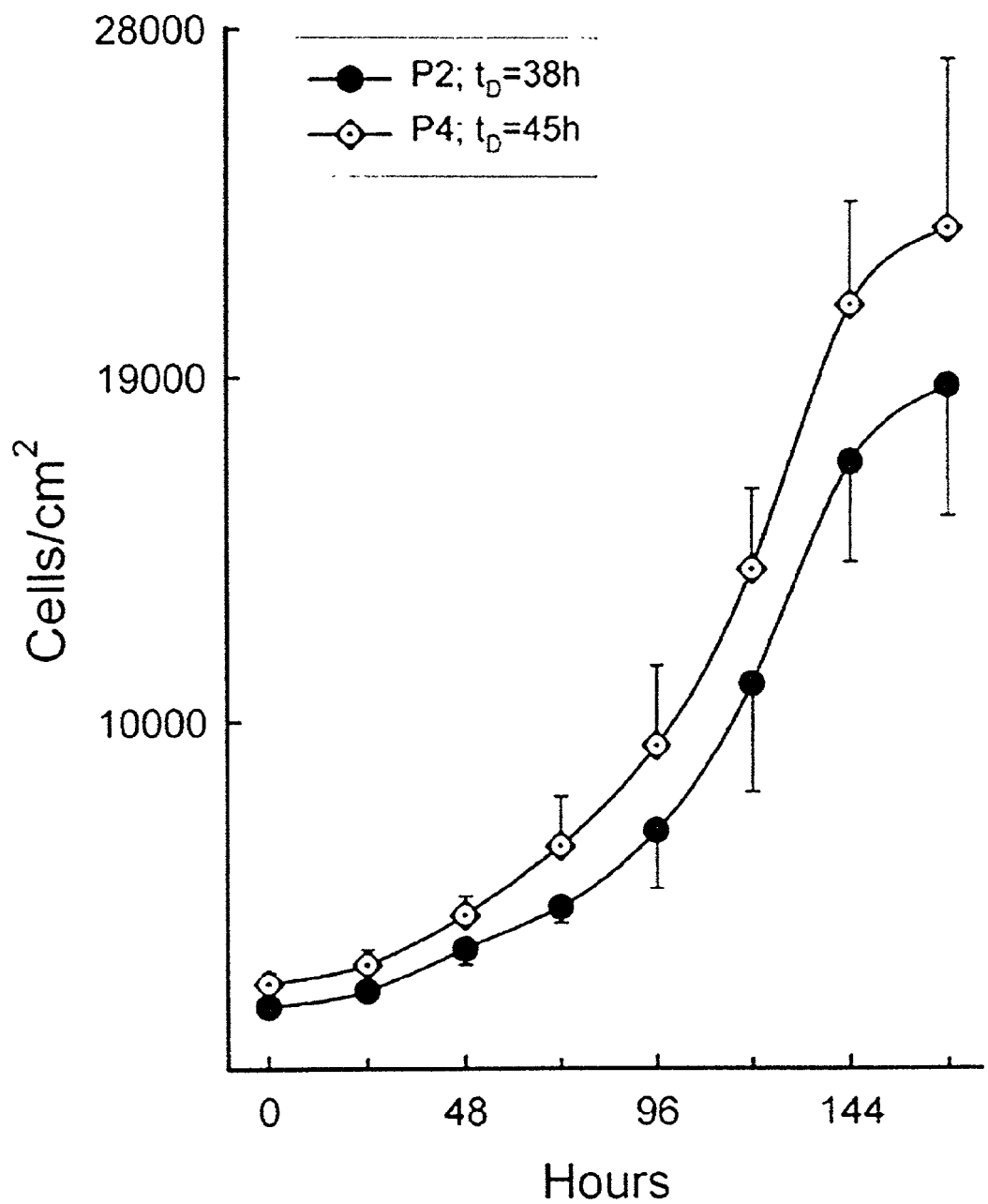

FIG. 42: Growth Rate of c-kit$^{POS}$-Derived Cells. Exponential growth curves of cells at P2 and P4; $t_D$, time required by the cells to double in number. Each point corresponds to 5 or 6 independent determinations. Vertical bars, SD.

Figure 43:
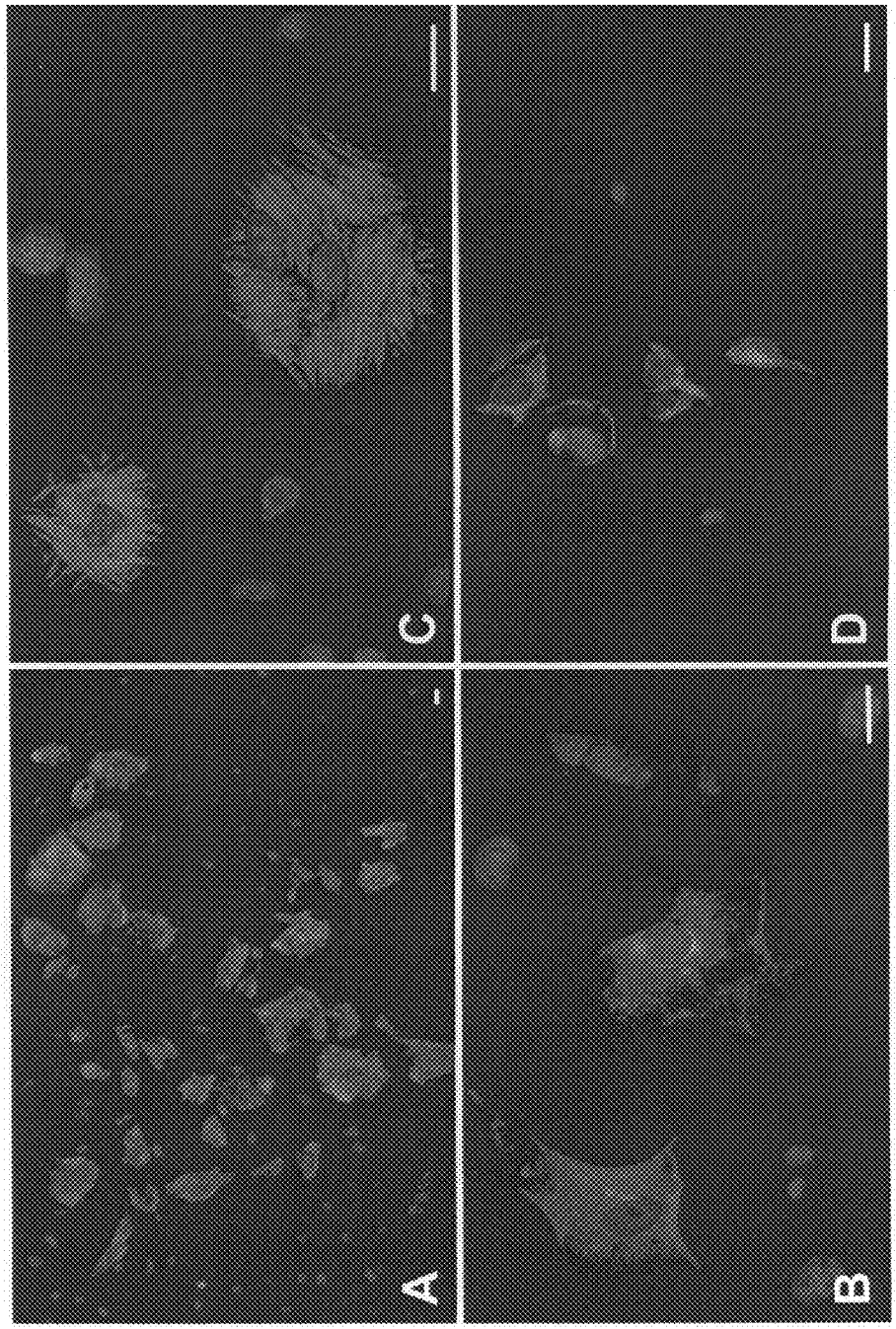

FIG. 43: Identification and Growth of Cardiac Lin$^-$c-kit$^{POS}$ Cells. In DM at P3, the cytoplasm (green) of M (A), EC (B), SMC (C) and F (D) is stained by cardiac myosin, factor VIII, α-smooth muscle actin and vimentin (factor VIII negative), respectively. Nuclei=red. Confocal microscopy; bars=10 μm.

Figure 44:
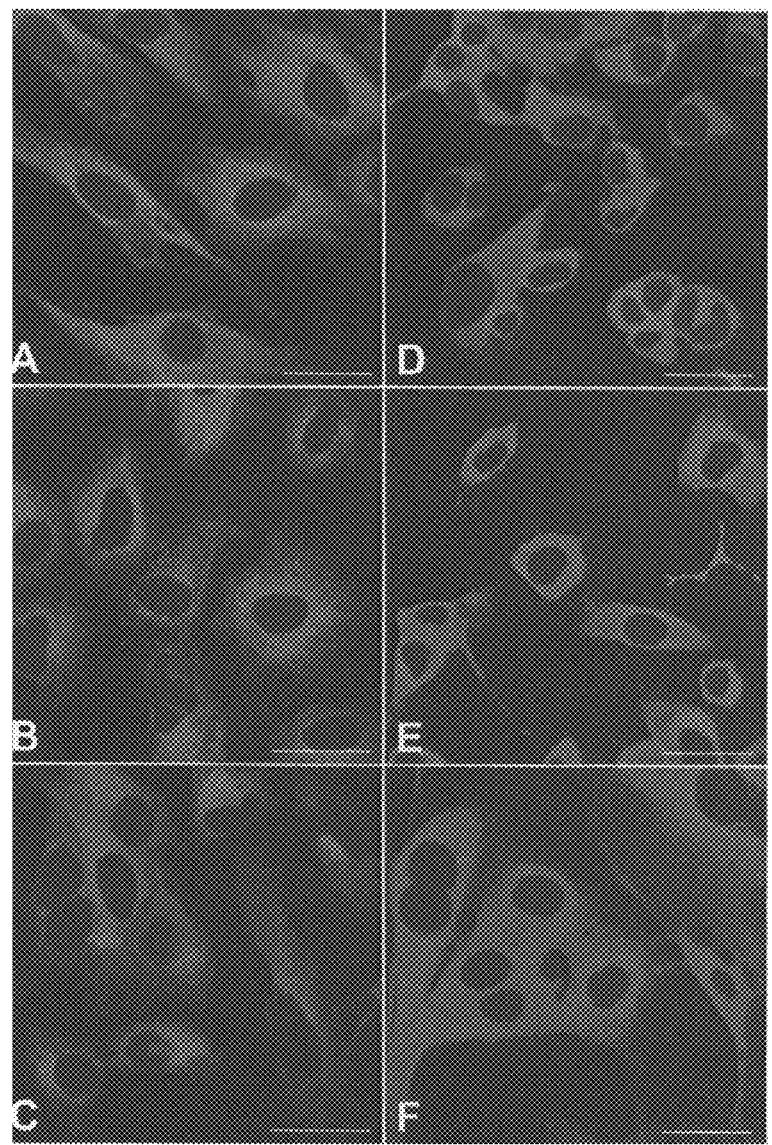

FIG. 44: Cytoplasmic Markers of Neural Cells. Panels A-C shows cells in DM at P1 (red fluorescence, α-sarcomeric actin; blue fluorescence, PI labeling). Panels D-F illustrate positive controls for MAP1b (D, neuron2A cell line), nerofilament 200 (E, neuron2A cell line), and GFAP (F, astrocyte type III, clone C8-D30) by green fluorescence in the cytoplasm (blue fluorescence, PI labeling). c-kit$^{POS}$-derived cells were negative for these neural proteins. Confocal microscopy; bar=10 μm.

Figure 45:
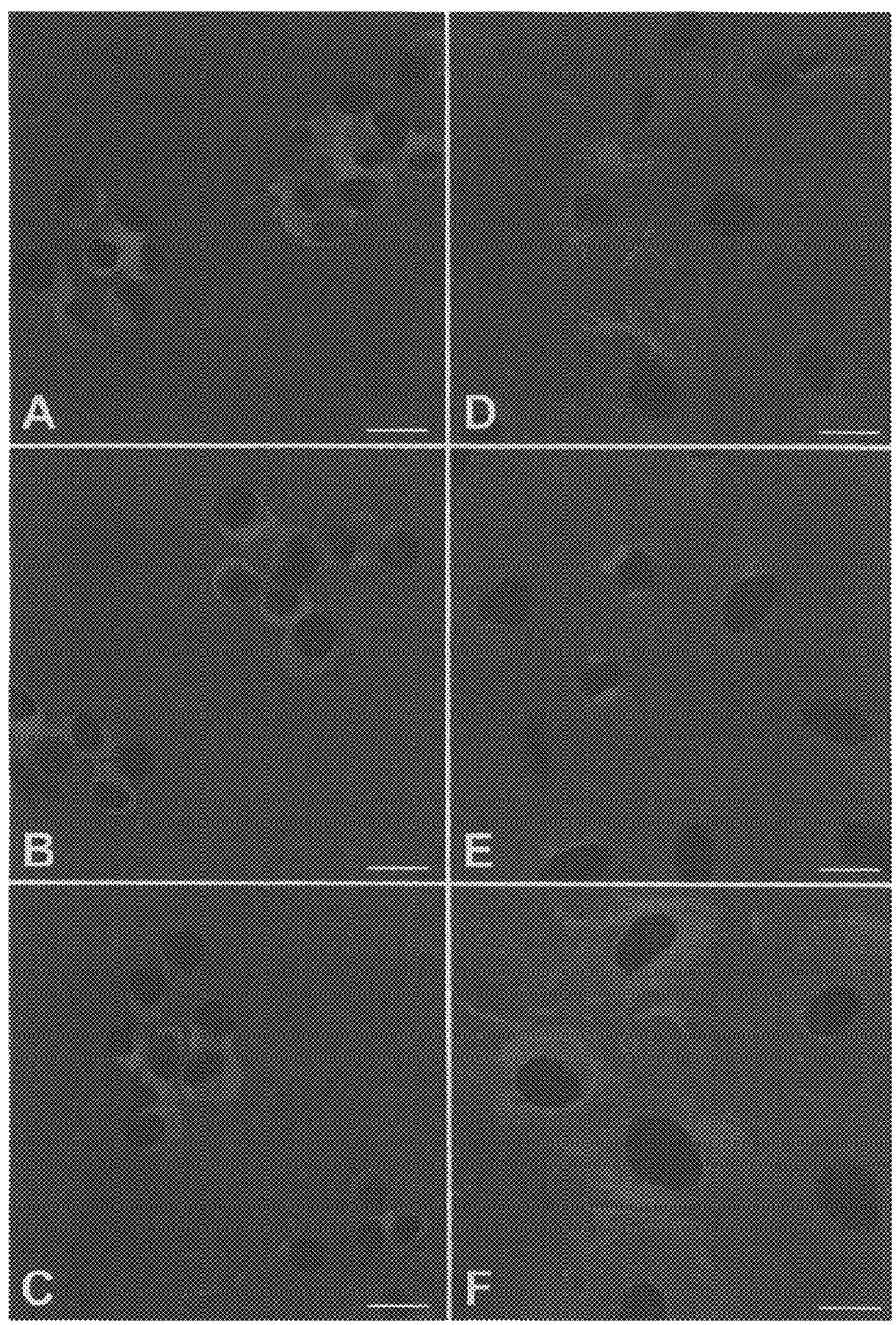

FIG. 45: Cytoplasmic Markers of Fibroblasts. Panels A-C shows small colonies of undifferentiated cells in NSCM (green fluorescence, c-kit; blue fluorescence, PI labeling). Panels D-F illustrate positive controls (rat heart fibroblasts) for fibronectin (D), procollagen type I (E), and vimentin (F) by red fluorescence in the cytoplasm (blue fluorescence, PI labeling). c-kit$^{POS}$-derived cells were negative for these fibroblast proteins. Confocal microscopy; bar=10 μm.

Figure 46:
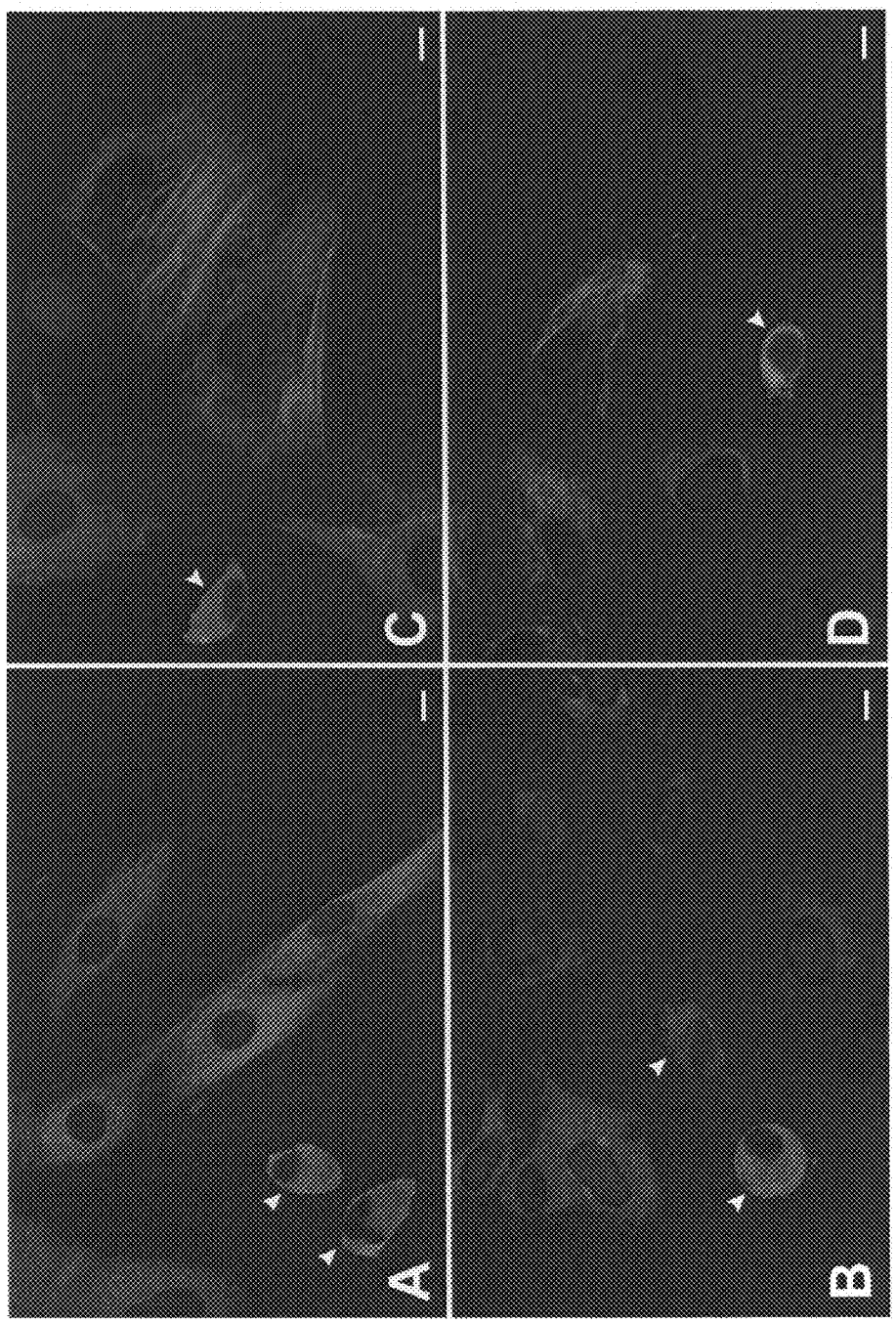

FIG. 46: FACS-Isolated c-kit$^{POS}$ Cells: Multipotentiality of Clonogenic Cells. In a clone, the cytoplasm (red) of M (A), EC (B), SMC (C) and F (D) is stained by cardiac myosin, factor VIII, α-smooth muscle actin and vimentin, respectively. Blue fluorescence, PI labeling of nuclei. Lin$^-$c-kit$^{POS}$ cells (green fluorescence, arrowheads) are present. Confocal microscopy; bar=10 μm.

Figure 47:
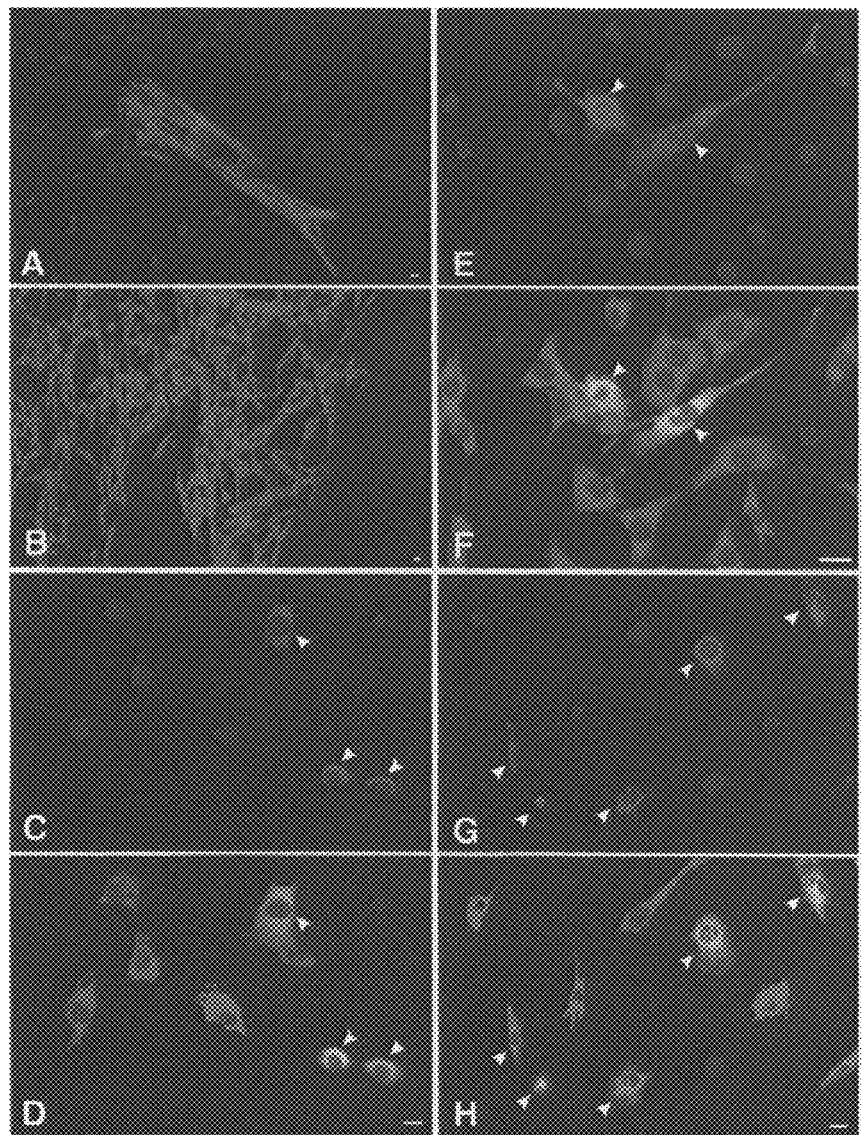

FIG. 47: Cardiac Cell Lineages in Early Differentiation. A,B, Expression of nestin alone (green fluorescence) in the cytoplasm of cells in early differentiation. C,D, Expression of nestin (green, C) and cardiac myosin (red, D) in developing myocytes (arrowheads). E,F, Expression of nestin (green, E) and factor VIII (red, F) in developing endothelial cells (arrowheads). G,H, Expression of nestin (green, G) and α-smooth muscle actin (red, H) in developing smooth muscle cells (arrowheads). Confocal microscopy; bars=10 μm.

Figure 48:
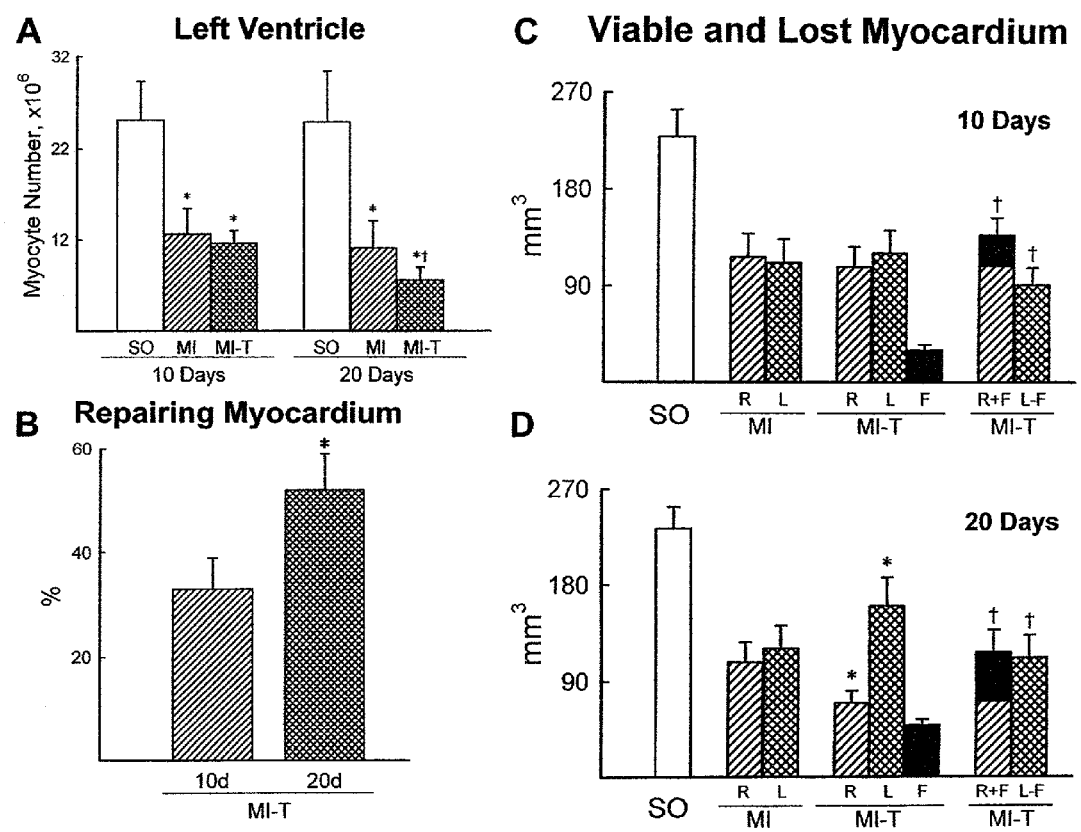

FIG. 48: Infarct Size and Myocardial Repair. A, At 10 days, coronary artery occlusion resulted in the loss of 49% and 53% of the number of myocytes in the left ventricle of untreated (MI) and treated (MI-T) rats, respectively. At 20 days, coronary artery occlusion resulted in the loss of 55% and 70% of the number of myocytes in the left ventricle of untreated (MI) and treated (MI-T) rats, respectively. SO, sham-operated animals. *$P<0.05$ vs SO. †$P<0.05$ vs MI. B, Percentage of newly formed myocardium within the infarcted region of the wall at 10 and 20 days (d) after coronary artery occlusion in animals treated with cell implantation (MI-T). *$P<0.05$ vs 10 d. C,D, The amount of new myocardium formed (F) at 10 and 20 days by cell implantation was measured morphometrically (solid bar). The remaining (R) and lost (L) myocardium after infarction is depicted by hatched bar and crosshatched bar, respectively. The generated tissue (F) increased the remaining myocardium (R+F) and decreased the lost myocardium (L−F) by the same amount. As a consequence, cardiac repair reduced infarct size in both groups of rats treated with cell implantation. Results are mean±SD. *$P<0.05$ vs MI. †$P<0.05$ vs Lo and Fo in MI-T.

Figure 49:
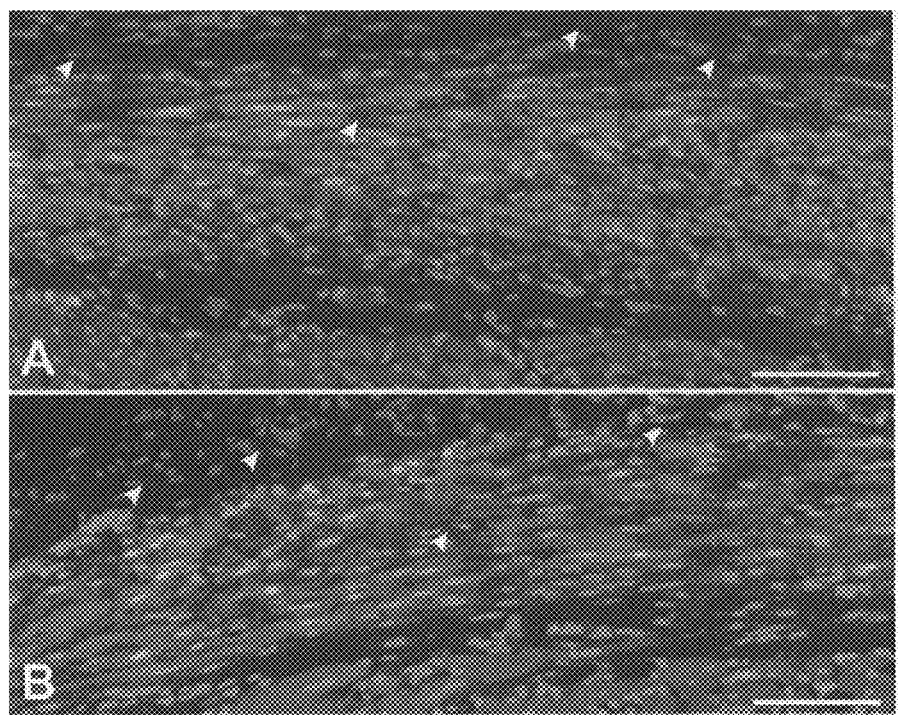

FIG. 49: Myocardial Repair. A,B, Bands of regenerating myocardium in two infarcted treated hearts. Red fluorescence corresponds to cardiac myosin antibody staining of newly formed myocytes. Yellow-green fluorescence reflects PI labeling of nuclei. Blue fluorescence (arrowheads) illustrates small foci of collagen accumulation within the infarcted region of the wall. Confocal microscopy; bar=100 µm.

Figure 50:
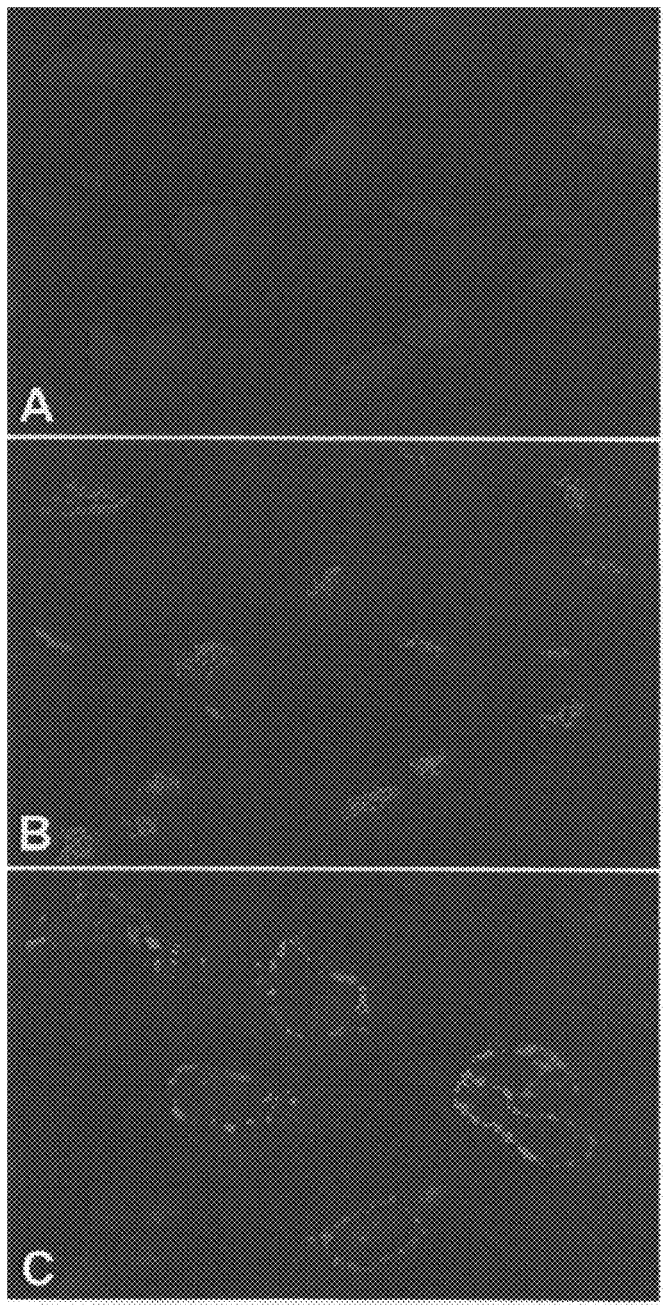

FIG. 50: Neoformation of Capillaries. The differentiation of implanted cells in capillary profiles was identified by BrdU labeling of endothelial cells. A, PI labeling of nuclei (blue); B, BrdU labeling of nuclei (green); C, Capillary endothelium (red) and endothelial cell nuclei labeled by BrdU (blue and green). Confocal microscopy; bar=10 µm.

Figure 51:
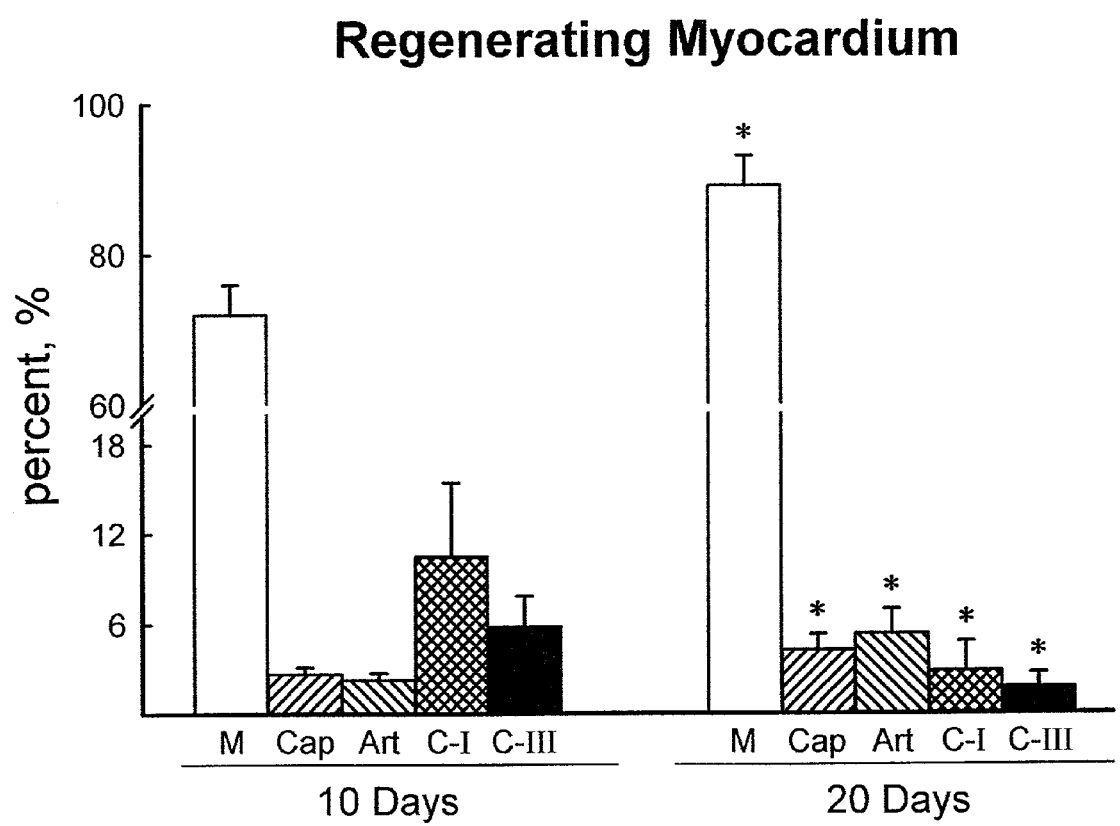

FIG. 51: Volume Composition of Regenerating Myocardium. During the interval from 10 to 20 days, the volume fraction of myocytes A), capillaries (Cap) and arterioles (Art) increased 25%, 62% and 140%, respectively. Conversely, the volume percent of collagen type I (C-I) and collagen type III (C-III) decreased 73% and 71%, respectively. Results are mean±SD. *$P<0.05$ vs 10 days.

Figure 52:
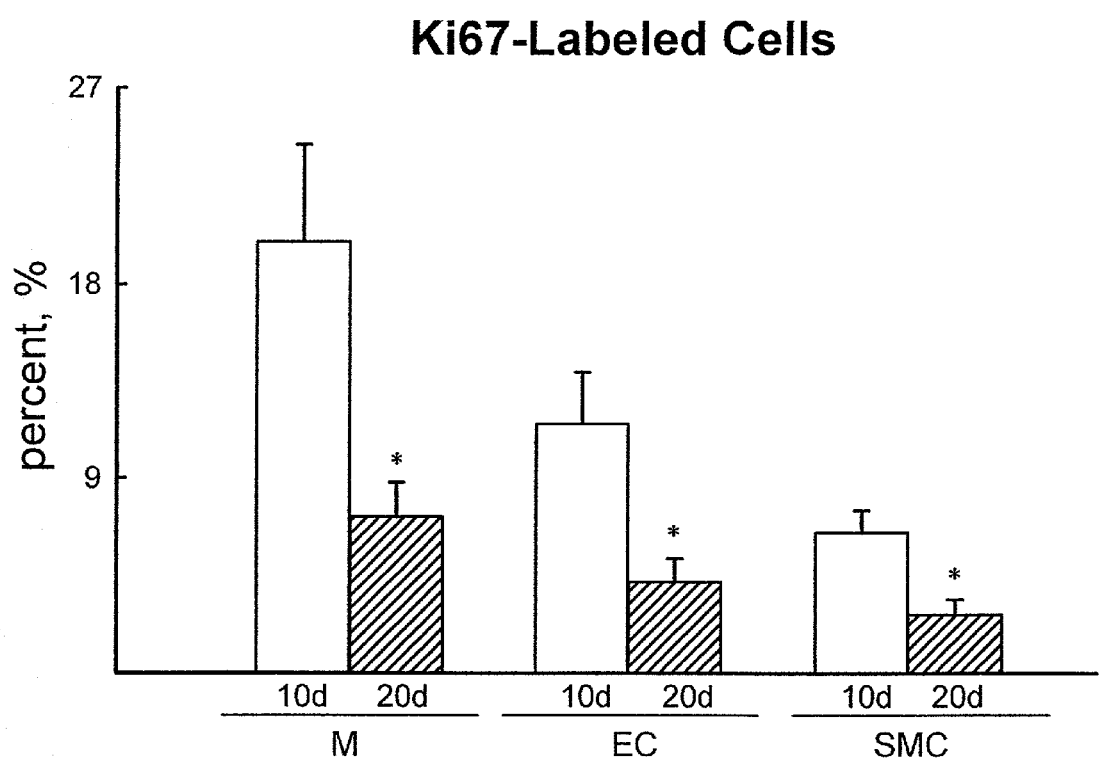

FIG. 52: Cell Proliferation in the Regenerating Myocardium. During the interval from 10 to 20 days, the fraction of myocytes (M), endothelial cells (EC) and smooth muscle cells (SMC) labeled by Ki67 decreased 64%, 63% and 59% respectively. Results are mean±SD. *$P<0.05$ vs 10 days.

Figure 53:
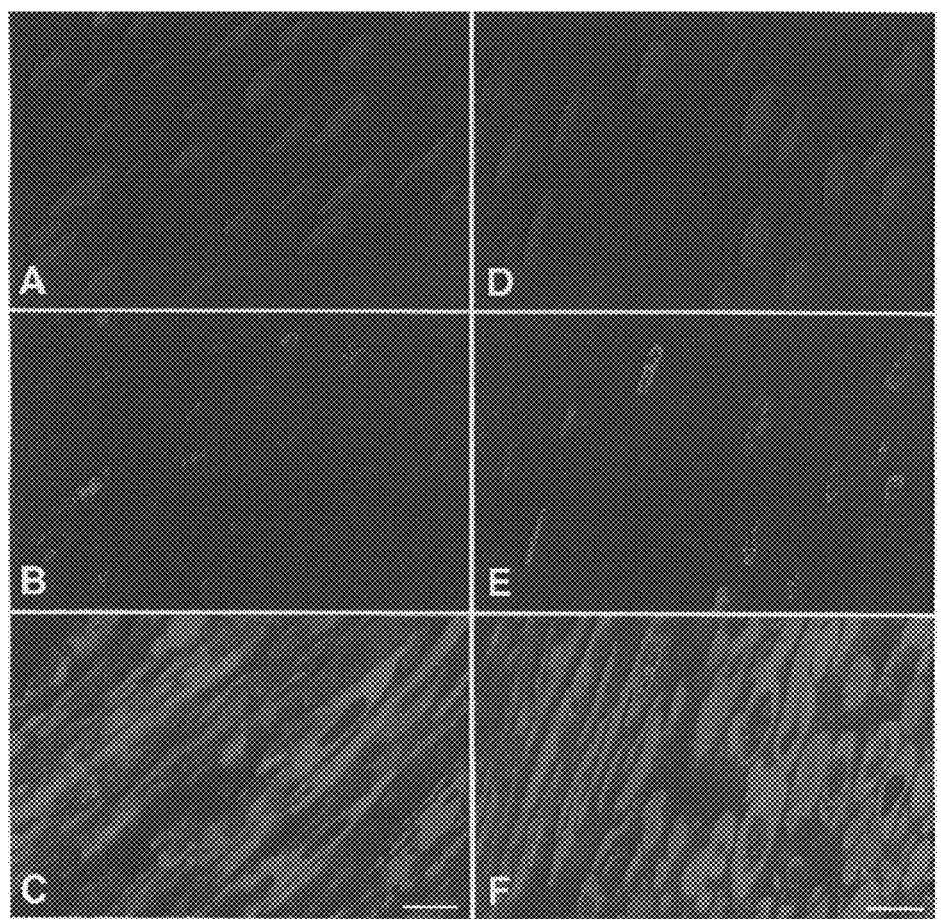

FIG. 53: Identification of Regenerating Myocytes by BrdU Labeling. A,D, Nuclei are illustrated by the blue fluorescence of PI. B,E, Green fluorescence documents BrdU labeling of nuclei. C,F, Myocyte cytoplasm is recognized by the red fluorescence of α-cardiac actinin (C) or α-sarcomeric actin (F). In new myocytes, dark and light blue fluorescence reflects the combination of PI and BrdU labeling of myocyte nuclei (C,F). Confocal microscopy; bar=10 µm.

Figure 54:
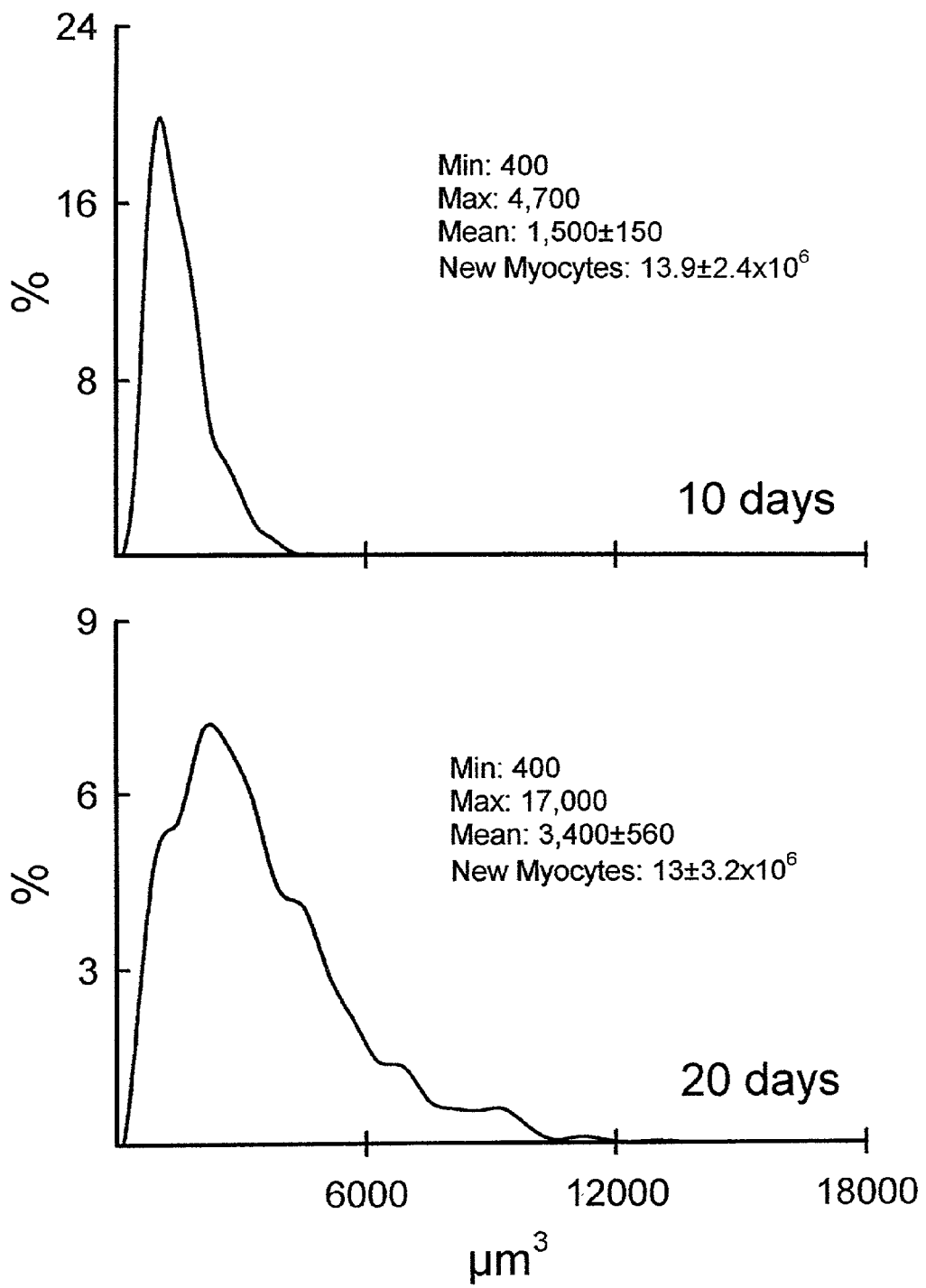

FIG. 54: Effects of Time on Number and Volume of Newly Formed Myocytes. During the interval from 10 to 20 days, developing myocytes increased significantly in size. However, cell number remained essentially constant. The size distribution was wider at 20 than at 10 days.

Figure 55:
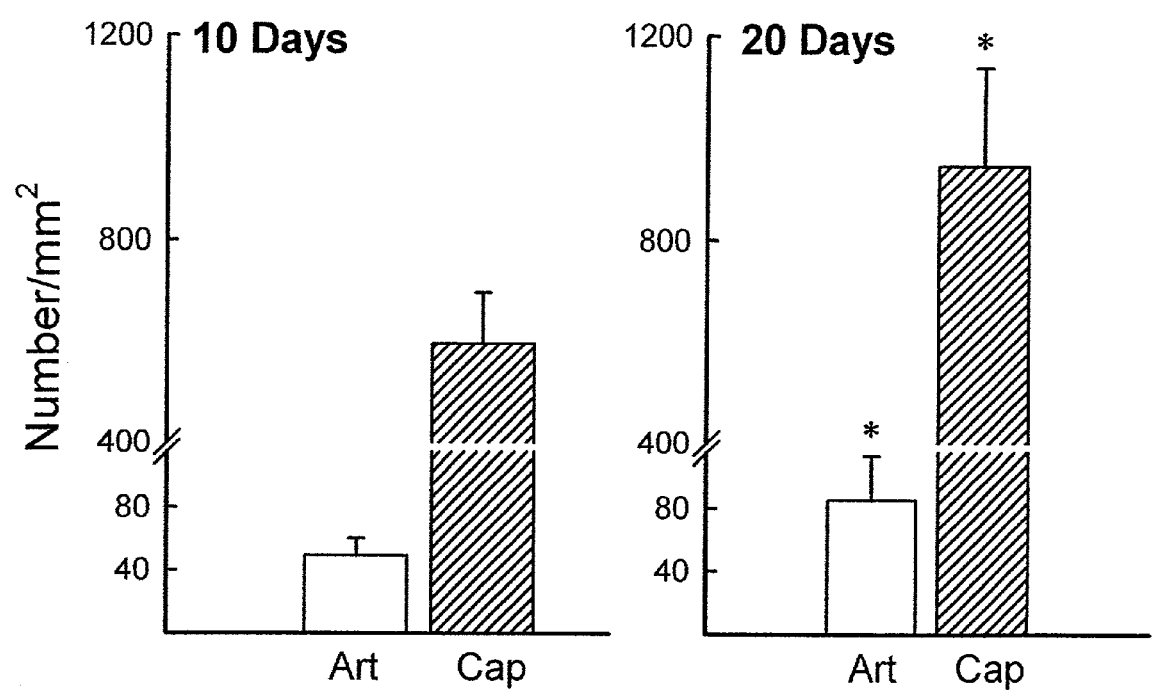

FIG. 55: Effects of Time on the Development of Newly Formed Coronary Vasculature. The numerical density of newly formed arterioles (Art) and capillaries (Cap) increased significantly during the interval from 10 to 20 days. Results are mean±SD. *$P<0.05$ vs 10 days.

Figure 56:
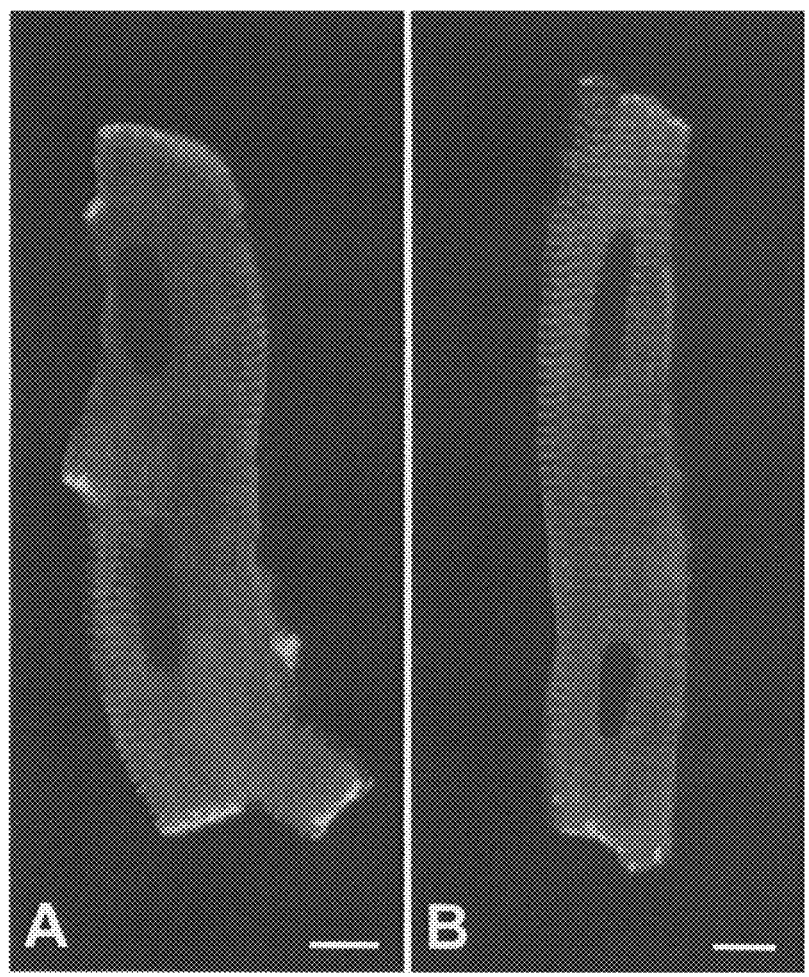

FIG. 56: Spared Myocytes in the Infarcted Ventricle. A,B, Large, hypertrophied myocytes isolated from the remaining viable tissue of the left ventricle and interventricular septum. Red fluorescence corresponds to cardiac myosin antibody staining and blue fluorescence to PI labeling. Yellow fluorescence at the edges of the cells reflects connexin 43 (A) and N-cadherin (B). Confocal microscopy; bar=10 µm.

Figure 57:
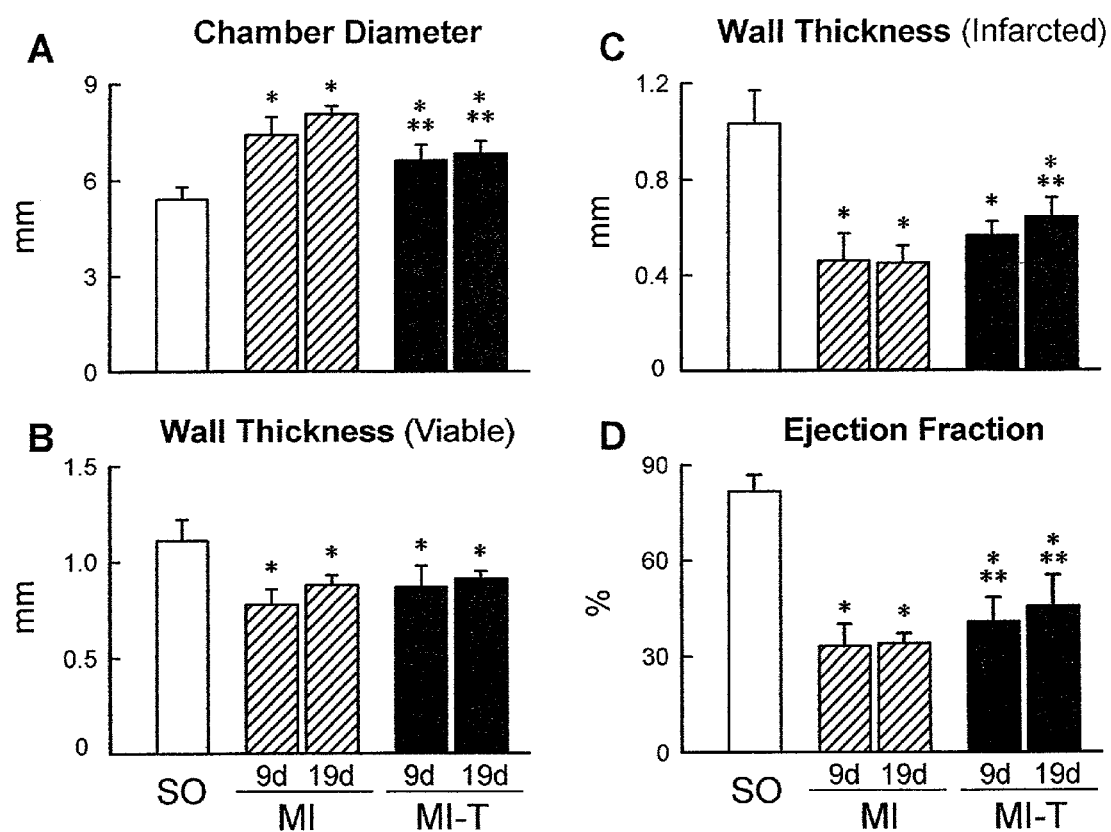

FIG. 57: Cell Implantation and Echocardiography. Myocardial regeneration attenuated ventricular dilation (A), had no effect on the thickness of the surviving portion of the wall (B), increased the thickness of the infarcted region of the ventricle (C) and improved ejection fraction (D). SO=sham-operated; MI=untreated infarcts; MI-T=treated infarcts. Results are mean±SD. *$P<0.05$ vs SO; **$P<0.05$ vs MI.

Figure 58:
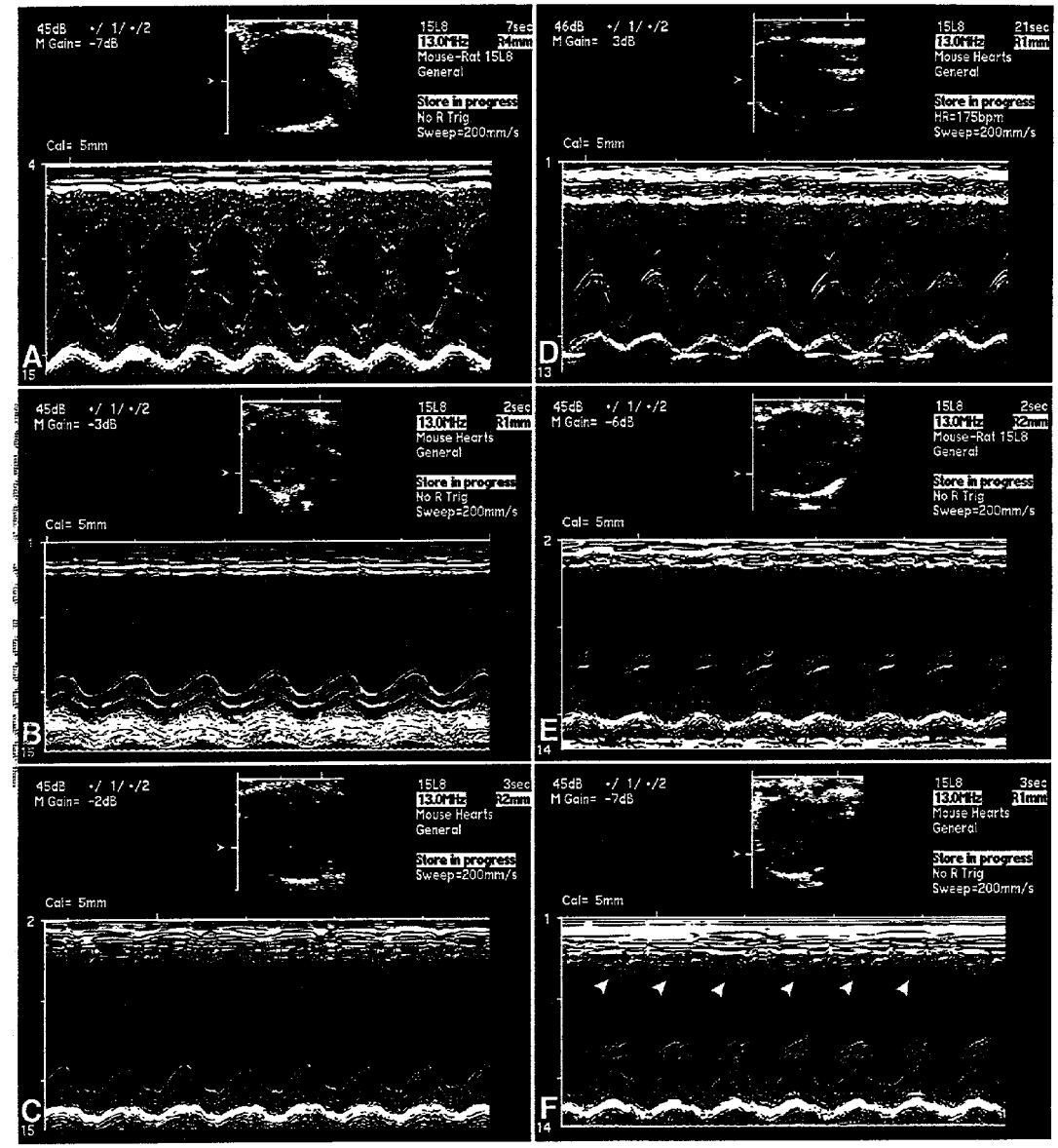

FIG. 58: Echocardiographic Tracing. Two-dimensional images and M-mode tracings of an untreated infarcted rat (A,B,C) and a treated infarcted rat (D,E,F). Panels A and D correspond to baseline conditions before coronary artery occlusion. The reappearance of contraction is evident in panel F (arrowheads).

Figure 59:
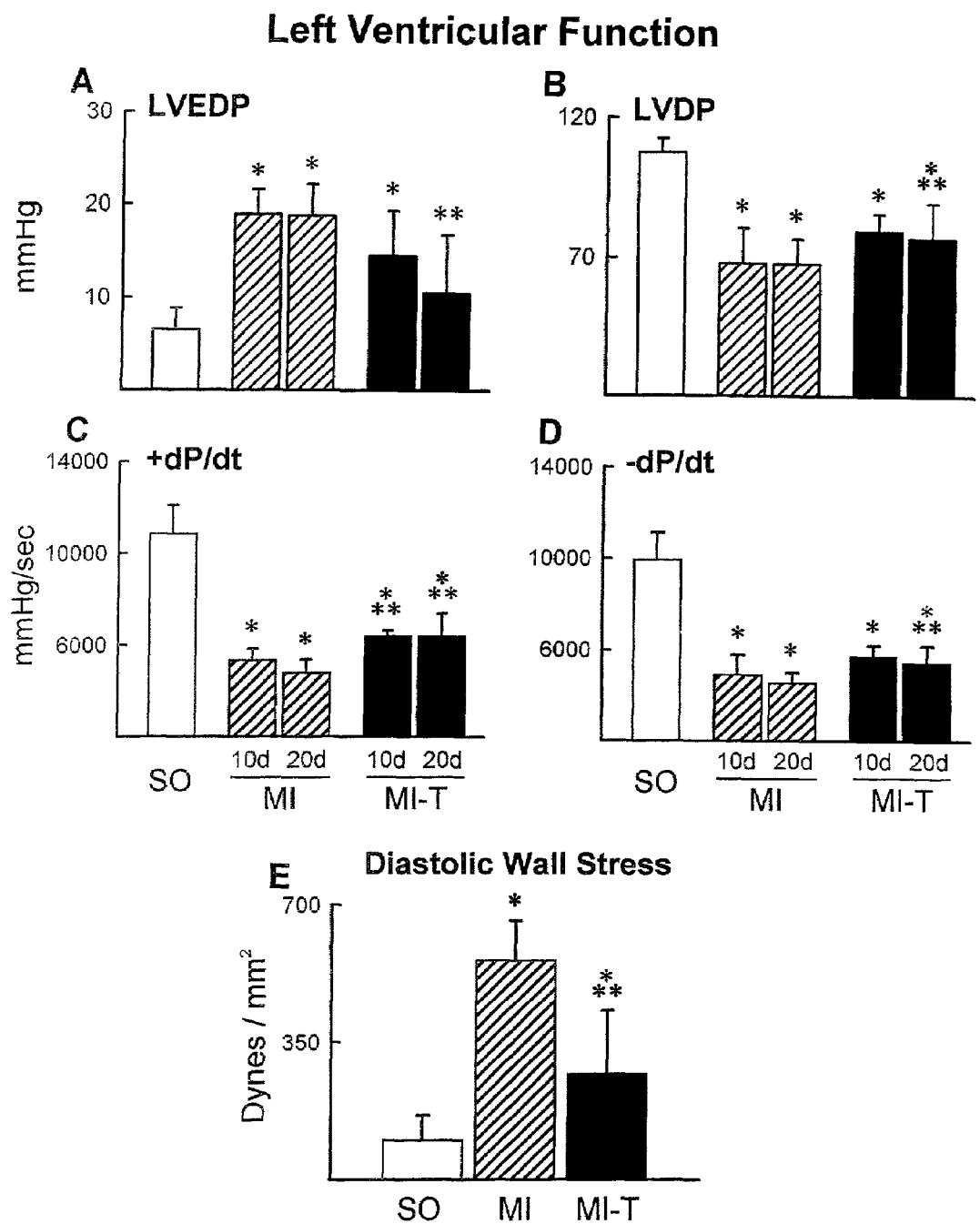

FIG. 59: Ventricular Function and Wall Stress. Cell implantation improved ventricular function (A-D) and attenuated the increase in diastolic wall stress (E) after infarction. SO=sham-operated; MI=untreated infarcts; MI-T=treated infarcts; LVEDP=left ventricular end-diastolic pressure; LVDP=left ventricular developed pressure; +dP/dt=rate of pressure rise; −dP/dt=rate of pressure decay. Results are mean±SD. *$P<0.05$ vs SO; **$P<0.05$ vs MI.

Figure 60:
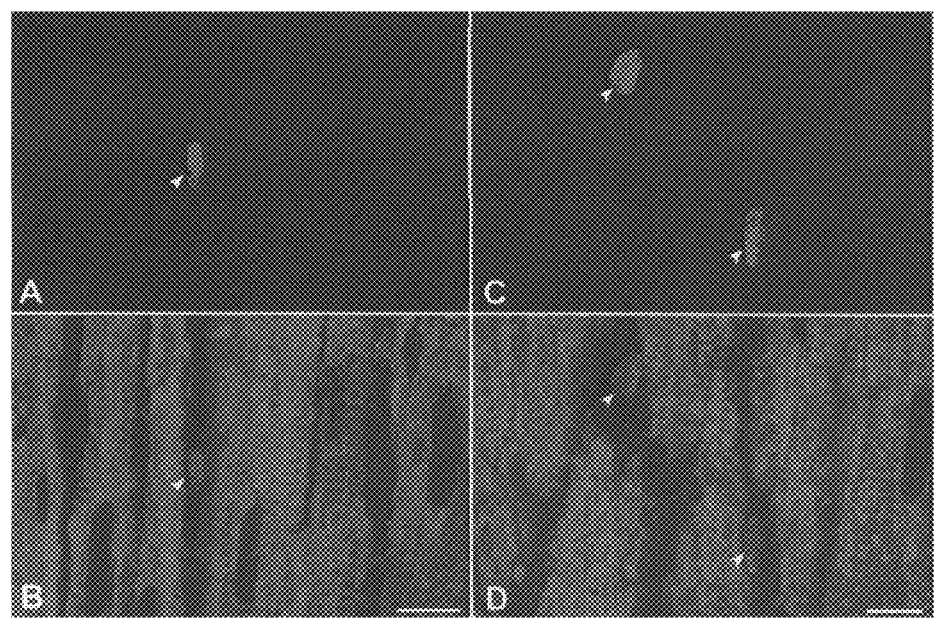

FIG. 60: Cell Implantation in Normal Myocardium. BrdU labeled cells obtained at P2 were injected in sham-operated rats. Twenty days later, only a few undifferentiated cells were identified. A,C, Green fluorescence documents BrdU labeling of nuclei. B,D, Myocyte cytoplasm is recognized by the red fluorescence of α-sarcomeric actin. Nuclei are illustrated by the blue fluorescence of PI. In injected cells (arrowheads), bright blue fluorescence reflects the combination of PI and BrdU labeling (B,D). Confocal microscopy; bar=10 µm.

Figure 61:
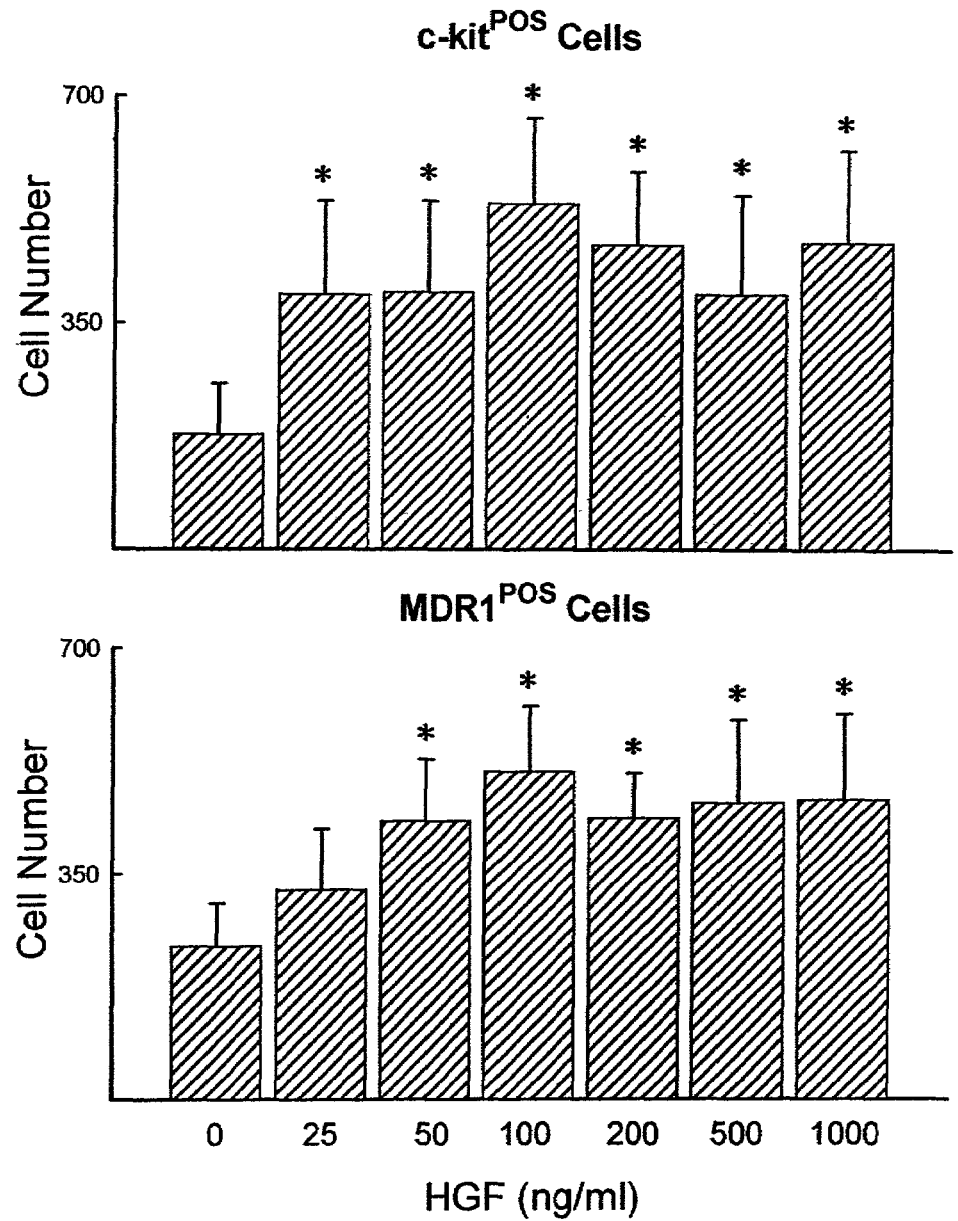
Figure 62:
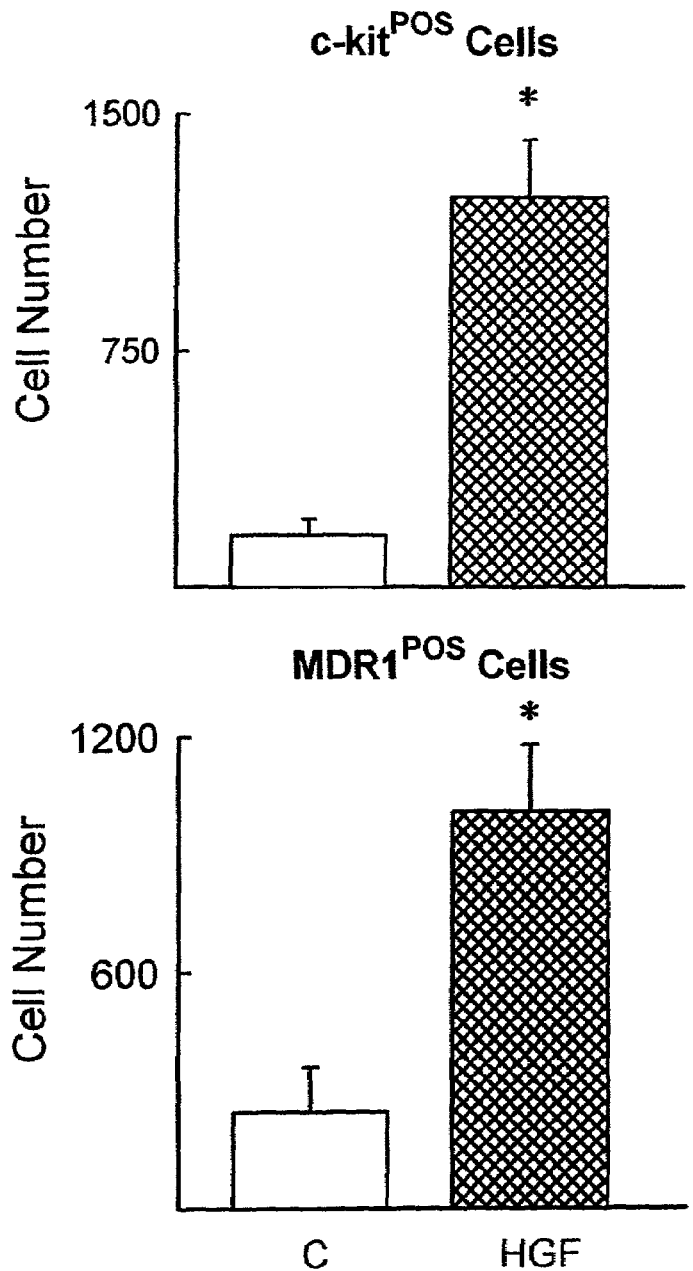

FIGS. 61 and 62. Migration and invasion assays. Results in are reported as the mean±SD. * indicates a statistical significant difference, i.e. $P<0.05$, from cells not exposed to the growth factor.

Figure 63:

FIG. 63. Matrix metalloproteinase activity assay. Digital photograph of the resulting gel from gelatin zymography, FIG. 64. Graphs of primitive cells expressing growth factor receptors. The distribution of c-met and IGF-1R on c-kit$^{POS}$ and MDR1$^{POS}$ cells in the various regions of the heart in sham-operated (SO), infarcted-treated (Treated) and infarcted-untreated (Untreated) mice sacrificed 7-8 hours after surgery and 2-3 hours after the administration of growth factors (Treated) or saline (SO; Untreated) is shown. These measurements include all c-kit$^{POS}$ and MDR1$^{POS}$ cells, independently of ongoing apoptosis. Abbreviations used are as follows: A, atria; LV, left ventricle; R, viable myocardium remote from the infarct; B, viable myocardium bordering the infarct; I, non-viable infarcted myocardium. All results are reported as the mean±SD.

Figure 65:
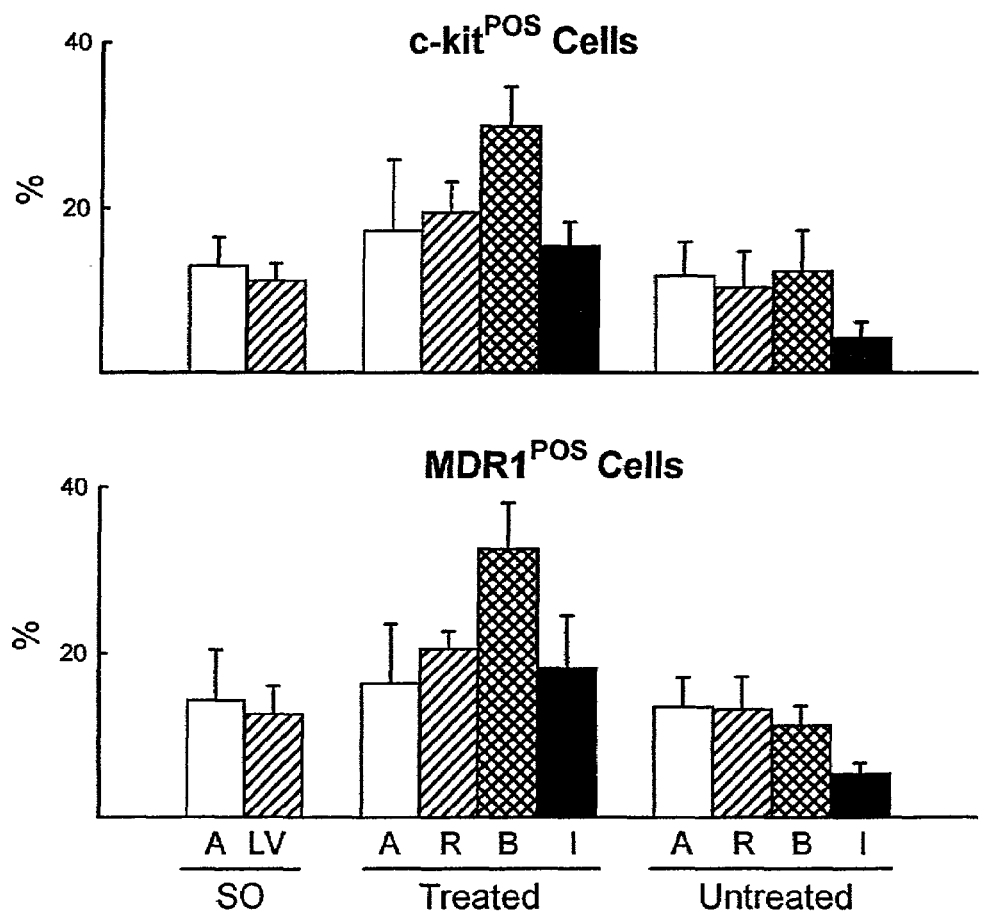

FIG. 65. Graphs showing the location of cycling primitive cells. The percentage of viable Ki67 labeled c-kit$^{POS}$ and MDR1$^{POS}$ cells in the various regions of the heart in sham-operated (SO), infarcted-treated (Treated) and infarcted-untreated (Untreated) mice sacrificed 7-8 hours after surgery and 2-3 hours after the administration of growth factors (Treated) or saline (SO; Untreated) is presented. Abbreviations used are as follows: A, atria; LV, left ventricle; R, viable myocardium remote from the infarct; B, viable myocardium bordering the infarct; I, non-viable infarcted myocardium. Results presented are means±SD.

Figure 66:
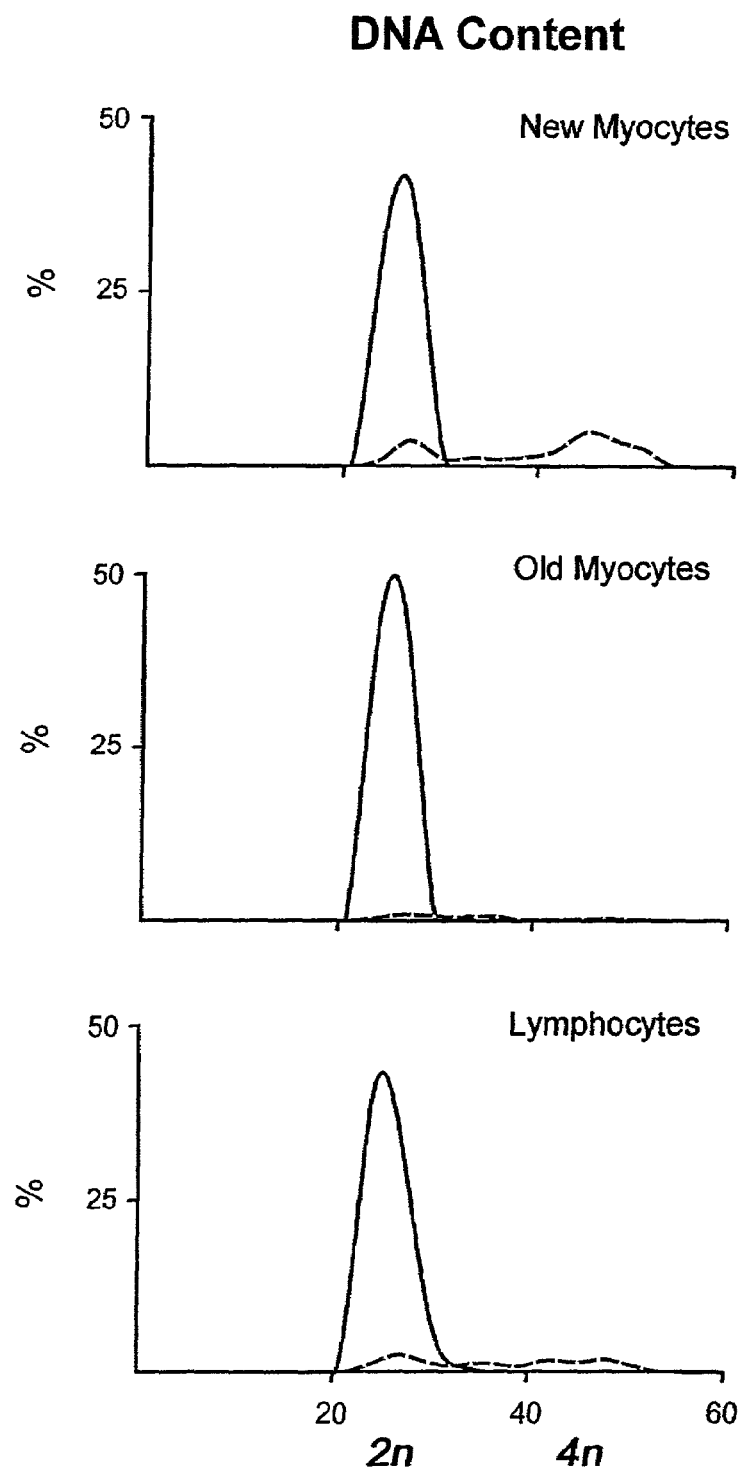

FIG. 66. Graphs showing the frequency distribution of DNA content in non-cycling (solid line) and cycling (broken line; Ki67 positive nuclei) myocytes. Both new and old myocytes showed an amount of chromatin corresponding to 2n chromosomes. A DNA content greater than 2n was restricted to cycling nuclei. The measured non-cycling nuclei displayed a fluorescence intensity comparable to that of diploid lymphocytes. Sampling included 600 new myocytes, 1,000 old myocytes and 1,000 lymphocytes.

Figure 67:
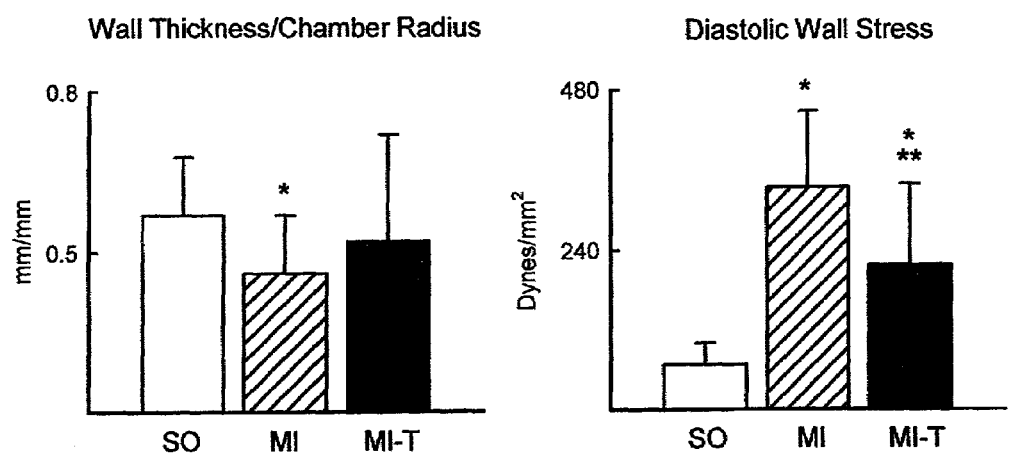

FIG. 67. Graphs showing the effects of myocardial infarction on the anatomy of the heart and diastolic load. Results are presented as the mean±SD. *,** indicate a value of p<0.05 vs. sham-operated mice (SO) and untreated infarcted mice (MI). MI-T refers to treated infarcted mice.

FIGS. 68. Graph showing the frequency distribution of myocyte sizes. The volume of newly generated myocytes was measured in sections stained with desmin and laminin antibodies and PI. Only longitudinally oriented cells with centrally located nuclei were included. The length and diameter across the nucleus were collected in each myocyte to compute cell volume, assuming a cylindrical shape. Four hundred cells were measured in each heart.

Figure 9:
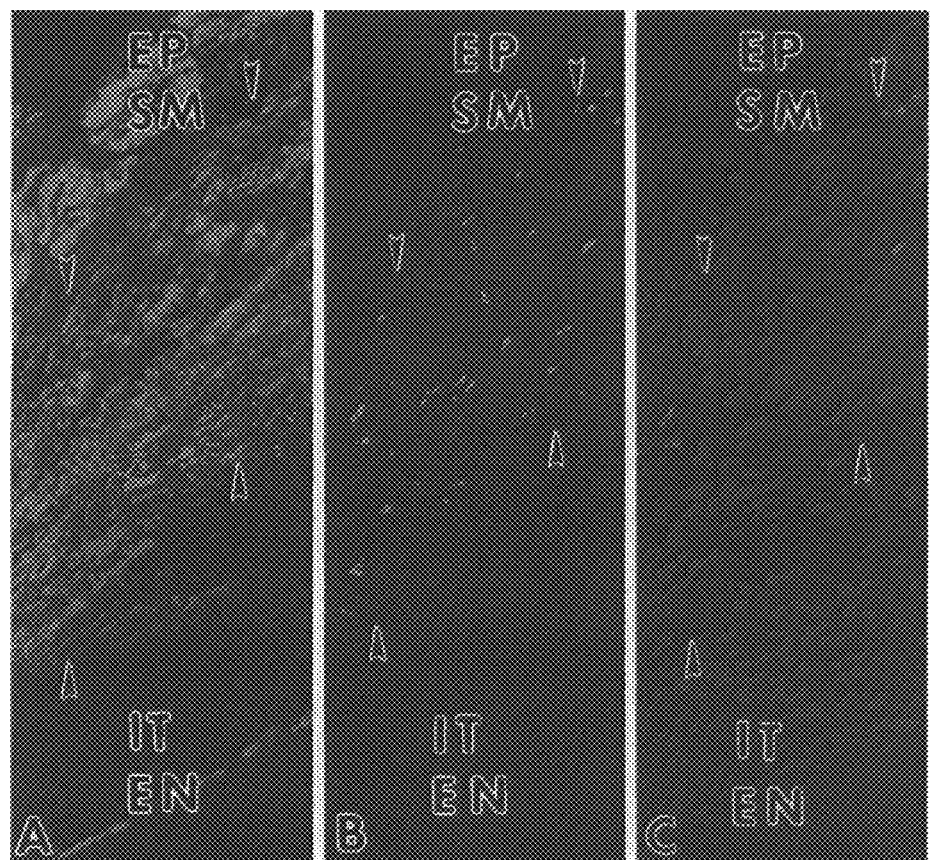
FIG. 9 (FIGS. 9A-C) shows photographs of tissue sections from MI induced mice, showing the area of MI injected with Lin⁻c-kit$^{POS}$ cells and showing regenerating myocardium (arrowheads).

FIG. 69: Graph showing cardiac repair. On the basis of the volume of LV in sham-operated (SO) mice and infarct size, 42% in untreated mice (MI) and 67% in treated mice (MI-T), the volume of myocardium destined to remain (R) and destined to be lost (L) was computed in the two groups of infarcted mice (FIG. 9). The volume of newly formed myocardium (F) was measured quantitatively in treated mice. Myocardial regeneration increased the volume of remaining myocardium (R+F) and decreased the volume of lost myocardium (L−F) by the same amount. Therefore, infarct size in treated mice was reduced by 15%.

DETAILED DESCRIPTION

The present invention provides methods and/or pharmaceutical composition comprising a therapeutically effective amount of somatic stem cells alone or in combination with a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), insulin-like growth factor (IGF-1) or Interleukin-3 or any cytokine capable of the stimulating and/or mobilizing stem cells. Cytokines may be administered alone or in combination or with any other cytokine or pharmaceutical agent capable of: the stimulation and/or mobilization of stem cells; the maintenance of early and late hematopoiesis (see below); the activation of monocytes (see below), macrophage/monocyte proliferation; differentiation, motility and survival (see below); treatment of cardiac or vascular conditions; and a pharmaceutically acceptable carrier, diluent or excipient (including combinations thereof).

The invention also provides methods and/or pharmaceutical compositions comprising a therapeutically effective amount of one or more cytokines for causing the migration and/or proliferation of cardiac stem cells or cardiac primative cells into circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta.

In a preferred aspect, the methods and/or compositions, including pharmaceutical compositions, comprise effective amounts of two or more cytokines. More specifically, the methods and/or compositions preferably comprise effective amounts of hepatocyte growth factor and insulin-like growth factor-1.

The cytokines in the pharmaceutical composition of the present invention may also include mediators known to be involved in the maintenance of early and late hematopoiesis such as IL-1 alpha and IL-1 beta, IL-6, IL-7, IL-8, IL-11 and IL-13; colony-stimulating factors, thrombopoietin, erythropoietin, stem cell factor, flt 3-ligand, hepatocyte cell growth factor, tumor necrosis factor alpha, leukemia inhibitory factor, transforming growth factors beta 1 and beta 3; and macrophage inflammatory protein 1 alpha), angiogenic factors (fibroblast growth factors 1 and 2, vascular endothelial growth factor) and mediators whose usual target (and source) is the connective tissue-forming cells (platelet-derived growth factor A, epidermal growth factor, transforming growth factors alpha and beta 2, oncostatin M and insulin-like growth factor-1), or neuronal cells (nerve growth factor) (Sensebe, L., et al., *Stem Cells* 1997; 15:133-43), VEGF polypeptides that are present in platelets and megacaryocytes (Wartiovaara, U., et al., *Thromb Haemost* 1998; 80:171-5; Mohle, R., *Proc Natl Acad Sci USA* 1997; 94:663-8) HIF-1, a potent transcription factor that binds to and stimulates the promoter of several genes involved in responses to hypoxia, endothelial PAS domain protein 1 (EPAS 1), monocyte-derived cytokines for enhancing collateral function such as monocyte chemotactic protein-1 (MCP-1).

In an additionally preferred aspect, the methods and/or compositions, including pharmaceutical compositions, comprise effective amounts of two or more cytokines in combination with an appropriate pharmaceutical agent useful in treating cardiac and/or vascular conditions.

In a preferred aspect, the pharmaceutical composition of the present invention is delivered via injection. These routes for administration (delivery) include, but are not limited to subcutaneous or parenteral including intravenous, intraarterial, intramuscular, intraperitoneal, intramyocardial, transendocardial, trans-epicardial, intranasal administration as well as intrathecal, and infusion techniques. Hence, preferably the pharmaceutical composition is in a form that is suitable for injection.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

The pharmaceutical composition of the present invention, e.g., comprising a therapeutic compound, can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, iontophoretic, polymer matrices, liposomes, and microspheres.

The pharmaceutical composition utilized in the present invention can be administered orally to the patient. Conventional methods such as administering the compounds in tablets, suspensions, solutions, emulsions, capsules, powders, syrups and the like are usable. Known techniques which deliver the compound orally or intravenously and retain the biological activity are preferred.

In one embodiment, a composition of the present invention can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The patient's levels are then maintained by an oral dosage form, although other forms of administration, dependent upon the patient's condition, can be used.

It is noted that humans are treated generally longer than the mice or other experimental animals which treatment has a length proportional to the length of the disease process and drug effectiveness. The doses may be single doses or multiple doses over a period of several days, but single doses are preferred. Thus, one can scale up from animal experiments, e.g., rats, mice, and the like, to humans, by techniques from this disclosure and documents cited herein and the knowledge in the art, without undue experimentation.

The treatment generally has a length proportional to the length of the disease process and drug effectiveness and the patient being treated.

The quantity of the pharmaceutical composition to be administered will vary for the patient being treated. In a preferred embodiment, $2\times10^4$-$1\times10^5$ stem cells and 50-500 µg/kg per day of a cytokine were administered to the patient. While there would be an obvious size difference between the hearts of a mouse and a human, it is possible that $2\times10^4$-$1\times10^5$ stem cells would be sufficient in a human as well. However, the precise determination of what would be considered an effective dose may be based on factors individual to each patient, including their size, age, size of the infarct, and amount of time since damage. Therefore, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Additionally, one of skill in the art would be able to ascertain without undue experimentation the appropriate pharmaceutical agent to be used in combination with one or more cytokines; and, one of skill in the art would be able to make the precise determination of what would be considered an effective dose based on factors individual to each patient, including their size, age, size of the infarct, and amount of time since damage. Therefore, dosages can be readily ascertained by those skilled in the art from this disclosure and the knowledge in the art.

Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. Accordingly, the invention involves the administration of stem cells as herein discussed, alone or in combination with one or more cytokine, as herein discussed, for the treatment or prevention of any one or more of these conditions or other conditions involving weakness in the heart, as well as compositions for such treatment or prevention, use of stem cells as herein discussed, alone or in combination with one or more cytokine, as herein discussed, for formulating such compositions, and kits involving stem cells as herein discussed, alone or in combination with one or more cytokine, as herein discussed, for preparing such compositions and/or for such treatment, or prevention. And, advantageous routes of administration involves those best suited for treating these conditions, such as via injection, including, but are not limited to subcutaneous or parenteral including intravenous, intraarterial, intramuscular, intraperitoneal, intramyocardial, transendocardial, trans-epicardial, intranasal administration as well as intrathecal, and infusion techniques.

The pharmaceutical compositions of the present invention may be used as therapeutic agents—i.e. in therapy applications. As herein, the terms "treatment" and "therapy" include curative effects, alleviation effects, and prophylactic effects.

As used herein, "patient" may encompass any vertebrate including but not limited to humans, mammals, reptiles, amphibians and fish. However, advantageously, the patient is a mammal such as a human, or an animal mammal such as a domesticated mammal, e.g., dog, cat, horse, and the like, or production mammal, e.g., cow, sheep, pig, and the like As used herein "somatic stem cell" or "stem cell" or "hematopoietic cell" refers to either autologous or allogenic stem cells, which may be obtained from the bone marrow, peripheral blood, or other source.

As used herein, "adult" stem cells refers to stem cells that are not embryonic in origin nor derived from embryos or fetal tissue.

As used herein "recently damaged myocardium" refers to myocardium which has been damaged within one week of treatment being started. In a preferred embodiment, the myocardium has been damaged within three days of the start of treatment. In a further preferred embodiment, the myocardium has been damaged within 12 hours of the start of treatment. It is advantageous to employ stem cells alone or in combination with cytokine(s) as herein disclosed to a recently damaged myocardium.

As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein, "home" refers to the attraction and mobilization of somatic stem cells towards damaged myocardium and/or myocardial cells.

As used herein, "assemble" refers to the assembly of differentiated somatic stem cells into functional structures i.e., myocardium and/or myocardial cells, coronary arteries, arterioles, and capillaries etc. This assembly provides functionality to the differentiated myocardium and/or myocardial cells, coronary arteries, arterioles and capillaries.

Thus, the invention involves the use of somatic stem cells. These are present in animals in small amounts, but methods of collecting stem cells are known to those skilled in the art.

In another aspect of the invention, the stem cells are selected to be lineage negative. The term "lineage negative" is known to one skilled in the art as meaning the cell does not express antigens characteristic of specific cell lineages.

Advantageously, the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

The invention further involves a therapeutically effective dose or amount of stem cells applied to the heart. An effective dose is an amount sufficient to effect a beneficial or desired clinical result. Said dose could be administered in one or more administrations. In the examples that follow, $2 \times 10^4$-$1 \times 10^5$ stem cells were administered in the mouse model. While there would be an obvious size difference between the hearts of a mouse and a human, it is possible that this range of stem cells would be sufficient in a human as well. However, the precise determination of what would be considered an effective dose may be based on factors individual to each patient, including their size, age, size of the infarct, and amount of time since damage. One skilled in the art, specifically a physician or cardiologist, would be able to determine the number of stem cells that would constitute an effective dose without undue experimentation.

In another aspect of the invention, the stem cells are delivered to the heart, specifically to the border area of the infarct. As one skilled in the art would be aware, the infarcted area is visible grossly, allowing this specific placement of stem cells to be possible.

The stem cells are advantageously administered by injection, specifically an intramyocardial injection. As one skilled in the art would be aware, this is the preferred method of delivery for stem cells as the heart is a functioning muscle. Injection of the stem cells into the heart ensures that they will not be lost due to the contracting movements of the heart.

In a further aspect of the invention, the stem cells are administered by injection transendocardially or trans-epicardially. This preferred embodiment allows the stem cells to penetrate the protective surrounding membrane, necessitated by the embodiment in which the cells are injected intramyocardially.

A preferred embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

Further embodiments of the invention require the stem cells to migrate into the infarcted region and differentiate into myocytes, smooth muscle cells, and endothelial cells. It is known in the art that these types of cells must be present to restore both structural and functional integrity. Other approaches to repairing infarcted or ischemic tissue have involved the implantation of these cells directly into the heart, or as cultured grafts, such as in U.S. Pat. Nos. 6,110,459, and 6,099,832.

Another embodiment of the invention includes the proliferation of the differentiated cells and the formation of the cells into cardiac structures including coronary arteries, arterioles, capillaries, and myocardium. As one skilled in the art is aware, all of these structures are essential for proper function in the heart. It has been shown in the literature that implantation of cells including endothelial cells and smooth muscle cells will allow for the implanted cells to live within the infarcted region, however they do not form the necessary structures to enable the heart to regain full functionality. The ability to restore both functional and structural integrity is yet another aspect of this invention.

Another aspect of the invention relates to the administration of a cytokine. This cytokine may be chosen from a group of cytokines, or may include combinations of cytokines. Stem cell factor (SCF) and granulocyte-colony stimulating factor (G-CSF) are known by those skilled in the art as stimulating factors which cause the mobilization of stem cells into the blood stream (Bianco et al, 2001, Clutterbuck, 1997, Kronenwett et al, 2000, LaIuppa et al, 1997, Patchen et al, 1998). Stromal cell-derived factor-1 has been shown to stimulate stem cell mobilization chemotactically, while steel factor has both chemotactic and chemokinetic properties (Caceres-Cortes et al, 2001, Jo et al, 2000, Kim and Broxmeyer, 1998, Ikuta et al, 1991). Vascular endothelial growth factor has been surmised to engage a paracrine loop that helps facilitate migration during mobilization (Bautz et al, 2000, Janowska-Wieczorek et al, 2001). Macrophage colony stimulating factor and granulocyte-macrophage stimulating factor have been shown to function in the same manner of SCF and G-CSF, by stimulating mobilization of stem cells. Interleukin-3 has also been shown to stimulate mobilization of stem cells, and is especially potent in combination with other cytokines.

The cytokine can be administered via a vector that expresses the cytokine in vivo. A vector for in vivo expression can be a vector or cells or an expression system as cited in any document incorporated herein by reference or used in the art, such as a viral vector, e.g., an adenovirus, poxvirus (such as vaccinia, canarypox virus, MVA, NYVAC, ALVAC, and the like), lentivirus or a DNA plasmid vector; and, the cytokine can also be from in vitro expression via such a vector or cells or expression system or others such as a baculovirus expression system, bacterial vectors such as *E. coli*, and mammalian cells such as CHO cells. See, e.g., U.S. Pat. Nos. 6,265,189, 6,130,066, 6,004,777, 5,990,091, 5,942,235, 5,833,975. The cytokine compositions may lend themselves to administration by routes outside of those stated to be advantageous or preferred for stem cell preparations; but, cytokine compositions may also be advantageously administered by routes stated to be advantageous or preferred for stem cell preparations.

A further aspect of the invention involves administration of a therapeutically effective dose or amount of a cytokine. An effective dose is an amount sufficient to effect a beneficial or desired clinical result. Said dose could be administered in one or more administrations. In a preferred embodiment, the dose would be given over the course of about two or three days following the beginning of treatment. However, the precise determination of what would be considered an effective dose may be based on factors individual to each patient, including their size, age, size of the infarct, the cytokine or combination of cytokines being administered, and amount of time since damage. One skilled in the art, specifically a physician or cardiologist, would be able to determine a sufficient amount of cytokine that would constitute an effective dose without being subjected to undue experimentation.

The invention also involves the administration of the therapeutically effective dose or amount of a cytokine being delivered by injection, specifically subcutaneously or intravenously. A person skilled in the art will be aware that subcutaneous injection or intravenous delivery are extremely common and offer an effective method of delivering the specific dose in a manner which allows for timely uptake and circulation in the blood stream.

A further aspect of the invention includes the administered cytokine stimulating the patient's stem cells and causing mobilization into the blood stream. As mentioned previously, the given cytokines are well-known to one skilled in the art for their ability to promote said mobilization.

Advantageously, once the stem cells have mobilized into the bloodstream, they home to the damaged area of the heart, as will become clear through the following examples.

Further embodiments of the invention involve the stem cells migrating into the infarcted region and differentiating into myocytes, smooth muscle cells, and endothelial cells. It is known in the art that these types of cells must be present to restore both structural and functional integrity.

A further embodiment of the invention includes administering an effective amount of one or more cytokines to the infarcted region. An effective dose is an amount sufficient to effect a beneficial or desired clinical result. Said dose could be administered in one or more administrations. However, the precise determination of what would be considered an effective dose may be based on factors individual to each patient, including their size, age, size of the infarct, the cytokine or combination of cytokines being administered, and amount of time since damage. One skilled in the art, specifically a physician or cardiologist, would be able to determine a sufficient amount of cytokine that would constitute an effective dose without being subjected to undue experimentation.

A still further embodiment of the invention includes the administering of an effective amount of one or more cytokines to the heart by injection. Preferably, the cytokines are delivered to the infarcted region or to the area bordering the infarcted region. As one skilled in the art would be aware, the infarcted area is visible grossly, allowing this specific placement of cytokines to be possible.

The cytokines are advantageously administered by injection, specifically an intramyocardial injection. As one skilled in the art would be aware, this is the preferred method of delivery for cytokines as the heart is a functioning muscle. Injection of the cytokines into the heart ensures that they will not be lost due to the contracting movements of the heart.

In a further aspect of the invention, the cytokines are administered by injection transendocardially or trans-epicardially. This preferred embodiment allows the cytokines to penetrate the protective surrounding membrane, necessitated by the embodiment in which the cytokines are injected intramyocardially.

A preferred embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

A further embodiment of the invention includes the delivery of the cytokines by a single administration. A still further embodiment of the invention includes multiple administrations of the same dosage of cytokines to the heart. A still further embodiment of the invention includes administration of multiple doses of the cytokines to the heart, such that a gradient is formed.

A still further embodiment of the invention includes the stimulation, migration, proliferation and/or differentiation of the resident cardiac stem cells.

Another embodiment of the invention includes the proliferation of the differentiated cells and the formation of the cells into cardiac structures including coronary arteries, arterioles, capillaries, and myocardium. As one skilled in the art is aware, all of these structures are important for proper function in the heart. It has been shown in the literature that implantation of cells including endothelial cells and smooth muscle cells will allow for the implanted cells to live within the infarcted region, however they do not form the necessary structures to enable the heart to regain full functionality. The ability to restore both functional and structural integrity or better functional and structural integrity than previously achieved in the art is yet another aspect of this invention.

It is a preferred in the practice of the invention to utilize both the administration of stem cells and that of a cytokine to ensure the most effective method of repairing damaged myocardium.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

In certain embodiments, a therapeutically effective dose of stem cells is applied, delivered, or administered to the heart or implanted into the heart. An effective dose or amount is an amount sufficient to effect a beneficial or desired clinical result. Said dose could be administered in one or more administrations. In the examples that follow, $2 \times 10^4$-$1 \times 10^5$ stem cells were administered in the mouse model. While there would be an obvious size difference between the hearts of a mouse and a human, it is possible that $2 \times 10^4$-$1 \times 10^5$ stem cells would be sufficient in a human as well. However, the precise determination of what would be considered an effective dose may be based on factors individual to each patient, including their size, age, size of the infarct, and amount of time since damage. One skilled in the art, specifically a physician or cardiologist, would be able to determine the number and type (or types) of stem cells which would constitute an effective dose without being subjected to undue experimentation, from this disclosure and the knowledge in the art; and, in this regard and in general in regard to preparing formulations and administering formulations or components thereof, mention is made of the teachings in the Examples and that the skilled artisan can scale dosages, amounts and the like based on the weight of the patient to be treated in comparison to the weight of any animal employed in the Examples. The stem cells are advantageously bone marrow or are cardiac stem cells; and even more advantageously, the stem cells are adult bone marrow (hematopoietic stem cells) or adult cardiac stem cells or a combination thereof or a combination of cardiac stem cells such as adult cardiac stem cells and another type of stem cell such as another type of adult stem cells.

In another aspect of the invention, the stem cells are delivered to the heart, specifically to the border area of the infarct. As one skilled in the art would be aware, the infarcted area is visible grossly, allowing this specific placement of stem cells to be possible.

The stem cells are advantageously administered by injection, specifically an intramyocardial injection. As one skilled in the art would be aware, this is the preferred method of delivery for stem cells as the heart is a functioning muscle. Injection of the stem cells into the heart ensures that they will not be lost due to the contracting movements of the heart.

In other aspects of the invention, the stem cells are administered by injection transendocardially or trans-epicardially. This preferred embodiment allows the stem cells to penetrate the protective surrounding membrane, necessitated by the embodiment in which the cells are injected intramyocardially.

A preferred embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

Embodiments of the invention can involve the administration of a cytokine. This cytokine may be chosen from a group of cytokines, or may include combinations of cytokines.

A further aspect of the invention involves administration of a therapeutically effective dose of a cytokine. An effective dose or amount is an amount sufficient to effect a beneficial or desired clinical result. Said dose could be administered in one or more administrations. In a preferred embodiment, the dose would be given over the course of about two or three days following the beginning of treatment. However, the precise determination of what would be considered an effective dose may be based on factors individual to each patient, including their size, age, size of the infarct, the cytokine or combination of cytokines being administered, and amount of time since damage. One skilled in the art, specifically a physician or cardiologist, would be able to determine a sufficient amount of cytokine that would constitute an effective dose without being subjected to undue experimentation, especially in view of the disclosure herein and the knowledge in the art.

The administration of the therapeutically effective dose of at least one cytokine is advantageously by injection, specifically subcutaneously or intravenously. A person skilled in the art will be aware that subcutenous injection or intravenous delivery are extremely common and offer an effective method of delivering the specific dose in a manner which allows for timely uptake and circulation in the blood stream.

A further aspect of the invention includes the administered cytokine stimulating the patient's stem cells and causing mobilization into the blood stream. As mentioned previously, the given cytokines are well known to one skilled in the art for their ability to promote said mobilization. Again, once the stem cells have mobilized into the bloodstream, they home to the damaged area of the heart. Thus in certain embodiments, both the implanted stem cells and the mobilized stem cells migrate into the infarct region and differentiate into myocytes, smooth muscle cells, and endothelial cells. It is known in the art that these types of cells are advantageously present to restore both structural and functional integrity.

Another embodiment of the invention includes the proliferation of the differentiated cells and the formation of the cells into cardiac structures including coronary arteries, arterioles, capillaries, and myocardium. As one skilled in the art is aware, all of these structures are essential for proper function in the heart. It has been shown in the literature that implantation of cells including endothelial cells and smooth muscle cells will allow for the implanted cells to live within the infarcted region, however they do not form the necessary structures to enable the heart to regain full functionality. Cardiac structures can be generated ex vivo and then implanted in the form of a graft; with the implantation of the graft being alone or in combination with stem cells or stem cells and at least one cytokine as in this disclosure, e.g., advantageously adult or cardiac or hematopoietic stem cells such as adult cardiac and/or adult hematpoietic stem cells or adult cardiac stem cells with another type of stem cell e.g. another type of adult stem cell. The means of generating and/or regenerating myocardium ex vivo, may incorporate somatic stem cells and heart tissue being cultured in vitro, optionally in the presence of a ctyokine. The somatic stem cells differentiate into myocytes, smooth muscle cells and endothelial cells, and proliferate in vitro, forming myocardial tissue and/or cells. These tissues and cells may assemble into cardiac structures including arteries, arterioles, capillaries, and myocardium. The tissue and/or cells formed in vitro may then be implanted into a patient, e.g. via a graft, to restore structural and functional integrity.

Additionally or alternatively, the source of the tissue being grafted can be from other sources of tissue used in grafts of the heart.

The restoration or some restoration of both functional and structural integrity of cardiac tissue—advantageously over that which has occurred previously—is yet another aspect of this invention.

Accordingly, the invention comprehends, in further aspects, methods for preparing compositions such as pharmaceutical compositions including somatic stem cells and/or at least one cytokine, for instance, for use in inventive methods for treating cardiovascular disease or conditions or cardiac conditions.

The present invention is additionally described by way of the following, non-limiting examples, that provide a better understanding of the present invention and of its many advantages.

All of the materials, reagents, chemicals, assays, cytokines, antibodies, and miscellaneous items referred to in the following examples are readily available to the research community through commercial suppliers, including but not limited to, Genzyme, Invitrogen, Gibco BRL, Clonetics, Fisher Scientific, R & D Systems, MBL International Corporation, CN Biosciences Corporate, Sigma Aldrich, and CedarLane Laboratories, Limited.

For example,
 stem cell factor is available under the name SCF (multiple forms of recombinant human, recombinant mouse, and antibodies to each), from R & D Systems (614 McKinley Place N.E., Minneapolis, Minn. 55413);

granulocyte-colony stimulating factor is available under the name G-CSF (multiple forms of recombinant human, recombinant mouse, and antibodies to each), from R & D Systems;

stem cell antibody-1 is available under the name SCA-1 from MBL International Corporation (200 Dexter Avenue, Suite D, Watertown, Mass. 02472);

multidrug resistant antibody is available under the name Anti-MDR from CN Biosciences Corporate;

c-kit antibody is available under the name c-kit (Ab-1) Polyclonal Antibody from CN Biosciences Corporate (Affiliate of Merck KgaA, Darmstadt, Germany. Corporate headquarters located at 10394 Pacific Center Court, San Diego, Calif. 92121).

EXAMPLES

Example 1

Hematopoietic Stem Cell (HSC) Repair of Infarcted Myocardium

A. Harvesting of Hematopoietic Stem Cells

Figure 1:
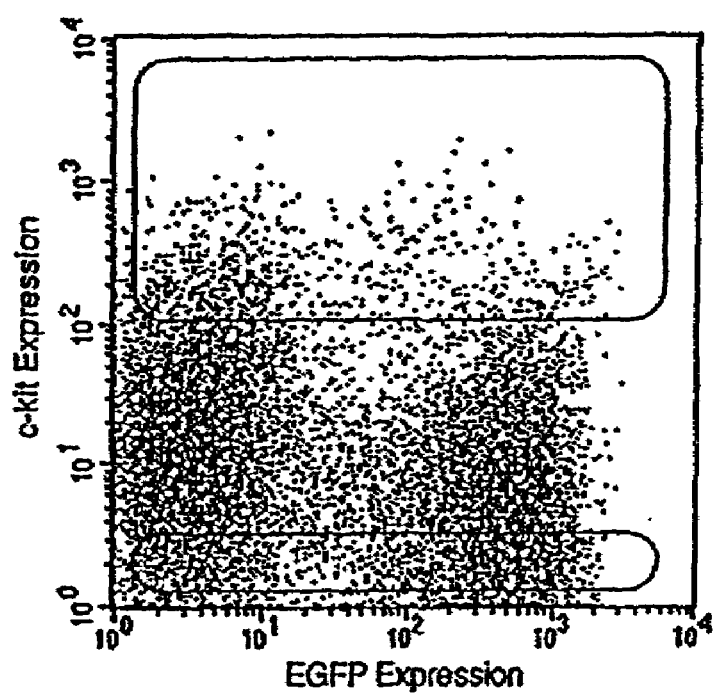
FIG. 1 shows a log-log plot showing Lin$^-$bone marrow cells from EGFP transgenic mice sorted by FACS based on c-kit expression (The fraction of c-kit$^{POS}$ cells (upper gate) was 6.4%. c-kit$^{NEG}$ cells are shown in the lower gate. c-kit$^{POS}$ cells were 1-2 logs brighter than c-kit$^{NEG}$ cells)

Bone marrow was harvested from the femurs and tibias of male transgenic mice expressing enhanced green fluorescent protein (EGFP). After surgical removal of the femurs and tibias, the muscle was dissected and the upper and lower surface of the bone was cut on the surface to allow the collecting buffer to infiltrate the bone marrow. The fluid containing buffer and cells was collected in tubes such as 1.5 ml Epindorf tubes. Bone marrow cells were suspended in PBS containing 5% fetal calf serum (FCS) and incubated on ice with rat anti-mouse monoclonal antibodies specific for the following hematopoietic lineages: CD4 and CD8 (T-lymphocytes), B-220 (B-lymphocytes), Mac-1 (macrophages), GR-1 (granulocytes) (Caltag Laboratories) and TER-119 (erythrocytes) (Pharmingen). Cells were then rinsed in PBS and incubated for 30 minutes with magnetic beads coated with goat anti-rat immunoglobulin (Polysciences Inc.). Lineage positive cells ($Lin^+$) were removed by a biomagnet and lineage negative cells ($Lin^-$) were stained with ACK-4-biotin (anti-c-kit mAb). Cells were rinsed in PBS, stained with streptavidin-conjugated phycoerythrin (SA-PE) (Caltag Labs.) and sorted by fluorescence activated cell sorting (FACS) using a FACSVantage instrument (Becton Dickinson). Excitation of EGFP and ACK-4-biotin-SA-EP occurred at a wavelength of 488 nm. The $Lin^-$ cells were sorted as c-kit positive ($c\text{-}kit^{POS}$) and c-kit negative ($c\text{-}kit^{NEG}$) with a 1-2 log difference in staining intensity (FIG. 1). The $c\text{-}kit^{POS}$ cells were suspended at $2\times10^4$ to $1\times10^5$ cells in 5 µl of PBS and the $c\text{-}kit^{NEG}$ cells were suspended at a concentration of $1\times10^5$ in 5 µl of PBS.

B. Induction of Myocardial Infarction in Mice

Figure 2:
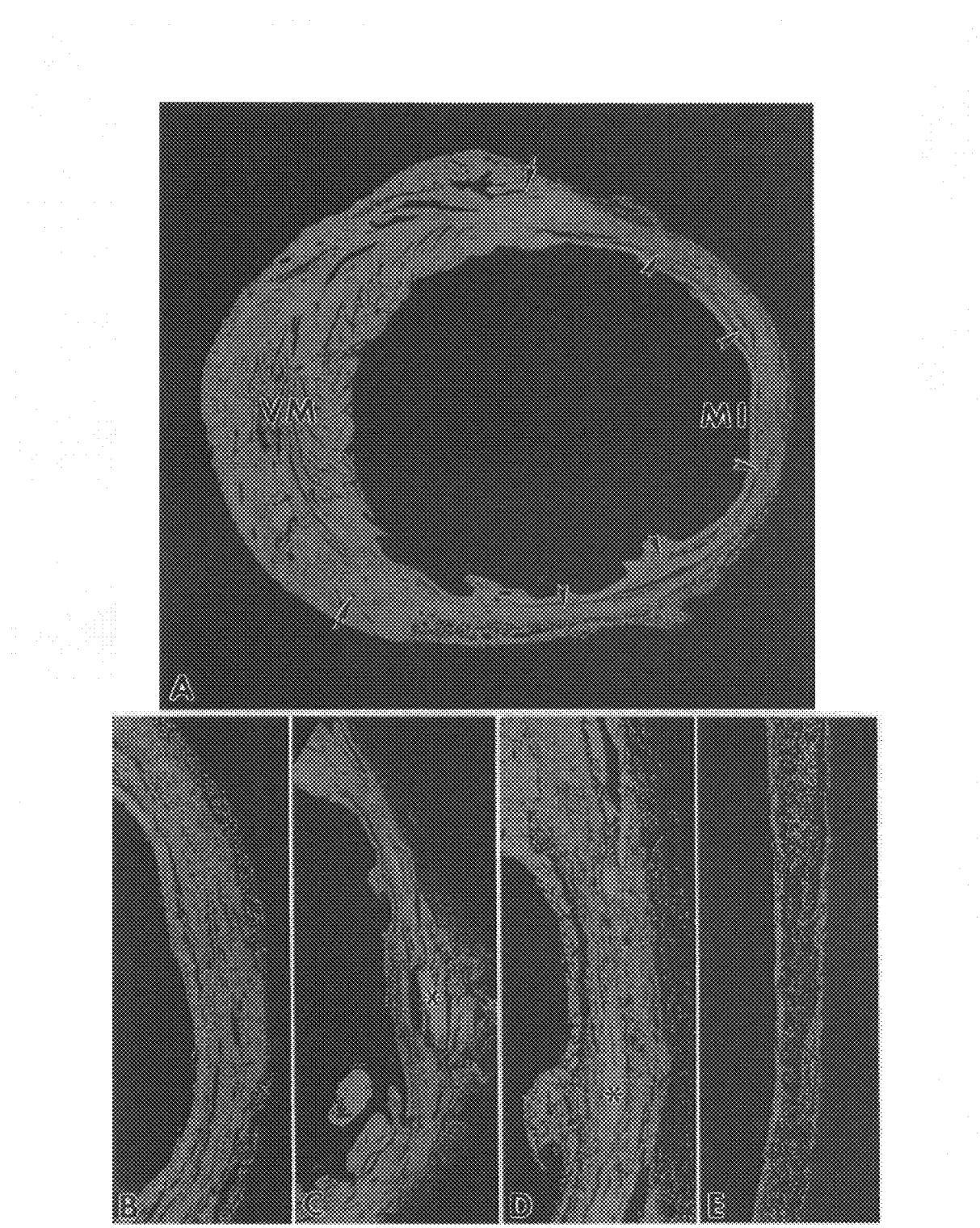
FIG. 2A shows a photograph of a tissue section from a MI induced mouse (The photograph shows the area of myocardial infarct (MI) injected with Lin$^-$c-kit$^{POS}$ cells from bone marrow (arrows), the remaining viable myocardium (VM), and the regenerating myocardium (arrowheads). Magnification is 12×)
FIG. 2B shows a photograph of the same tissue section of FIG. 2A at a higher magnification, centering on the area of the MI with magnification being 50×.
FIGS. 2C, D show photographs of a tissue section at low and high magnifications of the area of MI, injected with Lin$^-$c-kit$^{POS}$ cells, with the magnification of 2C being 25×, and the magnification of 2D being 50×.
FIG. 2E shows a photograph of a tissue section of the area of MI injected with Lin$^-$c-kit$^{NEG}$ cells wherein only healing is apparent and the magnification is 50× (*Necrotic myocytes. Red=cardiac myosin; green=PI labeling of nuclei)

Myocardial infarction was induced in female C57BL/6 mice at 2 months of age as described by Li et al. (1997). Three to five hours after infarction, the thorax of the mice was reopened and 2.5 µl of PBS containing $Lin^-c\text{-}kit^{POS}$ cells were injected in the anterior and posterior aspects of the viable myocardium bordering the infarct (FIG. 2). Infarcted mice, left uninjected or injected with $Lin^-c\text{-}kit^{NEG}$ cells, and sham-operated mice i.e., mice where the chest cavity was opened but no infarction was induced, were used as controls. All animals were sacrificed 9±2 days after surgery. Protocols were approved by institutional review board. Results are presented as mean±SD. Significance between two measurements was determined by the Student's t test, and in multiple comparisons was evaluated by the Bonferroni method (Scholzen and Gerdes, 2000). P<0.05 was considered significant.

Injection of male $Lin^-c\text{-}kit^{POS}$ bone marrow cells in the peri-infarcted left ventricle of female mice resulted in myocardial regeneration. The peri-infarcted region is the region of viable myocardium bordering the infarct. Repair was obtained in 12 of 30 mice (40%). Failure to reconstitute infarcts was attributed to the difficulty of transplanting cells into tissue contracting at 600 beats per minute (bpm). However, an immunologic reaction to the histocompatibility antigen on the Y chromosome of the donor bone marrow cells could account for the lack of repair in some of the female recipients. Closely packed myocytes occupied 68±11% of the infarcted region and extended from the anterior to the posterior aspect of the ventricle (FIGS. 2A-2D). New myocytes were not found in mice injected with $Lin^-c\text{-}kit^{NEG}$ cells (FIG. 2E).

C. Determination of Ventricular Function

Figure 3:
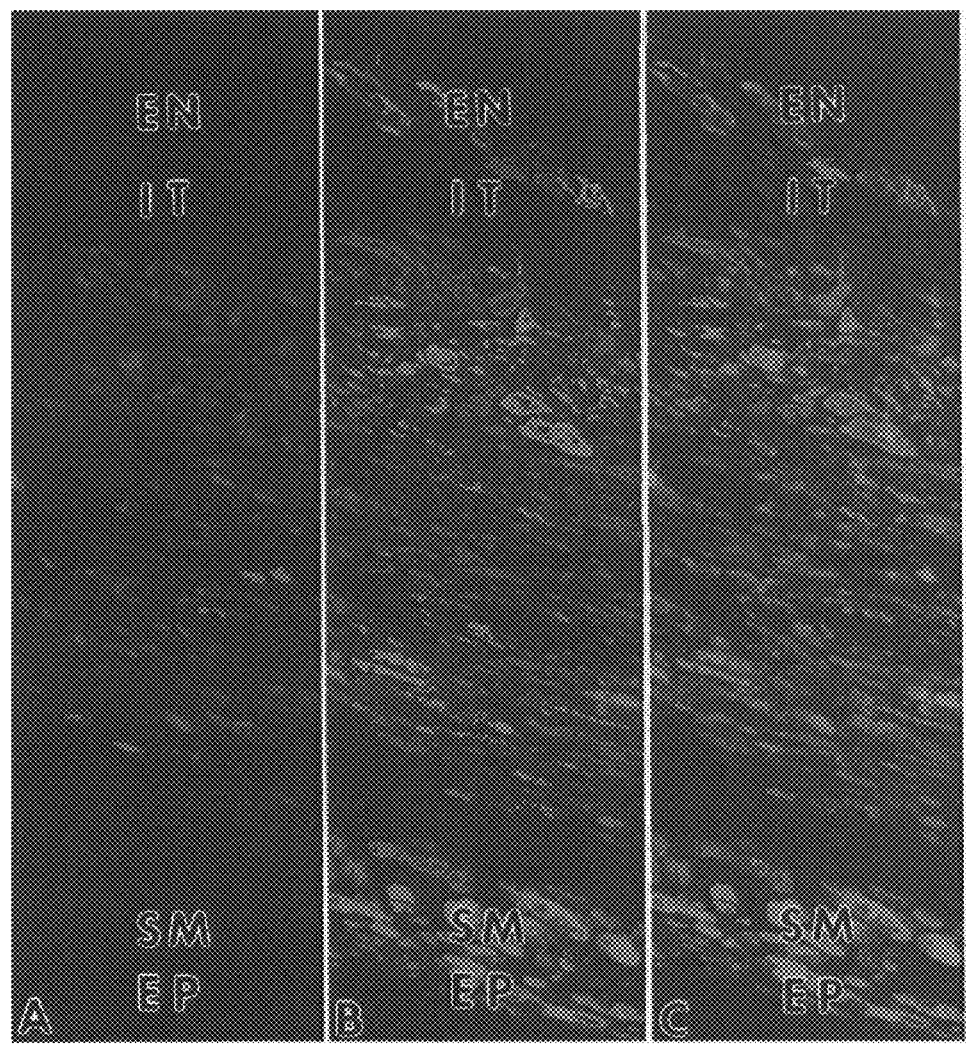
FIGS. 3A-C show photographs of a section of tissue from a MI induced mouse, showing the area of MI injected with Lin⁻c-kit$^{POS}$ cells (Visible is a section of regenerating myocardium from endocardium (EN) to epicardium (EP). All photographs are labeled to show the presence of infarcted tissue in the subendocardium (IT) and spared myocytes in the subendocardium (SM).
Figure 4:
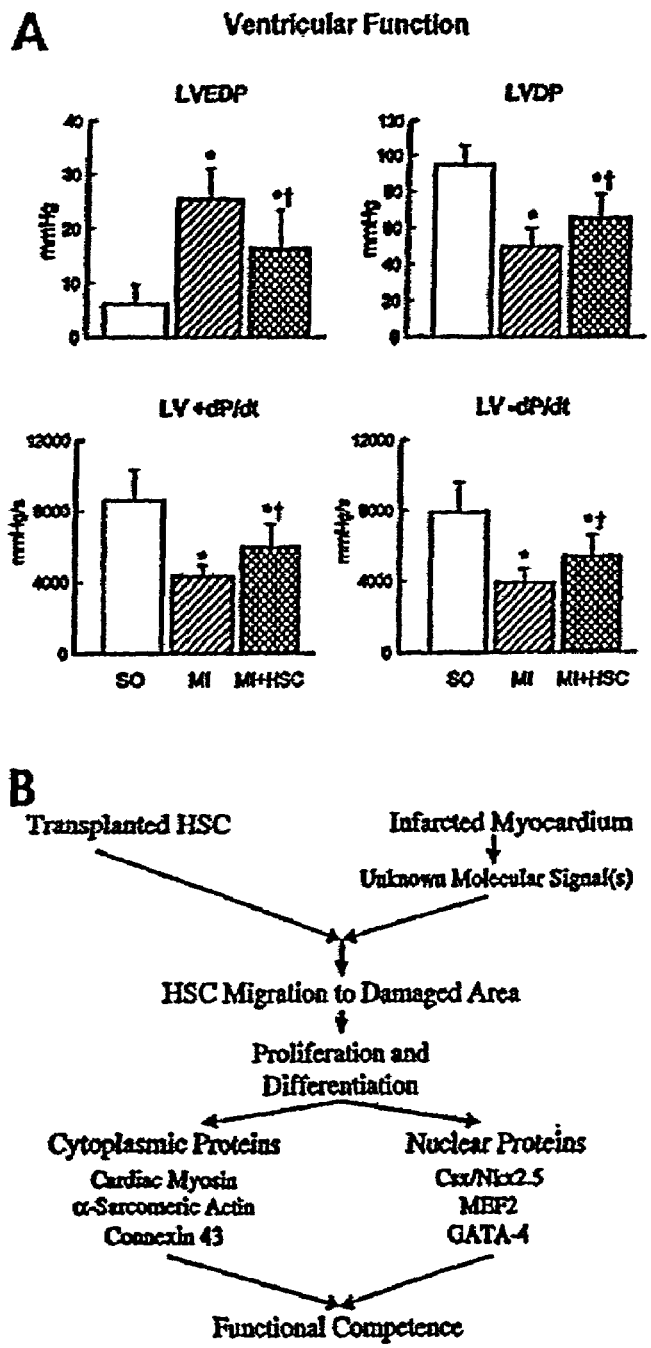
FIG. 4A shows of grafts depicting the effects of myocardial infarction on left ventricular end-diastolic pressure (LVEDP), developed pressure (LVDP), LV+rate of pressure rise (dP/dt), and LV−rate of pressure decay (dP/dt) (From left to right, bars indicate: sham-operated mice (SO, n=11); mice non-injected with Lin⁻c-kit$^{POS}$ cells (MI, n=5 injected with Lin⁻c-kit$^{NEG}$ cells; n=6 non-injected); mice injected with Lin⁻c-kit$^{POS}$ cells (MI+BM, n=9). Error bars are the standard deviation. *, †p<0.05 vs SO and MI)
FIG. 4B shows a drawing of a proposed scheme for Lin⁻c-kit$^{POS}$ cell differentiation in cardiac muscle and functional implications.

Mice were anesthetized with chloral hydrate (400 mg/kg body weight, i.p.), and the right carotid artery was cannulated with a microtip pressure transducer (model SPR-671, Millar) for the measurements of left ventricular (LV) pressures and LV + and −dP/dt in the closed-chest preparation to determine whether developing myocytes derived from the HSC transplant had an impact on function. Infarcted mice non-injected or injected with $Lin^-c\text{-}kit^{NEG}$ cells were combined in the statistics. In comparison with sham-operated groups, the infarcted groups exhibited indices of cardiac failure (FIG. 3). In mice treated with $Lin\text{-}c\text{-}kit^{POS}$ cells, LV end-diastolic pressure (LVEDP) was 36% lower, and developed pressure (LVDP) and LV + and −dP/dt were 32%, 40%, and 41% higher, respectively (FIG. 4A).

D. Determination of Cell Proliferation and EGFP Detection

The abdominal aorta was cannulated, the heart was arrested in diastole by injection of cadmium chloride ($CdCl_2$), and the myocardium was perfused retrogradely with 10% buffered formalin. Three tissue sections, from the base to the apex of the left ventricle, were stained with hematoxylin and eosin. At 9±2 days after coronary occlusion, the infarcted portion of the ventricle was easily identifiable grossly and histologically (see FIG. 2A). The lengths of the endocardial and epicardial surfaces delimiting the infarcted region, and the endocardium and epicardium of the entire left ventricle were measured in each section. Subsequently, their quotients were computed to yield the average infarct size in each case. This was accomplished at 4× magnification utilizing an image analyzer connected to a microscope. The fraction of endocardial and epicardial circumference delimiting the infarcted area (Pfeffer and Braunwald, 1990; Li et al., 1997) did not differ in untreated mice, 78±18% (n=8) and in mice treated with $Lin^-c\text{-}kit^{POS}$ cells (n=12), 75±14% or $Lin^-c\text{-}kit^{NEG}$ cells (n=11), 75±15%.

Figure 5:
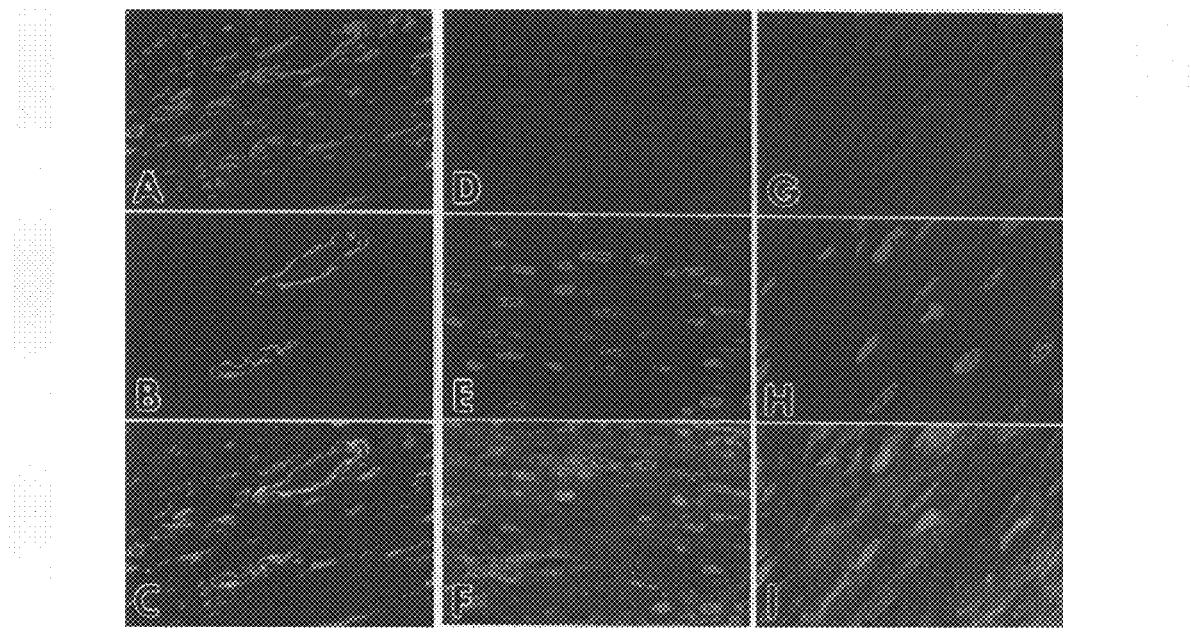
FIGS. 5A-I show photographs of a tissue sections from a MI induced mouse depicting regenerating myocardium in the area of the MI which has been injected with Lin⁻c-kit$^{POS}$ cells (FIG. 5A is stained to show the presence of EGFP (green). Magnification is 300×.
Figure 6:
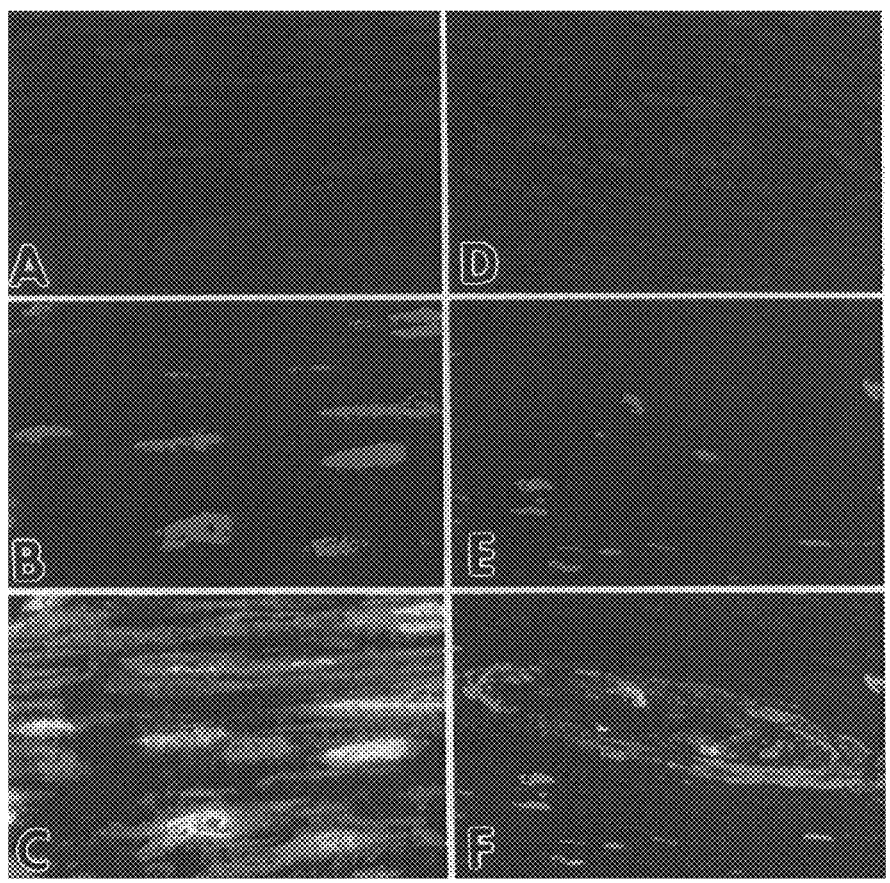
FIG. 6 (FIGS. 6A-F) shows photographs of tissue sections from MI induced mice, showing regenerating myocardium in the area of the MI injected with Lin⁻c-kit$^{POS}$ cells (FIGS. 6A-C show tissue which has been incubated in the presence of antibodies to BrdU.

To establish whether $Lin^-c\text{-}kit^{POS}$ cells resulted in myocardial regeneration, BrdU (50 mg/kg body weight, i.p.) was administered daily to the animals for 4-5 consecutive days before sacrifice to determine cumulative cell division during active growth. Sections were incubated with anti-BrdU antibody and BrdU labeling of cardiac cell nuclei in the S phase was measured. Moreover, expression of Ki67 in nuclei (Ki67 is expressed in cycling cells in G1, S, G2, and early mitosis) was evaluated by treating samples with a rabbit polyclonal anti-mouse Ki67 antibody (Dako Corp.). FITC-conjugated goat anti-rabbit IgG was used as secondary antibody. (FIGS. 5 and 6). EGFP was detected with a rabbit polyclonal anti-GFP (Molecular Probes). Myocytes were recognized with a mouse monoclonal anti-cardiac myosin heavy chain (MAB 1548; Chemicon) or a mouse monoclonal anti-α-sarcomeric actin (clone 5C5; Sigma), endothelial cells with a rabbit polyclonal anti-human factor VIII (Sigma) and smooth muscle cells with a mouse monoclonal anti-α-smooth muscle actin (clone 1A4; Sigma). Nuclei were stained with propidium iodide (PI), 10 μg/ml. The percentages of myocyte (M), endothelial cell (EC) and smooth muscle cell (SMC) nuclei labeled by BrdU and Ki67 were obtained by confocal microscopy. This was accomplished by dividing the number of nuclei labeled by the total number of nuclei examined. Number of nuclei sampled in each cell population was as follows; BrdU labeling: M=2,908; EC=2,153; SMC=4,877. Ki67 labeling: M=3,771; EC=4,051; SMC=4,752. Number of cells counted for EGFP labeling: M=3,278; EC=2,056; SMC=1, 274. The percentage of myocytes in the regenerating myocardium was determined by delineating the area occupied by cardiac myosin stained cells divided by the total area represented by the infarcted region in each case. Myocyte proliferation was 93% (p<0.001) and 60% (p<0.001) higher than in endothelial cells, and 225% (p<0.001 and 176% (p<0.001) higher than smooth muscle cells, when measured by BrdU and Ki67, respectively.

Figure 7:
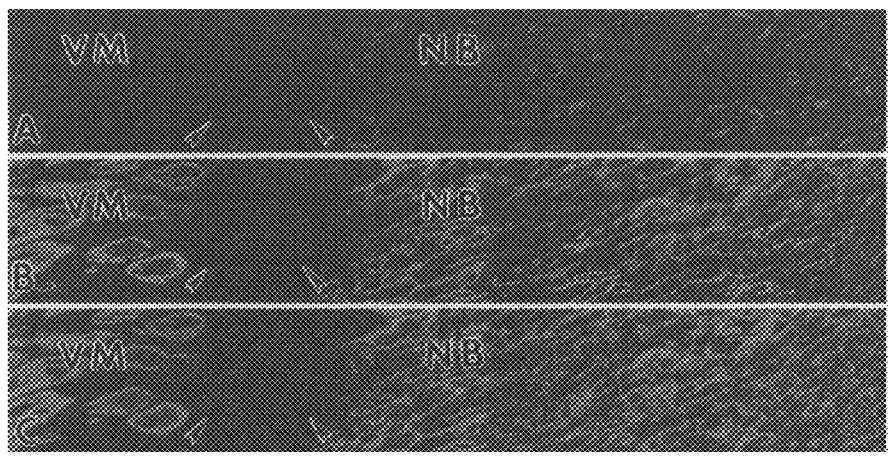
FIG. 7 (FIGS. 7A-C) shows photographs of tissue sections from MI induced mice, showing the area of MI injected with Lin⁻c-kit$^{POS}$ cells (Depicted are the border zone, viable myocardium (VM) and the new band (NB) of myocardium separated by an area of infarcted non-repairing tissue (arrows).
Figure 8:
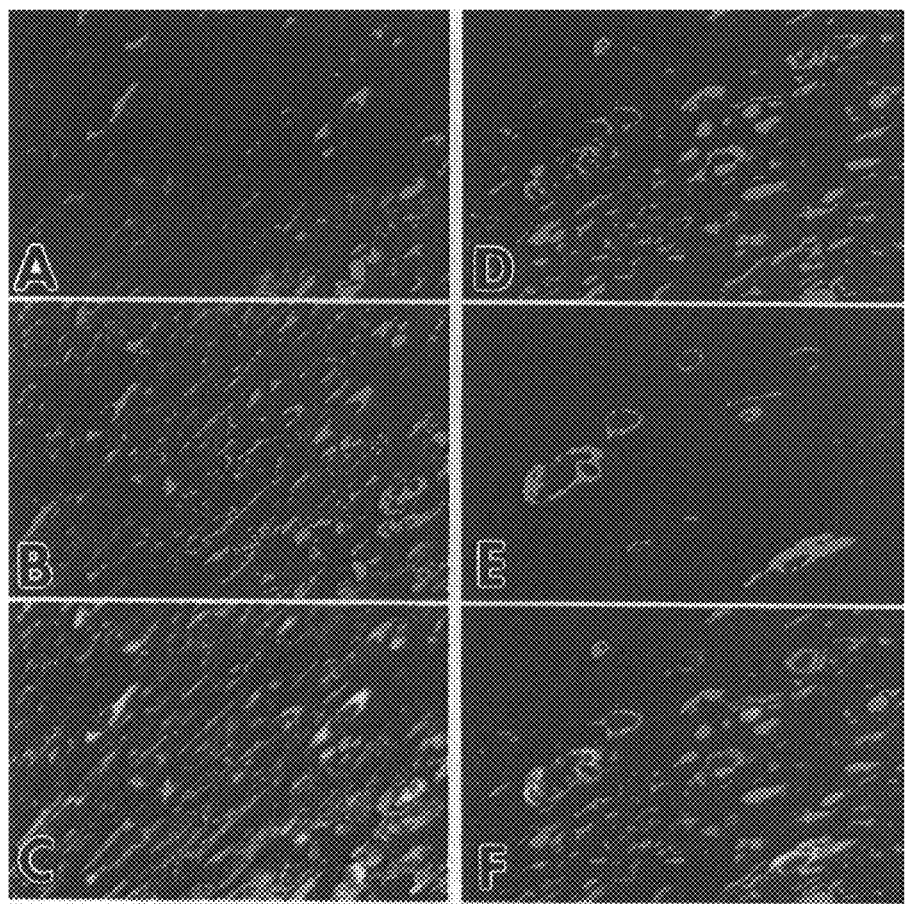
FIG. 8 (FIGS. 8A-F) shows photographs of tissue sections from MI induced mice, showing regenerating myocardium in the area of MI injected with Lin⁻c-kit$^{POS}$ cells (FIG. 8A is stained to show the presence of EGFP (green). Magnification is 650×.

The origin of the cells in the forming myocardium was determined by the expression of EGFP (FIGS. 7 and 8). EGFP expression was restricted to the cytoplasm and the Y chromosome to nuclei of new cardiac cells. EGFP was combined with labeling of proteins specific for myocytes, endothelial cells and smooth muscle cells. This allowed the identification of each cardiac cell type and the recognition of endothelial cells and smooth muscle cells organized in coronary vessels (FIGS. 5, 7, and 8). The percentage of new myocytes, endothelial cells and smooth muscle cells that expressed EGFP was 53±9% (n=7), 44±6% (n=7) and 49±7% (n=7), respectively. These values were consistent with the fraction of transplanted Lin$^-$c-kit$^{POS}$ bone marrow cells that expressed EGFP, 44±10% (n=6). An average 54±8% (n=6) of myocytes, endothelial cells and smooth muscle cells expressed EGFP in the heart of donor transgenic mice.

E. Detection of the Y-Chromosome

For the fluorescence in situ hybridization (FISH) assay, sections were exposed to a denaturing solution containing 70% formamide. After dehydration with ethanol, sections were hybridized with the DNA probe CEP Y (satellite III) Spectrum Green (Vysis) for 3 hours. Nuclei were stained with PI.

Y-chromosomes were not detected in cells from the surviving portion of the ventricle. However, the Y-chromosome was detected in the newly formed myocytes, indicating their origin as from the injected bone marrow cells (FIG. 9).

F. Detection of Transription Factors and Connexin 43

Sections were incubated with rabbit polyclonal anti-MEF2 (C-21; Santa Cruz), rabbit polyclonal anti-GATA-4 (H-112; Santa Cruz), rabbit polyclonal anti-Csx/Nkx2.5 (obtained from Dr. Izumo) and rabbit polyclonal anti-connexin 43 (Sigma). FITC-conjugated goat anti-rabbit IgG (Sigma) was used as secondary antibody.

Figure 10:
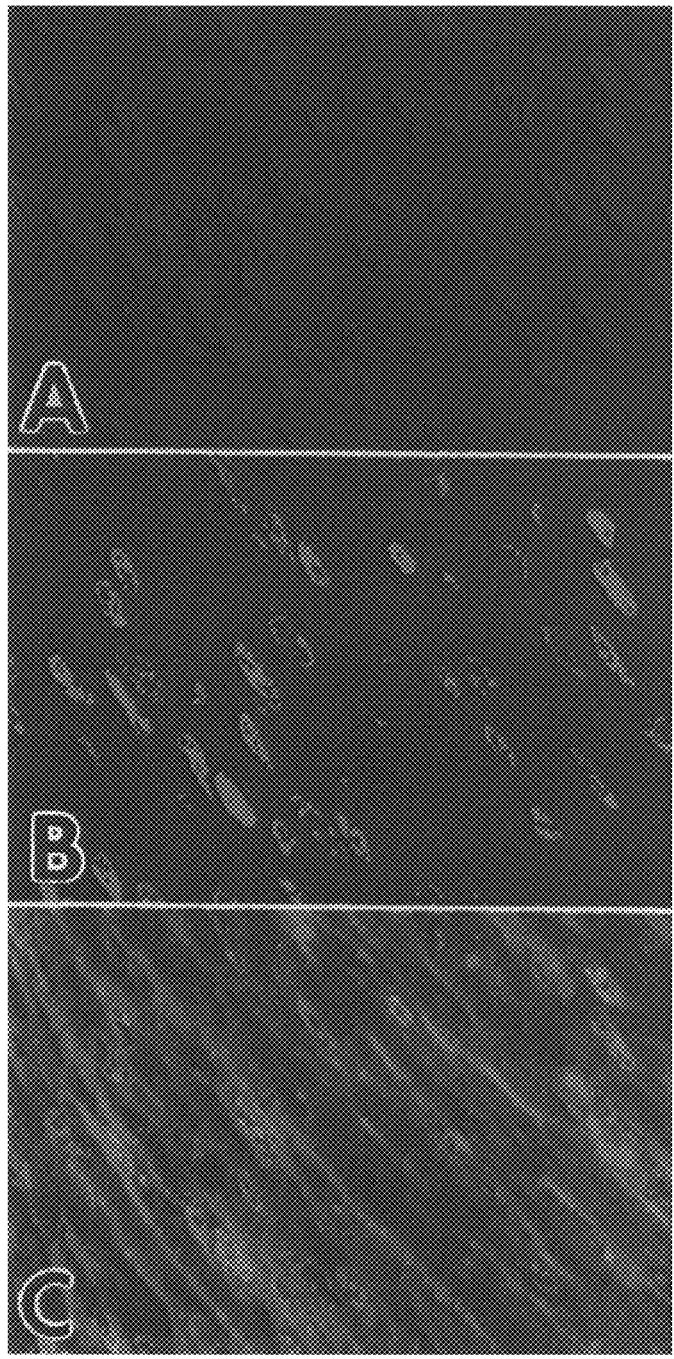
FIG. 10 (FIGS. 10A-C) shows photographs of tissue sections from MI induced mice, showing GATA-4 in cardiac myosin positive cells (FIG. 10A shows PI-stained nuclei (blue). Magnification is 650×.
Figure 11:
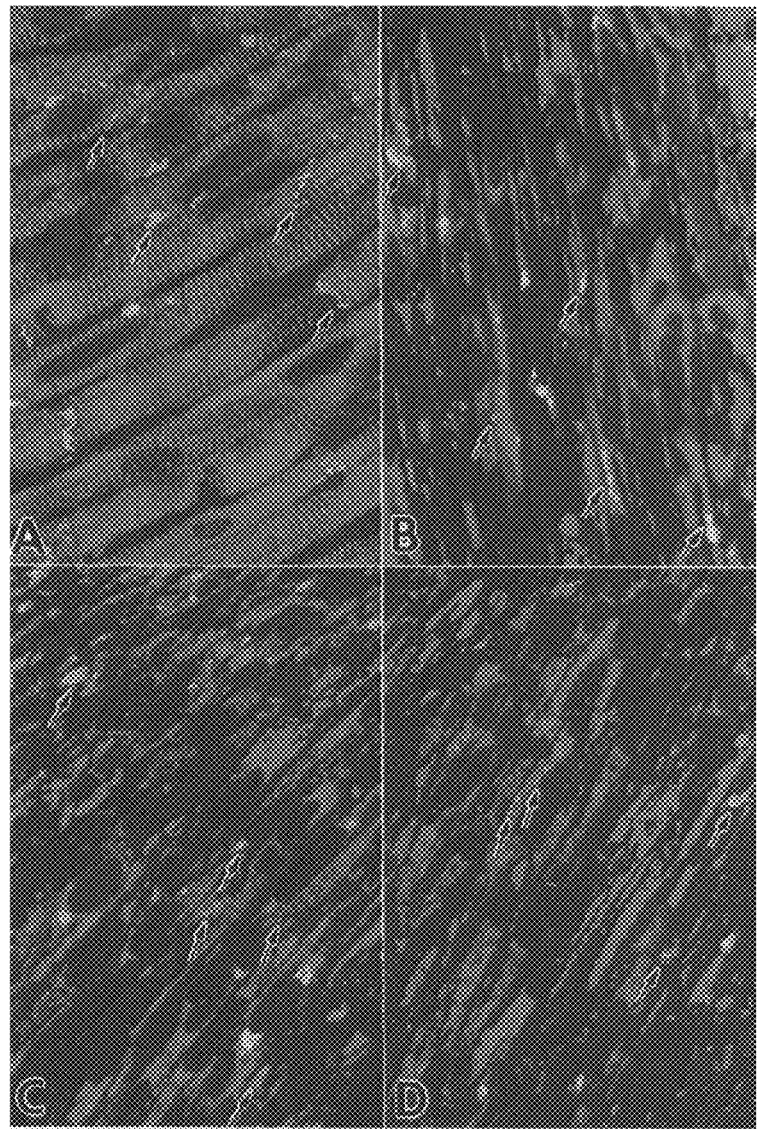
FIG. 11 (FIG. 11A-D) shows photograph of tissue sections from a MI induced mouse (FIG. 11A shows the border zone between the infarcted tissue and the surviving tissue. Magnification is 500×.
Figure 12:
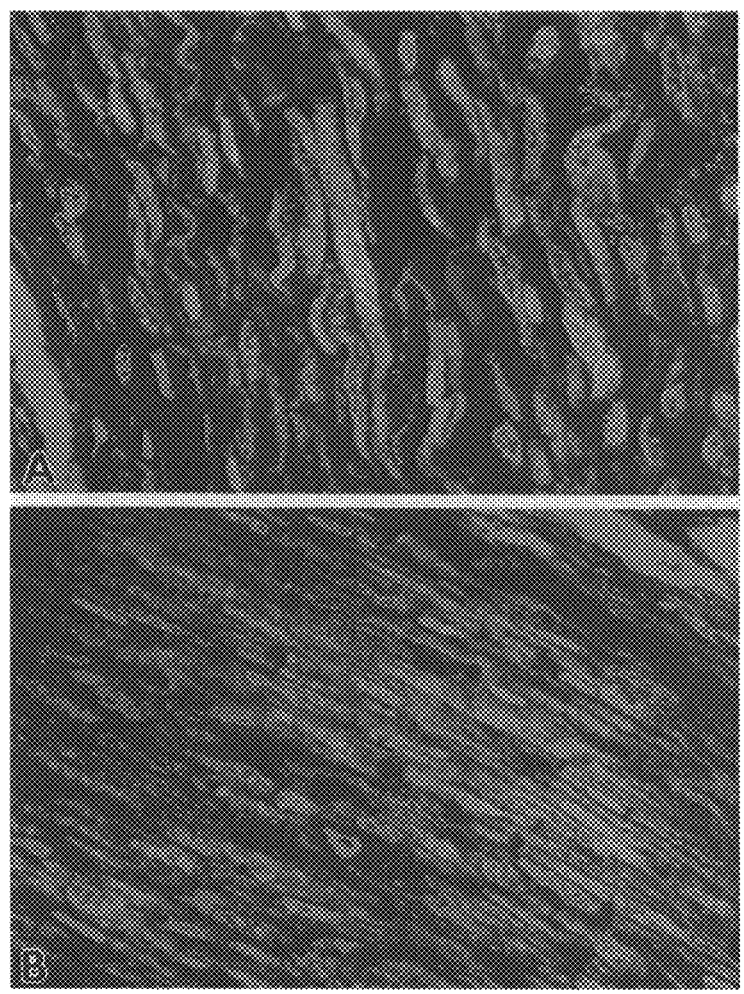
FIG. 12 (FIGS. 12A-B) shows photographs of tissue sections from a MI induced mouse showing the area of MI that was injected with Lin⁻c-kit$^{POS}$ cells and now shows regenerating myocytes (FIG. 12A is stained to show the presence of cardiac myosin (red) and PI-labeled nuclei (yellow-green). Magnification is 1,000.

To confirm that newly formed myocytes represented maturing cells aiming at functional competence, the expression of the myocyte enhancer factor 2 (MEF2), the cardiac specific transcription factor GATA-4 and the early marker of myocyte development Csx/Nkx2.5 was examined. In the heart, MEF2 proteins are recruited by GATA-4 to synergistically activate the promoters of several cardiac genes such as myosin light chain, troponin T, troponin I, α-myosin heavy chain, desmin, atrial natriuretic factor and α-actin (Durocher et al., 1997; Morin et al., 2000). Csx/Nkx2.5 is a transcription factor restricted to the initial phases of myocyte differentiation (Durocher et al., 1997). In the reconstituting heart, all nuclei of cardiac myosin labeled cells expressed MEF2 (FIGS. 7D-7F) and GATA-4 (FIG. 10), but only 40±9% expressed Csx/Nkx2.5 (FIGS. 7G-7I). To characterize farther the properties of these myocytes, the expression of connexin 43 was determined. This protein is responsible for intercellular connections and electrical coupling through the generation of plasma membrane channels between myocytes (Beardsle et al., 1998; Musil et al., 2000); connexin 43 was apparent in the cell cytoplasm and at the surface of closely aligned differentiating cells (FIGS. 11A-11D). These results were consistent with the expected functional competence of the heart muscle phenotype. Additionally, myocytes at various stages of maturation were detected within the same and different bands (FIG. 12).

Example 2

Mobilization of Bone Marrow Cells to Repair Infarcted Myocardium

A. Myocardial Infarction and Cytokines.

Fifteen C57BL/6 male mice at 2 months of age were splenectomized and 2 weeks later were injected subcutaneously with recombinant rat stem cell factor (SCF), 200 μg/kg/day, and recombinant human granulocyte colony stimulating factor (G-CSF), 50 μg/kg/day (Amgen), once a day for 5 days (Bodine et al., 1994; Orlic et al., 1993). Under ether anesthesia, the left ventricle (LV) was exposed and the coronary artery was ligated (Orlic et al., 2001; Li et al., 1997; Li et al., 1999). SCF and G-CSF were given for 3 more days. Controls consisted of splenectomized infarcted and sham-operated (SO) mice injected with saline. BrdU, 50 mg/kg body weight, was given once a day, for 13 days, before sacrifice; mice were killed at 27 days. Protocols were approved by New York Medical College. Results are mean±SD. Significance was determined by the Student's t test and Bonferroni method (Li et al., 1999). Mortality was computed with log-rank test. P<0.05 was significant.

Given the ability of bone marrow Lin$^-$c-kit$^{POS}$ cells to transdifferentiate into the cardiogenic lineage (Orlic et al., 2001), a protocol was used to maximize their number in the peripheral circulation in order to increase the probability of their homing to the region of dead myocardium. In normal animals, the frequency of Lin$^-$c-kit$^{POS}$ cells in the blood is only a small fraction of similar cells present in the bone marrow (Bodine et al., 1994; Orlic et al., 1993). As documented previously, the cytokine treatment used here promotes a marked increase of Lin$^-$c-kit$^{POS}$ cells in the bone marrow and a redistribution of these cells from the bone marrow to the peripheral blood. This protocol leads to a 250-fold increase in Lin$^-$c-kit$^{POS}$ cells in the circulation (Bodine et al., 1994; Orlic et al., 1993).

Figure 13:
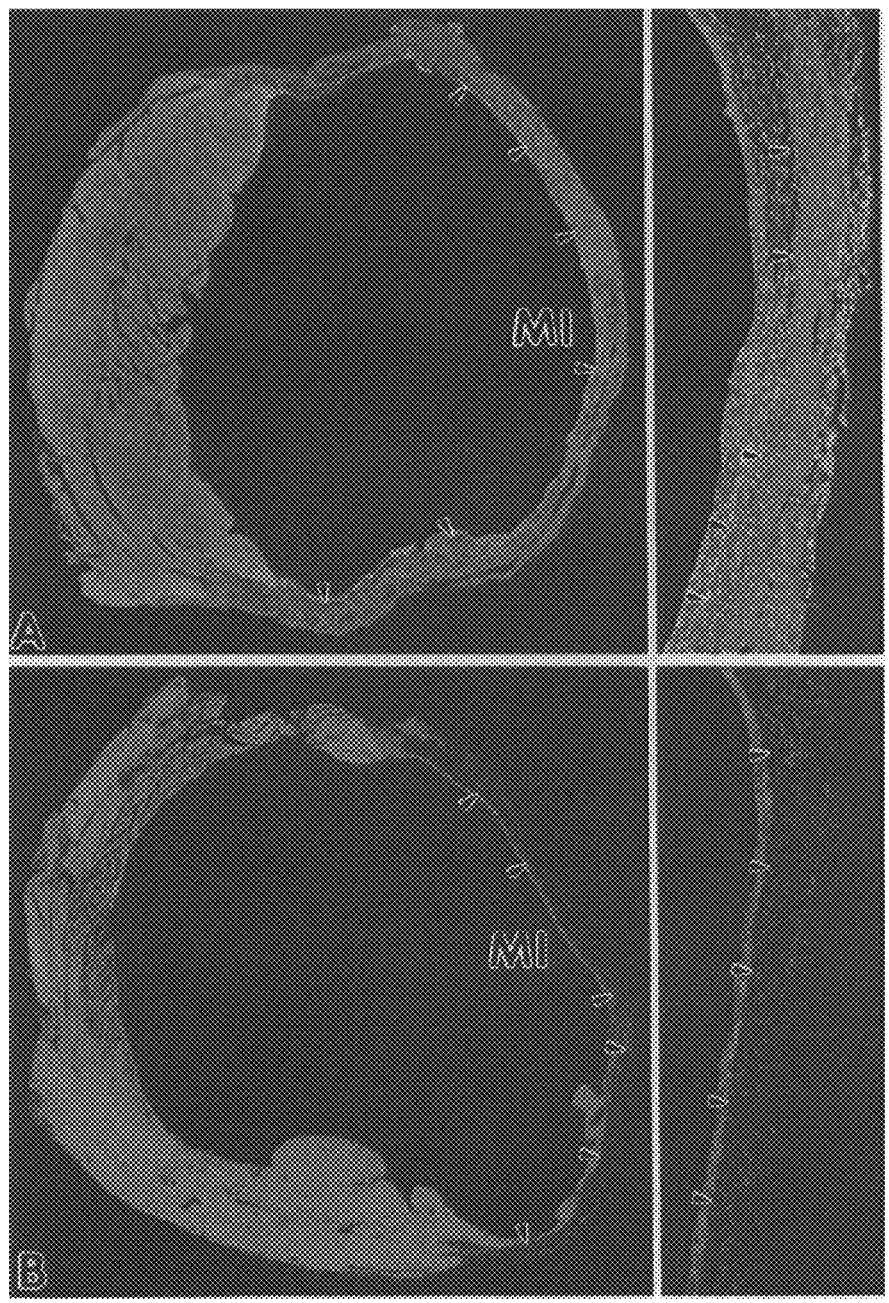
FIGS. 13A-B show photographs of tissue sections from MI induced mice (FIG. 13A shows a large infarct (MI) in a cytokine-treated mouse with forming myocardium (arrowheads) (Magnification is 50×) at higher magnification (80×—adjacent panel).
FIG. 13C shows a graph showing the mortality and myocardial regeneration in treated and untreated MI induced mice (Cytokine-treated infarcted mice, n=15; untreated infarcted mice, n=52. Log-rank test: p<0.0001)
Figure 14:
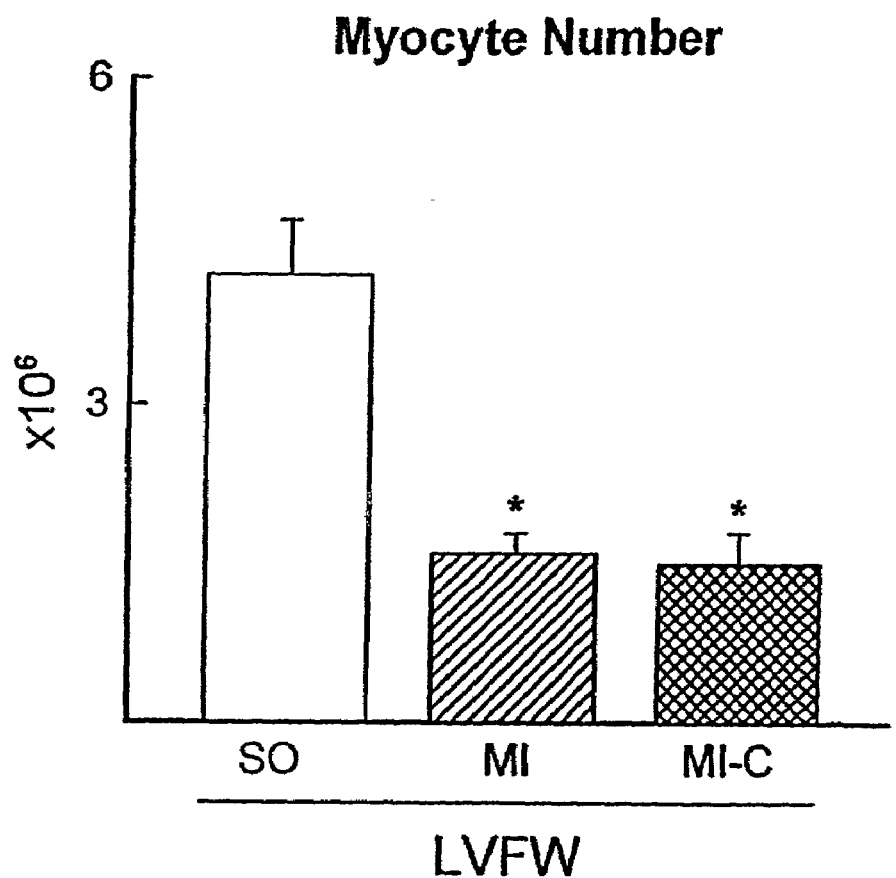
FIG. 14 shows a graph showing quantitative measurement of infarct size (Total number of myocytes in the left ventricular free wall (LVFW) of sham-operated (SO, n=9), infarcted non-treated (MI, n=9) and cytokine-treated (MI-C, n=11) mice at sacrifice, 27 days after infarction or sham operation. The percentage of myocytes lost equals infarct size. X±SD, *p<0.05 vs SO)

In the current study, BMC mobilization by SCF and G-CSF resulted in a dramatic increase in survival of infarcted mice; with cytokine treatment, 73% of mice (11 of 15) survived 27 days, while mortality was very high in untreated infarcted mice (FIG. 13A). A large number of animals in this group died from 3 to 6 days after myocardial infarction (MI) and only 17% (9 of 52) reached 27 days (p<0.001). Mice that died within 48 hours post-MI were not included in the mortality curve to minimize the influence of the surgical trauma. Infarct size was similar in the cytokine-, 64±11% (n=11), and saline-, 62±9% (n=9), injected animals as measured by the number of myocytes lost in the left ventricular free wall (LVFW) at 27 days (FIG. 14).

Importantly, bone marrow cell mobilization promoted myocardial regeneration in all 11 cytokine-treated infarcted mice, sacrificed 27 days after surgery (FIG. 13B). Myocardial growth within the infarct was also seen in the 4 mice that died prematurely at day 6 (n=2) and at day 9 (n=2). Cardiac repair was characterized by a band of newly formed myocardium occupying most of the damaged area. The developing tissue extended from the border zone to the inside of the injured region and from the endocardium to the epicardium of the LVFW. In the absence of cytokines, myocardial replacement was never observed and healing with scar formation was apparent (FIG. 13C). Conversely, only small areas of collagen accumulation were detected in treated mice.

B. Detection of BMC Mobilization by Echocardiography and Hemodynamics.

Echocardiography was performed in conscious mice using a Sequoia 256c (Acuson) equipped with a 13-MHz linear transducer (15L8). The anterior chest area was shaved and two dimensional (2D) images and M-mode tracings were recorded from the parasternal short axis view at the level of papillary muscles. From M-mode tracings, anatomical parameters in diastole and systole were obtained (Pollick et al., 1995). Ejection fraction (EF) was derived from LV cross sectional area in 2D short axis view (Pollick et al., 1995): EF=[(LVDA-LVSA)/LVDA]*100 where LVDA and LVSA correspond to LV areas in diastole and in systole. Mice were anesthetized with chloral hydrate (400 mg/kg body weight, ip) and a microtip pressure transducer (SPR-671, Millar) connected to a chart recorder was advanced into the LV for the evaluation of pressures and + and −dP/dt in the closed-chest preparation (Orlic et al., 2001; Li et al., 1997; Li et al., 1999).

Figure 15:
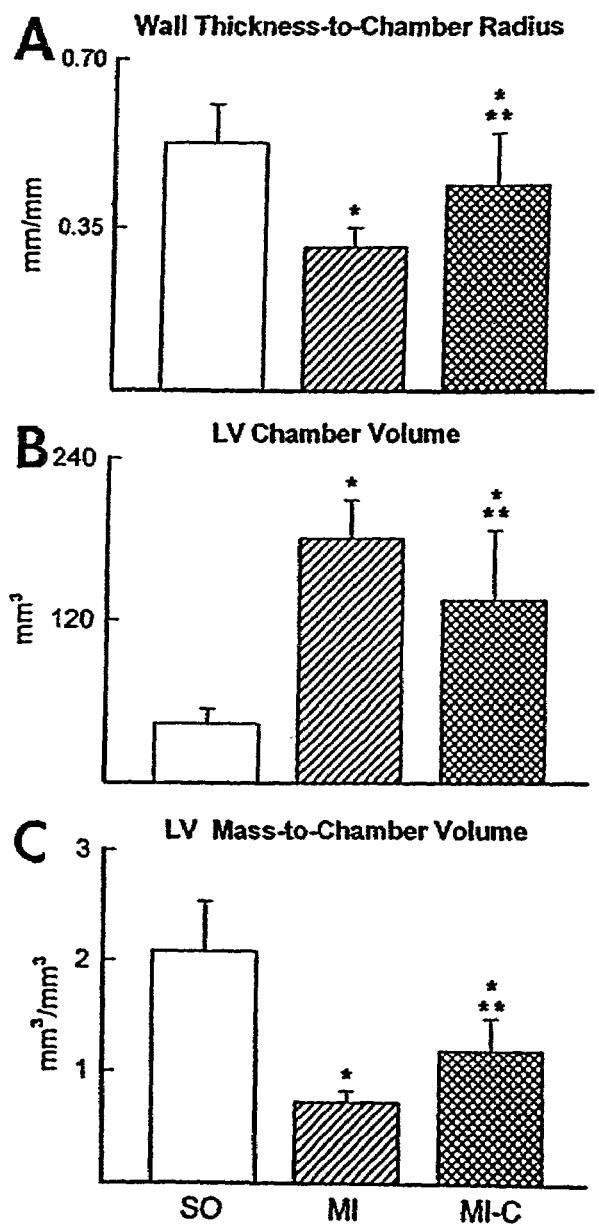
FIGS. 15A-C show graphs comparing aspects of myocardial infarction, cardiac anatomy and function (FIGS. 15A-C depict LV dimensions at sacrifice, 27 days after surgery; sham-operated (SO, n=9), non-treated infarcted (MI, n=9) and cytokine-treated infarcted (MI-C, n=10))
FIG. 15D shows EF by echocardiography; (SO, n=9; MI, n=9; and MI-C, n=9)
FIGS. 15E-M show M-mode echocardiograms of SO (e-g), MI (h-j) and MI-C (k-m) (Newly formed contracting myocardium (arrows))
FIG. 15N shows a graph showing wall stress; SO (n=9), MI (n=8) and MI-C (n=9) (Results are mean±SD. *,**p<0.05 vs SO and MI, respectively)
Figure 15:
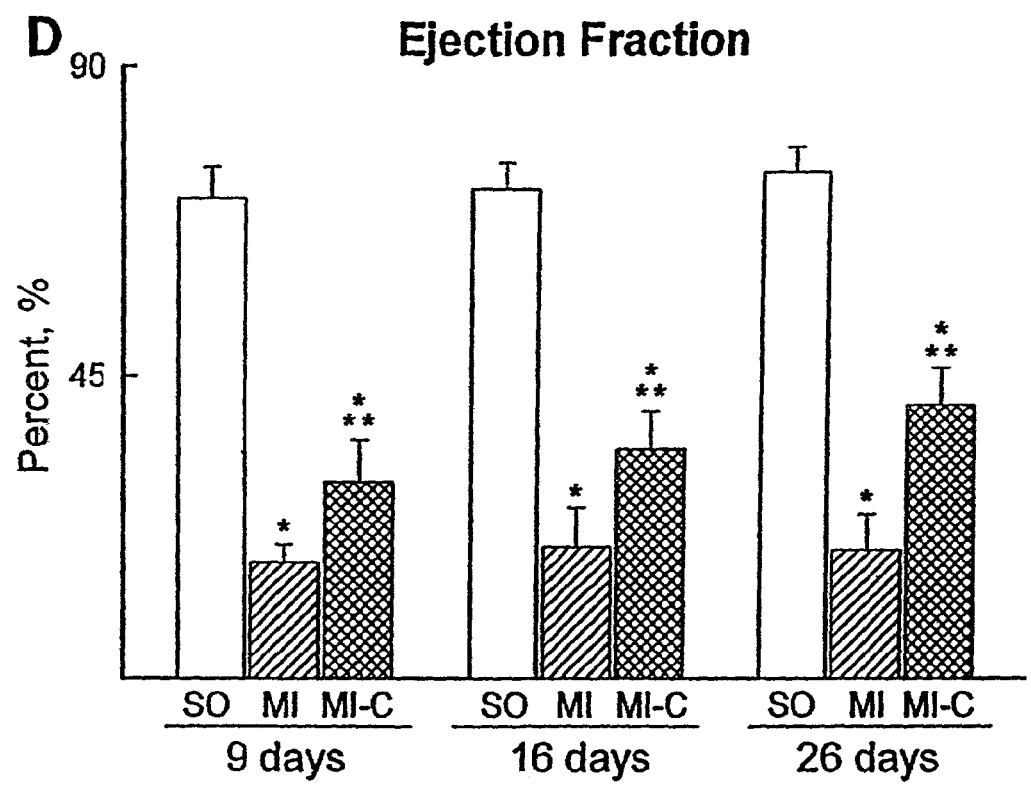
Figure 15:
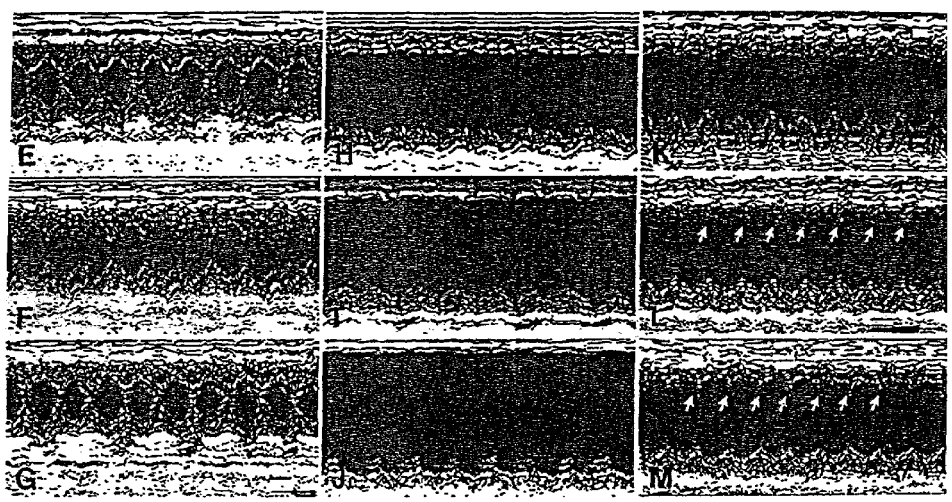
Figure 15:
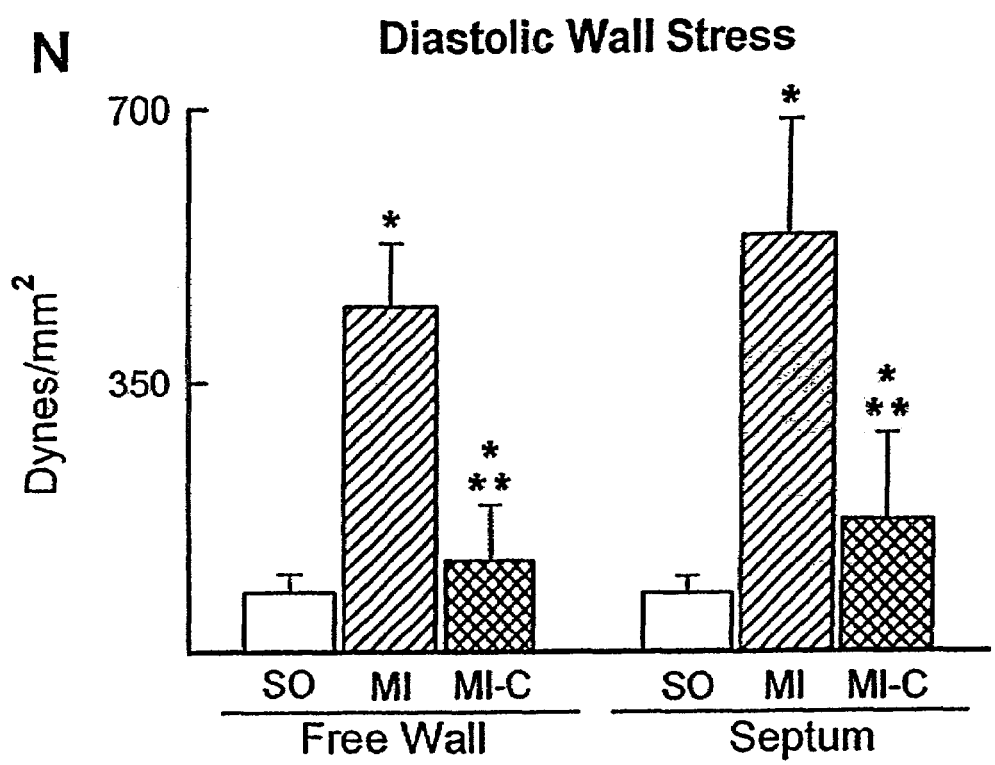

EF was 48%, 62% and 114% higher in treated than in non-treated mice at 9, 16 and 26 days after coronary occlusion, respectively (FIG. 15D). In mice exposed to cytokines, contractile function developed with time in the infarcted region of the wall (FIGS. 15E-M; FIGS. 16H-P, www.pnas.org). Conversely, LV end-diastolic pressure (LVEDP) increased 76% more in non-treated mice. The changes in LV systolic pressure (not shown), developed pressure (LVDP), + and −dP/dt were also more severe in the absence of cytokine treatment (FIGS. 17A-D). Additionally, the increase in diastolic stress in the zone bordering and remote from infarction was 69-73% lower in cytokine-treated mice (FIG. 15N). Therefore, cytokine-mediated infarct repair restored a noticeable level of contraction in the regenerating myocardium, decreasing diastolic wall stress and increasing ventricular performance. Myocardial regeneration attenuated cavitary dilation and mural thinning during the evolution of the infarcted heart in vivo.

Figure 16:
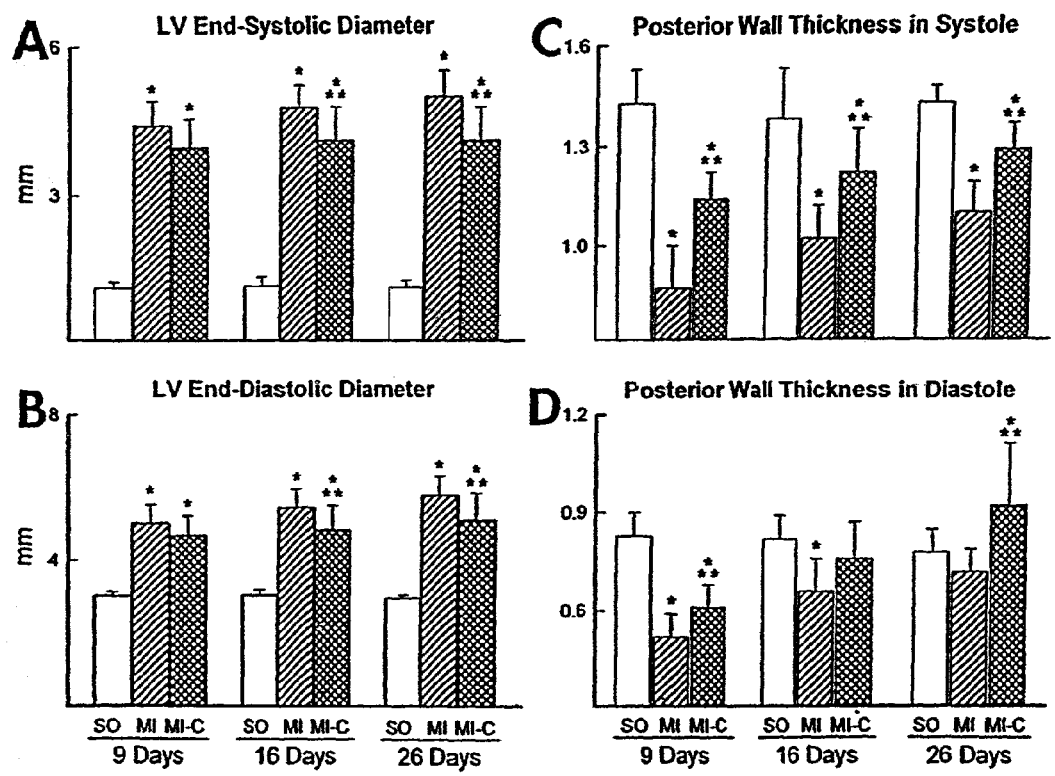
FIGS. 16A-G show grafts depicting aspects of myocardial infarction, cardiac anatomy and ventricular function (FIGS. 16A-D show echocardiographic LVESD (a), LVEDD (b), PWST (c) and PWDT (d) in SO (n=9), MI (n=9) and MI-C (n=9).
FIGS. 16H-P show two dimensional (2D) images and M-mode tracings of SO (h-j), MI (k-m) and MI-C (n-p)
Figure 16:
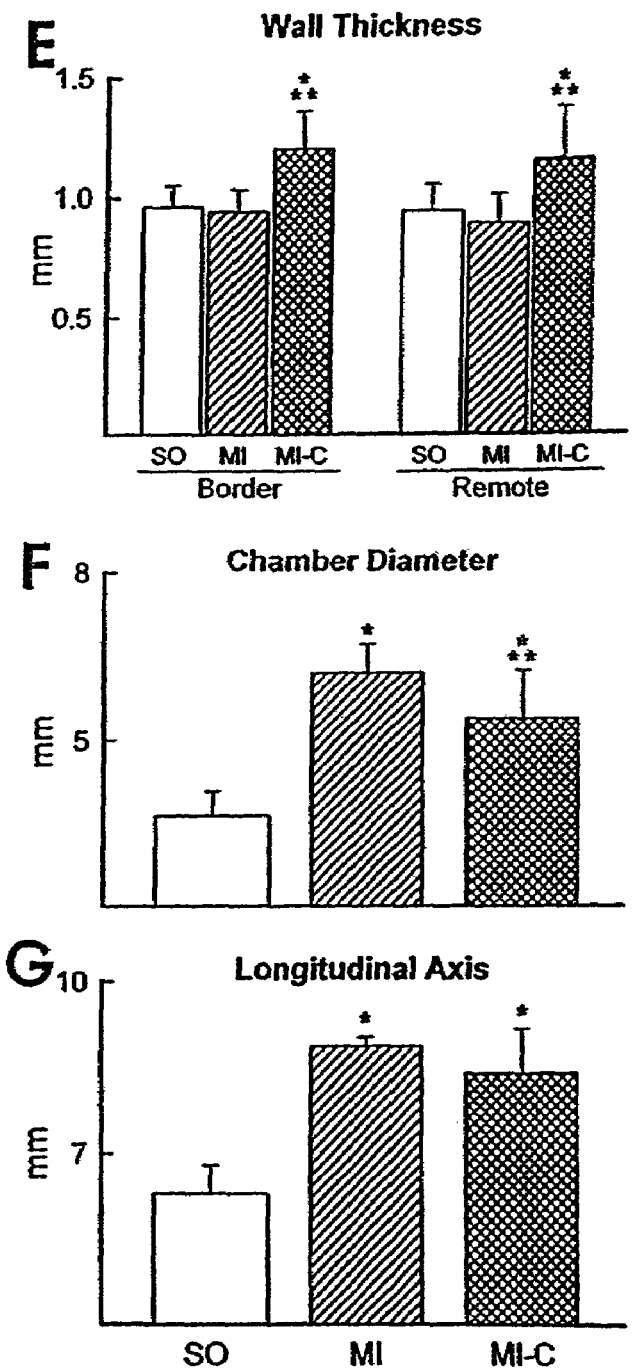
Figure 16:
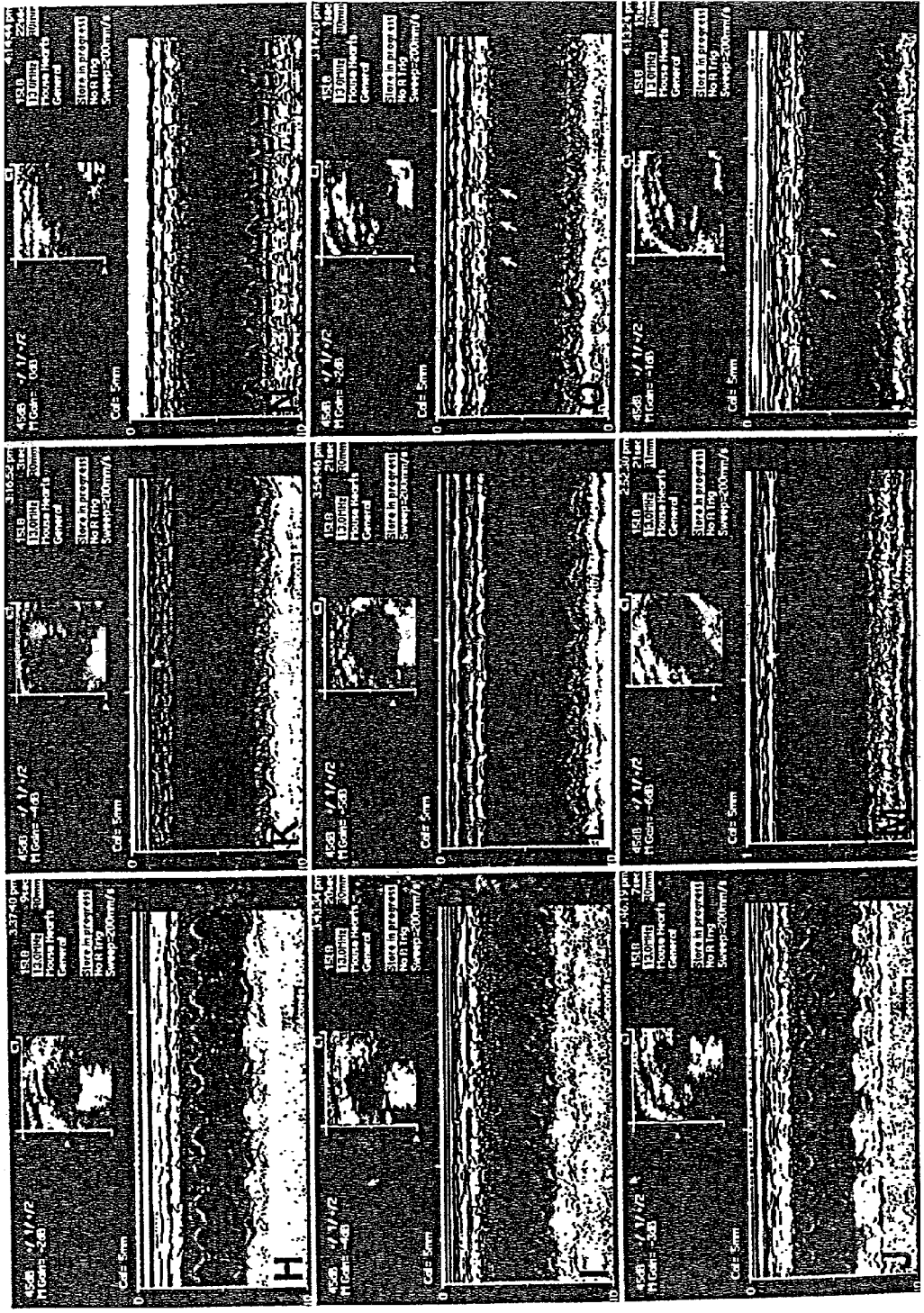
Figure 17:
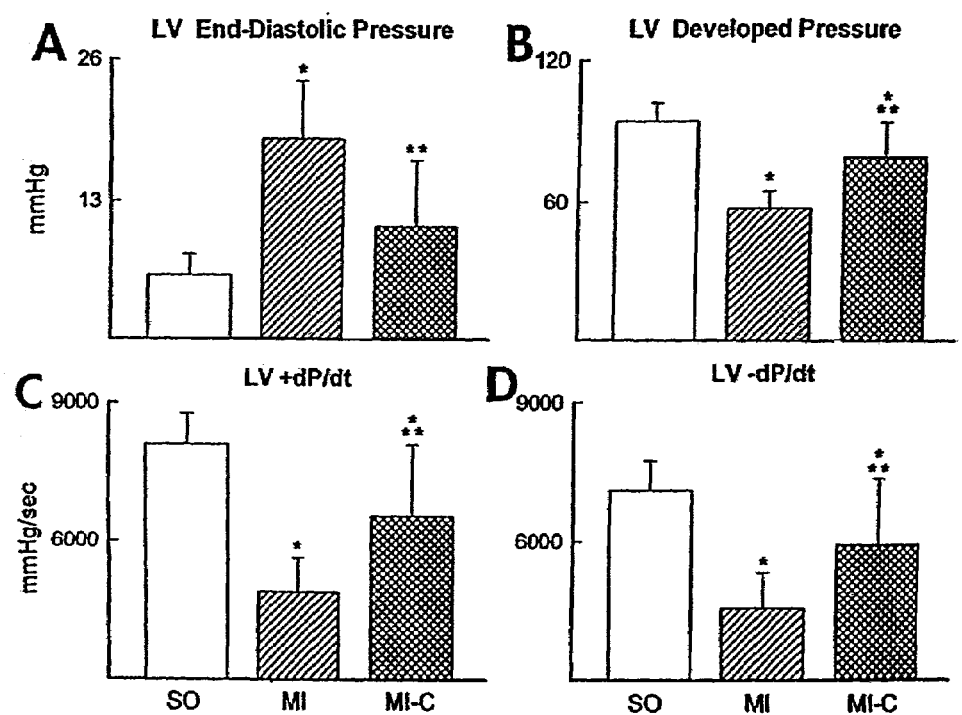
FIG. 17 (FIGS. 17A-D) shows graphs depicting aspects of ventricular function (FIGS. 17A-D show LV hemodynamics in anesthetized mice at sacrifice, 27 days after infarction or sham operation; SO (n=9), MI (n=9) and MI-C (n=10). For symbols and statistics, see also FIG. 13)

Echocardiographically, LV end-systolic (LVESD) and end-diastolic (LVEDD) diameters increased more in non-treated than in cytokine-treated mice, at 9, 16 and 26 days after infarction (FIGS. 16A-B). Infarction prevented the evaluation of systolic (AWST) and diastolic (AWDT) anterior wall thickness. When measurable, the posterior wall thickness in systole (PWST) and diastole (PWDT) was greater in treated mice (FIGS. 16C-D). Anatomically, the wall bordering and remote from infarction was 26% and 22% thicker in cytokine-injected mice (FIG. 16E). BMC-induced repair resulted in a 42% higher wall thickness-to-chamber radius ratio (FIG. 15A). Additionally, tissue regeneration decreased the expansion in cavitary diameter, −14%, longitudinal axis, −5% (FIGS. 16F-G), and chamber volume, −26% (FIG. 15B). Importantly, ventricular mass-to-chamber volume ratio was 36% higher in treated animals (FIG. 15C). Therefore, BMC mobilization that led to proliferation and differentiation of a new population of myocytes and vascular structures attenuated the anatomical variables which define cardiac decompensation.

C. Cardiac Anatomy and Determination of Infarct Size.

Following hemodynamic measurements, the abdominal aorta was cannulated, the heart was arrested in diastole with $CdCl_2$ and the myocardium was perfused with 10% formalin. The LV chamber was filled with fixative at a pressure equal to the in vivo measured end-diastolic pressure (Li et al., 1997; Li et al., 1999). The LV intracavitary axis was measured and three transverse slices from the base, mid-region and apex were embedded in paraffin. The mid-section was used to measure LV thickness, chamber diameter and volume (Li et al., 1997; Li et al., 1999). Infarct size was determined by the number of myocytes lost from the LVFW (Olivetti et al., 1991; Beltrami et al., 1994).

Figure 18:
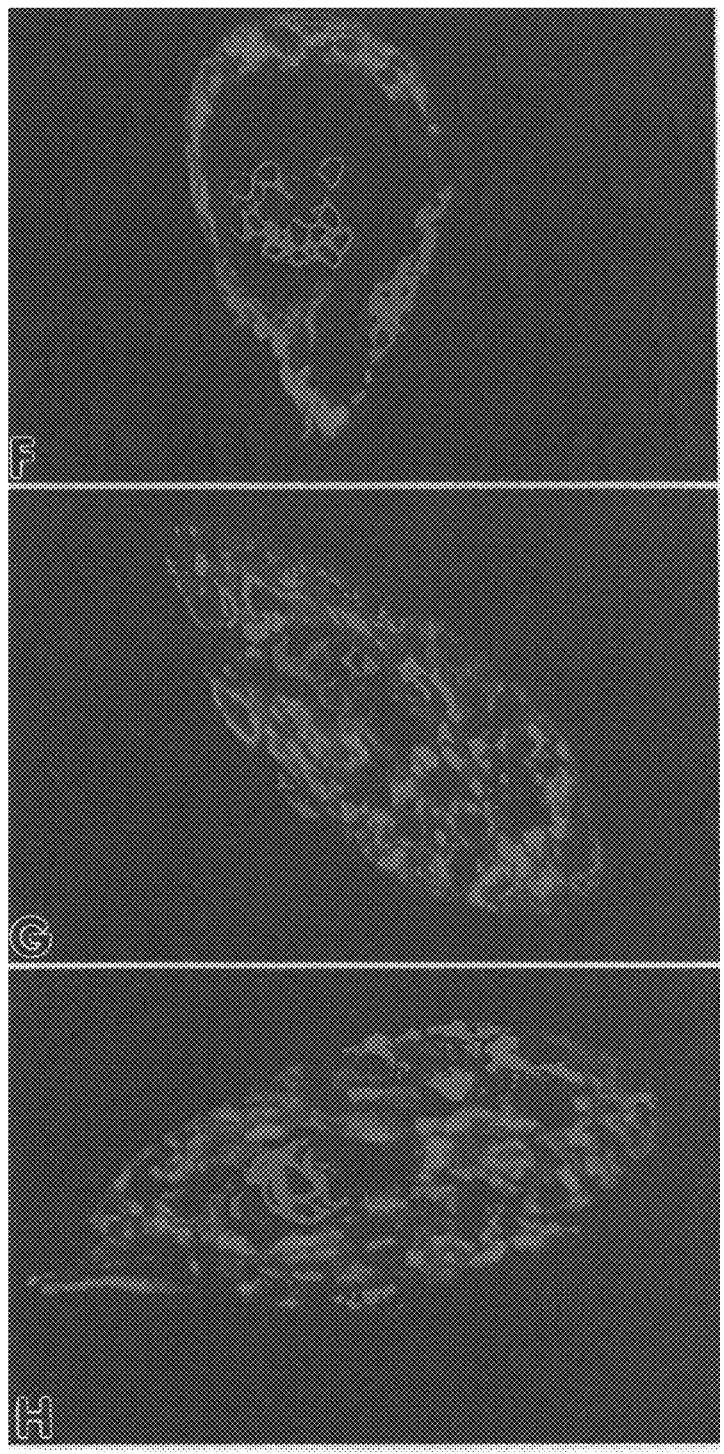
FIG. 18A-E shows graphs of aspects of myocardial regeneration (FIG. 18A classifies the cells in the tissue as remaining viable (Re), lost (Lo) and newly formed (Fo) myocardium in LVFW at 27 days in MI and MI-C; SO, myocardium without infarct.
FIGS. 18F-H show photographs of tissue sections from MI induced mice depicting arterioles with TER-119 labeled erythrocyte membrane (green fluorescence); blue fluorescence=PI staining of nuclei; red fluorescence=α-smooth muscle actin in SMC (FIG. 18F is magnified at 800×.

To quantify the contribution of the developing band to the ventricular mass, firstly the volume of the LVFW (weight divided by 1.06 g/ml) was determined in each group of mice. The data was $56\pm2$ $mm^3$ in sham operated (SO), $62\pm4$ $mm^3$ (viable FW=$41\pm3$; infarcted FW=$21\pm4$) in infarcted non-treated animals, and $56\pm9$ $mm^3$ (viable FW=$37\pm8$; infarcted FW=$19\pm5$) in infarcted cytokine-treated mice. These values were compared to the expected values of spared and lost myocardium at 27 days, given the size of the infarct in the non-treated and cytokine-treated animals. From the volume of the LVFW (56 $mm^3$) in SO and infarct size in non-treated, 62%, and treated, 64%, mice, it was possible to calculate the volume of myocardium destined to remain (non-treated=21 $mm^3$; treated=20 $mm^3$) and destined to be lost (non-treated=35 $mm^3$; treated=36 $mm^3$) 27 days after coronary occlusion (FIG. 18A). The volume of newly formed myocardium was detected exclusively in cytokine-treated mice and found to be 14 $mm^3$ (FIG. 18A). Thus, the repair band reduced infarct size from 64% (36 $mm^3$/56 $mm^3$=64%) to 39% [(36 $mm^3$−14 $mm^3$)/56 $mm^3$=39%]. Since the spared portion of the LVFW at 27 days was 41 and 37 $mm^3$ in non-treated and treated mice (see above), the remaining myocardium, shown in FIG. 18a, underwent 95% ($p<0.001$) and 85% ($p<0.001$) hypertrophy, respectively. Consistently, myocyte cell volume increased 94% and 77% (FIG. 18B).

D. Determination the Total Volume of Formed Myocardium

The volume of regenerating myocardium was determined by measuring in each of three sections the area occupied by the restored tissue and section thickness. The product of these two variables yielded the volume of tissue repair in each section. Values in the three sections were added and the total volume of formed myocardium was obtained. Additionally, the volume of 400 myocytes was measured in each heart. Sections were stained with desmin and laminin antibodies and propidium iodide (PI). Only longitudinally oriented cells with centrally located nuclei were included. The length and diameter across the nucleus were collected in each myocyte to compute cell volume, assuming a cylindrical shape (Olivetti et al., 1991; Beltrami et al., 1994). Myocytes were divided in classes and the number of myocytes in each class was calculated from the quotient of total myocyte class volume and average cell volume (Kajstura et al., 1995; Reiss et al., 1996). Number of arteriole and capillary profiles per unit area of myocardium was measured as previously done (Olivetti et al., 1991; Beltrami et al., 1994).

Sections were incubated with BrdU or Ki67 antibody. Myocytes (M) were recognized with a mouse monoclonal anti-cardiac myosin, endothelial cells (EC) with a rabbit polyclonal anti-factor VIII and smooth muscle cells (SMC) with a mouse monoclonal anti-α-smooth muscle actin myosin. The fractions of M, EC and SMC nuclei labeled by BrdU and Ki67 were obtained by confocal microscopy (Orlic et al., 2001). Nuclei sampled in 11 cytokine-treated mice; BrdU: M=3,541; EC=2,604; SMC=1,824. Ki67: M=3,096; EC=2,465; SMC=1,404.

Figure 19:
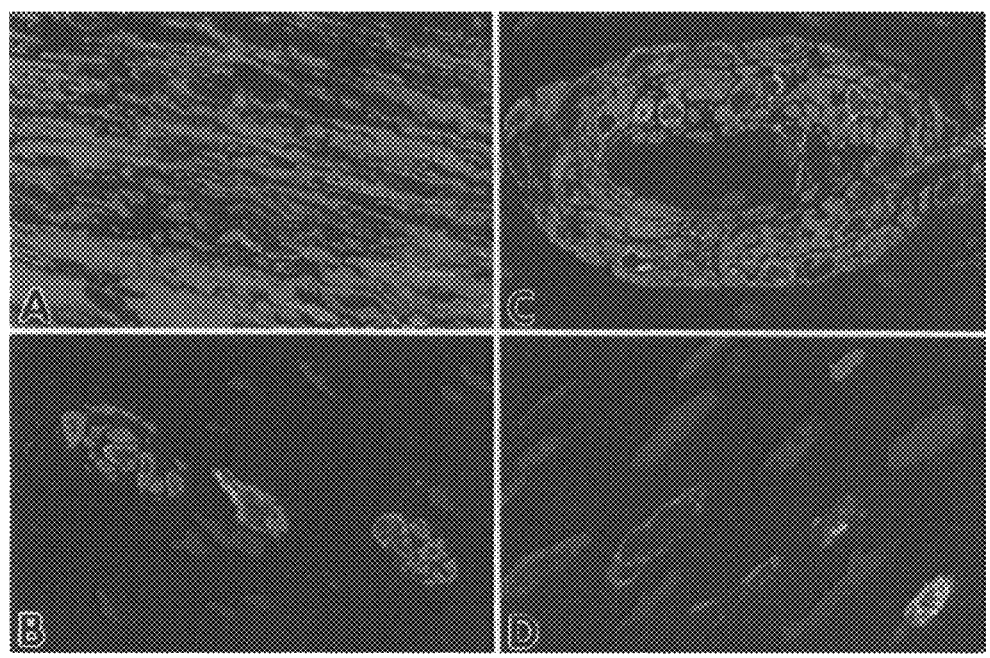
FIG. 19 (FIGS. 19A-D) shows photographs of tissue sections from MI induced mice that were incubated with antibodies to Ki67 (A,B) and BrdU (C,D) (FIG. 19A shows labeling of myocytes by cardiac myosin. Bright fluorescence of nuclei reflects the combination of PI and Ki67. Magnification is 800×.

BrdU was injected daily between days 14 to 26 to measure the cumulative extent of cell proliferation while Ki67 was assayed to determine the number of cycling cells at sacrifice. Ki67 identifies cells in G1, S, G2, prophase and metaphase, decreasing in anaphase and telophase (Orlic et al., 2001). The percentages of BrdU and Ki67 positive myocytes were 1.6- and 1.4-fold higher than EC, and 2.8- and 2.2-fold higher than SMC, respectively (FIG. 18C, 19). The forming myocardium occupied 76±11% of the infarct; myocytes constituted 61±12%, new vessels 12±5% and other components 3±2%. The band contained $15 \times 10^6$ regenerating myocytes that were in an active growing phase and had a wide size distribution (FIGS. 18D-E). EC and SMC growth resulted in the formation of 15±5 arterioles and 348±82 capillaries per mm² of new myocardium. Thick wall arterioles with several layers of SMC and luminal diameters of 10-30 μm represented vessels in early differentiation. At times, incomplete perfusion of the coronary branches within the repairing myocardium during the fixation procedure led to arterioles and capillaries containing erythrocytes (FIGS. 18F-H). These results provided evidence that the new vessels were functionally competent and connected with the coronary circulation. Therefore, tissue repair reduced infarct size and myocyte growth exceeded angiogenesis; muscle mass replacement was the prevailing feature of the infarcted heart.

E. Determination of Cell Differentiation

Cytoplasmic and nuclear markers were used. Myocyte nuclei: rabbit polyclonal Csx/Nkx2.5, MEF2, and GATA4 antibodies (Orlic et al., 2001; Lin et al., 1997; Kasahara et al., 1998); cytoplasm: mouse monoclonal nestin (Kachinsky et al., 1995), rabbit polyclonal desmin (Hermann and Aebi, 1998), cardiac myosin, mouse monoclonal α-sarcomeric actin and rabbit polyclonal connexin 43 antibodies (Orlic et al., 2001). EC cytoplasm: mouse monoclonal flk-1, VE-cadherin and factor VIII antibodies (Orlic et al., 2001; Yamaguchi et al., 1993; Breier et al., 1996). SMC cytoplasm: flk-1 and α-smooth muscle actin antibodies (Orlic et al., 2001; Couper et al., 1997). Scar was detected by a mixture of collagen type I and type III antibodies.

Figure 20:
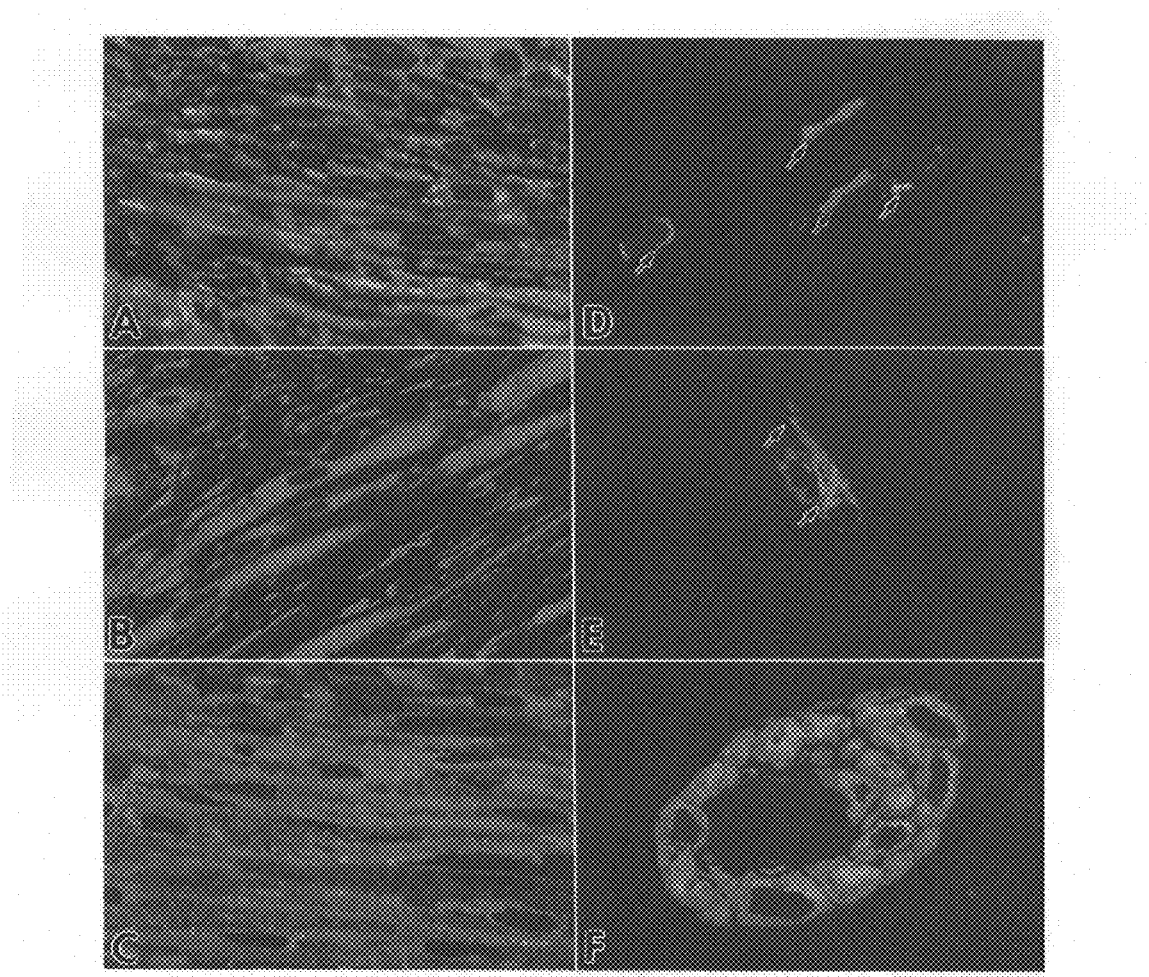
FIG. 20 (FIGS. 20A-F) shows photographs of tissue sections from MI induced mice showing markers of differentiating cardiac cells (FIG. 20A is stained to show labeling of myocytes by nestin (yellow)). Red fluorescence indicates cardiac myosin. Magnification is 1,200×.
Figure 21:
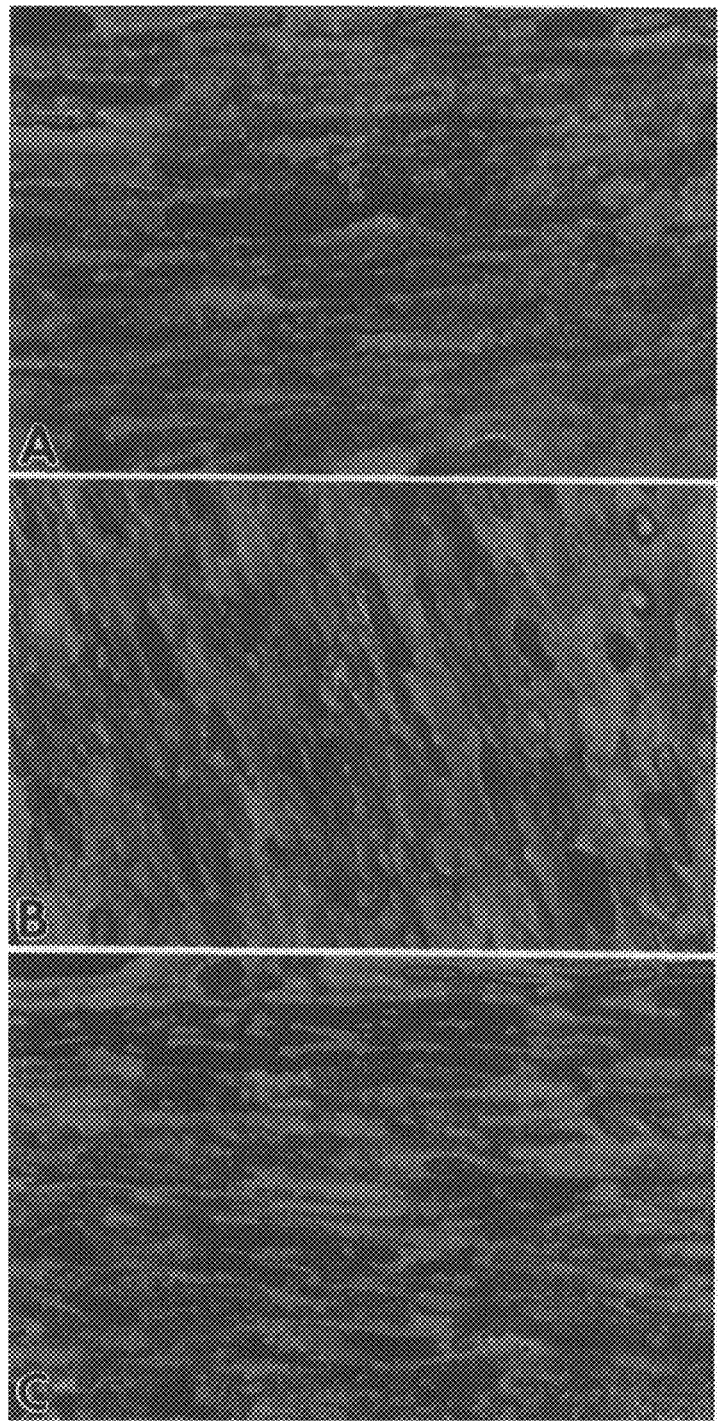
FIGS. 21A-C show tissue sections from MI induced mice (FIG. 21A uses bright fluorescence to depict the combination of PI labeling of nuclei with Csx/Nkx2.5. Magnification is 1,400×.

Five cytoplasmic proteins were identified to establish the state of differentiation of myocytes (Orlic et al., 2001; Kachinsky et al., 1995; Hermann and Aebi, 1998): nestin, desmin, α-sarcomeric actin, cardiac myosin and connexin 43. Nestin was recognized in individual cells scattered across the forming band (FIG. 20A). With this exception, all other myocytes expressed desmin (FIG. 20B), α-sarcomeric actin, cardiac myosin and connexin 43 (FIG. 20C). Three transcription factors implicated in the activation of the promoter of several cardiac muscle structural genes were examined (Orlic et al., 2001; Lin et al., 1997; Kasahara et al., 1998): Csx/Nkx2.5, GATA-4 and MEF2 (FIGS. 21A-C). Single cells positive for flk-1 and VE-cadherin (Yamaguchi et al., 1993; Breier et al., 1996), two EC markers, were present in the repairing tissue (FIGS. 20D,E); flk-1 was detected in SMC isolated or within the arteriolar wall (FIG. 20F). This tyrosine kinase receptor promotes migration of SMC during angiogenesis (Couper et al., 1997). Therefore, repair of the infarcted heart involved growth and differentiation of all cardiac cell populations resulting in de novo myocardium.

Example 3

Migration of Primitive Cardiac Cells in the Adult Mouse Heart

To determine whether a population of primitive cells was present in the adult ventricular myocardium and whether these cells possessed the ability to migrate, three major growth factors were utilized as chemoattractants: hepatocyte growth factor (HGF), stem cell factor (SCF) and granulocyte monocyte colony stimulating factor (GM-CSF). SCF and GMCSF were selected because they have been shown to promote translocation of herriatopoietic stem cells. Although HGF induces migration of hematopoietic stem cells, this growth factor is largely implicated in mitosis, differentiation and migration of cardiac cell precursors during early cardiogenesis. On this basis, enzymatically dissociated cells from the mouse heart were separated according to their size. Methods for dissociating cardiac cells from heart tissue are well-known to those skilled in the art and therefore would not involve undue experimentation (Cf U.S. Pat. No. 6,255,292 which is herein incorporated by reference in its entirety) A homogenous population of the dissociated cardiac cells containing small undifferentiated cells, 5-7 μm in diameter, with a high nucleus to cytoplasm ratio were subjected to migration assay in Boyden microchambers characterized by gelatin-coated filters containing pores, 5 μm (Boyden et al., 1962, J. Exptl. Med. 115:453-456)

No major differences in the dose-response curve of migrated cells in the presence of the three growth factors were detected. However, HGF appeared to mobilize a larger number of cells at a concentration of 100 ng/ml. In addition, the cells that showed a chemotactic response to HGF consisted of 15% of c-kit positive (c-kit$^{POS}$) cells, 50% of multidrug resistance-1 (MDR-1) labeled cells and 30% of stem cell antigen-1 (Sca-1) expressing cells. When the mobilized cells were cultured in 15% fetal bovine serum, they differentiated into myocytes, endothelial cells, smooth muscle cells and fibroblasts. Cardiac myosin positive myocytes constituted 50% of the preparation, while factor VIII labeled cells included 15%, alpha-smooth muscle actin stained cells 4%, and vimentin positive factor VIII negative fibroblasts 20%. The remaining cells were small undifferentiated and did not stain with these four antibodies. In conclusion, the mouse heart possesses primitive cells which are mobilized by growth factors. HGF translocates cells that in vitro differentiate into the four cardiac cell lineages.

Example 4

Cardiac C-Kit Positive Cells Proliferate In Vitro and Generate New Myocardium Vivo To determine whether primitive c-kit$^{POS}$ cells were present in senescent Fischer 344 rats, dissociated cardiac cells were exposed to magnetic beads coated with c-kit receptor antibody (ACK-4-biotin, anti-c-kit mAb). Following separation, these small undifferentiated cells were cultured in 10% fetal calf serum. Cells attached in a few days and began to proliferate at one week. Confluence was reached at 7-10 days. Doubling time, established at passage P2 and P4, required 30 and 40 hours, respectively. Cells grew up to P18 (90th generation) without reaching senescence. Replicative capacity was established by Ki67 labeling: at P2, 88±14% of the cells contained Ki67 protein in nuclei. Additional measurements were obtained between P1 and P4; 40% of cells expressed alpha-sarcomeric actin or cardiac myosin, 13% desmin, 3% alpha-smooth muscle actin, 15% factor VIIII or CD31, and 18% nestin. Under these in vitro conditions, cells showed no clear myofibrillar organization with properly aligned sarcomeres and spontaneous contraction was never observed. Similarly, Ang II, norepinephrine, isoprotererol, mechanical stretch and electrical field stimulation failed to initiate contractile function. On this basis, it was decided to evaluate whether these cells pertaining to the myogenic, smooth muscle cell and endothelial cell lineages had lost permanently their biological properties or their role could be reestablished in vivo. Following BrdU labeling of cells at P2, infarcted Fischer 344 rats were injected with these BrdU positive cells in the damaged region, 3-5 hours after coronary artery occlusion. Two weeks later, animals were sacrificed and the characteristics of the infarcted area were examined. Myocytes containing parallel arranged myofibrils along their longitudinal axis were recognized, in combination with BrdU labeling of nuclei. Moreover, vascular structures comprising arterioles and capillary profiles were present and were also positive to BrdU. In conclusion, primitive c-kit positive cells reside in the senescent heart and maintain the ability to proliferate and differentiate into parenchymal cells and coronary vessels when implanted into injured functionally depressed myocardium.

Example 5

Cardiac Stem Cells Mediate Myocyte Replication in the Young and Senescent Rat Heart The heart is not a post-mitotic organ but contains a subpopulation of myocytes that physiologically undergo cell division to replace dying cells. Myocyte multiplication is enhanced during pathologic overloads to expand the muscle mass and maintain cardiac performance. However, the origin of these replicating myocytes remains to be identified. Therefore, primitive cells with characteristics of stem/progenitor cells were searched for in the myocardium of of Fischer 344 rats. Young and old animals were studied to determine whether aging had an impact on the size population of stem cells and dividing myocytes. The numbers of c-kit and MDR1 positive cells in rats at 4 months were 11±3, and 18±6/100 mm$^2$ of tissue, respectively. Values in rats at 27 months were 35±10, and 42±13/100 mm$^2$. A number of newly generated small myocytes were identified that were still c-kit or MDR1 positive. Ki67 protein, which is expressed in nuclei of cycling cells was detected in 1.3±0.3% and 4.1±1.5% of myocytes at 4 and 27 months, respectively. BrdU localization following 6 or 56 injections included 1.0±0.4% and 4.4±1.2% at 4 months, and 4.0±1.5% and 16±4% at 27 months. The mitotic index measured in tissue sections showed that the fraction of myocyte nuclei in mitosis comprised 82±28/10$^6$ and 485±98/10$^6$ at 4 and 27 months, respectively. These determinations were confirmed in dissociated myocytes to obtain a cellular mitotic index. By this approach, it was possible to establish that all nuclei of multinucleated myocytes were in mitosis simultaneously. This information could not be obtained in tissue sections. The collected values showed that 95±31/10$^6$ myocytes were dividing at 4 months and 620±98/10$^6$ at 27 months. At both age intervals, the formation of the mitotic spindle, contractile ring, disassembly of the nuclear envelope, karyokinesis and cytokinesis were documented. In conclusion, primitive undifferentiated cells reside in the adult heart and their increase with age is paralleled by an increase in the number of myocytes entering the cell cycle and undergoing karyokinesis and cytokinesis. This relationship suggests that cardiac stem cells may regulate the level and fate of myocyte growth in the aging heart.

Example 6

Chimerism of the Human Heart and the Role of Stem Cells

The critical role played by resident primitive cells in the remodeling of the injured heart is well appreciated when organ chimerism, associated with transplantation of a female heart in a male recipient, is considered. For this purpose, 8 female hearts implanted in male hosts were analyzed. Translocation of male cells to the grafted female heart was identified by FISH for Y chromosome (see Example 1E). By this approach, the percentages of myocytes, coronary arterioles and capillary profiles labeled by Y chromosome were 9%, 14% and 7%, respectively. Concurrently, the numbers of undifferentiated c-kit and multidrug resistance-1 (MDR1) positive cells in the implanted female hearts were measured. Additionally, the possibility that these cells contained the Y chromosome was established. Cardiac transplantation involves the preservation of portions of the atria of the recipient on which the donor heart with part of its own atria is attached. This surgical procedure is critical for understanding whether the atria from the host and donor contained undifferentiated cells that may contribute to the complex remodeling process of the implanted heart. Quantitatively, the values of c-kit and, MDR1 labeled cells were very low in control non-transplanted hearts: 3 c-kit and 5 MDR1/100 mm$^2$ of left ventricular myocardium. In contrast, the numbers of c-kit and MDR1 cells in the atria of the recipient were 15 and 42/100 mm$^2$. Corresponding values in the atria of the donor were 15 and 52/100 mm$^2$ and in the ventricle 11 and 21/100 mm$^2$. Transplantation was characterized by a marked increase in primitive undifferentiated cells in the heart. Stem cells in the atria of the host contained Y chromosome, while an average of 55% and 63% of c-kit and MDR1 cells in the donor's atria and ventricle, respectively, expressed the Y chromosome. All c-kit and MDR1 positive cells were negative for CD45. These observations suggest that the translocation of male cells to the implanted heart has a major impact on the restructuring of the donor myocardium. In conclusion, stem cells are widely distributed in the adult heart and because of their plasticity and migration capacity generate myocytes, coronary arterioles and capillary structures with high degree of differentiation.

Example 7

Identification and Localization of Stem Cells in the Adult Mouse Heart

Turnover of myocytes occurs in the normal heart, and myocardial damage leads to activation of myocyte proliferation and vascular growth. These adaptations raise the possibility that multipotent primitive cells are present in the heart and are implicated in the physiological replacement of dying myocytes and in the cellular growth response following injury. On this basis, the presence of undifferentiated cells in the normal mouse heart was determined utilizing surface markers including c-kit, which is the receptor for stem cell factor, multidrug resistance-1 (MDR1), which is a P-glycoprotein capable of extruding from the cell dyes, toxic substances and drugs, and stem cell antigen-1 (Sca-1), which is involved in cell signaling and cell adhesion. Four separate regions consisting of the left and right atria, and the base, mid-section and apical portion of the ventricle were analyzed. From the higher to the lower value, the number of c-kit positive cells was 26±11, 15±5, 10±7 and 6±3/100 mm² in the atria, and apex, base and mid-section of the ventricle, respectively. In comparison with the base and mid-section, the larger fraction of c-kit positive cells in the atria and apex was statistically significant. The number of MDR1 positive cells was higher than those expressing c-kit, but followed a similar localization pattern; 43±14, 29±16, 14±7 and 12±10/100 mm² in the atria, apex, base and mid-section. Again, the values in the atria and apex were greater than in the other two areas. Sca-1 labeled cells showed the highest value; 150±36/100 mm² positive cells were found in the atria. Cells positive for c-kit, MDR1 and Sca-1 were negative for CD45, and for myocyte, endothelial cell, smooth muscle cell and fibroblast cytoplasmic proteins. Additionally, the number of cells positive to both c-kit and MDR1 was measured to recognize cells that possessed two stem cell markers. In the entire heart, 36% of c-kit labeled cells expressed MDR1 and 19% of MDR1 cells had also c-kit. In conclusion, stem cells are distributed throughout the mouse heart, but tend to accumulate in the regions at low stress, such as the atria and the apex.

Example 8

Repair of Infarcted Myocardium by Resident Cardiac Stem Cells

Migration, Invasion and Expression Assays

The receptor of HGF, c-Met, has been identified on hematopoietic and hepatic stem cells (126, 90) and, most importantly, on satellite skeletal muscle cells (92) and embryonic cardiomyocytes (127). These findings prompted us to determine whether c-Met was present in CSCs and its ligand HGF had a biological effect on these undifferentiated cells. The hypothesis was made that HGF promotes migration and invasion of CSCs in vitro and favors their translocation from storage areas to sites of infarcted myocardium in vivo. HGF influences cell migration (128) through the expression and activation of matrix metalloproteinase-2 (94, 95). This enzyme family may destroy barriers in the extracellular matrix facilitating CSC movement, homing and tissue restoration.

IGF-1 is mitogenic, antiapoptotic and is necessary for neural stem cell multiplication and differentiation (96, 97, 98). If CSCs express IGF-1R, IGF-1 may impact in a comparable manner on CSCs protecting their viability during migration to the damaged myocardium. IGF-1 overexpression is characterized by myocyte proliferation in the adult mouse heart (65) and this form of cell growth may depend on CSC activation, differentiation and survival.

In the initial part of this study, migration and invasion assays were conducted to establish the mobility properties of c-kit$^{POS}$ and MDR1$^{POS}$ cells in the presence of the chemotactic HGF. Cardiac cells were enzymatically dissociated and myocytes were discarded (124). Small cells were resuspended in serum-free medium (SFM). Cell migration was measured by using a modified Boyden chamber that had upper and lower wells (Neuro Probe, Gaithersburg, Md.). The filter for the 48-well plate consisted of gelatin-coated polycarbonate membrane with pores of 5 µm in diameter. The bottom well was filled with SFM containing 0.1% BSA and HGF at increasing concentrations; 50 µl of small cell suspension were placed in the upper well. Five hours later, filters were fixed in 4% paraformaldheyde for 40 minutes and stained with PI, and c-kit and MDR1 antibodies. FITC-conjugated anti-IgG was used as a secondary antibody. Six separate experiments were done at each HGF concentration. Forty randomly chosen fields were counted in each well in each assay to generate a dose-response curve (FIG. 61). The motogenic effects of IGF-1 on small cells was excluded by performing migration assays with IGF-1 alone or in combination with HGF (data not shown). Invasion assays were done utilizing a chamber with 24-wells and 12 cell culture inserts (Chemicon, Temecula, Calif.). A thin layer of growth factor-depleted extracellular matrix was spread on the surface of the inserts. Conversely, 100 ng/ml of HGF were placed in the lower chamber. Invading cells digested the coating and clung to the bottom of the polycarbonate membrane. The number of translocated cells was measured 48 hours later following the same protocol described in the migration assay. Four separate experiments were done (FIG. 62). Consistent with the results obtained in the migration assay, IGF-1 had no effects on cell invasion (data not shown).

Migration was similar in both cell types and reached its peak at 100 ng/ml HGF. At 5 hours, the number of c-kit$^{POS}$ and MDR1$^{POS}$ cells transmigrated into the lower chamber was 3-fold and 2-fold higher than control cells, respectively. Larger HGF concentrations did not improve cell migration (FIGS. 61 and 62). On this basis, HGF at 100 ng/ml was also employed to determine the ability of c-kit$^{POS}$ and MDR1$^{POS}$ cells to penetrate the synthetic extracellular matrix of the invasion chamber. In 48 hours, the growth factor increased by 8-fold and 4-fold the number of c-kit$^{POS}$ and MDR1$^{POS}$ cells in the lower portion of the chamber (FIGS. 61 and 62), respectively. IGF-1 had no effect on the mobility of these CSCs at concentrations varying from 25 to 400 ng/ml. The addition of IGF-1 to HGF did not modify the migration and invasion characteristics of c-kit$^{POS}$ and MDR1$^{POS}$ cells obtained by HGF alone.

Small, undifferentiated c-Met$^{POS}$ cells were collected with immunomagnetic beads and the ability of these cells to cleave gelatin was evaluated by zymography (FIG. 63). Briefly, small cells were isolated from the heart (n=4) and subsequently separated by microbeads (Miltenyi, Auburn, Calif.) coated with c-Met antibody. Cells were exposed to HGF, 100 ng/ml, for 30 minutes at 37° C. Cell lysates were run onto 10% polyacrylamide gels copolymerized with 0.1% gelatin (Invitrogen, Carlsbad, Calif.). The gels were incubated in Coomassie blue staining solution (0.5%) and areas of gelatinolytic activity were detected as clear bands against a gray background. This was done to demonstrate whether c-Met$^{POS}$ cells expressed matrix metalloproteinases (MMPs) and were capable of digesting the substrate present in the gel (94, 95). Positive results were obtained (FIG. 63), suggesting that the mobility of these primitive cells was due, at least in part, to activation of MMPs. Together, these in vitro assays point to the chemotactic function of HGF on CSCs. Such a role of HGF appears to be mediated by its binding to c-Met receptors and the subsequent stimulation of MMP synthesis (94, 95).

Myocardial Infarction in Mice

Myocardial infarction was produced in mice and 5 hours later 4 separate injections of a solution containing HGF and IGF-1 were performed from the atria to the border zone. HGF was administrated at increasing concentrations to create a chemotactic gradient between the stored CSCs and the dead tissue. This protocol was introduced to enhance homing of CSCs to the injured area and to generate new myocardium. If this were the case, large infarcts associated with animal death may be rapidly reduced and the limits of infarct size and survival extended by this intervention.

Female 129 SV-EV mice were used. Following anesthesia (150 mg ketamine-1 mg acepromazine/kg b.w., i.m.), mice were ventilated, the heart was exposed and the left coronary artery was ligated (61, 87). Coronary ligation in animals to be treated with growth factors was performed as close as possible to the aortic origin to induce very large infarcts. Subsequently, the chest was closed and animals were allowed to recover. Five hours later, mice were anesthetized, the chest was reopened and four injections of HGF-IGF-1, each of 2.5 µl, were made from the atria to the region bordering the infarct. The last two injections were done at the opposite sides of the border zone. The concentration of HGF was increased progressively in the direction of the infarct, from 50 to 100 and 200 ng/ml. IGF-1 was administered at a constant concentration of 200 ng/ml. Mice were injected with BrdU (50 mg/kg b.w.) from day 6 to day 16 to identify small, newly formed, proliferating myocytes during this interval. Sham-operated and infarcted-untreated mice were injected with normal saline in the same four sites.

Figure 64:
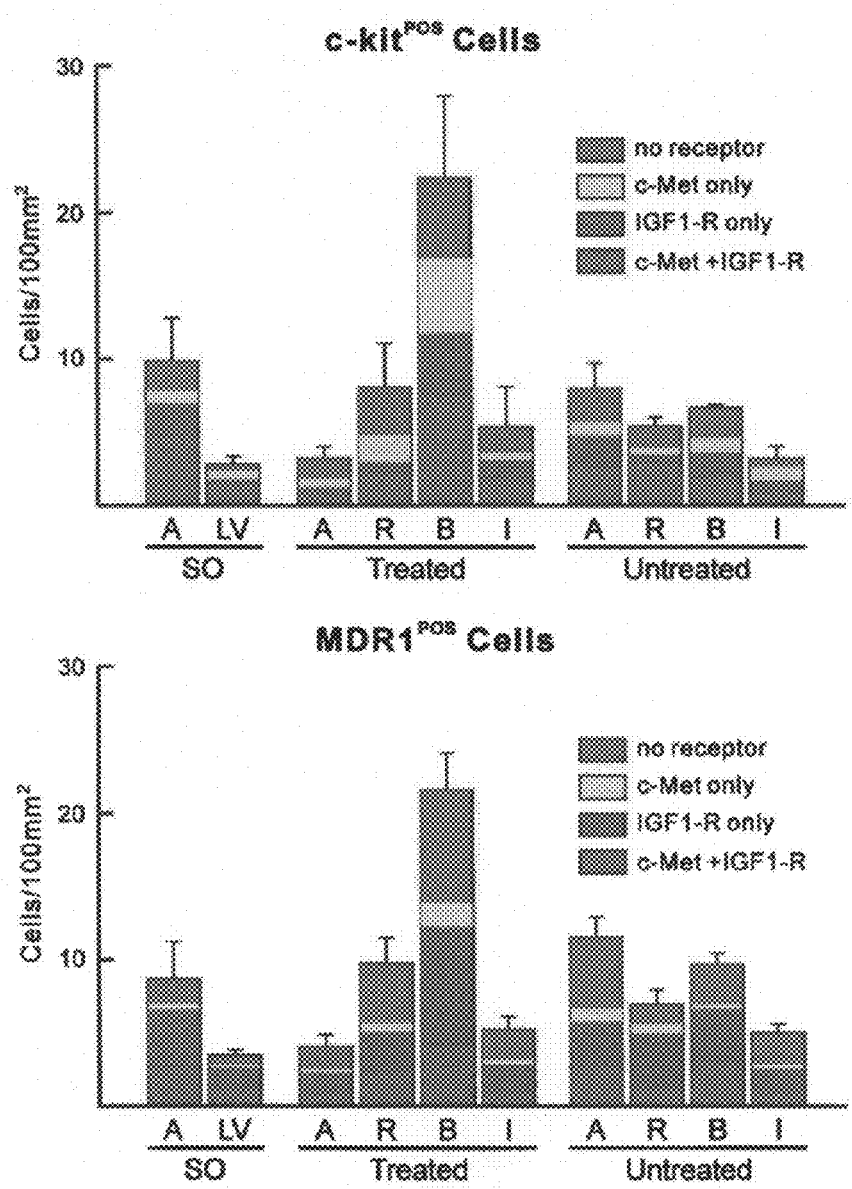

Before discussing the effects of CSCs on organ repair the presence of c-Met and IGF-1R on cells expressing c-kit and MDR1 was measured in the atria and left ventricle (LV) of control mice. An identical analysis was done in the atria and infarcted and non-infarcted LV of mice subjected to coronary artery occlusion. This determination was performed 2-3 hours following the administration of growth factors, which reflected 7-8 hours after coronary occlusion (The objective was to document that primitive cells invaded the dead tissue and the surrounding viable myocardium and that HGF and IGF-1 were implicated in this process.

c-Met and IGF-1R were detected in c-kit$^{POS}$ and MDR1$^{POS}$ cells dispersed in regions of the normal (n=5), infarcted-treated (n=6) and infarcted-untreated (n=5) heart (FIG. 22, A to F). A large fraction of c-kit$^{POS}$ and MDR1$^{POS}$ cells expressed c-Met and IGF-1R alone or in combination. Myocardial infarction and the administration of growth factors did not alter in a consistent manner the relative proportion of CSCs with and without c-Met and IGF-1R in the myocardium (FIG. 64). Hairpin 1 (apoptosis) and hairpin 2 (necrosis) labeling and Ki67 expression in nuclei (cycling cells) were used to establish the viability and activation of c-kit$^{POS}$ and MDR1$^{POS}$ cells in the various portions of the damaged and non-damaged heart, respectively (FIG. 22, G to L).

CSCs were more numerous in the atria than in the ventricle of control mice. Acute myocardial infarction and growth factor administration markedly changed the number and the distribution of primitive cells in the heart. Viable c-kit$^{POS}$ and MDR1$^{POS}$ cells significantly increased in the spared myocardium of the border zone and remote tissue as well as in the dead myocardium of the infarcted region. Importantly, CSCs decreased in the atria (FIG. 22, M and N), suggesting that a translocation of primitive cells occurred from this site of storage to the stressed viable and dead myocardium. A different phenomenon was noted in infarcted-untreated mice, in which viable CSCs remained higher in the atria than in the ventricle. In control animals and infarcted-treated mice, apoptosis and necrosis were not detected in c-kit$^{POS}$ and MDR1$^{POS}$ cells within the infarct and surrounding myocardium. Ki67 labeling was identified in nearly 35% and 20% of undifferentiated cells distributed in the border zone and in the infarct, respectively (FIG. 65). In infarcted-untreated mice, the majority of c-kit$^{POS}$ and MDR1$^{POS}$ cells in the infarct were apoptotic (FIG. 22, M and N). Necrosis was not seen. An apoptotic CSC death gradient was observed from the infarct to the distant myocardium and atrial tissue. In these mice, only 10-14% of the viable c-kit$^{POS}$ and MDR1$^{POS}$ cells expressed Ki67 (FIG. 65).

Thus, these results support the notion that CSCs express c-Met and IGF-1R and, thereby, HGF and IGF-1 have a positive impact on the colonization, proliferation and survival of CSCs in the infarcted heart. On the basis of in vitro and in vivo data, HGF appears to have a prevailing role in cell migration and IGF-1 in cell division and viability. In infarcted-untreated mice, however, CSCs do not translocate to the infarcted region and the pre-existing primitive cells die by apoptosis. The important question was then whether CSCs located within the infarct were capable of differentiating in the various cardiac cell lineages and reconstitute dead myocardium. A positive finding would provide a mechanism for cardiac repair in infarcted-treated mice and a potential explanation for the absence of myocardial regeneration in infarcted-untreated mice.

For anatomical measurements, the heart was arrested in diastole with $CdCl_2$, and the myocardium was perfused with 10% formalin. The LV chamber was filled with fixative at a pressure equal to the in vivo measured end-diastolic pressure. The LV intracavitary axis was determined and the mid-section was used to obtain LV thickness and chamber diameter. Infarct size was measured by the number of myocytes lost from the LV inclusive of the interventricular septum (87).

Myocardial infarction at 16 days resulted in a 42% (n=15) and 67% (n=22) loss of myocytes in the left ventricle and septum of untreated and HGF-IGF-1-treated mice, respectively (FIG. 23A). In spite of a 60% larger infarct, mice exposed to growth factors had a better preservation of cardiac function (FIG. 23B). HGF-IGF-1 led to a smaller elevation in LV end-diastolic pressure and a lesser decrease in +dP/dt and −dP/dt. The difference in infarct size did not influence mortality, which was similar in the two groups of mice: 43% in untreated and 40% in treated. Importantly, 14 of the 22 mice that received growth factors survived with infarcts affecting more than 60% of the LV. Seven of these mice had infarcts that involved 75% to 86% of LV. Untreated mice had infarcts that never exceeded 60% (FIG. 23, C and D). In contrast to injected mice, a portion of the posterior aspect of the LV wall and the entire interventricular septum had to be preserved for untreated animals to survive. An infarct larger than 60% is incompatible with life in mice, rats, dogs and any other mammalian species. Irreversible cardiogenic shock and death supervene in humans with a 46% infarct (99).

From the volume of LV in sham-operated mice and infarct size in untreated and treated animals it was possible to calculate the volume of myocardium destined to remain and destined to be lost 16 days after coronary artery occlusion. The volume of newly formed myocardium inclusive of myocytes, vascular structures and other tissue components was detected exclusively in growth factor-treated mice and found to be 8 mm$^3$. Thus, the repair band reduced infarct size from 67% to 57% (FIGS. 68 and 69).

The chemotactic and mitogenic properties of HGF-IGF-1 resulted in the mobilization, proliferation and differentiation of primitive cells in the infarcted region of the wall creating new myocardium. In spite of the complexity of this methodological approach in small animals, the formation of a myocardial band within the infarct was obtained in 85% of the cases (22 of 26 mice). The band occupied 65±8% of the damaged area and was located in the mid-portion of the infarct equally distant from the inner and outer layer of the wall. In very large infarcts, the entire thickness of the wall was replaced by developing myocardium (FIG. 23, E to H). Anatomically, the longitudinal axis and the chamber diameter were similar in the two groups of infarcted mice indicating that the therapeutic intervention promoted positive ventricular remodeling. This notion was consistent with the 60% larger infarct size in treated mice. Additionally, the wall thickness-to-chamber radius ratio decreased less in treated than in untreated mice. This relationship, in combination with the smaller increase in LV end-diastolic pressure in treated mice significantly attenuated the increase of diastolic wall stress in this group (FIG. 67).

Primitive cells were labeled with monoclonal c-kit and MDR1 antibodies (82, 83). BrdU incorporation was detected by BrdU antibody (61, 87). Endothelial cells were recognized with anti-factor VIII and smooth muscle cells with anti-α-smooth muscle actin. For myocyte differentiation, nestin, desmin, cardiac myosin, α-sarcomeric actin, N-cadherin and connexin 43 antibodies were utilized. Scar formation in the infarct was detected by a mixture of anti-collagen type I and type III (83, 61, 87).).

The composition of the repairing myocardium was evaluated morphometrically. Antibodies specific for myocytes, endothelial cells and smooth muscle cells were employed for the recognition of parenchymal cells and vessel profiles (61, 87). Moreover, BrdU labeling of cells was used as a marker of regenerating tissue over time. Myocytes occupied 84±3% of the band, the coronary vasculature 12±3%, and other structural components 4±1%. New myocytes varied from 600 to 7,200 μm$^3$, with an average volume of 2,200±400 μm$^3$ (FIGS. 68 and 69). Together, 3.1±1.1 million myocytes were formed to compensate for a loss of 2.4±0.8 million cells. This slight excess in cell regeneration was at variance with myocyte size. In sham-operated hearts, myocyte volume, 18,000±3,600 μm$^3$, was 8.2-fold larger than growing cells. Importantly, 16% of the muscle mass lost was reconstituted 16 days after infarction (lost muscle mass: $18,000 \times 2.4 \times 10^6 = 43$ mm$^3$ regenerated muscle mass: $2,200 \times 3.1 \times 10^6 = 7.0$ mm$^3$; 7.0:43=16%). The new myocytes were still maturing, but functionally competent as demonstrated echocardiographically in vivo and mechanically in vitro.

Echocardiography was performed in conscious mice by using an Acuson Sequoia 256c equipped with a 13-MHz linear transducer (87). Two-dimensional images and M-mode tracings were recorded from the parasternal short axis view at the level of papillary muscles. Ejection fraction (EF) was derived from LV cross-sectional area in 2D short axis view: EF=[(LVDA−LVSA)/LVDA]×100, where LVDA and LVSA correspond to LV areas in diastole and systole. For hemodynamics, mice were anesthetized and a Millar microtip pressure transducer connected to a chart recorder was advanced into the LV for the evaluation of pressures and + and − dP/dt in the closed-chest preparation. Echocardiography performed at day 15 showed that contractile activity was partially restored in the regenerating portion of the wall of treated infarcts. Ejection fraction was also higher in treated than in untreated mice (FIG. 24, A to E). Thus, structural repair was coupled with functional repair.

To confirm that new myocytes reached functional competence and contributed to the amelioration of ventricular performance, these cells were enzymatically dissociated from the regenerating myocardium of the infarcted region of the wall (129) and their contractile behavior was evaluated in vitro (124, 130). Myocytes isolated from infarcted treated mice (n=10) by collagenase digestion were placed in a cell bath (30±0.2° C.) containing 1.0 mM Ca$^{2+}$ and stimulated at 0.5 Hz by rectangular depolarizing pulses, 3-5 ms in duration in twice diastolic threshold in intensity. Parameters were obtained from video images stored in a computer (124, 130). Developing myocytes were small with myofibrils located at the periphery of the cell in the subsarcolemmal region. The new myocytes resembled neonatal cells actively replicating DNA. They were markedly smaller than the spared hypertrophied ventricular myocytes (FIG. 25, A and B). In comparison with surviving old myocytes, growing cells showed a higher peak shortening and velocity of shortening, and a lower time to peak shortening (FIG. 25, C to J).

The isolated newly generated myocytes were stained by Ki67 to determine whether these cells were cycling and, therefore, synthesizing DNA. An identical protocol was applied to the isolated surviving hypertrophied myocytes of infarcted-treated mice. On this basis, the DNA content of each myocyte nucleus in mononucleated and binucleated cells was evaluated by PI staining and confocal microscopy (see FIG. 25, A and B). Control diploid mouse lymphocytes were used as baseline. The objective was to establish if cell fusion occurred in CSCs before their commitment to cell lineages. This possibility has recently been suggested by in vitro studies (131, 132). Non-cycling new myocytes and enlarged spared myocytes had only diploid nuclei, excluding that such a phenomenon played a role in cardiac repair (FIG. 66).

To establish the level of differentiation of maturing myocytes within the band, the expression of nestin, desmin, cardiac myosin heavy chain, α-sarcomeric actin, N-cadherin and connexin 43 was evaluated. N-cadherin identifies the fascia adherens and connexin 43 the gap junctions in the intercalated discs. These proteins are developmentally regulated. Connexin 43 is also critical for electrical coupling and synchrony of contraction of myocytes. These 6 proteins were detected in essentially all newly formed myocytes (FIG. 26, A to N). The percentage of myocytes labeled by BrdU was 84±9%, indicating that cell proliferation was ongoing in the regenerating tissue. Cardiac repair included the formation of capillaries and arterioles (FIG. 27, A to D). The presence of red blood cells within the lumen indicated that the vessels were connected with the coronary circulation. This phase of myocardial restoration, however, was characterized by a prevailing growth of resistance arterioles than capillary structures. There were 59±29 arterioles and 137±80 capillaries per mm$^2$ of new myocardium.

The current findings indicate that resident CSCs can be mobilized from their region of storage to colonize the infarcted myocardium where they differentiate into cardiac cell lineages resulting in tissue regeneration. The intervention utilized here was capable of salvaging animals with infarct size normally incompatible with life in mammals.

Example 9

Cardiac Stem Cells Differentiate In Vitro Acquiring Functional Competence In Vivo A. Collection and Cloning of Cells Cardiac cells were isolated from female Fischer rats at 20-25 months of age (111, 112). Intact cells were separated and myocytes were discarded. Small cells were resuspended and aggregates removed with a strainer. Cells were incubated with a rabbit c-kit antibody (H-300, Santa Cruz) which recognizes the N-terminal epitope localized at the external aspect of the membrane (121). Cells were exposed to magnetic beads coated with anti-rabbit IgG (Dynal) and c-kit$^{POS}$ cells were collected with a magnet (n=13). For FACS (n=4), cells were stained with r-phycoerythrin-conjugated rat monoclonal anti-c-kit (Pharmingen). With both methods, c-kit$^{POS}$ cells varied from 6-9% of the small cell population.

c-kit$^{POS}$ cells scored negative for myocyte (α-sarcomeric actin, cardiac myosin, desmin, α-cardiac actinin, connexin 43), endothelial cell (EC; factor VIII, CD31, vimentin), smooth muscle cell (SMC; α-smooth muscle actin, desmin)

and fibroblast (F; vimentin) cytoplasmic proteins. Nuclear markers of myocyte lineage (Nkx2.5, MEF2, GATA-4) were detected in 7-10% and cytoplasmic proteins in 1-2% of the cells. c-kit$^{POS}$ cells did not express skeletal muscle transcription factors (MyoD, myogenin, Myf5) or markers of the myeloid, lymphoid and erythroid cell lineages (CD45, CD45RO, CD8, TER-119), indicating the cells were Lin$^-$c-kit$^{POS}$ cells.

c-kit$^{POS}$ cells were plated at 1-2×10$^4$ cells/ml NSCM utilized for selection and growth of neural stem cells (122). This was composed by Dulbecco's MEM and Ham's F12 (ratio 1:1), bFGF, 10 ng/ml, EGF, 20 ng/ml, HEPES, 5 mM, insulin-transferrin-selenite. c-kit$^{POS}$ cells attached in two weeks and began to proliferate (FIG. 28a,b). NSCM was then substituted with differentiating medium (DM) and confluence was reached in 7-10 days. Cells were passaged by trypsinization. Cycling cells, as determined by Ki67 expression, varied from 74±12% to 84±8% at passages (P) P1-P5 (n=5 at each P). Doubling time at P2 and P4 averaged 41 hours. Cells continued to divide up to P23 without reaching growth arrest and senescence, at which time cells were frozen. Cardiac lineages were identified from P0 to P23. At P0 (n=7), P3 (n=10), P10 (n=13) and P23 (n=13), myocytes were 29-40%, EC 20-26%, SMC 18-23% and F 9-16%. Aliquots of P23 grown after 6 months in liquid nitrogen expressed the same phenotypes as the parental cells.

At P0 and P1 when grown in DM, 50% of the cells exhibited Nkx2.5, 60% MEF2, 30% GATA-4 and 55% GATA-5 (FIG. 28c-f). Conversely, skeletal muscle (MyoD, myogenin, Myf5), blood cell (CD45, CD45RO, CD8, TER-119) and neural (MAP1b, neurofilament 200, GFAP) markers were not identified.

For cloning, cells were seeded at 10-50 cells/ml NSCM (FIG. 28g) (109, 110). After one week, colonies derived from a single cell were recognized (FIG. 28h); fibronectin, procollagen type I and vimentin were absent excluding the fibroblast lineage. Individual colonies were detached with cloning cylinders and plated. Multiple clones developed and one clone in each preparation was chosen for characterization. MEM containing 10% FCS and 10$^{-8}$ M dexamethasone was employed to induce differentiation (DM). For subcloning, cells from multiple clones were plated at 10-50 cells/ml NSCM. Single subclones were isolated and plated in DM. At each subcloning step, an aliquot of cells was grown in suspension to develop clonal spheres.

Each clone contained groups of 2-3 Lin$^-$c-kit$^{POS}$ cells (FIG. 29a), although the majority of these cells (~20-50) were dispersed among c-kit$^{NEG}$ cells. Some cells were Ki67 positive and occasionally in mitosis (FIG. 29b-d). Myocytes expressing cardiac myosin and α-sarcomeric actin, EC expressing factor VIII, CD31 and vimentin, SMC expressing α-smooth muscle actin and F expressing vimentin alone were identified in each clone (FIG. 29e-h). Aggregates of small cells containing nestin were also present (Supplementary Information). Thus, Lin$^-$c-kit$^{POS}$ cells isolated from the myocardium possessed the properties expected for stem cells. They were clonogenic, self-renewing and multipotent and gave origin to the main cardiac cell types. Subclonal analysis of several primary clones confirmed the stability of the phenotype of the primary clones: clonogenicity, self-renewal and multipotentiality. The phenotype of most subclones was indistinguishable from that of the primary clones. However, in two of eight subclones, only myocytes were obtained in one case and exclusively EC were identified in the other.

Clonogenic cells, grown in suspension in Corning untreated dishes generated spherical clones (FIG. 30a). This anchorage independent growth is typical of stem cells[14,15].

Spheroids consisted of clusters of c-kit$^{POS}$ and c-kit$^{NEG}$ cells and large amounts of nestin (FIG. 30b-d). Similarly to other stem cells[14,15], following plating in DM, spheroids readily attached, and cells migrated out of the spheres and differentiated (FIG. 30e-h).

Cells were fixed in 4% paraformaldehyde and undifferentiated cells were labeled with c-kit antibody. Markers for myocytes included Nkx2.5, MEF2, GATA-4, GATA-5, nestin, α-sarcomeric actin, α-cardiac actinin, desmin and cardiac myosin heavy chain. Markers for SMC comprised α-smooth muscle actin and desmin, for EC factor VIII, CD31 and vimentin, and for F vimentin in the absence of factor VIII, fibronectin and procollagen type I. MyoD, myogenin and Myf5 were utilized as markers of skeletal muscle cells. CD45, CD45RO, CD8 and TER-119 were employed to exclude hematopoietic cell lineages. MAP1b, neurofilament 200 and GFAP were used to recognize neural cell lineages. BrdU and Ki67 were employed to identify cycling cells (61, 87). Nuclei were stained by PI.

Myocytes and SMC failed to contract in vitro. Angiotensin II, isoproterenol, norepinephrine and electrical stimulation did not promote contraction. EC did not express markers of full differentiation such as eNOS.

B. Myocardial Infarction and Cell Implantation

BrdU labeled cells (P2; positive cells=88±6%) were implanted. Myocardial infarction was produced in female Fischer rats at 2 months of age (111). Five hours later, 22 rats were injected with 2×10$^5$ cells in two opposite regions bordering the infarct; 12 rats were sacrificed at 10 days and 10 rats at 20 days. At each interval, 8-9 infarcted and 10 sham-operated rats were injected with saline and 5 with Lin$^-$c-kit$^{NEG}$ cells and used as controls. Under ketamine anesthesia, echocardiography was performed at 9 and 19 days, only in rats killed at 20 days. From M-mode tracings, LV end-diastolic diameter and wall thickness were obtained. Ejection fraction was computed (87). At 10 and 20 days, animals were anesthetized and LV pressures and + and − dP/dt were evaluated in the closed-chest preparation (111). Mortality was lower but not statistically significant in treated than in untreated rats at 10 and 20 days after surgery, averaging 35% in all groups combined. Protocols were approved by the institutional review board.

C. Anatomic and Functional Results

Hearts were arrested in diastole and fixed with formalin. Infarct size was determined by the fraction of myocytes lost from the left ventricle (87), 53±7% and 49±10% (NS) in treated and untreated rats at 10 days, and 70±9% and 55±10% (P<0.001) in treated and untreated rats at 20 days, respectively. The volume of 400 new myocytes was measured in each heart. Sections were stained with desmin and laminin and PI. In longitudinally oriented myocytes with centrally located nuclei, cell length and diameter across the nucleus were collected to compute cell volume (87).

Sections were incubated with BrdU and Ki67 antibodies. A band of regenerating myocardium was identified in 9 of 12 treated infarcts at 10 days, and in all 10 treated infarcts at 20 days. At 10 days, the band was thin and discontinuous and, at 20 days, was thicker and present throughout the infarcted area (FIG. 31a-c). Myocytes (M), EC, SMC and F were identified by cardiac myosin, factor VIII, α-smooth muscle actin and vimentin in the absence of factor VIII, respectively. Myocytes were also identified by cardiac myosin antibody and propidium iodide (PI). At 10 and 20 days, 30 and 48 mm$^3$ of new myocardium were measured, respectively. Tissue regeneration reduced infarct size from 53±7% to 40±5% (P<0.001) at 10 days, and from 70±9% to 48±7% (P<0.001) at 20 days Cells labeled by BrdU and Ki67 were identified by confocal microscopy (103, 105). The number of nuclei sampled for BrdU labeling were: M=5,229; EC=3,572; SMC=4,010; F=5,529. Corresponding values for Ki67 were: M=9,290; EC=9,103; SMC=8,392. Myocyte differentiation was established with cardiac myosin, α-sarcomeric actin, α-cardiac actinin, N-cadherin and connexin 43. Collagen was detected by collagen type I and type III antibodies.

Since implanted cells were labeled by BrdU, the origin of the cells in the developing myocardium was identified by this marker. Myocytes, arterioles (FIG. 31f-n) and capillary profiles were detected. At 10 days, the proportion of myocytes, capillaries and arterioles was lower, and collagen was higher than at 20 days. Cell growth evaluated by Ki67 was greater at 10 days decreasing at 20 days (Supplementary Information).

Cardiac myosin, α-sarcomeric actin, α-cardiac actinin, N-cadherin and connexin 43 were detected in myocytes (FIG. 31o-p; Supplementary Information). At 10 days, myocytes were small, sacromeres were rarely detectable and N-cadherin and connexin 43 were mostly located in the cytoplasm (FIG. 31o). Myocyte volume averaged 1,500 $\mu m^3$ and 13.9× $10^6$ myocytes were formed. At 20 days, myocytes were closely packed and myofibrils were more abundant; N-cadherin and connexin 43 defined the fascia adherens and nexuses in intercalated discs (FIG. 31p). Myocyte volume averaged 3,400 $\mu m^3$ and 13×$10^6$ myocytes were present.

Myocyte apoptosis was measured by in situ ligation of hairpin oligonucleotide probe with single base overhang. The number of nuclei sampled for apoptosis was 30,464 at 10 days and 12,760 at 20 days. The preservation of myocyte number from 10 to 20 days was consistent with a decrease in Ki67 labeling and an increase in apoptosis (0.33±0.23% to 0.85±0.31%, P<0.001).

Thus, myocyte proliferation prevailed early and myocyte hypertrophy later. From 10-20 days, the number of vessels nearly doubled.

Procedures for determining mechanical properties of the new myocytes have been previously described[30]. Myocytes isolated from infarcted treated rats (n=4) were placed in a cell bath (30±0.2° C.) containing 1.0 mM $Ca^{2+}$ and stimulated at 0.5 Hz by rectangular depolarizing pulses, 3-5 ms in duration in twice diastolic threshold in intensity. Mechanical parameters were obtained from video images stored in a computer. The mechanical behavior of myocytes isolated from the infarcted and non-infarcted regions of treated hearts was measured at 20 days (FIG. 32a-e). New cells were calcium tolerant and responded to stimulation. However, in comparison with spared myocytes, maturing cells showed a decreased peak shortening and velocity of shortening; time to peak shortening and time to 50% re-lengthening were similar in the two groups of cells (FIG. 33a-l). Developing myocytes had myofibrils mostly distributed at the periphery; sarcomere station was apparent (FIG. 32a-e).

Cell implantation reduced infarct size and cavitary dilation, and increased wall thickness and ejection fraction. Contraction reappeared in the infarcted ventricular wall and end-diastolic pressure, developed pressure and + and − dP/dt improved at 20 days. Diastolic stress was 52% lower in treated rats (Supplementary Information). Thus, structural and functional modifications promoted by cardiac repair decreased diastolic load and ameliorated ventricular performance. This beneficial effect occurred in spite of the fact that infarct size was similar in the two groups of rats.

Colonization, replication, differentiation of the transplanted cells and tissue regeneration required c-kit$^{POS}$ cells and damaged myocardium. c-kit$^{POS}$ cells injected in sham-operated rats grafted poorly and did not differentiate. Injection of c-kit$^{NEG}$ cells in the border of infarcts had no effect on cardiac repair.

The multipotent phenotype of the Lin$^-$c-kit$^{POS}$ cell reported here is in apparent contrast with cardiac cell lineage determinations in chicken (113), zebrafish (114) and mammals (115) concluding that myocytes, SMC, and EC each originates from a separate lineage. However, not all studies are in agreement (116). Because these experiments (113, 114, 115, 116) did not address the developmental potential of any of the cells marked, as has been done here, the different outcomes likely represent another example of the difference between normal developmental fate and developmental potential. Additionally, the plasticity of human embryonic stem cells (117), progenitor endothelial cells (101) and clonogenic cells (52) as means to repair damaged myocardium has recently been documented (101,52).

Example 10

Mobilization of Cardiac Stem Cells (CSC) by Growth Factors Promotes Repair of Infarcted Myocardium Improving Regional and Global Cardiac Function in Conscious Dogs The methods of the previous non-limiting examples were used with exceptions as described below.

Myocardial regeneration after infarction in rodents by stem cell homing and differentiation has left unanswered the question whether a similar type of cardiac repair would occur in large mammals. Moreover, whether new myocardium can affect the functional abnormality of infarcted segments restoring contraction is not known. For this purpose, dogs were chronically instrumented for measurements of hemodynamics and regional wall function. Stroke volume and EF were also determined. Myocardial infarction was induced by inflating a hydraulic occluder around the left anterior descending coronary artery. Four hours later, HGF and IGF-1 were injected in the border zone to mobilize and activate stem cells; dogs were then monitored up to 30 days. Growth factors induced chronic cardiac repair reversing bulging of the infarct: segment shortening increased from −2.0±0.7% to +5.5±2.2%, stroke work from −18±11 to +53±10 mm×mmHg, stroke volume from 22±2 to 45±4 ml and ejection fraction from 39±3 to 64±4%. In treated dogs at 8 hours after infarction, the number of primitive cells increased from 240±40 c-kit positive cells at baseline to 1700±400 (remote myocardium), 4400±1200 (border zone) and 3100±900 c-kit positive cells/100 $mm^2$ (infarcted area). Ki67 labeling was detected in 48%, 46% and 26% of c-kit positive cells in the remote, border and infarcted myocardium, respectively. Thus, high levels of these cells were replicating. These effects were essentially absent in infarcted untreated dogs. Acute experiments were complemented with the quantitative analysis of the infarcted myocardium defined by the implanted crystals 10-30 days after coronary occlusion. Changes from paradoxical movement to regular contraction in the new myocardium were characterized by the production of myocytes, varying in size from 400 to 16,000 with a mean volume of 2,000±640 $\mu m^3$. Resistance vessels with BrdU-labeled endothelial and smooth muscle cells were 87±48 per $mm^2$ of tissue. Capillaries were 2-3-fold higher than arterioles. Together, 16±9% of the infarct was replaced by healthy myocardium. Thus, canine resident primitive cells can be mobilized from the site of storage to reach dead myocardium. Stem cell activation and differentiation promotes repair of the infarcted heart improving local wall motion and systemic hemodynamics.

Example 11

Mobilization of Resident Cardiac Stem Cells Constitutes an Important Additional Treatment to Angiotensin II Blockade in the Infarcted Heart The methods of the previous non-limiting examples were used with exceptions as described below.

Two of the major complicating factors of myocardial infarction (MI) are the loss of muscle mass and cavitary dilation, which both contribute to negative left ventricular (LV) remodeling and to the depression in cardiac performance. In an attempt to interfere with these deleterious effects of MI, resident cardiac stem cells (CSC) were mobilized and activated to promote tissue regeneration, and the $AT_1$ receptor blocker losartan (Los) was administered, 20 mg/kg body weight/day, to attenuate cellular hypertrophy, and, thereby, the expansion in chamber volume. On this basis, MI was produced in mice and the animals were subdivided in four groups: 1. Sham-operated (SO); 2. MI only; 3. MI-Los; 4. MI-Los-CSC. One month after MI, animals were sacrificed, and LV function, infarct dimension and cardiac remodeling were evaluated. Myocardial regeneration was also measured in mice treated with CSC. Infarct size, based on the number of myocytes lost by the LV was 47% in MI, 51% MI-Los and 53% MI-Los-CSC. In comparison with MI and MI-Los, MI treated with Los and CSC resulted in a more favorable outcome of the damaged heart in terms of chamber diameter: −17% vs MI and −12% vs MI-Los; longitudinal axis: −26% ($p<0.001$) vs MI and −8% ($p<0.02$) vs MI-Los; and chamber volume: −40% ($p<0.01$) vs MI and −35% ($p<0.04$) vs MI-Los. The LV-mass-to-chamber volume ratio was 47% ($p<0.01$) and 56% ($p<0.01$) higher in MI-Los-CSC than in MI and MI-Los, respectively. Tissue repair in MI-Los-CSC was made of $10\times10^6$ new myocytes of 900 µm$^3$. Moreover, there were 70 arterioles and 200 capillaries per mm$^2$ of myocardium in this group of mice. The production of 9 mm$^3$ of new myocardium reduced MI size by 22% from 53% to 41% of LV. Echocardiographically, contractile function reappeared in the infarcted region of the wall of mice with MI-Los-CSC. Hemodynamically, MI-Los-CSC mice had a lower LVEDP, and higher + and − dP/dt. In conclusion, the positive impact of losartan on ventricular remodeling is enhanced by the process of cardiac repair mediated by translocation of CSC to the infarcted area. Mobilized CSC reduce infarct size and ventricular dilation and, thereby, ameliorate further the contractile behavior of the infarcted heart.

Example 12

Hepatocyte Growth Factor (HGF) Induces the Translocation of c-met to the Nucleus Activating the Expression of GATA-4 and Cardiac Stem Cell (CSC) Differentiation The methods of the previous non-limiting examples were used with exceptions as described below.

In preliminary studies we were able to document that CSCs positive for c-kit or MDR-1 expressed the surface receptor c-met. c-met is the receptor of HGF and ligand binding promoted cell motility via the synthesis of matrix metalloproteinases. However, it was unknown whether c-met activation had additional effects on CSCs biology and function. For this purpose, we tested whether c-met on CSCs exposed to 50 ng/ml of HGF in NSCM responded to the growth factor by internalization and translocation within the cell. Surprisingly, a localization of c-met in the nucleus was detected by confocal microscopy in these stimulated cells which maintained primitive characteristics. This unusual impact of HGF on c-met raised the possibility that the mobilized receptor could interact with other nuclear proteins participating in cell growth and differentiation of CSCs. Because of the critical role of the cardiac specific transcription factor GATA-4 in the commitment of cell lineage. By immunoprecipitation and Western blot, a protein complex made by c-met and GATA-4 was identified. A time-dependent analysis following a single HGF stimulation showed a progressive increase in c-met-GATA-4 complex from 15 minutes to 3 days. Time was also coupled with differentiation of primitive cells into myocytes and other cardiac cells. To establish a molecular interaction at the DNA level between GATA-4 and c-met, a gel retardation assay was performed on nuclear extracts isolated from cells stimulated with HGF for 1 hour. A shifted band was obtained utilizing a probe containing the GATA sequence. However, the addition of GATA-4 antibody resulted in a supershifted band. Conversely, the inclusion of c-met antibody attenuated the optical density of the GATA band. Since a GATA sequence upstream to the TATA box was identified in the c-met promoter, a second mobility shift assay was performed. In this case, nuclear extracts from HGF stimulated cells resulted in a shifted band which was diminished by c-met antibody. In contrast, GATA-4 antibody induced a supershifted band. Thus, HGF-mediated translocation of c-met at the level of the nucleus may confer to c-met a function of transcription factor and future studies will demonstrate whether this DNA binding enhances the expression of GATA-4 leading to the differentiation of immature cardiac cells.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. American Heart Association. 2001 *Heart and Stroke Statistical Update*. Dallas, Tex.: American Heart Association, 2000.
2. Bautz, F. et al., "Expression and secretion of vascular endothelial growth factor-A by cytokine stimulated hematopoietic progenitor cells. Possible role in the hematopoietic microenvironment." *Exp Hematol* 2000 June; 28(6):700-6.
3. Beardsle, M. A. et al., "Rapid turnover of connexin43 in the adult rat heart." *Circ. Res.* (1998) 83, 629-635.
4. Beltrami, C. A. et al., "Structural basis of end-stage failure in ischemic cardiomyopathy in humans." *Circulation* (1994) 89, 151-163.
5. Bianco, P. et al. "Bone marrow stromal stem cells: nature, biology, and potential applications." *Stem Cells* (2001) 19:180-192.
6. Blume et al., "A review of autologous hematopoetic cell transplantation." Biology of Blood & Marrow Transplantation, (2000) 6: 1-12.
7. Bodine, D. M. et al., "Efficient retrovirus transduction of mouse pluripotent hematopoietic stem cells mobilized into the peripheral blood by treatment with granulocyte colony-stimulating factor and stem cell factor." *Blood* (1994) 84, 1482-1491.
8. Breier, G. et al., "Molecular cloning and expression of murine vascular endothelial-cadherin in early stage development of cardiovascular system." *Blood* (1996) 87, 630-641.
9. Brugger et al., "Ex vivo manipulation of hematopoetic stem and progenitor cells. Seminars in Hematology." (2000), 37 (1): 42-49.
10. Caceres-Cortes, J. R. et al., "Steel factor sustains SCL expression and the survival of purified CD34+ bone marrow cells in the absence of detectable cell differentiation." *Stem Cells* (2001) January; 19(1):59-70.
11. Caplan A. I. and Haynesworth S. E., "Method for enhancing the implantation and differentiation of marrow-derived mesenchymal cells." Filed Nov. 16, 1990. U.S. Pat. No. 5,197,985
12. Chiu et al., "Cellular Cardiomyoplasty: Myardial Regeneration With Satellite Cell Implantation." *Ann. Thorac. Surg.*(1995) 60: 12-18.
13. Clutterbuck, R. D. et al., "G-CSF mobilization of haemopoietic cell populations in SCID mice engrafted with human leukaemia." *Bone Marrow Transplant* (1997) August; 20(4):325-32.
14. Coles, J. G. et al., "Inhibition of Human Xenogenic or Allogenic Antibodies to Reduce Xenograft or Allograft Rejection in Human Recipients". Patent No. WO 95/34581A1, published Dec. 21, 1995.
15. Couper, L. L. et al., "Vascular endothelial growth factor increases the mitogenic response to fibroblast growth factor-2 in vascular smooth muscle cells in vivo via expression of fms-like tyrosine kinase-1." (1997) *Circ. Res.* 81, 932-939.
16. Dinsmore, J. "Procine Cardiomyocytes and Their Use in Treatment of Insufficient Cardiac Function". Patent No. WO 96/38544, published Dec. 5, 1996.
17. Durocher, D. et al., "The cardiac transciption factors Nkx2-5 and GATA-4 are mutual cofactors." *EMBO J.* 16, 5687-5696 (1997).
18. Field L. J. "Non-human mammal having a graft and methods of delivering protein to myocardial tissue." Filed Nov. 16, 1992. U.S. Pat. No. 5,602,301.
19. Field L. J. "Myocardial grafts and cellular compositions." Filed Jun. 7, 1995. U.S. Pat. No. 5,733,727.
20. Field, L. J. "Myocardial Grafts and Cellular Compositions Useful for Same." Patent No. WO 95/14079A1, published May 26, 1995.
21. Fielding et al., "Autologous bone marrow transplantation." Curr. Opin. Hematology, 1994, 1: 412-417.
22. Gillis S. "Method for improving autologous transplantation." Filed Sep. 26, 1991. U.S. Pat. No. 5,199,942
23. Gussoni et al., "Normal dystrophin transcripts detected in Duchenne muscular dystrophy patients after myoblast transplantation." Nature 356:435-438 (1992).
24. Hermann, H. and Aebi, U. "In Subcellular Biochemistry: Intermediate Filaments."Vol. 31 (ed. Herrmann, H. & Harris, E.) 319-362 (Plenum Press, New York, 1998).
25. Huang H. M. et al., "Optimal proliferation of a hematopoietic progenitor cell line requires either costimulation with stem cell factor or increase of receptor expression that can be replaced by overexpression of Bcl-2. Blood." 1999 Apr. 15; 93(8):2569-77.
26. Ikuta, K et al., "Mouse hematopoietic stem cells and the interaction of c-kit receptor and steel factor." *International Journal of Cell Cloning* 1991; 9:451-460.
27. Janowska-Wieczorek, A. et al., "Autocrine/paracrine mechanisms in human hematopoiesis." *Stem Cells* 2001; 19:99-107.
28. Jo, D. Y. et al., "Chemotaxis of primitive hematopoietic cells in response to stromal cell-derived factor-1." *The Journal of Clinical Investigation* 2000 January; 105(1): 101-111.
29. Kachinsky, A. M. et al., "Intermediate filaments in cardiac myogenesis: nestin in the developing mouse heart." (1995) *J. Histochem. Cytochem.* 43, 843-847.
30. Kanj et al., "Myocardial ischemia associated with high-dose carmustine infusion." Cancer, 1991, 68 (9): 1910-1912.
31. Kajstura, J. et al., "The cellular basis of pacing-induced dilated cardiomyopathy. Myocyte cell loss and myocyte cellular reactive hypertrophy." (1995) *Circulation* 92, 2306-2317.
32. Kasahara, H. et al, "Cardiac and extracardiac expression of Csx/Nkx2.5 homeodomain protein." (1998) *Circ. Res.* 82, 936-946.
33. Kedes, L. H. et al., "Compositions and Methods for Transduction of Cells." Patent No. WO 95/12979A1, published May 18, 1995.
34. Keil F. et al., "Effect of interleukin-3, stem cell factor and granulocyte-macrophage colony-stimulating factor on committed stem cells, long-term culture initiating cells and bone marrow stroma in a one-step long-term bone marrow culture." Ann Hematol. 2000 May; 79(5):243-8.
35. Kempermann, G. et al., "Activity-dependent regulation of neuronal plasticity and self repair." *Prog Brain Res* 2000; 127:35-48.
36. Kim, C. H. and Broxmeyer H. E., "In vitro behavior of hematopoietic progenitor cells under the influence of chemoattractants: stromal cell-derived factor-1, steel factor, and the bone marrow environment." *Blood* 1998 Jan. 1; 91(1):100-10.
37. Kocher, A. A. et al., "Neovascularization of ischemic myocardium by human bone-marrow-derived angioblasts prevents cardiomyocyte apoptosis reduces remodeling and improves cardiac function." *Nature Medicine* 2001 April; 7(4):430-436.
38. Koh et al., "Differentiation and long-term survival of C2C12 myoblast grafts in heart." Journal of Clinical Investigation 92:1548-1554 (1993).
39. Krause, D. S. et al., "Multi-organ, multi-lineage engraftment by a single bone marrow-derived stem cell." *Cell* (2001) May; 105(3)369-370.
40. Kronenwett, R. et al., "The role of cytokines and adhesion molecules for mobilization of peripheral blood stem cells." *Stem Cells* 2000; 18:320-330.
41. LaIuppa, J. A. et al., "Evaluation of cytokines for expansion of the megakaryocyte and ranulocyte lineages." *Stem Cells* (1997) May:15(3):198-206.
42. Leor et al., "Transplantation of Fetal Myocardial Tissue Into the Infarcted Myocardium of Rat, A Potential Method for Repair of Infarcted Myocardium?" Circulation 94: (Supplement II) II-332-II-336 (1996).
43. Li et al., "Method of Culturing Cardiomyocytes from Human Pediatric Ventricular Myocardium." (1992) *J. Tiss. Cult. Meth.;* 93-100.
44. Li, Q. et al. "Overexpression of insulin-like growth factor-1 in mice protects from myocyte death after infarction, attenuating ventricular dilation, wall stress, and cardiac hypertrophy." *J Clin Invest.* 100, 1991-1999 (1997).
45. Li, B et al., "Insulin-like growth factor-1 attenuates the detrimental impact of nonocclusive coronary artery constriction on the heart." (1999) *Circ. Res.* 84, 1007-1019.

46. Li et al., J. Mol. Cell. Cardiol., 26:A162 (1994).
47. Li et al., Cardiovascular Res. 32:362-373 (1996).
48. Li et al., "In Vivo Survival and Function of Transplanted Rat Cardiomyocytes" *Circulation Research* 78:283-288 (1996).
49. Li et al., "Cardiomyocyte Transplantation Improves Heart Function" (1996) *The Society of Thoracic Surgeons;* 62: 654-661.
50. Li et al., "Human Pediatric and Adult Ventricular Cardiomyocytes in Culture: Assessment of Phenotypic Changes with Passaging" Feb. 20, 1996 *Cardiovascular Research;* 1-12.
51. Lin, Q. et al., "Control of mouse cardiac morphogenesis and myogenesis by transcription factor MEF2C." (1997) *Science* 276, 1404-1407.
52. Malouf, N. N. et al., "Adult derived stem cells from the liver become myocytes in the heart in vivo." *Am J Pathology* 2001 June; 158(6)1929-35.
53. Menasche, P. et al., (2000) *Lancet* 357, 279-280.
54. Morin, S. et al., "GATA-dependent recruitment of MEF2 proteins to target promoters." (2000) *EMBO J.* 19, 2046-2055.
55. Murray et al., "Skeletal Myobalst Transplantation for Repair of Myocardial Necrosis" J. Clin. Invest. 98:2512-2523 (1996).
56. Musil, L. S. et al., "Regulation of connexin degradation as a mechanism to increase gap junction assembly and function." (2000) *J. Biol. Chem.* 275, 25207-25215.
57. National Institutes of Health. "Stem Cells: A Primer." *National Insitutes of Health:* May 2000.
58. Noishiki et al., "Angiogenic growth factor release system for in vivo tissue engineering: a trial of bone marrow transplantation into ischemic myocardium."(1999) *J. Artif. Organs,* 2: 85-91.
59. Olivetti, G. et al., "Cellular basis of chronic ventricular remodeling after myocardial infarction in rats." (1991) *Circ. Res.* 68(3), 856-869.
60. Orlic, D. et al., (1993) *Blood* 91, 3247-3254.
61. Orlic, D. et al., "Bone marrow cells regenerate infarcted myocardium." (2001) *Nature* 410, 701-705.
62. Patchen, M L et al. "Mobilization of peripheral blood progenitor cells by Betafectin® PGG-glucan alone and in combination with granulocyte colony-stimulating factor." *Stem Cells* (1998) May; 16(3):208-217.
63. Pfeffer, M. A. and Braunwald, E. "Ventricular remodeling after myocardial infarction." *Circulation* 81, 1161-1172 (1990).
64. Pollick, C. et al., "Echocardiographic and cardiac Doppler assessment of mice." (1995) *J. Am. Soc. Echocardiogr.* 8, 602-610 (1995).
65. Reiss, K et al., "Overexpression of insulin-like growth factor-1 in the heart is coupled with myocyte proliferation in transgenic mice." (1996) *Proc. Natl. Acad. Sci. USA* 93(16), 8630-8635.
66. Roberts M. M., et al., "Prolonged release and c-kit expression of haemopoietic precursor cells mobilized by stem cell factor and granulocyte colony stimulating factor." Br J Haematol. 1999 March; 104(4):778-84.
67. Rosenthal, N. and Tsao, L. "Helping the heart to heal with stem cells." *Nature Medicine* 2001 April; 7(4):412-413.
68. Scholzen, T., and Gerdes, J. "The ki-67 protein: from the known and the unknown." *J. Cell. Physiol.* 182, 311-322 (2000).
69. Shimomura T., et al., "Thrombopoietin stimulates murine lineage negative, Sca-1+, C-Kit+, CD34-cells: comparative study with stem cell factor or interleukin-3." *Int J Hematol.* (2000) January; 71(1):33-9.
70. Soonpaa et al. "Formation of nascent intercalated disks between grafted fetal cardiomyocytes and host myocardium." (1994) *Science* 264(5155):98-101.
71. Silver J. et al., "Methods of reducing glial scar formation and promoting axon and blood vessel growth and/or regeneration through the use of activated immature astrocytes." Filed Oct. 27, 1989. U.S. Pat. No. 5,202,120.
72. Simnett et al. "Autologous stem cell translantation for malignancy: a systemic review of the literature." Clin. Lab Haem. 2000, 22:61-72.
73. Smith D. A. et al., "Method for inducing human myocardial cell proliferation." Filed Apr. 4, 1995. U.S. Pat. No. 5,580,779
74. Smith D. A. and Townsend L E. "Method of isolation, culture and proliferation of human atrial myocytes." Filed Sep. 21, 1995. U.S. Pat. No. 5,543,318
75. Strobel, E S et al. "Adhesion and migration are differentially regulated in hematopoietic progenitor cells by cytokines and extracellular matrix." *Blood* (1997) November 1; 90(9):3524-3532.
76. Taylor, D. A. et al. (1998) *Nature Med.* 4, 929-933.
77. Temple, S. "Opinion: Stem cell plasticity—building the brain of our dreams." *Nat Rev Neurosci* 2001 July; 2(7): 513-520.
78. Thompson et al. *Science* 257:868-870 (1992).
79. Tomita, S et al. (1999) *Circulation* 100(suppl II), II-247-II-256.
80. Vaughn et al. "Incorporating bone marrow transplantation into NCCN guidelines." (1998) *Oncology,* 12 (11A): 390-392.
81. Yamaguchi, T. P. et al., "Flk-1, an flt-related receptor tyrosine kinase is an early marker for endothelial cell precursors. Development." (1993) *Development* 118(2), 489-498.
82. Quaini, F. et al. "Chimerism of the transplanted heart." (2002) *N Engl J Med.* 346(1):5-15 N.
83. Anversa, P. and Nadal-Ginard, B., "Myocyte renewal and ventricular remodelling." *Nature.* (2002); 415(6868):240-3.
84. Beltrami, A. P. et al., "Chimerism of the transplanted heart." N Engl J Med. (2002) 346(1):5-15.
85. Reya, T. et al., "Stem cells, cancer, and cancer stem cells." (2001) *Nature* 414(6859):105-11. Jackson, K. A. et al., "Hematopoietic potential of stem cells isolated from murine skeletal muscle." *Proc Natl Acad Sci USA.* (1999) 96(25):14482-6.
86. Orlic, D. et al., "Mobilized bone marrow cells repair the infarcted heart, improving function and survival." *Proc Natl Acad Sci* USA. (2001) 98(18):10344-9.
87. Blau, H. M. et al., "The evolving concept of a stem cell: entity or function?" *Cell.* (2001); 105(7):829-41.
88. S. P. Monga, S. P. et al. "Expansion of hepatic and hematopoietic stem cells utilizing mouse embryonic liver explants." (2001) *Cell Transplant.* January-February; 10(1), 81-89.
89. Weimar, I. S. et al., ",Hepatocyte growth factor/scatter factor (HGF/SF) is produced by human bone marrow stromal cells and promotes proliferation, adhesion and survival of human hematopoietic progenitor cells (CD34+)." *Exp Hematol.* (1998) 26(9):885-94.
90. Yu, C. Z. et al., *Stem Cells* 16, 66 (1998).
91. Birchmeier, C. and Brohmann, H., *Curr. Opin. Cell Biol.* 12, 725 (2001).
92. Xing, X. et al., *Am. J. Pathol.* 158, 1111 (2001).
93. Hamasuna, R. et al. "Regulation of matrix metalloproteinase-2 (MMP-2) by hepatocyte growth factor/scatter factor (HGF/SF) in human glioma cells: HGF/SF enhances MMP-2 expression and activation accompanying up-regulation of membrane type-1 MMP." *Int J Cancer.* (1999) 82(2):274-81.
94. Wang, H. and Keiser, J. A., "Hepatocyte growth factor enhances MMP activity in human endothelial cells." *Biochem Biophys Res Commun.* 2000; 272(3):900-5.
95. Arsenijevic, Y. et al., "Insulin-like growth factor-I is necessary for neural stem cell proliferation and demonstrates distinct actions of epidermal growth factor and fibroblast growth factor-2." *J Neurosci.* (2001) 21(18):7194-202
96. Arsenijevic, Y. and Weiss, S., J. Neurosci. "Insulin-like growth factor-I is a differentiation factor for postmitotic CNS stem cell-derived neuronal precursors: distinct actions from those of brain-derived neurotrophic factor." *J Neurosci.* (1998) 18(6):2118-28.
97. Brooker, G. J. et al., "Endogenous IGF-1 regulates the neuronal differentiation of adult stem cells." *J Neurosci Res.* (2000) 59(3):332-41.
98. Page, D. L. et al., "Myocardial changes associated with cardiogenic shock." *N Engl J Med.* (1971) 285(3):133-7.
99. Pasumarthi, K. B. S. et al., "Coexpression of mutant p53 and p193 renders embryonic stem cell-derived cardiomyocytes responsive to the growth-promoting activities of adenoviral E1A." *Circ Res.* (2001) 88(10):1004-11.
100. Condorelli, G. et al.,"Cardiomyocytes induce endothelial cells to trans-differentiate into cardiac muscle: implications for myocardium regeneration." *Proc Natl Acad Sci USA.* (2001) 98(19):10733-8.
101. Beltrami, A. P. et al. "Evidence that human cardiac myocytes divide after myocardial infarction." *N Engl J Med.* (2001) 344(23):1750-7.
102. Jackson, K. A. et al., *J. Clin. Invest.* (2001) 107, 1395.
103. MacLellan, W. R. and Schneider, M. D. "Genetic dissection of cardiac growth control pathways." *Annu. Rev. Physiol.* (2000) 62, 289-319.
104. Hidemasa, O. et al. "Telomerase reverse transcriptase promotes cardiac muscle cell proliferation, hypertrophy, and survival."*Proc. Natl. Acad. Sci. USA* 98, 10308-10313 (2001).
105. Anversa, P. and Kajstura, J. "Ventricular myocytes are not terminally differentiated in the adult mammalian heart." *Circ. Res.* (1998) 83, 1-14.
106. Rao, M. S. and Mattson, M. P. "Stem cells and aging: expanding the possibilities.*Mech. Ageing Dev.* (1998) 122, 713-734.
107. Zaucha, J. M. et al. "Hematopoietic responses to stress conditions in young dogs compared with elderly dogs." *Blood* (2001) 98, 322-327.
108. Gritti, A. et al. "Epidermal and fibroblast growth factors behave as mitogenic regulators for a single multipotent stem cell-like population from the subventricular region of the adult mouse forebrain." *J. Neurosci.* (1999) 19, 3287-3297.
109. Shihabuddin, L. S. et al., "Adult spinal cord stem cells generate neurons after transplantation in the adult dentate gyrus." *J. Neurosci.* (2000) 20, 8727-8735.
110. Cheng, W. et al. "Aging does not affect the activation of the myocyte IGF-1 autocrine system after infarction and ventricular failure in Fischer 344 rats." *Circ. Res.* (1996) 78, 536-546.
111. Kajstura, J. et al. "Apoptotic and necrotic myocyte cell deaths are independent contributing variables of infarct size in rats." *Lab. Invest.* (1996) 74, 86-107.
112. Mikawa, T. & Fishman, D. A. "The polyclonal origin of myocyte lineages." *Annu. Rev. Physiol.* (1996) 58, 509-521.
113. Stainer, D. Y. R. et al., "Cardiovascular development in zebrafish. I. Myocardial fate and heart tube formation." *Development* (1993) 119, 31-40.
114. Hillebrands, J -L. et al. "Origin of neointimal endothelium and α-actin-positive smooth muscle cells in transplant arteriosclerosis." *J. Clin. Invest.* (2001) 107, 1411-1422.
115. Eisenberg, C. A & Bader, D. "QCE-6: a clonal cell line with cardiac myogenic and endothelial cell potentials." *Dev. Biol.* (1995) 167, 469-481.
116. Kehat, I. et al. "Human embryonic stem cells can differentiate into myocytes with structural and functional properties of myocytes." *J. Clin. Invest.* (2001) 108, 407-414.
117. Anderson, D. J. "Stem cells and pattern formation in the nervous system: the possible versus the actual." *Neuron* (2001) 30, 19-35.
118. Lee, J. Y. et al. "Clonal isolation of muscle-derived cells capable of enhancing muscle regeneration and bone healing." *J. Cell Biol.* (2000) 150, 1085-1099.
119. Seale, P. et al. "Pax7 is required for the specification of myogenic satellite cells." *Cell* (2000) 102, 777-786.
120. Broudy, V. C. "Stem cell factor and hematopoiesis." *Blood* (1997) 90, 1345-1364.
121. Tropepe, V. et al. "Distinct neural stem cells proliferate in response to EGF and FGF developing mouse telencephalon." *Dev. Biol.* (1999) 208, 166-188.
122. Li, P. et. al. "Myocyte performance during evolution of myocardial infarction in rats: effects of propionyl-L-carnitine." *Am. J. Physiol.* (1995) 208, H1702-H1713.
123. Beltrami, A. P. et al., Submitted (2002).
124. Bunting, K. D. et al., *Blood* 96, 902 (2000).
125. Block, G. D. et al., *J. Cell Biol.* 132, 1133 (1996).
126. Rappolee, D. A. et al., *Circ. Res.* 78, 1028 (1996).
127. Powell, E. M. et al., *Neuron.* 30, 79 (2001).
128. Leri, A. et al., *Circ. Res.* 84, 752 (1999).
129. Capasso, J. M. and Anversa, P., *Am. J. Physiol.* 263, H841 (1992).
130. Terada, N. et al. *Nature,* Advanced online publication DOI: nature730, (2002).
131. Ying, Q -L. et al., *Nature,* Advanced online publication DOI: nature729, (2002).

We claim:

1. A method for restoring functional and structural integrity to damaged myocardium in a subject in need thereof, the method comprising administering to the subject an effective amount of a cytokine to form a chemotactic gradient in the subject's heart sufficient to cause adult cardiac stem cells resident in the heart to migrate to the area of the damaged myocardium, wherein said gradient is formed by multiple injections of said cytokine from storage areas of said resident adult cardiac stem cells to a border zone of the damaged myocardium, and wherein the functional and structural integrity of the damaged myocardium is restored following the migration of adult cardiac stem cells to the area of damaged myocardium.

2. A method for restoring functional and structural integrity to damaged myocardium in a subject in need thereof, the method comprising administering to the subject an effective amount of at least one isolated cytokine to form a chemotactic gradient in the subject's heart sufficient to cause adult cardiac stem cells resident in the heart to replicate and migrate to the area of the damaged myocardium, wherein said gradient is formed by multiple injections of said at least one cytokine from storage areas of said resident adult cardiac stem cells to a border zone of the damaged myocardium, and wherein the functional and structural integrity of the damaged myocardium is restored following the migration of adult cardiac stem cells to the area of damaged myocardium.

3. The method of claim 2, wherein said stem cells are c-kit$^{POS}$.

4. The method of claim 2, wherein the injections are intramyocardial.

5. The method of claim 2, wherein the injections are transepicardial.

6. The method of claim 2, wherein the multiple injections comprise variable concentrations of one or more of said cytokines.

7. The method of claim 2, wherein the adult cardiac stem cells differentiate into myocytes, smooth muscle cells, and endothelial cells.

8. The method of claim 7 wherein at least some of the differentiated adult cardiac stem cells assemble into myocardial tissue and myocardial vessels.

9. The method of claim 2, wherein said method also regenerates cardiac vessels.

10. The method of claim 2, wherein the storage areas of said resident adult cardiac stem cells are one or more of the subject's myocardial apex, left atrium, and right atrium.

11. The method of claim 2, wherein at least two of the injections are done at opposite sides of the border zone.

12. The method of claim 2, wherein the at least one cytokine is capable of mobilizing adult stem cells in vitro.

13. The method of claim 12, wherein the at least one cytokine is selected from the group consisting of hepatocyte growth factor, stem cell factor, and granulocyte monocyte colony stimulating factor.

14. The method of claim 13, wherein the at least one cytokine is hepatocyte growth factor.

15. The method of claim 14, wherein said hepatocyte growth factor is administered at varying concentrations of between 0 and 400 ng/ml at different places of administration.

16. The method of claim 15, wherein the varying concentrations of the hepatocyte growth factor increase progressively in a direction towards the damaged myocardium.

17. The method of claim 14 wherein said hepatocyte growth factor is administered at varying concentrations of between 50 and 200 ng/ml at different places of administration.

18. The method of claim 2, further comprising administering a second cytokine, wherein the second cytokine induces proliferation of adult cardiac stem cells.

19. The method of claim 18, wherein the second cytokine is insulin-like growth factor-1.

20. The method of claim 19, wherein said insulin-like growth factor-1 is administered at a concentration less than 500 ng/ml.

21. The method of claim 19, wherein said insulin-like growth factor-1 is administered at a concentration of between 150 and 250 ng/ml.

22. The method of claim 19, wherein said insulin-like growth factor-1 is administered at a concentration of 200 ng/ml.

* * * * *

UNITED STATES PATENT AND TRADEMARK OFFICE
CERTIFICATE OF CORRECTION

PATENT NO. : 7,547,674 B2
APPLICATION NO. : 10/162796
DATED : June 16, 2009
INVENTOR(S) : Piero Anversa Page 1 of 1

It is certified that error appears in the above-identified patent and that said Letters Patent is hereby corrected as shown below:

Title Pg, Item [75], Inventors: delete "Donald Orlic, Bethesda, MD (US)" as an inventor.

Signed and Sealed this

Fourteenth Day of July, 2009

JOHN DOLL
*Acting Director of the United States Patent and Trademark Office*